(12) United States Patent
Luo et al.

(10) Patent No.: US 9,580,725 B2
(45) Date of Patent: Feb. 28, 2017

(54) METHODS AND COMPOSITIONS FOR MODIFYING PLANT FLAVONOID COMPOSITION AND DISEASE RESISTANCE

(71) Applicant: NORFOLK PLANT SCIENCES LIMITED, Norwich, Norfolk (GB)

(72) Inventors: Jie Luo, Norwich (GB); Eugenio Butelli, Norwich (GB); Jonathan Jones, Norwich (GB); Laurence Tomlinson, Norwich (GB); Catherine Rosemary Martin, Norwich (GB)

(73) Assignee: Norfolk Plant Sciences Limited, Norwich (GB)

( * ) Notice: Subject to any disclaimer, the term of this patent is extended or adjusted under 35 U.S.C. 154(b) by 167 days.

(21) Appl. No.: 14/315,366

(22) Filed: Jun. 26, 2014

(65) Prior Publication Data
US 2015/0074846 A1 Mar. 12, 2015

Related U.S. Application Data

(62) Division of application No. 12/918,248, filed as application No. PCT/GB2009/000431 on Feb. 18, 2009, now Pat. No. 8,802,925.

(60) Provisional application No. 61/029,416, filed on Feb. 18, 2008.

(51) Int. Cl.
| | |
|---|---|
| *C12N 15/82* | (2006.01) |
| *C07K 14/415* | (2006.01) |
| *C07K 14/47* | (2006.01) |

(52) U.S. Cl.
CPC ........ *C12N 15/8257* (2013.01); *C07K 14/415* (2013.01); *C07K 14/4702* (2013.01); *C12N 15/8201* (2013.01); *C12N 15/825* (2013.01)

(58) Field of Classification Search
CPC .......................... C12N 15/8257; C12N 15/825
See application file for complete search history.

(56) References Cited

U.S. PATENT DOCUMENTS 6,881,430 B2  4/2005  Kohler et al.

FOREIGN PATENT DOCUMENTS

| KR | 2009111404 A | 10/2009 |
|---|---|---|
| WO | WO 2006/062698 A2 | 6/2006 |

OTHER PUBLICATIONS

Mehrtens, F. et al., Plant Physiology (2005), vol. 138; pp. 1083-1096.*

(Continued)

*Primary Examiner* — Russell Kallis
(74) *Attorney, Agent, or Firm* — Williams Mullen, PC; David M. Saravitz

(57) ABSTRACT

The invention provides methods, compositions and transformation systems for modifying the levels of transcription factors in plants such as *Solanaceous* plants, and introducing disease resistance genes into plants, to produce products with elevated levels of antioxidant compounds, including but not limited to flavonols and chlorogenic acid, as well as exhibiting enhanced disease resistance, and optionally altered appearance. Preferred plants are those in which introduced genes are from *Solanaceous* species.

20 Claims, 38 Drawing Sheets

(56) References Cited

OTHER PUBLICATIONS

Allen, A., et al., "MYB Transcription Fac5tors that Colour our Fruit," *Trends in Plant Science*, Feb. 2008, pp. 99-102, vol. 13(3).
Du, H., et al., "Biochemical and Molecular Characterization of Plant MYB Transcription Factor Family," *Biochemistry* (Moscow), 2009, pp. 1-11, vol. 74(1).
Gonzalez, et al., "Regulation of the anthocyanin biosynthetic pathway by the TTG1/bHLH/Myb transcriptional complex in Arabidopsis seedlings," *The Plant Journal*, 2008, pp. 814-827, vol. 53.
Jung, et al., "The potato *developer* (*D*) locus encodes an R2R3 MYB transcription factor that regulates expression of multiple anthocyanin structural genes in tuber skin," *Theor. Appl. Genet.*, 2009, pp. 45-57, vol. 120(1).
Kinney, A., "Metabolic engineering in plants for human health and nutrition," *Current Opinion in Biotechnology*, 2006, pp. 130-138, vol. 17.
Luo, J., et al., "AtMYB12 regulates caffeoyl quinic acid and favonol synthesis in tomato: expression in fruit results in very high levels of both types of polyphenol," *The Plan Journal*, 2008, pp. 316-326, vol. 56.
Matthews, et al., "Activation Tagging in Tomato Identifies a Transcriptional Regulator of Anthocyanin Biosynthesis, Modification, and Transport," *The Plant Cell*, Aug. 2003, pp. 1689-1703, vol. 15.

Mehrtens, F., et al., "The Arabidopsis Transcription Factor MYB12 is a Flavonol-Specific Regulator of Phenylpropanoid Biosynthesis," *Plant Physiology*, Jun. 2005, pp. 1083-1096, vol. 138.
*Nature Reviews—Genetics*, 2003, Glossary Terms for Clegg et al., vol. 4 (March): pp. 206-215.
Stracke, R., et al., "Differential regulation of closely related R2R3-MYB transcription factors controls flavonol accumulation in different parts of the Arabidopsis thaliana seedling," *The Plant Journal*, 2007, pp. 660-677, vol. 50.
Oregon State University (2006, 2009), Dept. of Horticulture "Oregon Vegetables: Purple Tomato FAQ".
Pelegrini, et al., "Plant γ-thionins: Novel insights on the mechanism of action of a multi-functional class of defense proteins," *The International Journal of Biochemistry & Cell Biology*, 2005, pp. 2239-2253, vol. 37(11).
Schwinn, et al., "A small Family of *MYB*-Regulatory Genes Controls Floral Pigmentation Intensity and Patterning in the Genus *Antirrhinum*," *The Plant Cell*, 2006, pp. 831-851, vol. 18.
Shang, et al., "Methods for transient assay of gene function in floral tissues," *Plant Methods*, 2007, pp. 1-12, vol. 3(1).
USDA—Agriculture Research Service (2006). Germplasm Resources Information Network (ARS-GRIN), Genus "*Antirrhinum L.*"

\* cited by examiner

MGRTPCCEKVGIKRGRWTAEEDQILTNYIISNGEGSWRSLPKNAGLLRCGKSCRLRWINYLRS
DLKRGNITSQEEDIIIKLHATLGNRWSLIAEHLSGRTDNEIKNYWNSHLSRKVDSLRIPSDEKLP
KAVVDLAKKGIPKPIKKSSISRPKNKKSNLLEKEALCCTNMPACDSAMELMQEDLAKIEVPNS
WAGPIEAKGSLSSDSDIEWPRLEEIMPDVVIDDEDKNTNFILNCFREEVTSNNVGNSYSCIEEGN
KKISSDDEKIKLLMDWQDNDELVWPTLPWELETDIVPSWPQWDDTDTNLLQNCTNDNNNYEE
ATTMEINNQNHSTIVSWLLS

B

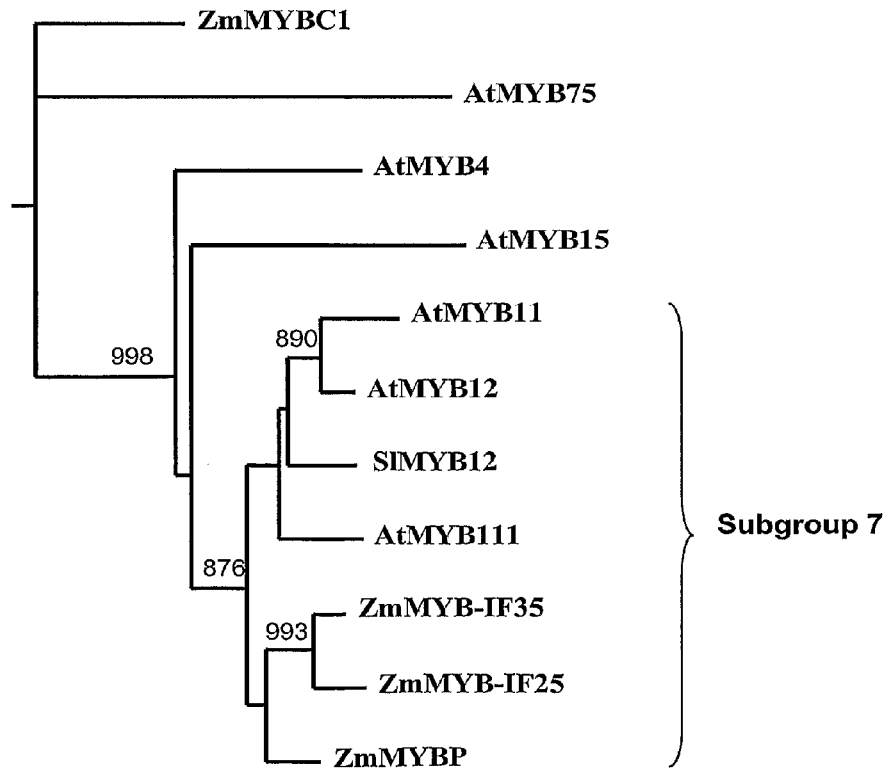

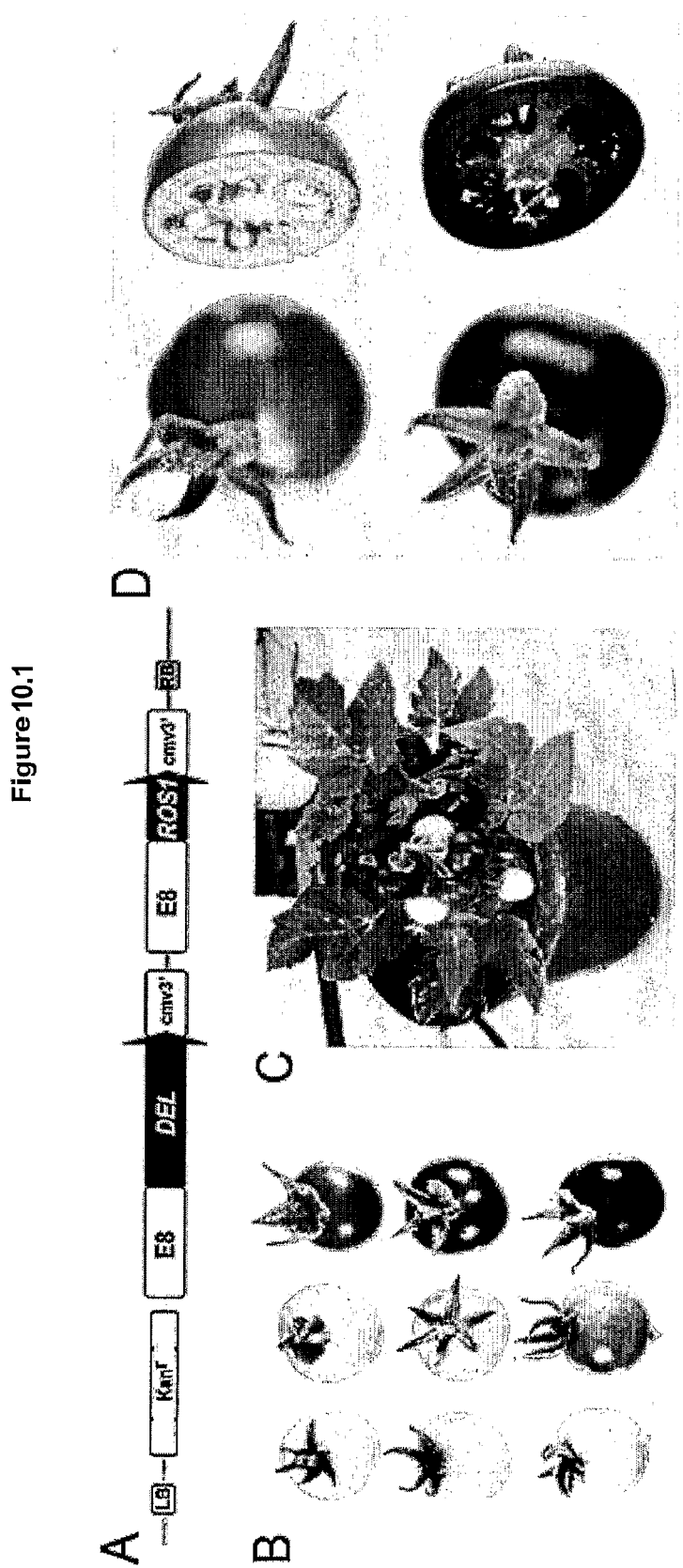
Figure 10.1

Figure 10.2
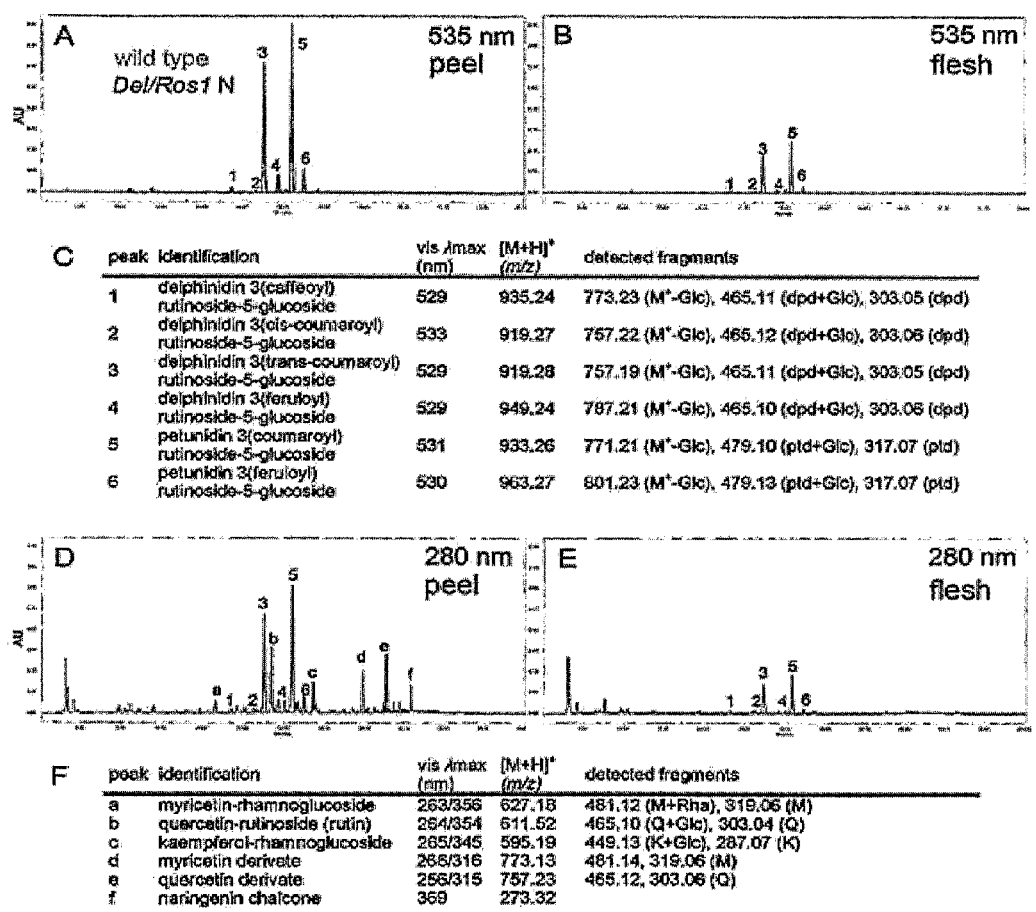

Figure 10.3
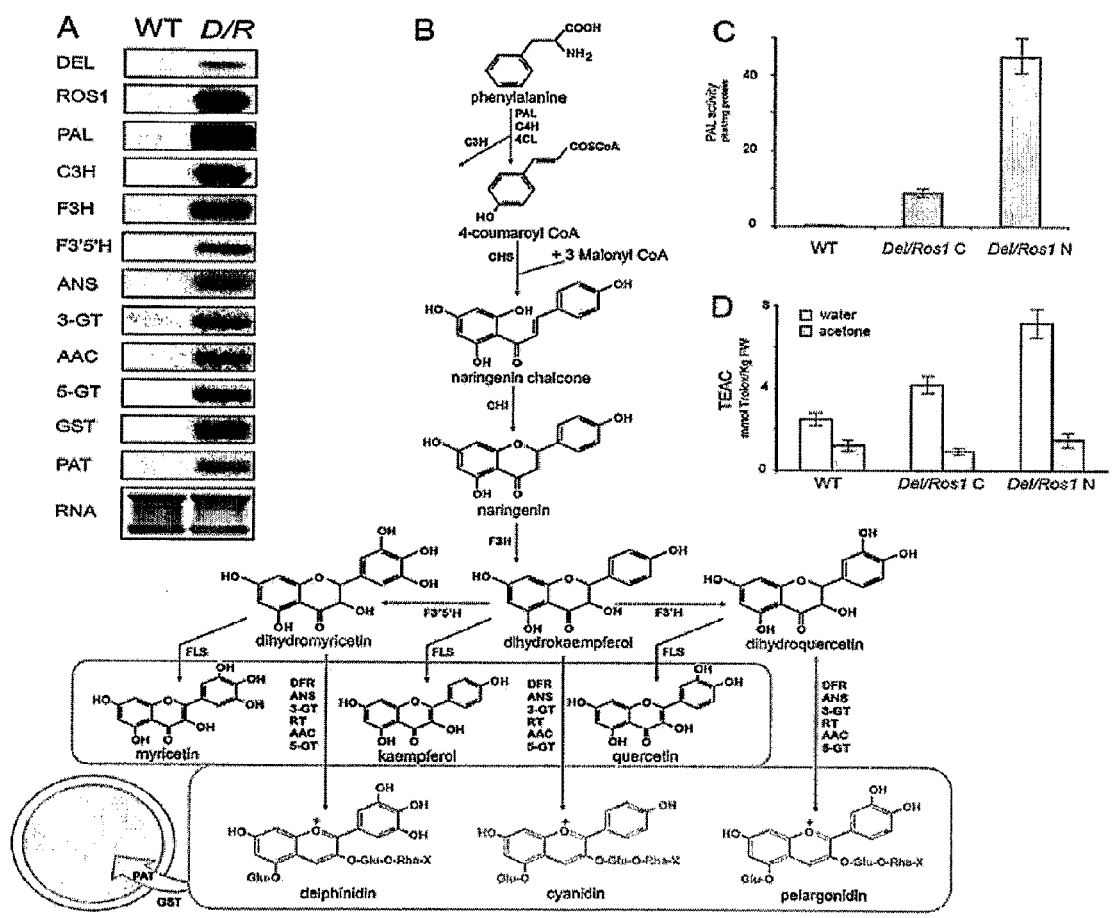

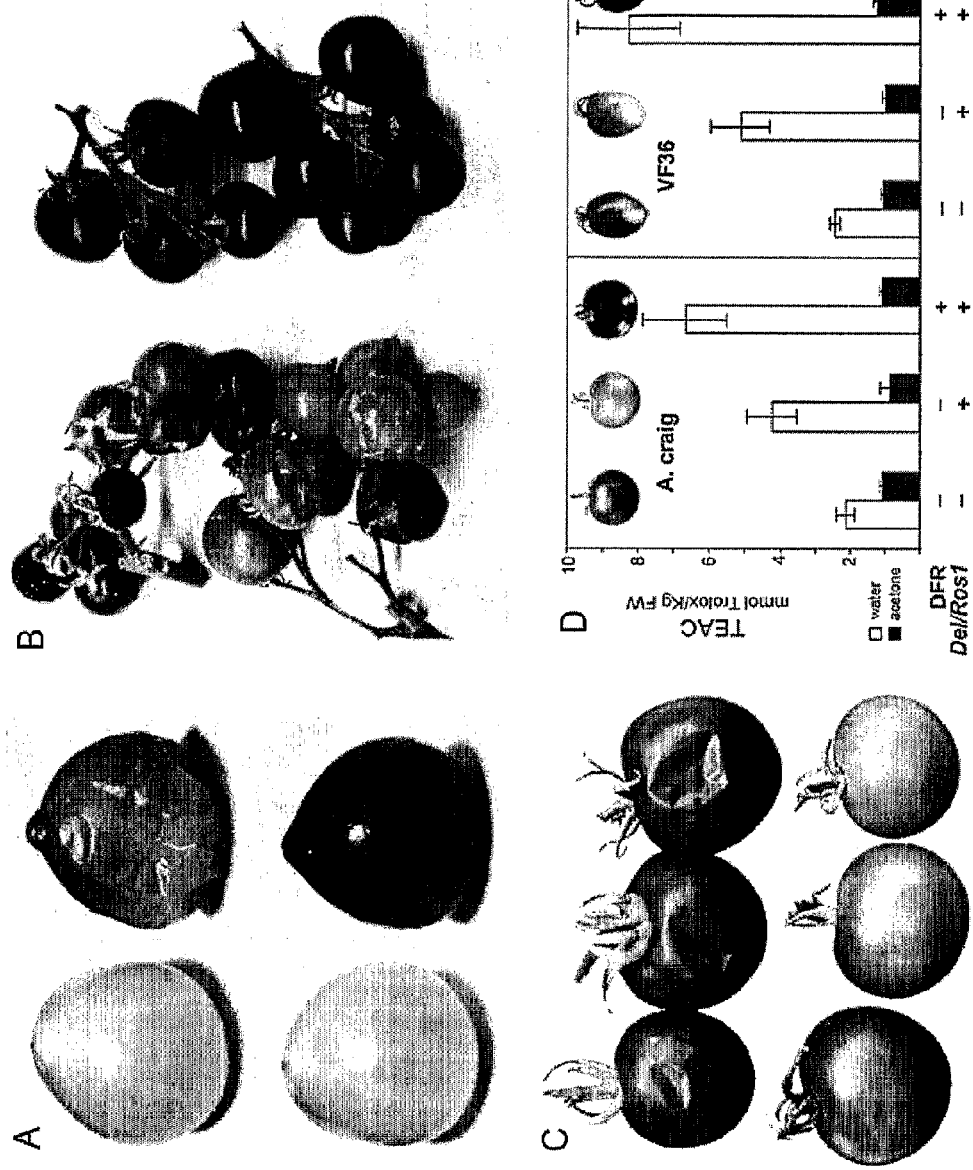
Figure 10.4

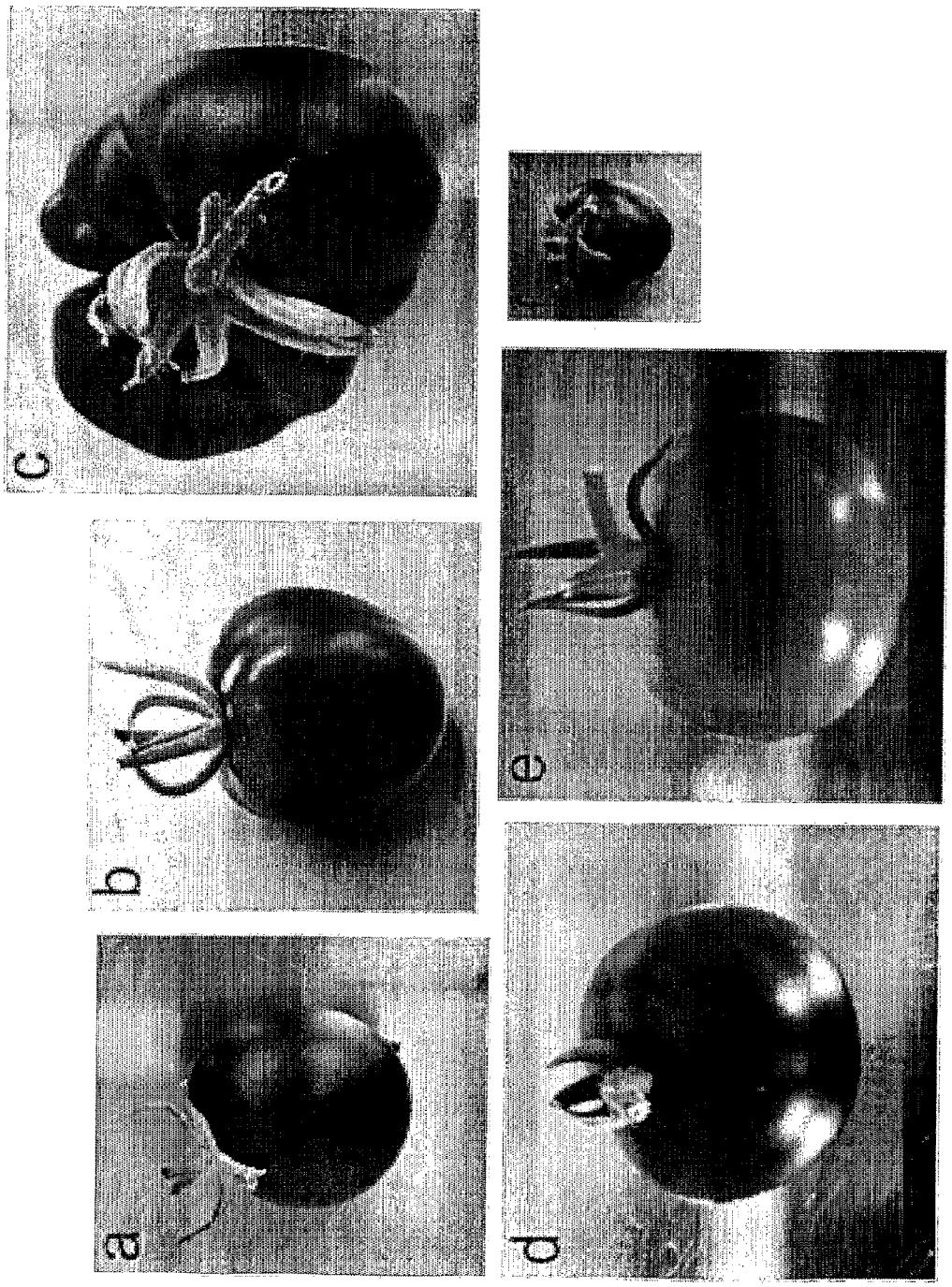
Figure 10.5

Figure 10.6
A
| Sample | Anthocyanin levels; mg per g fresh weight tomato |
|---|---|
| Control 1 | 0.008 ± 0.001 |
| Control 2 | 0.016 ± 0.003 |
| Del/Ros1 line C | 0.464 ± 0.062 |
| Del/Ros1 line N | 2.835 ± 0.456 |
| Del/Ros1 line Y | 0.458 ± 0.042 |
| Del/Ros1 line Z | 0.230 ± 0.029 |
B
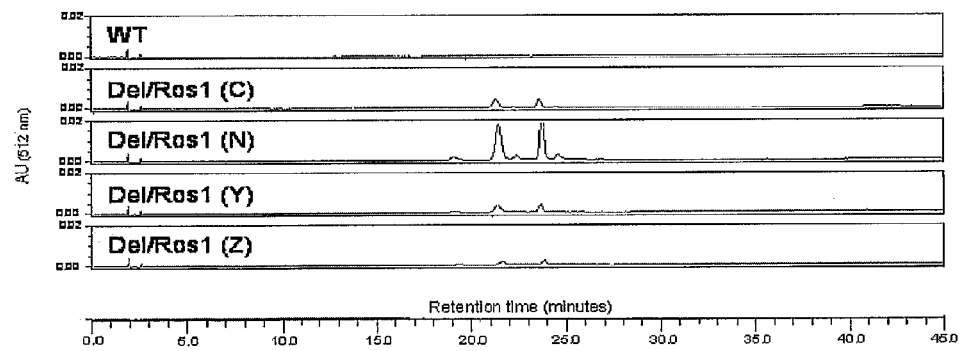
C
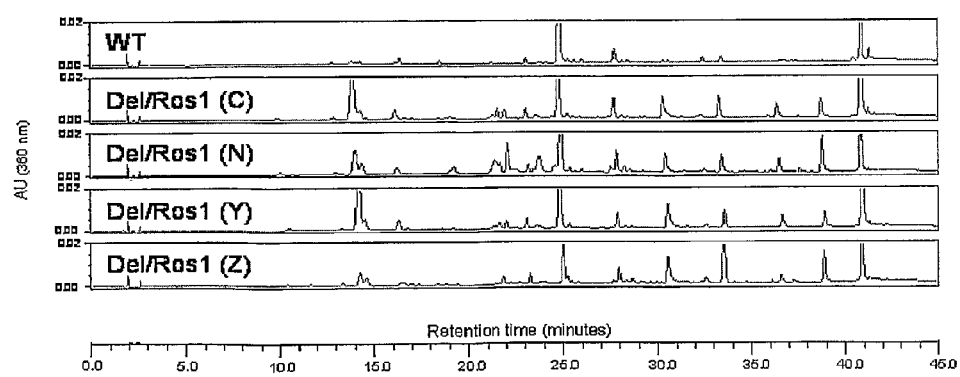

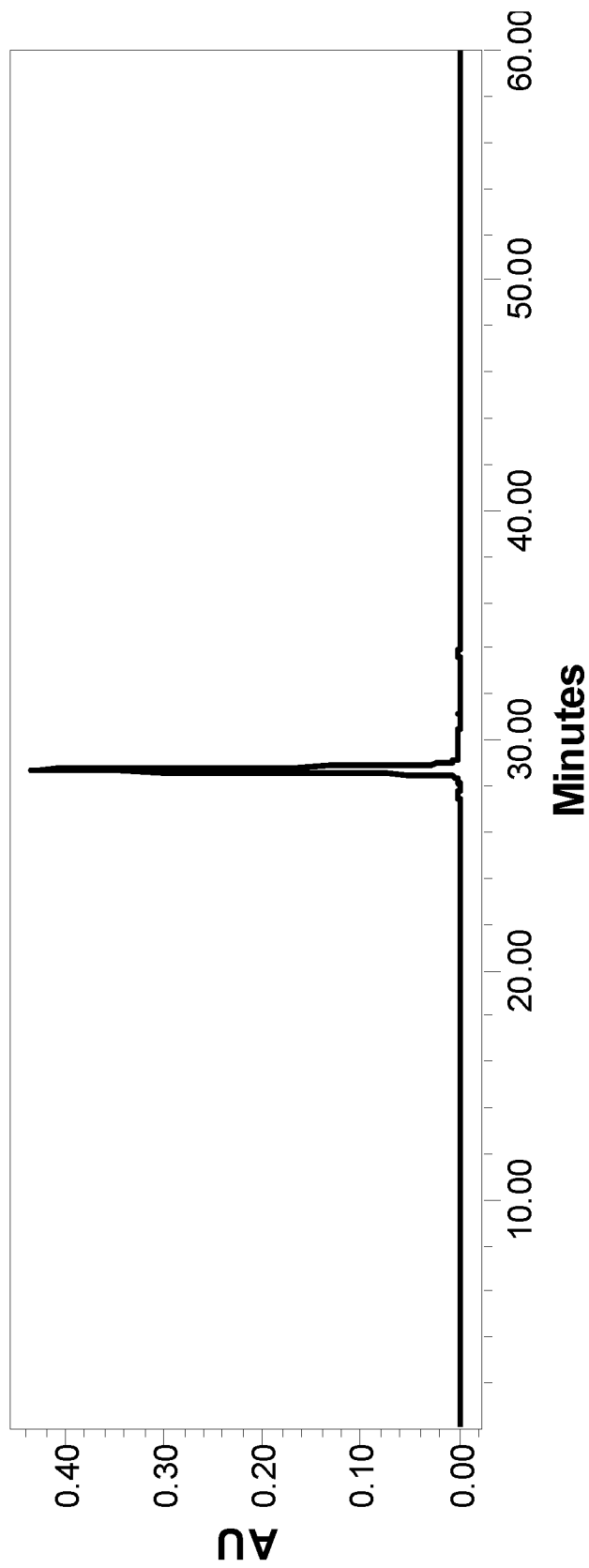
FIG. 10.7A

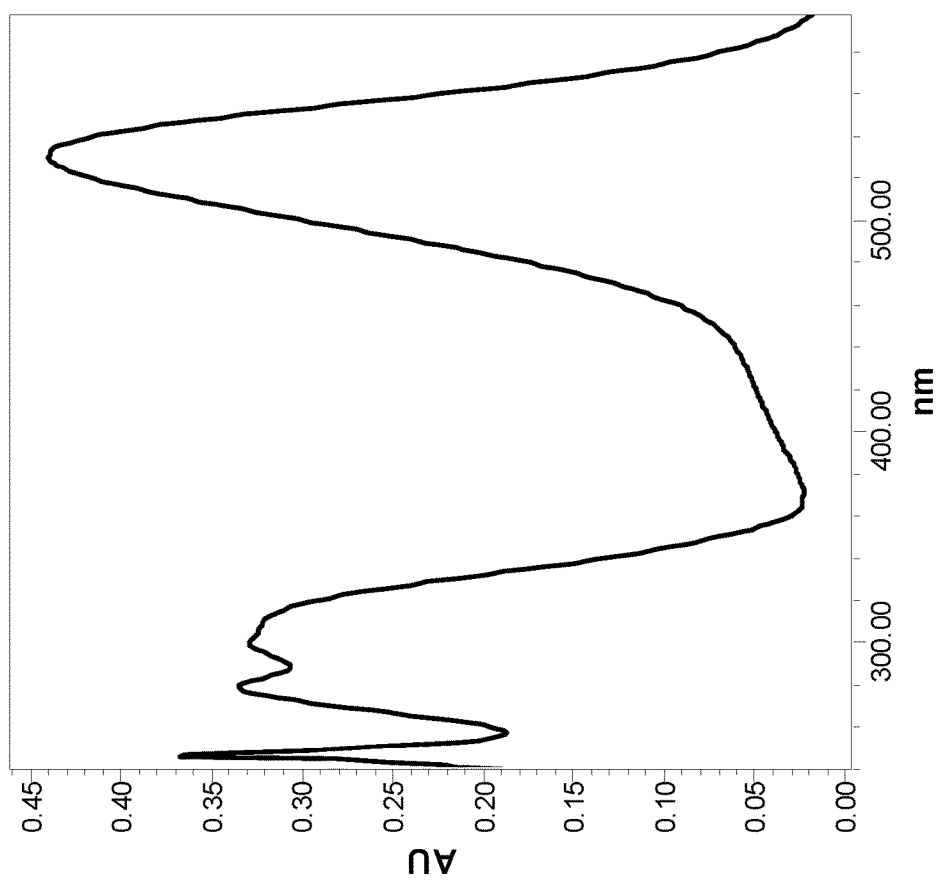
FIG. 10.7B

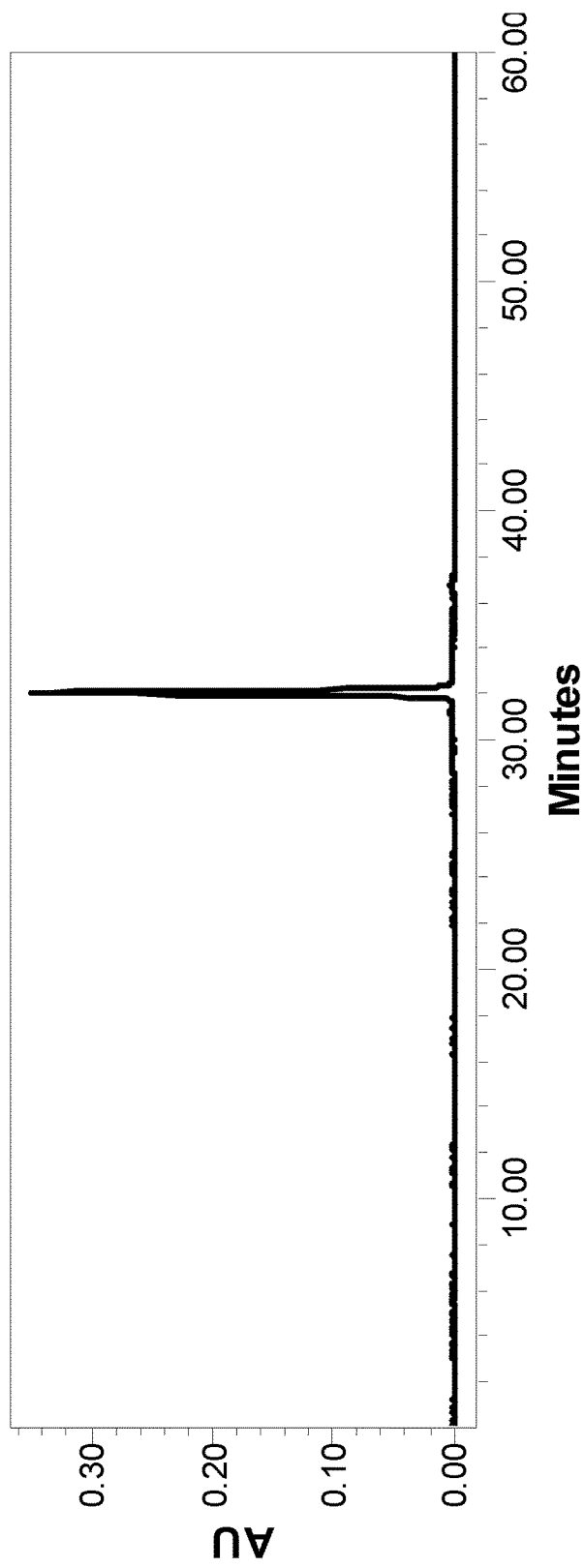
FIG. 10.7C

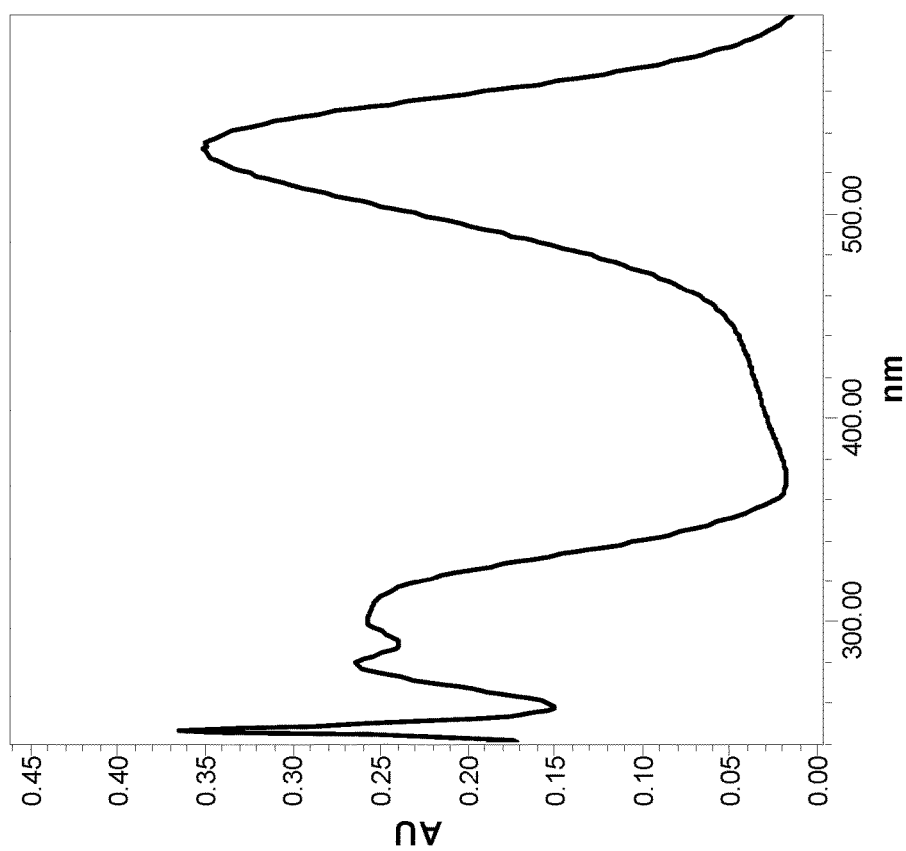
FIG. 10.7D

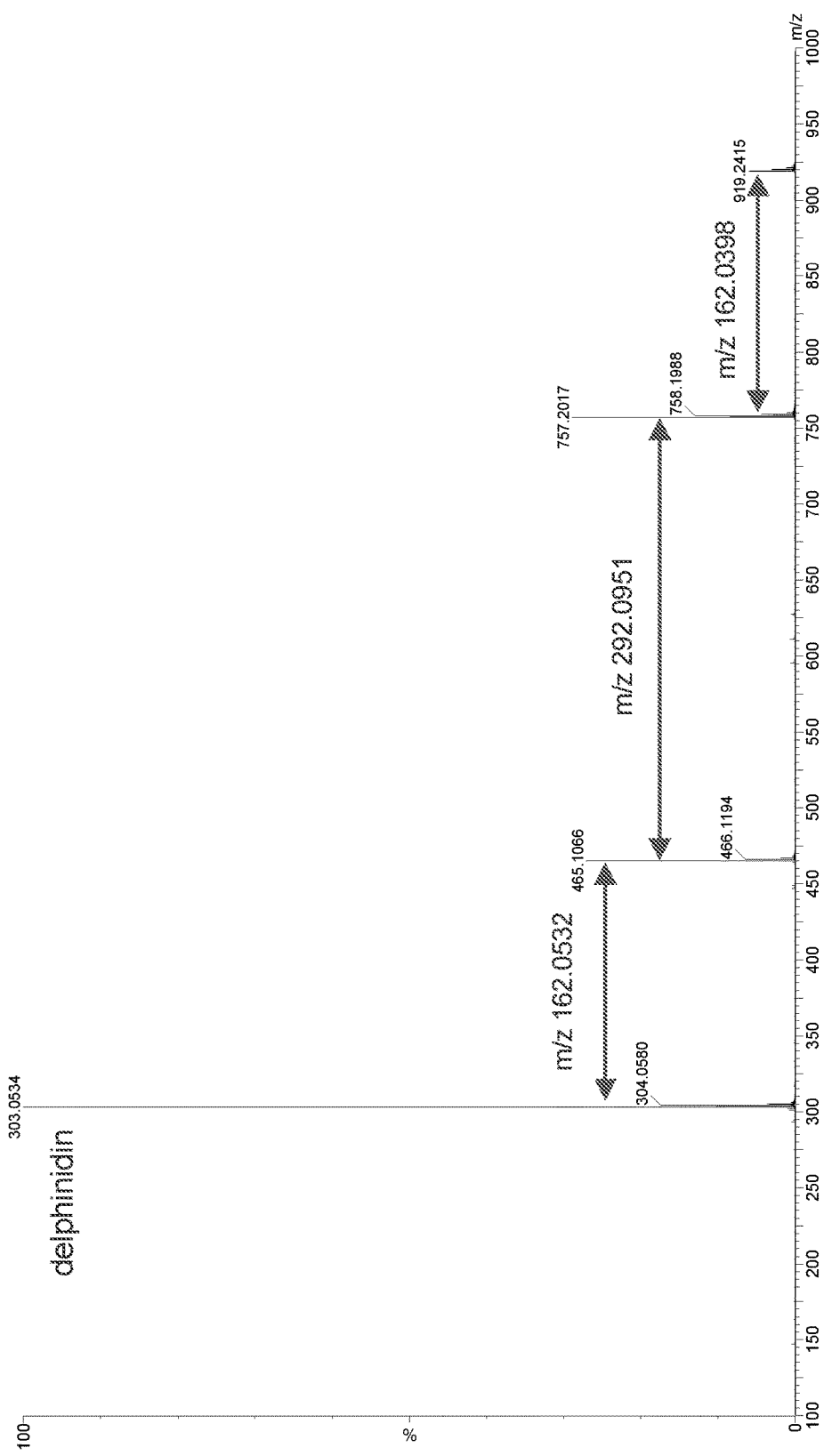
FIG. 10.7E

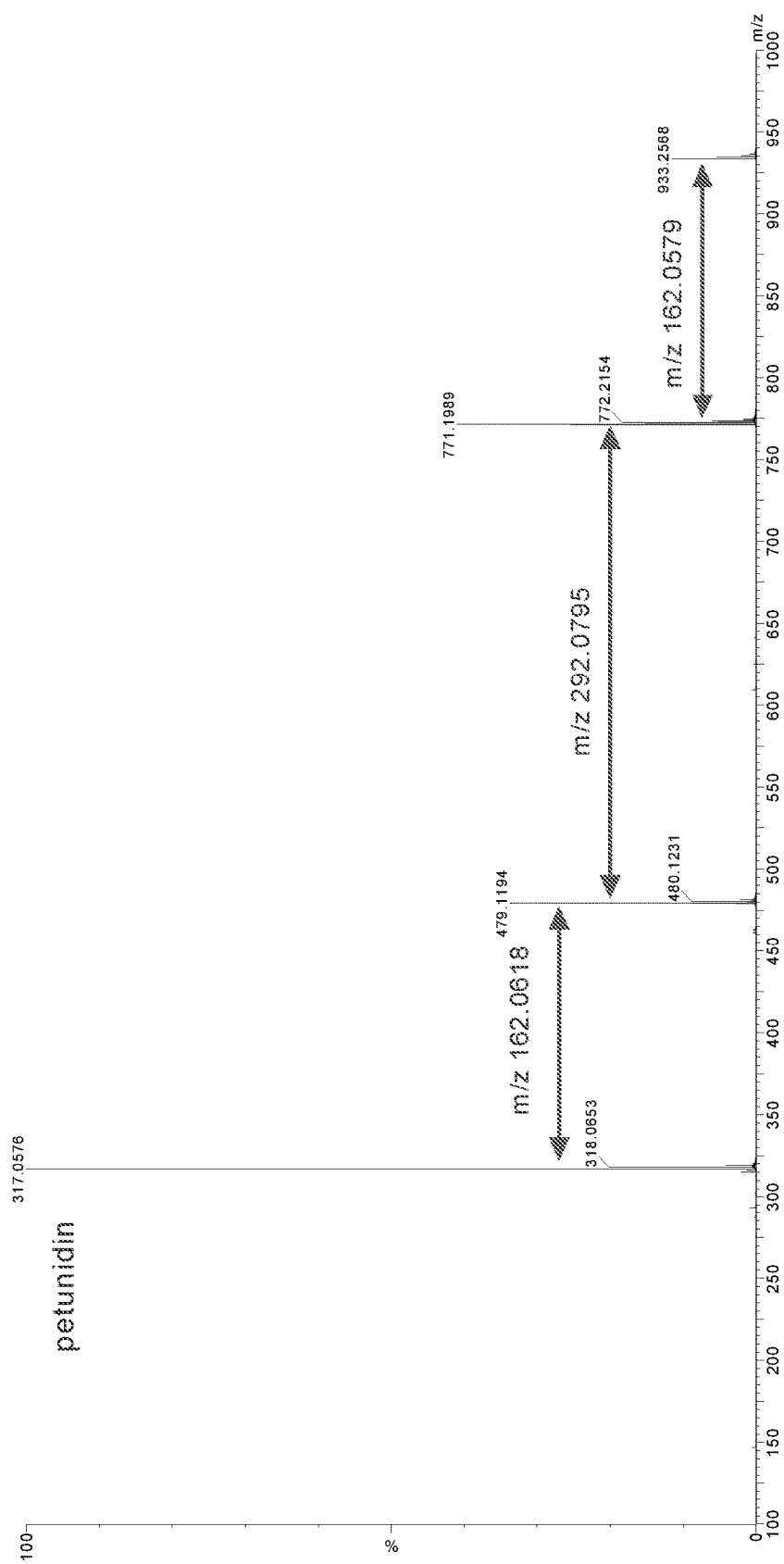
FIG. 10.7F

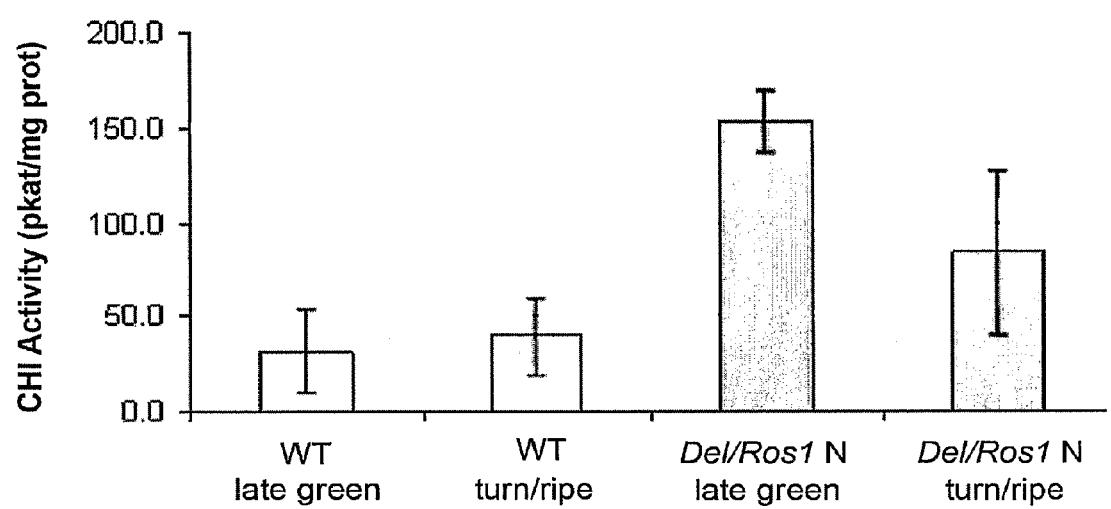
Figure 10.8

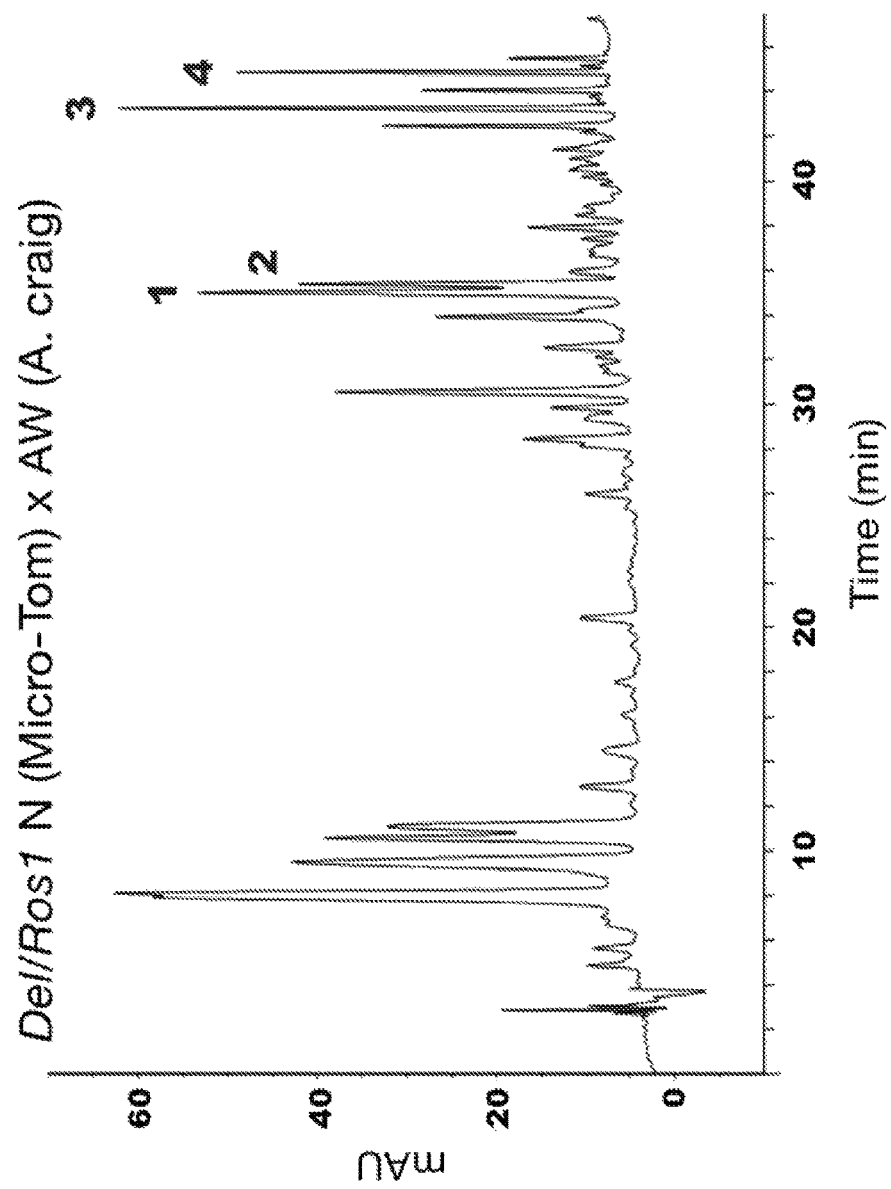
FIG. 10.9A

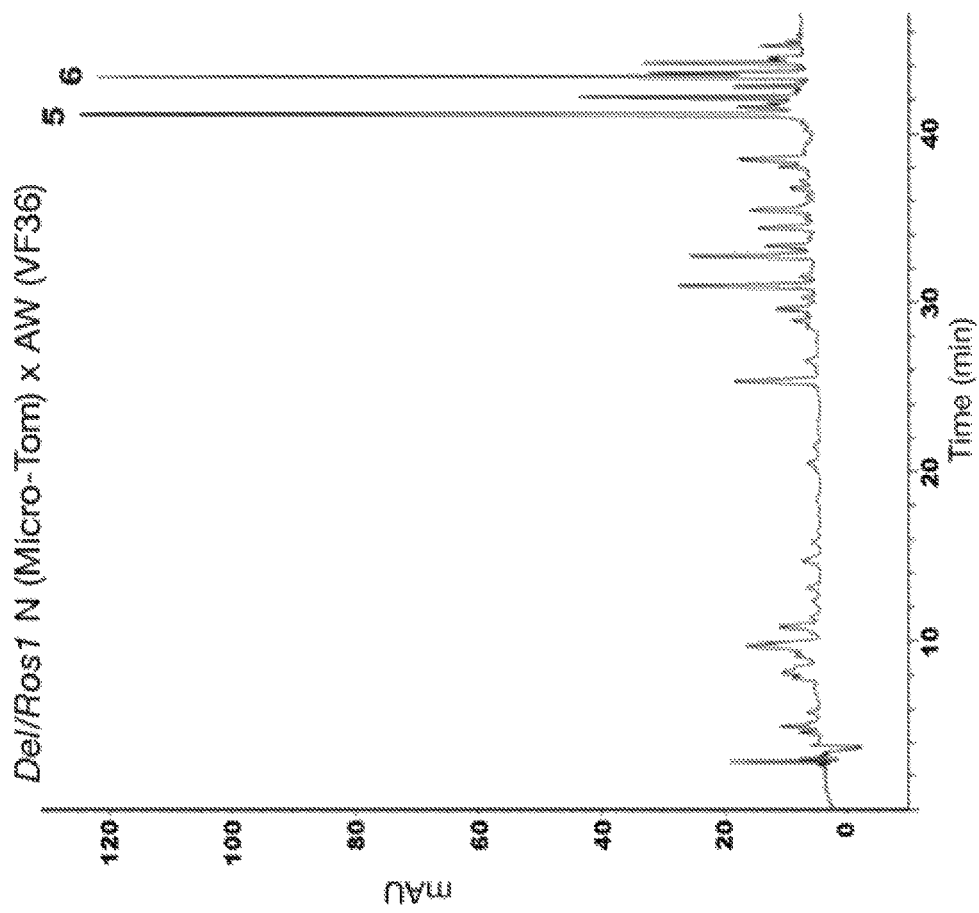
FIG. 10.9B

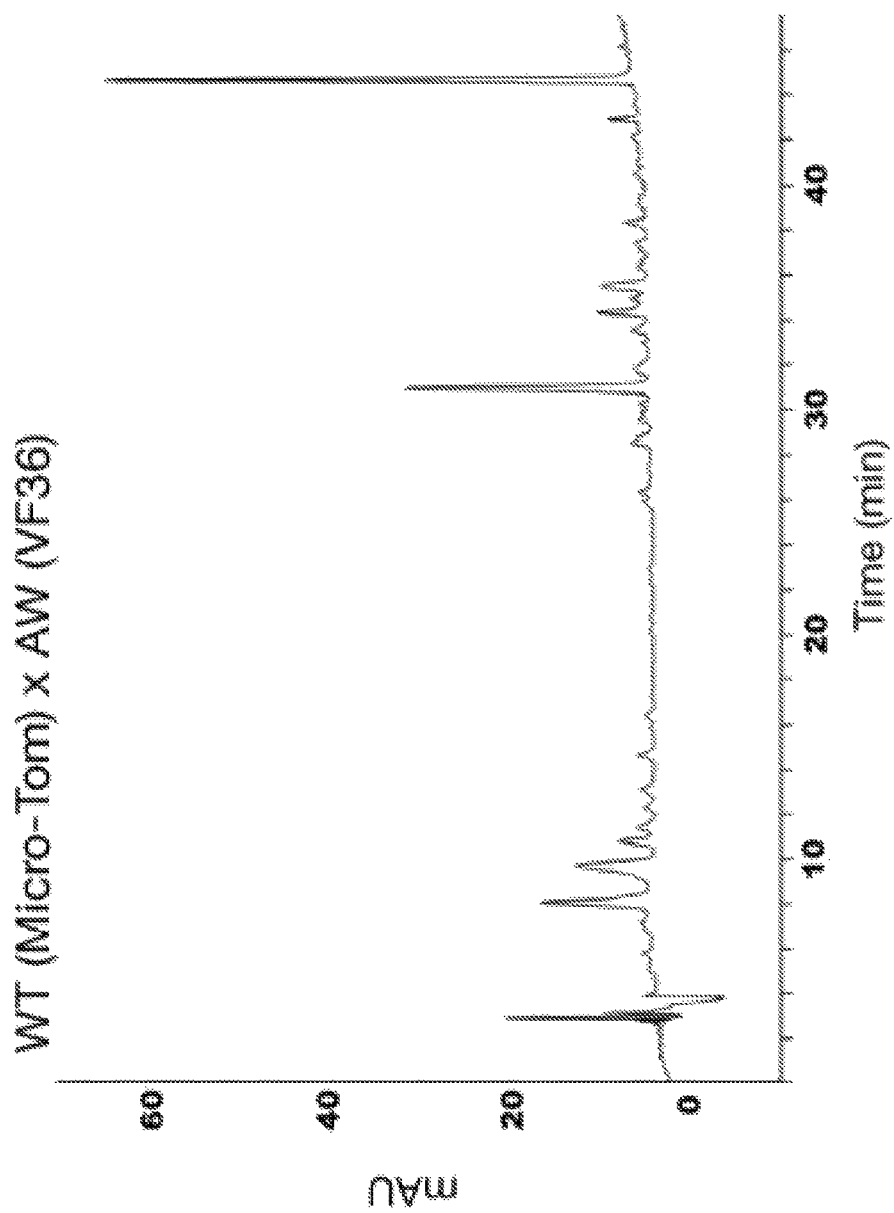
FIG. 10.9C

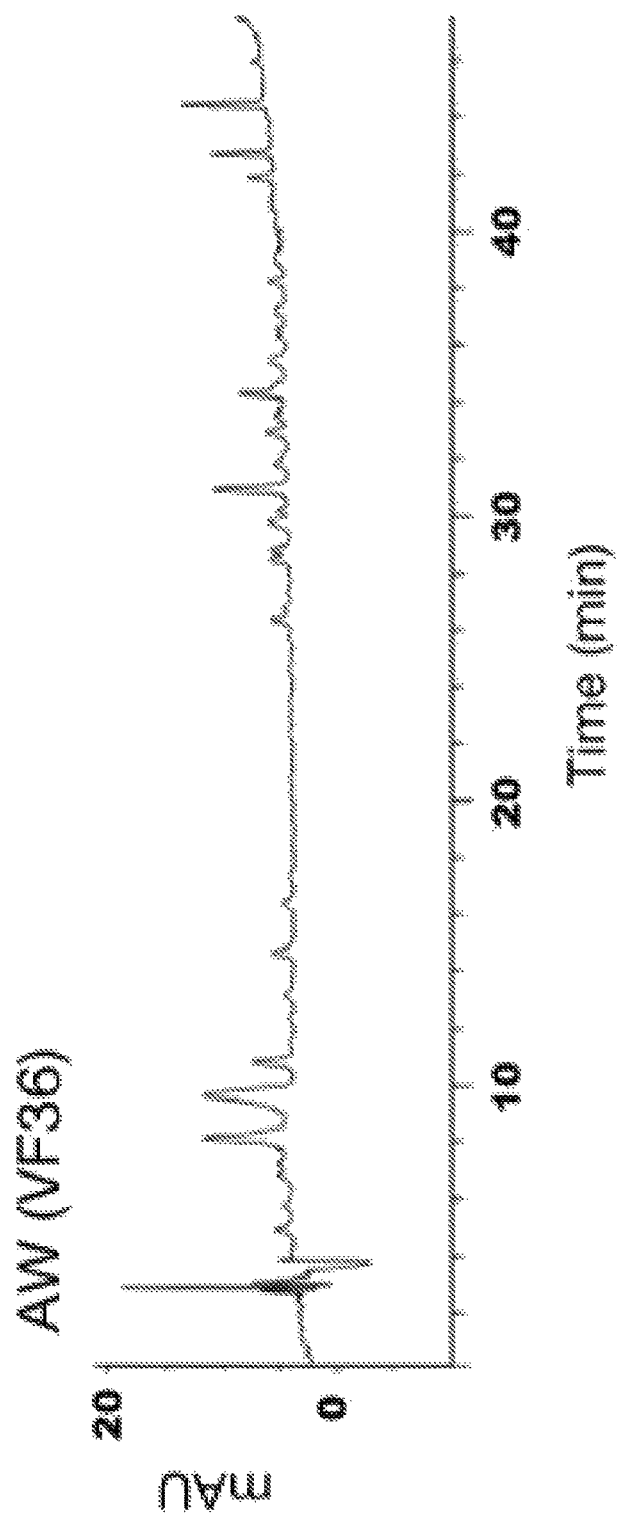
FIG. 10.9D

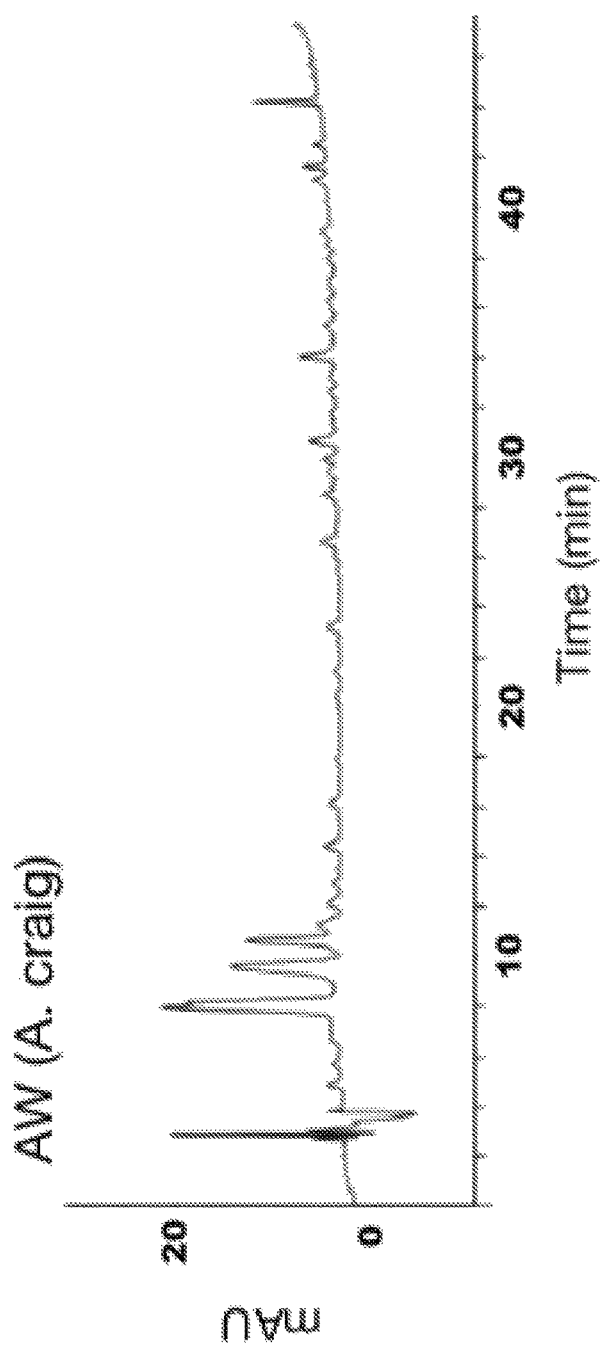
FIG. 10.9E

| peak | identification |
|---|---|
| 1 | Kaempferol-Glc-Rha |
| 2 | Kaempferol-Glc-Glc-Rha-Cou |
| 3 | Quercetin-Glc-Rha-Cou |
| 4 | Kaempferol-Glc-Rha-Cou |
| 5 | Myrlcetin-Glc-Rha-Cou |
| 6 | MeOH-Myrlcetin-Glc-Rha-Cou |

FIG. 10.9F

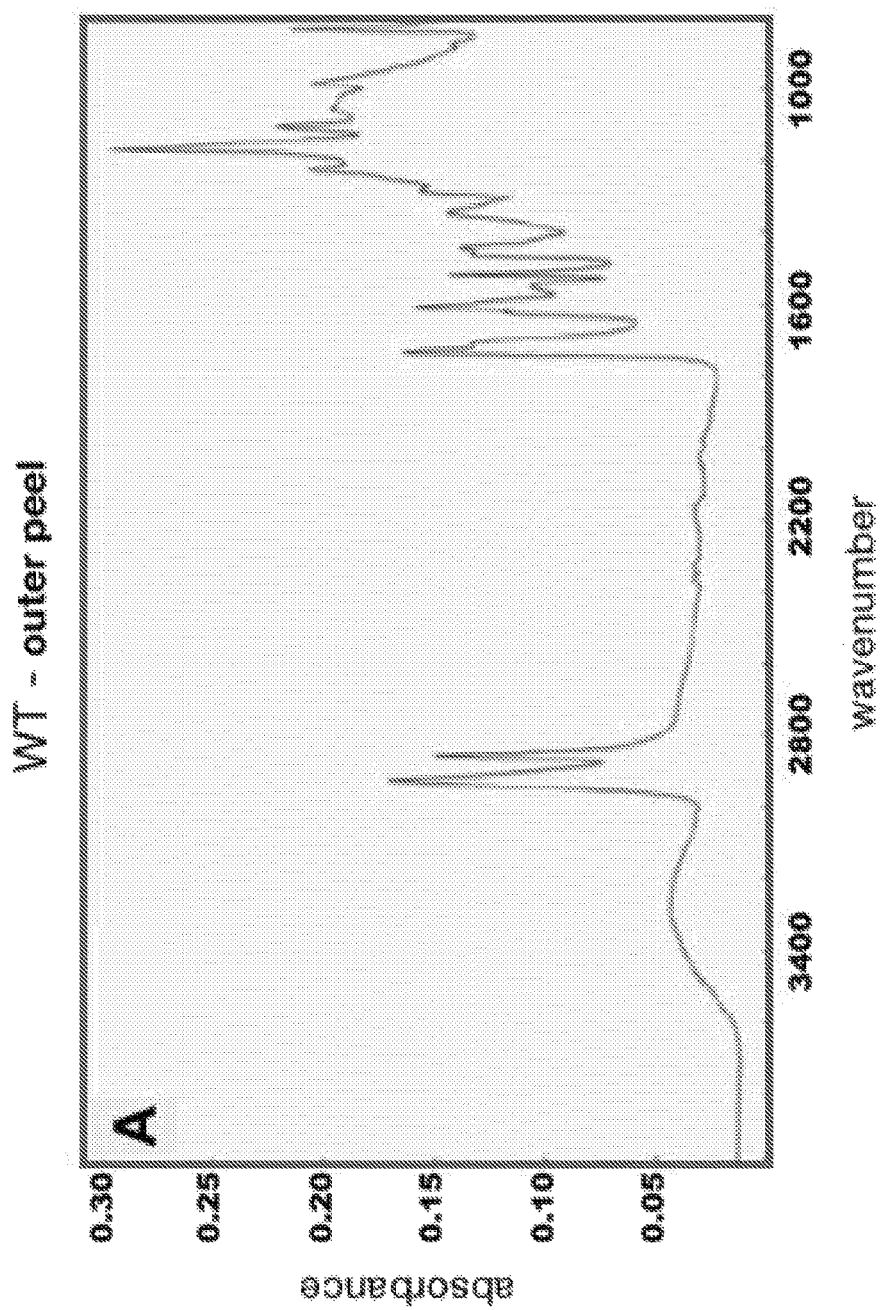
FIG. 10.10A

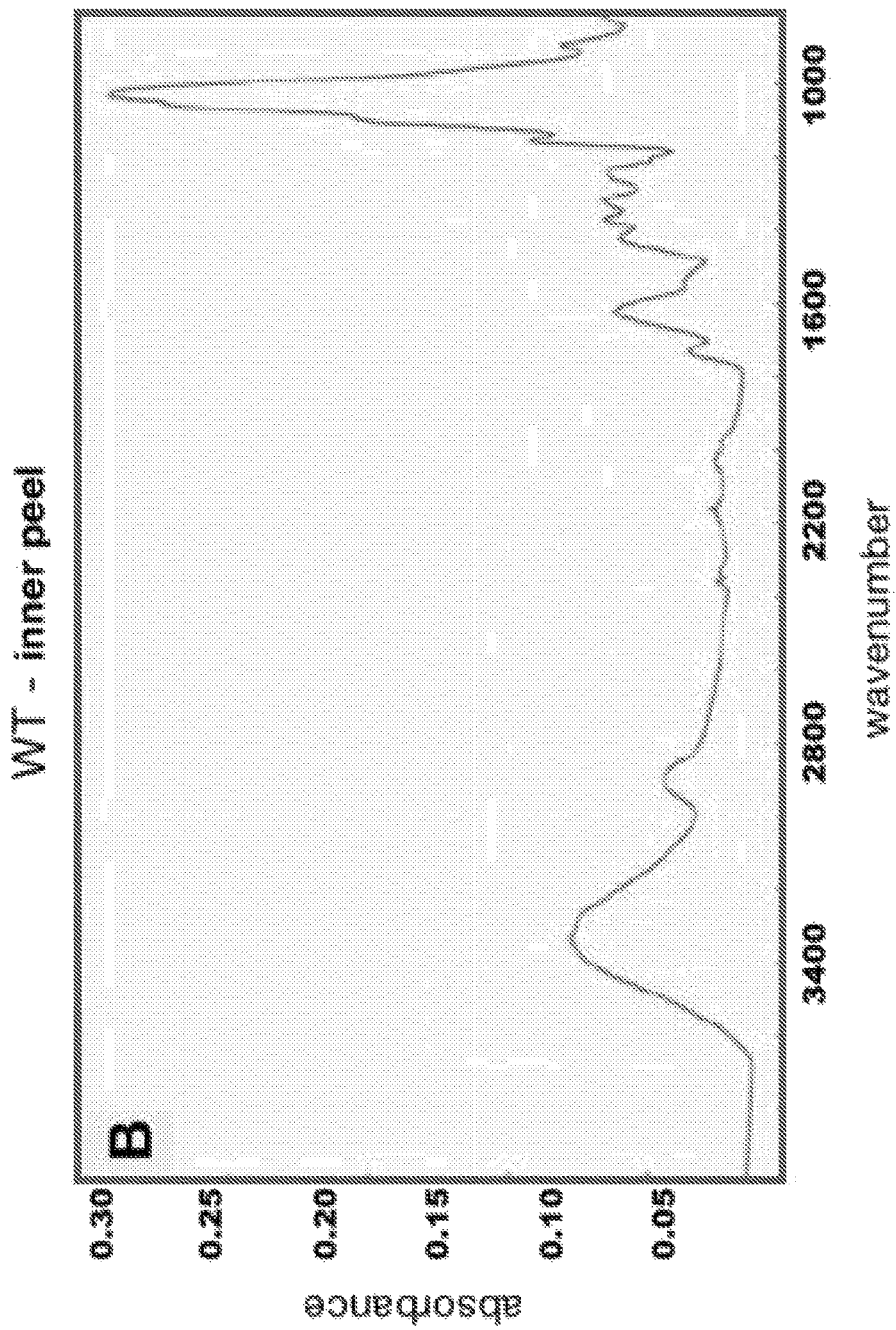
FIG. 10.10B

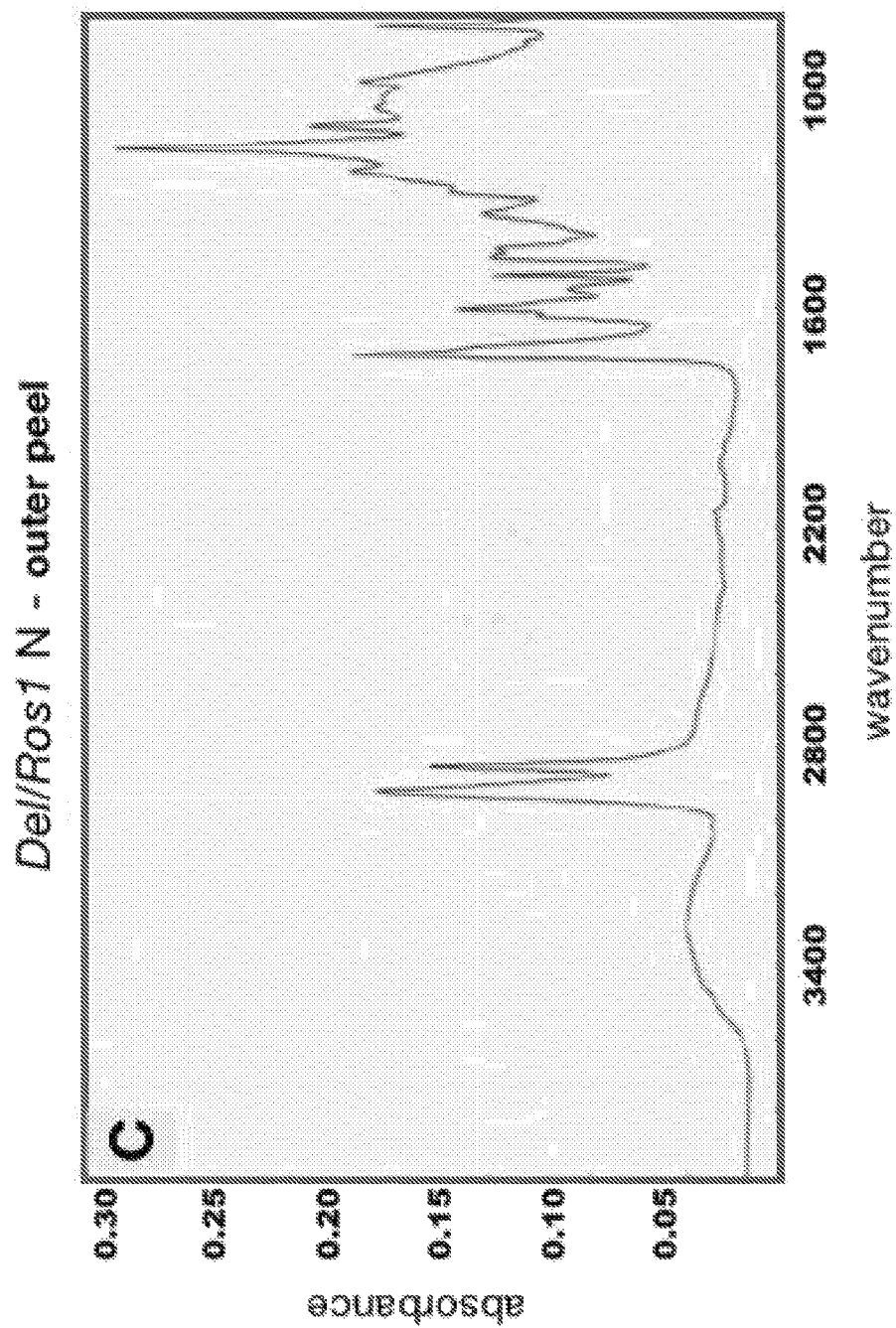
FIG. 10.10C

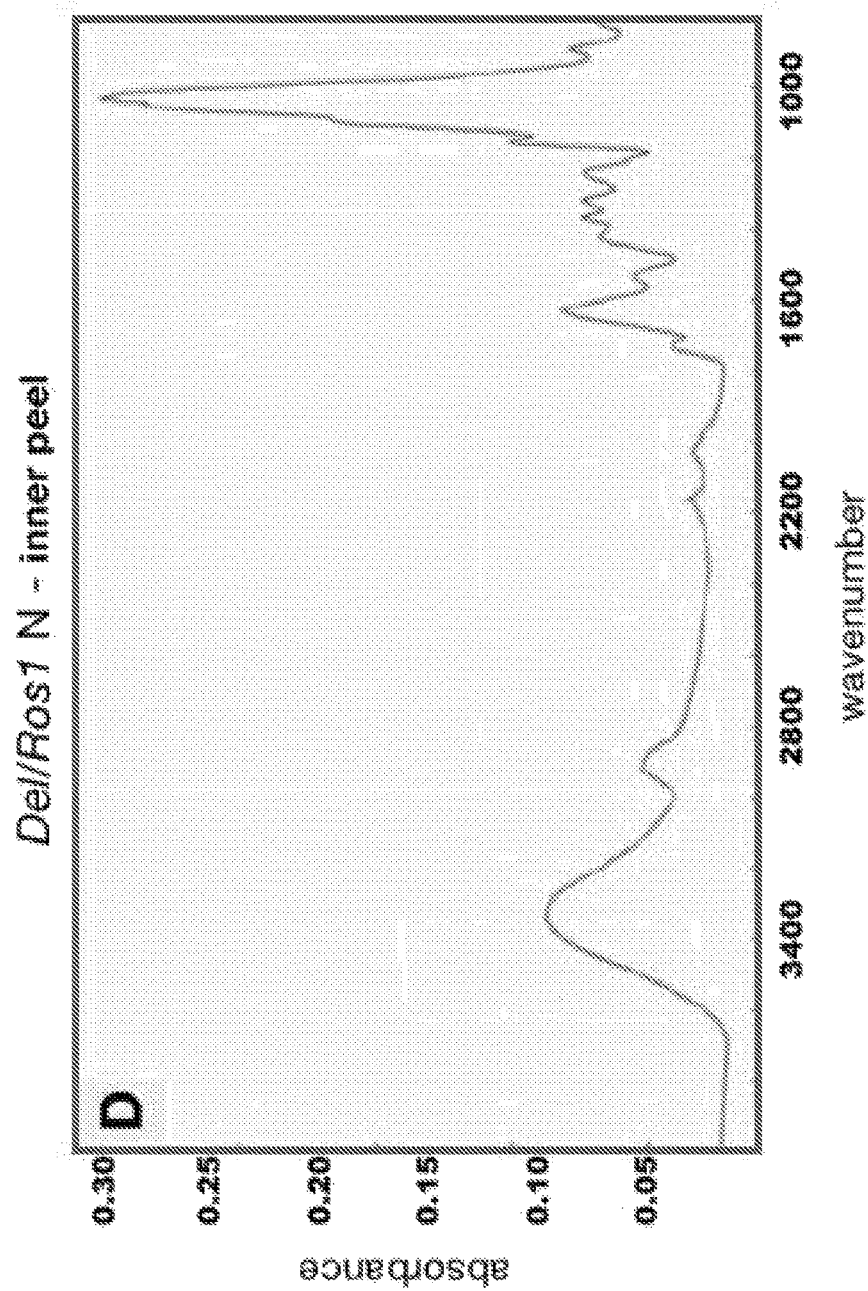
FIG. 10.10D

| material obtained in September 2004 | | | mg/gDW | |
|---|---|---|---|---|
| | | | | mean |
| flesh | WT | 1 | 2,15 | |
| | | 2 | 2,15 | 2,15 |
| | Del/Ros1N | 1 | 2,58 | |
| | | 2 | 2,89 | 2,73 |
| | Del/Ros1C | 1 | 2,23 | |
| | | 2 | 2,46 | 2,34 |
| peel | WT | 1 | 22,05 | |
| | | 2 | 21,04 | 21,54 |
| | Del/Ros1N | 1 | 22,53 | |
| | | 2 | 13,16 | 17,85 |
| | Del/Ros1C | 1 | 19,31 | |
| | | 2 | 21,95 | 20,63 |

| material obtained in November 2005 | | | mg/gFW | |
|---|---|---|---|---|
| | | | | mean |
| flesh | WT | 1 | 0,37 | |
| | | 2 | 0,32 | 0,35 |
| | Del/Ros1N | 1 | 0,22 | |
| | | 2 | 0,39 | 0,30 |
| peel | WT | 1 | 3,86 | |
| | | 2 | 4,86 | 4,36 |
| | Del/Ros1N | 1 | 3,60 | |
| | | 2 | 4,25 | 3,93 | e

FIG. 10.10E

Figure 10.11
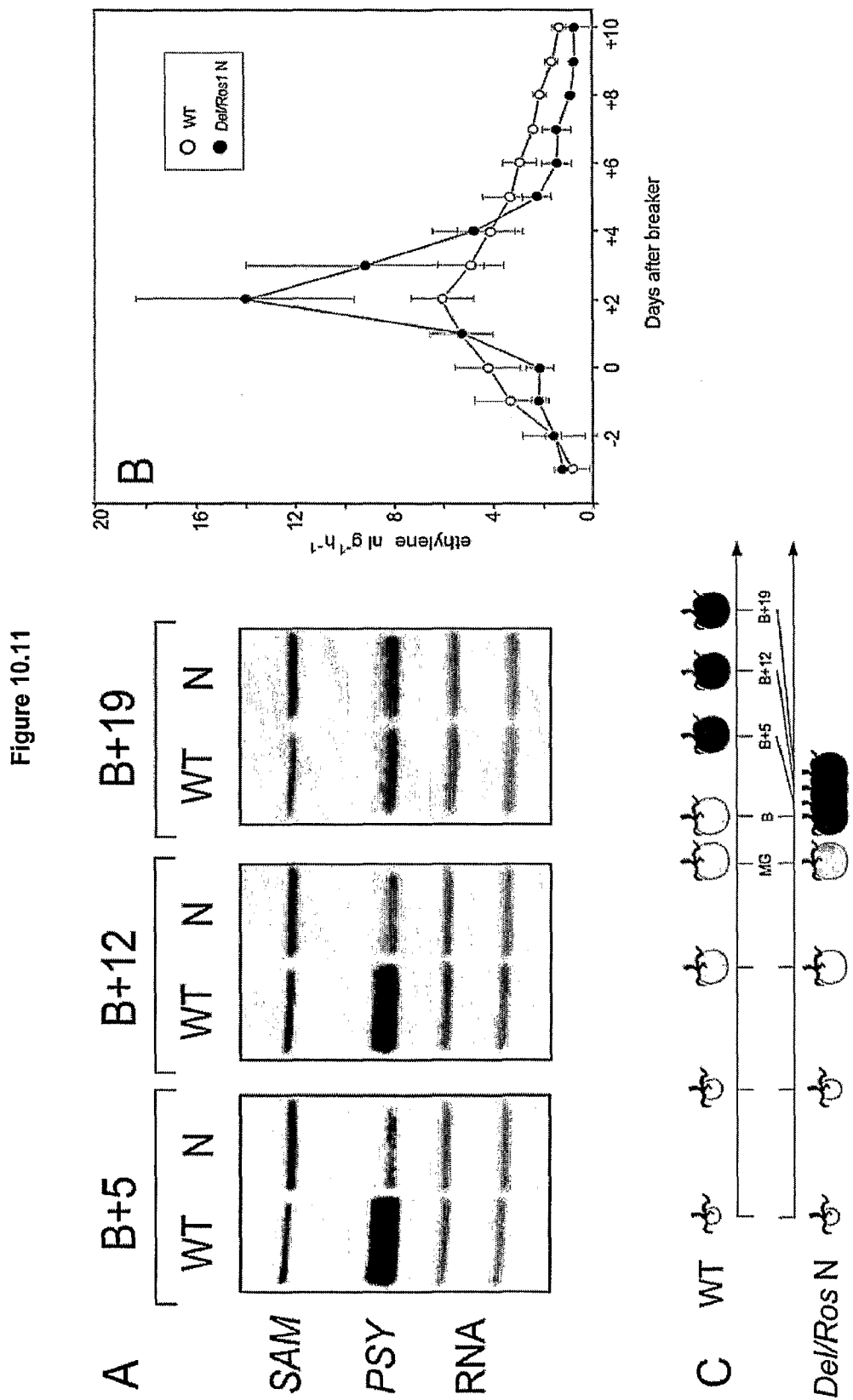

Figure 10.12
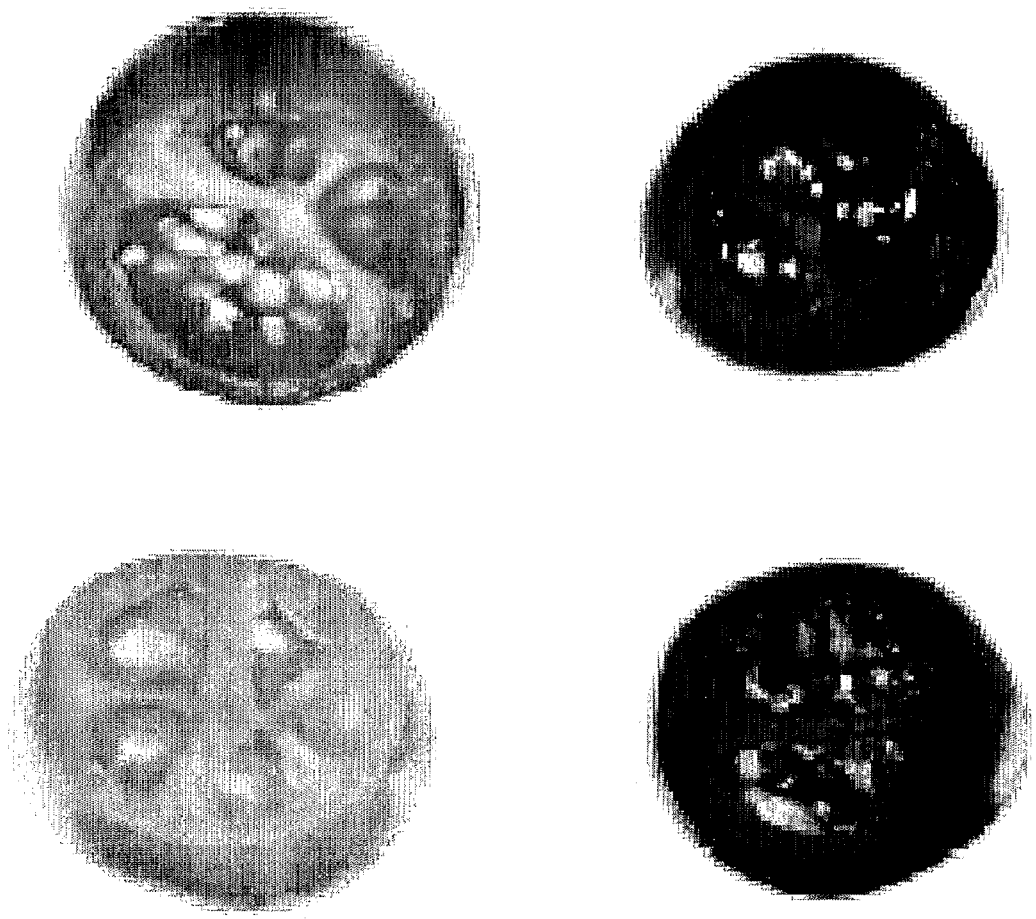

Figure 11.1
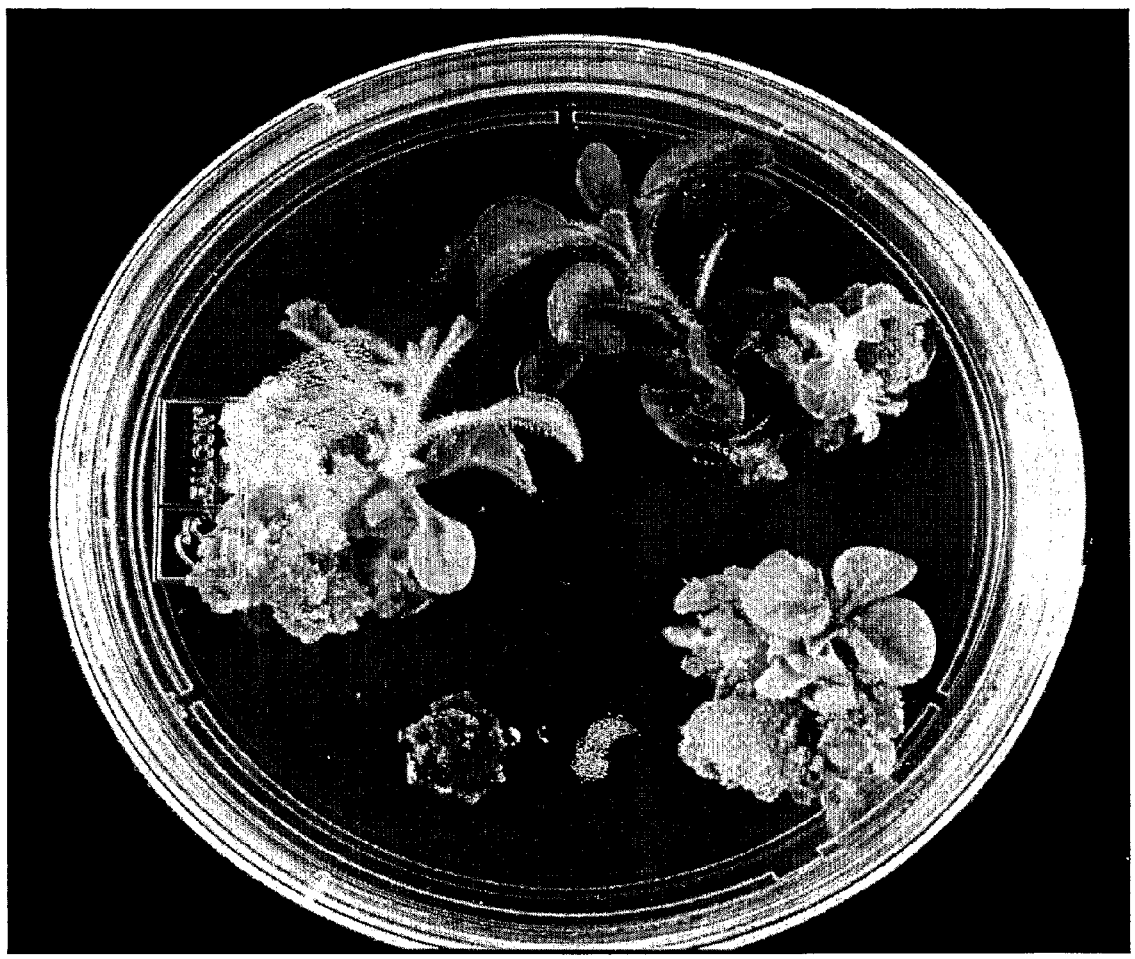

Figure 11.2
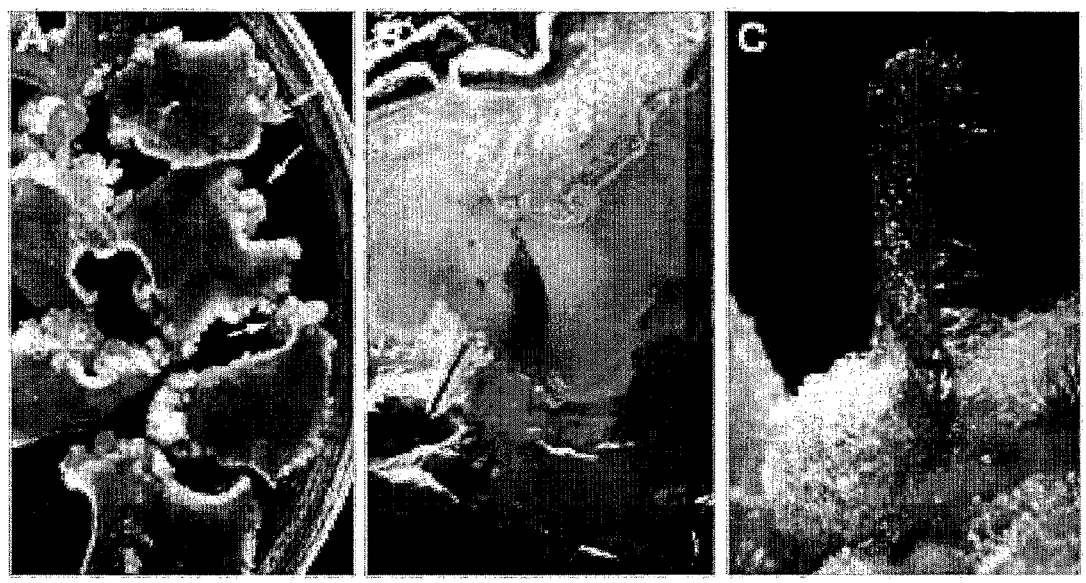

SEQUENCE LISTING

<160> NUMBER OF SEQ ID NOS: 86

<210> SEQ ID NO 1
<211> LENGTH: 2577
<212> TYPE: DNA
<213> ORGANISM: Solanum okadae

<400> SEQUENCE: 1

| | | | | | |
|---|---|---|---|---|---|
| atggctgaaa | ttcttctcac | agcagtcatc | aataaatcaa | tagaaatagc | tggaaatgta | 60 |
| ctctttcaag | aaggtacgcg | tttatattgg | ttgaaagagg | acatcgattg | gctccagaga | 120 |
| gaaatgagac | acattcgatc | atatgtagac | aatgcaaagg | caaggaagt | tggaggcgat | 180 |
| tcaagggtga | aaaacttatt | aaaagatatt | caacaactgg | caggtgatgt | ggaggatcta | 240 |
| ttagatgagt | ttcttccaaa | aattcaacaa | tccataagt | tcatttgttg | ccttaagacg | 300 |
| gtttcttttg | ccgatgagtt | tgctatggag | attgagaaga | taaaagaag | agttgctgat | 360 |
| attgaccgtg | taaggacaac | ttacagcatc | acagatacaa | gtaacaataa | tgatgattgc | 420 |
| attccattgg | accggagaag | attgttcctt | catgctgatg | aaacagaggt | catcggtctg | 480 |
| gaagatgact | tcaatacact | acaagccaaa | ttacttgatc | atgatttgcc | ttatggagtt | 540 |
| gtttcaatag | ttggcatgcc | cggtttggga | aaacaactc | ttgccaagaa | actttatagg | 600 |
| catgtctgtc | atcaatttga | gtgttcggga | ctggtctatg | tttcacaaca | gccaagggcg | 660 |
| ggagaaatct | tacatgacat | agccaaacaa | gttggactga | cggaagagga | aaggaaagaa | 720 |
| aacttggaga | caaacctacg | atcactcttg | aaaataaaaa | ggtatgttat | tctcttagat | 780 |
| gacatttggg | atgttgaaat | tgggatgat | ctaaaacttg | tccttcctga | atgtgattca | 840 |
| aaaattggca | gtaggataat | tataacctct | cgaaatagta | atgtaggcag | atacatagga | 900 |
| ggggatttct | caatccacgt | gttgcaaccc | ctagattcag | agaaaagctt | tgaactcttt | 960 |
| accaagaaaa | tctttaattt | tgttaatgat | aattgggcca | atgcttcacc | agacttggta | 1020 |
| aatattggta | gatgtatagt | tgagagatgt | ggaggtatac | cgctagcaat | tgtggtgact | 1080 |
| gcaggcatgt | taagggcaag | aggaagaaca | gaacatgcat | ggaacagagt | acttgagagt | 1140 |
| atggctcata | aaattcaaga | tggatgtggt | aaggtattgg | ctctgagtta | caatgatttg | 1200 |
| cccattgcat | taaggccatg | tttcttgtac | tttggtcttt | accccgagga | ccatgaaatt | 1260 |
| cgtgcttttg | atttgacaaa | tatgtggatt | gctgagaagc | tgatagttgt | aaatactggc | 1320 |
| aatgggcgag | aggctgaaag | tttggcggat | gatgtcctaa | atgatttggt | ttcaagaaac | 1380 |
| ttgattcaag | ttgccaaaag | gacatatgat | ggaagaattt | caagttgtcg | catacatgac | 1440 |
| ttgttacata | gtttgtgtgt | ggacttggct | aaggaaagta | acttctttca | cacggagcac | 1500 |
| aatgcatttg | gtgatcctag | caatgttgct | agggtgcgaa | ggattacatt | ctactctgat | 1560 |
| gataatgcca | tgaatgagtt | cttccattta | aatcctaagc | ctatgaagct | tcgttcactt | 1620 |
| ttctgtttca | caaagaccg | ttgcatattt | tctcaaatgg | ctcatcttaa | cttcaaatta | 1680 |
| ttgcaagtgt | tggttgtagt | catgtctcaa | aagggttatc | agcatgttac | tttccccaaa | 1740 |
| aaaattggga | acatgagttg | cctacgttat | gtgcgattgg | aggggcaat | tagagtaaaa | 1800 |
| ttgccaaata | gtattgtcaa | gctcaaatgt | ctagagaccc | tggatatatt | tcatagctct | 1860 |
| agtaaacttc | cttttggtgt | ttgggagtct | aaaatattga | acatctttg | ttacacagaa | 1920 |
| gaatgttact | gtgtctcttt | tgcaagtcca | ttttgccgaa | tcatgcctcc | taataatcta | 1980 |
| caaactttga | tgtgggtgga | tgataaattt | tgtgaaccaa | gattgttgca | ccgattgata | 2040 |
| aatttaagaa | cattgtgtat | aatggatgta | tccggttcta | ccattaagat | attatcagca | 2100 |

-continued

```
ttgagccctg tgcctagagc gttggaggtt ctgaagctca gattttttcaa gaacacgagt    2160 gagcaaataa acttgtcgtc ccatccaaat attgtcgagt tgggtttggt tggtttctca    2220
gcaatgctct tgaacattga agcattccct ccaaatcttg tcaagcttaa tcttgtcggc    2280
ttgatggtag acggtcatct attggcagtg cttaagaaat tgcccaaatt aaggatactt    2340
atattgcttt ggtgcagaca tgatgcagaa aaaatggatc tctctggtga tagctttccg    2400
caacttgaag ttttgtatat tgaggatgca caagggttgt ctgaagtaac gtgcatggat    2460
gatatgagta tgcctaaatt gaaaaagcta tttcttgtac aaggcccaaa catttcccca    2520
attagtctca gggtctcgga acggcttgca aagttgagaa tatcacaggt actataa      2577
```

<210> SEQ ID NO 2
<211> LENGTH: 2589
<212> TYPE: DNA
<213> ORGANISM: Solanum mochiquense

<400> SEQUENCE: 2

```
atggctgaaa ttcttcttac agcagtcatc aataaatctg tagaaatagc tggaaatgta     60
ctctttcaag aaggtacgcg tttatattgg ttgaaggagg atatagattg gctccaaaga    120
gaaatgagac acattcgatc atatgtagac aatgcaaagg ccaaggaagt tggaggtgat    180
tcaagggtga aaaacttatt aaaagatatt caacaactcg caggtgatgt ggaggatctc    240
ctagatgagt ttcttccaaa aattcaacaa tccagtaagt tcaaaggcgc aatttgttgc    300
cttaagaccg tttctttttgc ggatgagttt gctatggaga ttgagaagat aaaaagaagg    360
gttgtggaca ttgatcgtgt aaggacaact tacaacatca tggatacaaa taacaacaat    420
gattgcattc cattggacca gagaagattg ttccttcatg ttgatgaaac agaggtcatc    480
ggtttggatg atgacttcaa tacactacaa gccaaattac ttgaccaaga tttgccttat    540
ggagttgttt caatagttgg catgcccggt ctaggaaaaa caactcttgc caagaaactt    600
tataggcatg tccgtcataa atttgagtgt tcgggactgg tctatgtttc acaacagcca    660
agggcgggag aaatcttaat cgacatagcc aaacaagttg gactgacgga agacgaaagg    720
aaagaaaact tggagaacaa cctacggtca ctcttgaaaa gaaaaaggta tgttattctc    780
ttagatgaca tttgggatgt tgaaatttgg gatgatctaa aacttgtcct tcctgaatgt    840
gattcaaaaa ttggcagtag gataattata acctctcgaa atagtaatgt aggcagatac    900
ataggagggg atttctcaat tcacgtgttg caacctctaa attcggagaa cagttttgaa    960
ctctttacca agaaaatctt tattttttgat aacaataata attggaccaa tgcttccacca   1020 aacttggtag atattggtag aagtatagtt ggtagatgtg gtggtatacc actagccatt   1080
gtggtgactg caggcatgtt aagggcaaga gaaagaacag aacgtgcatg gaacaggtta   1140
cttgagagta tgagccataa agttcaagat ggatgtgcta aggtattggc tctgagttac   1200
aatgatttgc caattgcatt aaggccatgt tccttgtatt ttggccttta ccccgaggat   1260
catgaaattc gtgcttttga tttgacaaat atgtggattg ctgagaagtt gatagttgta   1320
aatagtggca atgggcgaga ggctgaaagt ttggcggatg atgtcctaaa tgatttggtt   1380
tcaagaaaca tgattcaagt tgccaaaagg acatatgatg aagaatttc aagttgtcgc   1440 atacatgact tgttacatag tttgtgtgtt gacttggcta aggaaagcaa cttctttcac   1500
accgagcaca atgcattggg tgatcccgga aatgttgcta ggctgcgaag gattacattc   1560
tactctgata ataatgccat gaatgagttc ttccgttcaa atcctaagct tgagaagctt   1620
```

-continued

```
cgtgcacttt tctgttttac agaagaccct tgcatatttt ctcaactggc tcatcttgat    1680
ttcaaattat tgcaagtgtt ggttgtagtc atctttgttg atgatatttg tggtgtcagt    1740
atcccaaaca catttgggaa catgaggtgc ttacgttatc tgcgattcca ggggcatttt    1800
tatgggaaac tgccaaattg tatggtgaag ctcaaacgtc tagagaccct cgatattggt    1860
tatagcttaa ttaaatttcc tactggtgtt tggaagtcta cacaattgaa acatcttcgt    1920
tatggaggtt ttaatcaagc atctaacagt tgcttttcta taagcccatt tttcccaaac    1980
ttgtactcat tgcctcataa taatgtacaa actttgatgt ggctggatga taaatttttt    2040
gaggcgggat tgttgcaccg attgatcaat ttaagaaaac tgggtatagc aggagtatct    2100
gattctacag ttaagatatt atcagcattg agccctgtgc aacggcgct ggaggttctg     2160 aagctcaaaa tttacaggga catgagtgag caaataaact tgtcgtccta tccaaatatt    2220
gttaagttgc gtttgaatgt ttgcggaaga atgcgcttga actgtgaagc atttcctcca    2280
aatcttgtca agcttactct tgtcggcgat gaggtagacg gtcatgtagt ggcagagctt    2340
aagaaattgc ccaaattaag gatacttaaa atgtttgggt gcagtcataa tgaagaaaag    2400
atggatctct ctggtgatgg tgatagcttt ccgcaacttg aagttctgca tattgatgaa    2460
ccagatgggt tgtctgaagt aacgtgtagg atgatgtca gtatgcctaa attgaaaaag     2520
ttgttacttg tacaacgccg cccttctcca attagtctct cagaacgtct tgcaaagctc    2580
agaatatga                                                           2589
```

<210> SEQ ID NO 3
<211> LENGTH: 2577
<212> TYPE: DNA
<213> ORGANISM: Solanum neorossii

<400> SEQUENCE: 3

```
atggctgaaa ttcttctcac agcagtcatc aataaatcaa tagaaatagc tggaaatgta     60
ctctttcaag aaggtacgcg tttatattgg ttgaaagagg acatcgattg gctccagaga    120
gaaatgagac acattcgatc atatgtagac aatgcaaagg caaggaagt tggaggcgat     180 tcaagggtga aaaacttatt aaaagatatt caacaactgg caggtgatgt ggaggatcta    240
ttagatgagt ttcttccaaa aattcaacaa tccataagt tcatttgttg ccttaagacg     300
gtttcttttg ccgatgagtt tgctatggag attgagaaga taaaaagaag agttgctgat    360
attgaccgtg taaggacaac ttacagcatc acagatacaa gtaacaataa tgatgattgc    420
attccattgg accggagaag attgttcctt catgctgatg aaacagaggt catcggtctg    480
gaagatgact tcaatacact acaagccaaa ttacttgatc atgatttgcc ttatggagtt    540
gtttcaatag ttggcatgcc cggtttggga aaaacaactc ttgccaagaa actttatagg    600
catgtctgtc atcaatttga gtgttcggga ctggtctatg tttcacaaca gccaagggcg    660
ggagaaatct tacatgacat agccaaacaa gttggactga cggaagagga aggaaagaa     720 aacttggaga acaacctacg atcactcttg aaaataaaaa ggtatgttat tctcttagat    780
gacatttggg atgttgaaat ttgggatgat ctaaaacttg tccttcctga atgtgattca    840
aaaattggca gtaggataat tataacctct cgaaatagta atgtaggcag atacatagga    900
ggggatttct caatccacgt gttgcaaccc ctagattcag agaaaagctt tgaactcttt    960
accaagaaaa tctttaattt tgttaatgat aattgggcca atgcttcacc agacttggta   1020
aatattggta gatgtatagt tgagagatgt ggaggtatac cgctagcaat tgtggtgact   1080
gcaggcatgt taagggcaag aggaagaaca gaacatgcat ggaacagagt acttgagagt   1140
```

-continued

```
atggctcata aaattcaaga tggatgtggt aaggtattgg ctctgagtta caatgatttg    1200
cccattgcat taaggccatg tttcttgtac tttggtcttt accccgagga ccatgaaatt    1260
cgtgcttttg atttgacaaa tatgtggatt gctgagaagc tgatagttgt aaatactggc    1320
aatgggcgag aggctgaaag tttggcggat gatgtcctaa atgatttggt ttcaagaaac    1380
ttgattcaag ttgccaaaag gacatatgat ggaagaattt caagttgtcg catacatgac    1440
ttgttacata gtttgtgtgt ggacttggct aaggaaagta acttctttca cacggagcac    1500
tatgcatttg gtgatcctag caatgttgct agggtgcgaa ggattacatt ctactctgat    1560
gataatgcca tgaatgagtt cttccattta aatcctaagc ctatgaagct tcgttcactt    1620
ttctgtttca caaagaccg ttgcatattt tctcaaatgg ctcatcttaa cttcaaatta    1680
ttgcaagtgt tggttgtagt catgtctcaa aaggggttatc agcatgttac tttccccaaa    1740
aaaattggga acatgagttg cctacgctat gtgcgattgg aggggggcaat tagagtaaaa    1800 ttgccaaata gtattgtcaa gctcaaatgt ctagagaccc tggatatatt tcatagctct    1860
agtaaacttc cttttggtgt ttgggagtct aaaatattga acatctttg ttacacagaa    1920 gaatgttact gtgtctcttt tgcaagtcca ttttgccgaa tcatgcctcc taataatcta    1980
caaactttga tgtgggtgga tgataaattt tgtgaaccaa gattgttgca ccgattgata    2040
aatttaagaa cattgtgtat aatggatgta tccggttcta ccattaagat attatcagca    2100
ttgagccctg tgcctaaagc gttggaggtt ctgaagctca gattttcaa gaacacgagt    2160 gagcaaataa acttgtcgtc ccatccaaat attgtcgagt tgggtttggt tggttttctca    2220 gcaatgctct tgaacattga agcattccct ccaaatcttg tcaagcttaa tcttgtcggc    2280
ttgatggtag acggtcatct attggcagtg cttaagaaat tgcccaaatt aaggatactt    2340
atattgcttt ggtgcagaca tgatgcagaa aaaatggatc tctctggtga tagctttccg    2400
caacttgaag ttttgtatat tgaggatgca caagggttgt ctgaagtaac gtgcatggat    2460
gatatgagta tgcctaaatt gaaaaagcta tttcttgtac aaggcccaaa catttcccca    2520
attagtctca gggtctcgga acggcttgca aagttgagaa tatcacaggt actataa    2577
```

<210> SEQ ID NO 4
<211> LENGTH: 858
<212> TYPE: PRT
<213> ORGANISM: Solanum okadae

<400> SEQUENCE: 4

```
Met Ala Glu Ile Leu Leu Thr Ala Val Ile Asn Lys Ser Ile Glu Ile
1               5                   10                  15

Ala Gly Asn Val Leu Phe Gln Glu Gly Thr Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Val Gly Gly Asp Ser Arg Val Lys
    50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Asn Lys Phe Ile Cys
                85                  90                  95

Cys Leu Lys Thr Val Ser Phe Ala Asp Glu Phe Ala Met Glu Ile Glu
            100                 105                 110

Lys Ile Lys Arg Arg Val Ala Asp Ile Asp Arg Val Arg Thr Thr Tyr
```

-continued

```
            115                 120                 125
Ser Ile Thr Asp Thr Ser Asn Asn Asp Asp Cys Ile Pro Leu Asp
    130                 135                 140

Arg Arg Arg Leu Phe Leu His Ala Asp Glu Thr Glu Val Ile Gly Leu
145                 150                 155                 160

Glu Asp Asp Phe Asn Thr Leu Gln Ala Lys Leu Leu Asp His Asp Leu
                165                 170                 175

Pro Tyr Gly Val Val Ser Ile Val Gly Met Pro Gly Leu Gly Lys Thr
            180                 185                 190

Thr Leu Ala Lys Lys Leu Tyr Arg His Val Cys His Gln Phe Glu Cys
            195                 200                 205

Ser Gly Leu Val Tyr Val Ser Gln Gln Pro Arg Ala Gly Glu Ile Leu
    210                 215                 220

His Asp Ile Ala Lys Gln Val Gly Leu Thr Glu Glu Arg Lys Glu
225                 230                 235                 240

Asn Leu Glu Asn Asn Leu Arg Ser Leu Leu Lys Ile Lys Arg Tyr Val
                245                 250                 255

Ile Leu Leu Asp Asp Ile Trp Asp Val Glu Ile Trp Asp Asp Leu Lys
            260                 265                 270

Leu Val Leu Pro Glu Cys Asp Ser Lys Ile Gly Ser Arg Ile Ile Ile
    275                 280                 285

Thr Ser Arg Asn Ser Asn Val Gly Arg Tyr Ile Gly Gly Asp Phe Ser
    290                 295                 300

Ile His Val Leu Gln Pro Leu Asp Ser Glu Lys Ser Phe Glu Leu Phe
305                 310                 315                 320

Thr Lys Lys Ile Phe Asn Phe Val Asn Asp Asn Trp Ala Asn Ala Ser
                325                 330                 335

Pro Asp Leu Val Asn Ile Gly Arg Cys Ile Val Glu Arg Cys Gly Gly
            340                 345                 350

Ile Pro Leu Ala Ile Val Val Thr Ala Gly Met Leu Arg Ala Arg Gly
    355                 360                 365

Arg Thr Glu His Ala Trp Asn Arg Val Leu Glu Ser Met Ala His Lys
370                 375                 380

Ile Gln Asp Gly Cys Gly Lys Val Leu Ala Leu Ser Tyr Asn Asp Leu
385                 390                 395                 400

Pro Ile Ala Leu Arg Pro Cys Phe Leu Tyr Phe Gly Leu Tyr Pro Glu
                405                 410                 415

Asp His Glu Ile Arg Ala Phe Asp Leu Thr Asn Met Trp Ile Ala Glu
            420                 425                 430

Lys Leu Ile Val Val Asn Thr Gly Asn Gly Arg Glu Ala Glu Ser Leu
    435                 440                 445

Ala Asp Asp Val Leu Asn Asp Leu Val Ser Arg Asn Leu Ile Gln Val
    450                 455                 460

Ala Lys Arg Thr Tyr Asp Gly Arg Ile Ser Ser Cys Arg Ile His Asp
465                 470                 475                 480

Leu Leu His Ser Leu Cys Val Asp Leu Ala Lys Glu Ser Asn Phe Phe
                485                 490                 495

His Thr Glu His Asn Ala Phe Gly Asp Pro Ser Asn Val Ala Arg Val
            500                 505                 510

Arg Arg Ile Thr Phe Tyr Ser Asp Asp Asn Ala Met Asn Glu Phe Phe
    515                 520                 525

His Leu Asn Pro Lys Pro Met Lys Leu Arg Ser Leu Phe Cys Phe Thr
    530                 535                 540
```

-continued

```
Lys Asp Arg Cys Ile Phe Ser Gln Met Ala His Leu Asn Phe Lys Leu
545                 550                 555                 560

Leu Gln Val Leu Val Val Met Ser Gln Lys Gly Tyr Gln His Val
            565                 570                 575

Thr Phe Pro Lys Lys Ile Gly Asn Met Ser Cys Leu Arg Tyr Val Arg
            580                 585                 590

Leu Glu Gly Ala Ile Arg Val Lys Leu Pro Asn Ser Ile Val Lys Leu
            595                 600                 605

Lys Cys Leu Glu Thr Leu Asp Ile Phe His Ser Ser Lys Leu Pro
610                 615                 620

Phe Gly Val Trp Glu Ser Lys Ile Leu Arg His Leu Cys Tyr Thr Glu
625                 630                 635                 640

Glu Cys Tyr Cys Val Ser Phe Ala Ser Pro Phe Cys Arg Ile Met Pro
                645                 650                 655

Pro Asn Asn Leu Gln Thr Leu Met Trp Val Asp Asp Lys Phe Cys Glu
            660                 665                 670

Pro Arg Leu Leu His Arg Leu Ile Asn Leu Arg Thr Leu Cys Ile Met
            675                 680                 685

Asp Val Ser Gly Ser Thr Ile Lys Ile Leu Ser Ala Leu Ser Pro Val
            690                 695                 700

Pro Arg Ala Leu Glu Val Leu Lys Leu Arg Phe Phe Lys Asn Thr Ser
705                 710                 715                 720

Glu Gln Ile Asn Leu Ser Ser His Pro Asn Ile Val Glu Leu Gly Leu
            725                 730                 735

Val Gly Phe Ser Ala Met Leu Leu Asn Ile Glu Ala Phe Pro Pro Asn
            740                 745                 750

Leu Val Lys Leu Asn Leu Val Gly Leu Met Val Asp Gly His Leu Leu
            755                 760                 765

Ala Val Leu Lys Lys Leu Pro Lys Leu Arg Ile Leu Ile Leu Leu Trp
770                 775                 780

Cys Arg His Asp Ala Glu Lys Met Asp Leu Ser Gly Asp Ser Phe Pro
785                 790                 795                 800

Gln Leu Glu Val Leu Tyr Ile Glu Asp Ala Gln Gly Leu Ser Glu Val
            805                 810                 815

Thr Cys Met Asp Asp Met Ser Met Pro Lys Leu Lys Lys Leu Phe Leu
            820                 825                 830

Val Gln Gly Pro Asn Ile Ser Pro Ile Ser Leu Arg Val Ser Glu Arg
            835                 840                 845

Leu Ala Lys Leu Arg Ile Ser Gln Val Leu
            850                 855
```

<210> SEQ ID NO 5
<211> LENGTH: 862
<212> TYPE: PRT
<213> ORGANISM: Solanum mochiquense

<400> SEQUENCE: 5

```
Met Ala Glu Ile Leu Leu Thr Ala Val Ile Asn Lys Ser Val Glu Ile
1               5                   10                  15

Ala Gly Asn Val Leu Phe Gln Glu Gly Thr Arg Leu Tyr Trp Leu Lys
            20                  25                  30

Glu Asp Ile Asp Trp Leu Gln Arg Glu Met Arg His Ile Arg Ser Tyr
            35                  40                  45

Val Asp Asn Ala Lys Ala Lys Glu Val Gly Gly Asp Ser Arg Val Lys
```

```
                50                  55                  60
Asn Leu Leu Lys Asp Ile Gln Gln Leu Ala Gly Asp Val Glu Asp Leu
 65                  70                  75                  80

Leu Asp Glu Phe Leu Pro Lys Ile Gln Gln Ser Ser Lys Phe Lys Gly
                 85                  90                  95

Ala Ile Cys Cys Leu Lys Thr Val Ser Phe Ala Asp Glu Phe Ala Met
                100                 105                 110

Glu Ile Glu Lys Ile Lys Arg Arg Val Val Asp Ile Asp Arg Val Arg
                115                 120                 125

Thr Thr Tyr Asn Ile Met Asp Thr Asn Asn Asn Asp Cys Ile Pro
130                 135                 140

Leu Asp Gln Arg Arg Leu Phe Leu His Val Asp Glu Thr Glu Val Ile
145                 150                 155                 160

Gly Leu Asp Asp Asp Phe Asn Thr Leu Gln Ala Lys Leu Leu Asp Gln
                165                 170                 175

Asp Leu Pro Tyr Gly Val Val Ser Ile Val Gly Met Pro Gly Leu Gly
                180                 185                 190

Lys Thr Thr Leu Ala Lys Lys Leu Tyr Arg His Val Arg His Lys Phe
                195                 200                 205

Glu Cys Ser Gly Leu Val Tyr Val Ser Gln Gln Pro Arg Ala Gly Glu
210                 215                 220

Ile Leu Ile Asp Ile Ala Lys Gln Val Gly Leu Thr Glu Asp Glu Arg
225                 230                 235                 240

Lys Glu Asn Leu Glu Asn Asn Leu Arg Ser Leu Leu Lys Arg Lys Arg
                245                 250                 255

Tyr Val Ile Leu Leu Asp Asp Ile Trp Asp Val Glu Ile Trp Asp Asp
                260                 265                 270

Leu Lys Leu Val Leu Pro Glu Cys Asp Ser Lys Ile Gly Ser Arg Ile
                275                 280                 285

Ile Ile Thr Ser Arg Asn Ser Asn Val Gly Arg Tyr Ile Gly Gly Asp
                290                 295                 300

Phe Ser Ile His Val Leu Gln Pro Leu Asn Ser Glu Asn Ser Phe Glu
305                 310                 315                 320

Leu Phe Thr Lys Lys Ile Phe Ile Phe Asp Asn Asn Asn Asn Trp Thr
                325                 330                 335

Asn Ala Ser Pro Asn Leu Val Asp Ile Gly Arg Ser Ile Val Gly Arg
                340                 345                 350

Cys Gly Gly Ile Pro Leu Ala Ile Val Val Thr Ala Gly Met Leu Arg
                355                 360                 365

Ala Arg Glu Arg Thr Glu Arg Ala Trp Asn Arg Leu Leu Glu Ser Met
                370                 375                 380

Ser His Lys Val Gln Asp Gly Cys Ala Lys Val Leu Ala Leu Ser Tyr
385                 390                 395                 400

Asn Asp Leu Pro Ile Ala Leu Arg Pro Cys Phe Leu Tyr Phe Gly Leu
                405                 410                 415

Tyr Pro Glu Asp His Glu Ile Arg Ala Phe Asp Leu Thr Asn Met Trp
                420                 425                 430

Ile Ala Glu Lys Leu Ile Val Asn Ser Gly Asn Gly Arg Glu Ala
                435                 440                 445

Glu Ser Leu Ala Asp Asp Val Leu Asn Asp Leu Val Ser Arg Asn Met
                450                 455                 460

Ile Gln Val Ala Lys Arg Thr Tyr Asp Gly Arg Ile Ser Ser Cys Arg
465                 470                 475                 480
```

```
Ile His Asp Leu Leu His Ser Leu Cys Val Asp Leu Ala Lys Glu Ser
            485                 490                 495

Asn Phe Phe His Thr Glu His Asn Ala Leu Gly Asp Pro Gly Asn Val
            500                 505                 510

Ala Arg Leu Arg Arg Ile Thr Phe Tyr Ser Asp Asn Asn Ala Met Asn
            515                 520                 525

Glu Phe Phe Arg Ser Asn Pro Lys Leu Glu Lys Leu Arg Ala Leu Phe
            530                 535                 540

Cys Phe Thr Glu Asp Pro Cys Ile Phe Ser Gln Leu Ala His Leu Asp
545                 550                 555                 560

Phe Lys Leu Leu Gln Val Leu Val Val Ile Phe Val Asp Asp Ile
                565                 570                 575

Cys Gly Val Ser Ile Pro Asn Thr Phe Gly Asn Met Arg Cys Leu Arg
            580                 585                 590

Tyr Leu Arg Phe Gln Gly His Phe Tyr Gly Lys Leu Pro Asn Cys Met
            595                 600                 605

Val Lys Leu Lys Arg Leu Glu Thr Leu Asp Ile Gly Tyr Ser Leu Ile
            610                 615                 620

Lys Phe Pro Thr Gly Val Trp Lys Ser Thr Gln Leu Lys His Leu Arg
625                 630                 635                 640

Tyr Gly Gly Phe Asn Gln Ala Ser Asn Ser Cys Phe Ser Ile Ser Pro
            645                 650                 655

Phe Phe Pro Asn Leu Tyr Ser Leu Pro His Asn Asn Val Gln Thr Leu
            660                 665                 670

Met Trp Leu Asp Asp Lys Phe Phe Glu Ala Gly Leu His Arg Leu
            675                 680                 685

Ile Asn Leu Arg Lys Leu Gly Ile Ala Gly Val Ser Asp Ser Thr Val
            690                 695                 700

Lys Ile Leu Ser Ala Leu Ser Pro Val Pro Thr Ala Leu Glu Val Leu
705                 710                 715                 720

Lys Leu Lys Ile Tyr Arg Asp Met Ser Glu Gln Ile Asn Leu Ser Ser
            725                 730                 735

Tyr Pro Asn Ile Val Lys Leu Arg Leu Asn Val Cys Gly Arg Met Arg
            740                 745                 750

Leu Asn Cys Glu Ala Phe Pro Pro Asn Leu Val Lys Leu Thr Leu Val
            755                 760                 765

Gly Asp Glu Val Asp Gly His Val Val Ala Glu Leu Lys Lys Leu Pro
            770                 775                 780

Lys Leu Arg Ile Leu Lys Met Phe Gly Cys Ser His Asn Glu Glu Lys
785                 790                 795                 800

Met Asp Leu Ser Gly Asp Gly Asp Ser Phe Pro Gln Leu Glu Val Leu
            805                 810                 815

His Ile Asp Glu Pro Asp Gly Leu Ser Glu Val Thr Cys Arg Asp Asp
            820                 825                 830

Val Ser Met Pro Lys Leu Lys Lys Leu Leu Val Gln Arg Arg Pro
            835                 840                 845

Ser Pro Ile Ser Leu Ser Glu Arg Leu Ala Lys Leu Arg Ile
            850                 855                 860

<210> SEQ ID NO 6
<211> LENGTH: 858
<212> TYPE: PRT
<213> ORGANISM: Solanum neorossii
```

```
<400> SEQUENCE: 6

Met Ala Glu Ile Leu Leu Thr Ala Val Ile Asn Lys Ser Ile Glu Ile
1               5                   10                  15

Ala Gly Asn Val Leu Phe Gln Glu Gly Thr Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Val Gly Gly Asp Ser Arg Val Lys
    50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Asn Lys Phe Ile Cys
                85                  90                  95

Cys Leu Lys Thr Val Ser Phe Ala Asp Glu Phe Ala Met Glu Ile Glu
            100                 105                 110

Lys Ile Lys Arg Arg Val Ala Asp Ile Asp Arg Val Arg Thr Thr Tyr
            115                 120                 125

Ser Ile Thr Asp Thr Ser Asn Asn Asp Asp Cys Ile Pro Leu Asp
        130                 135                 140

Arg Arg Arg Leu Phe Leu His Ala Asp Glu Thr Glu Val Ile Gly Leu
145                 150                 155                 160

Glu Asp Asp Phe Asn Thr Leu Gln Ala Lys Leu Leu Asp His Asp Leu
                165                 170                 175

Pro Tyr Gly Val Val Ser Ile Val Gly Met Pro Gly Leu Gly Lys Thr
            180                 185                 190

Thr Leu Ala Lys Lys Leu Tyr Arg His Val Cys His Gln Phe Glu Cys
            195                 200                 205

Ser Gly Leu Val Tyr Val Ser Gln Gln Pro Arg Ala Gly Glu Ile Leu
210                 215                 220

His Asp Ile Ala Lys Gln Val Gly Leu Thr Glu Glu Arg Lys Glu
225                 230                 235                 240

Asn Leu Glu Asn Asn Leu Arg Ser Leu Leu Lys Ile Lys Arg Tyr Val
            245                 250                 255

Ile Leu Leu Asp Asp Ile Trp Asp Val Glu Ile Trp Asp Asp Leu Lys
            260                 265                 270

Leu Val Leu Pro Glu Cys Asp Ser Lys Ile Gly Ser Arg Ile Ile Ile
            275                 280                 285

Thr Ser Arg Asn Ser Asn Val Gly Arg Tyr Ile Gly Gly Asp Phe Ser
290                 295                 300

Ile His Val Leu Gln Pro Leu Asp Ser Glu Lys Ser Phe Glu Leu Phe
305                 310                 315                 320

Thr Lys Lys Ile Phe Asn Phe Val Asn Asp Asn Trp Ala Asn Ala Ser
            325                 330                 335

Pro Asp Leu Val Asn Ile Gly Arg Cys Ile Val Glu Arg Cys Gly Gly
            340                 345                 350

Ile Pro Leu Ala Ile Val Val Thr Ala Gly Met Leu Arg Ala Arg Gly
            355                 360                 365

Arg Thr Glu His Ala Trp Asn Arg Val Leu Glu Ser Met Ala His Lys
370                 375                 380

Ile Gln Asp Gly Cys Gly Lys Val Leu Ala Leu Ser Tyr Asn Asp Leu
385                 390                 395                 400

Pro Ile Ala Leu Arg Pro Cys Phe Leu Tyr Phe Gly Leu Tyr Pro Glu
                405                 410                 415
```

-continued

```
Asp His Glu Ile Arg Ala Phe Asp Leu Thr Asn Met Trp Ile Ala Glu
            420                 425                 430

Lys Leu Ile Val Val Asn Thr Gly Asn Gly Arg Glu Ala Glu Ser Leu
            435                 440                 445

Ala Asp Asp Val Leu Asn Asp Leu Val Ser Arg Asn Leu Ile Gln Val
450                 455                 460

Ala Lys Arg Thr Tyr Asp Gly Arg Ile Ser Ser Cys Arg Ile His Asp
465                 470                 475                 480

Leu Leu His Ser Leu Cys Val Asp Leu Ala Lys Glu Ser Asn Phe Phe
                485                 490                 495

His Thr Glu His Tyr Ala Phe Gly Asp Pro Ser Asn Val Ala Arg Val
            500                 505                 510

Arg Arg Ile Thr Phe Tyr Ser Asp Asp Asn Ala Met Asn Glu Phe Phe
            515                 520                 525

His Leu Asn Pro Lys Pro Met Lys Leu Arg Ser Leu Phe Cys Phe Thr
            530                 535                 540

Lys Asp Arg Cys Ile Phe Ser Gln Met Ala His Leu Asn Phe Lys Leu
545                 550                 555                 560

Leu Gln Val Leu Val Val Met Ser Gln Lys Gly Tyr Gln His Val
                565                 570                 575

Thr Phe Pro Lys Lys Ile Gly Asn Met Ser Cys Leu Arg Tyr Val Arg
            580                 585                 590

Leu Glu Gly Ala Ile Arg Val Lys Leu Pro Asn Ser Ile Val Lys Leu
            595                 600                 605

Lys Cys Leu Glu Thr Leu Asp Ile Phe His Ser Ser Lys Leu Pro
610                 615                 620

Phe Gly Val Trp Glu Ser Lys Ile Leu Arg His Leu Cys Tyr Thr Glu
625                 630                 635                 640

Glu Cys Tyr Cys Val Ser Phe Ala Ser Pro Phe Cys Arg Ile Met Pro
                645                 650                 655

Pro Asn Asn Leu Gln Thr Leu Met Trp Val Asp Asp Lys Phe Cys Glu
            660                 665                 670

Pro Arg Leu Leu His Arg Leu Ile Asn Leu Arg Thr Leu Cys Ile Met
            675                 680                 685

Asp Val Ser Gly Ser Thr Ile Lys Ile Leu Ser Ala Leu Ser Pro Val
            690                 695                 700

Pro Lys Ala Leu Glu Val Leu Lys Leu Arg Phe Phe Lys Asn Thr Ser
705                 710                 715                 720

Glu Gln Ile Asn Leu Ser Ser His Pro Asn Ile Val Glu Leu Gly Leu
            725                 730                 735

Val Gly Phe Ser Ala Met Leu Leu Asn Ile Glu Ala Phe Pro Pro Asn
            740                 745                 750

Leu Val Lys Leu Asn Leu Val Gly Leu Met Val Asp Gly His Leu Leu
            755                 760                 765

Ala Val Leu Lys Lys Leu Pro Lys Leu Arg Ile Leu Ile Leu Leu Trp
            770                 775                 780

Cys Arg His Asp Ala Glu Lys Met Asp Leu Ser Gly Asp Ser Phe Pro
785                 790                 795                 800

Gln Leu Glu Val Leu Tyr Ile Glu Asp Ala Gln Gly Leu Ser Glu Val
            805                 810                 815

Thr Cys Met Asp Asp Met Ser Met Pro Lys Leu Lys Lys Leu Phe Leu
            820                 825                 830
```

Val Gln Gly Pro Asn Ile Ser Pro Ile Ser Leu Arg Val Ser Glu Arg
            835                 840                 845

Leu Ala Lys Leu Arg Ile Ser Gln Val Leu
        850                 855

<210> SEQ ID NO 7
<211> LENGTH: 2577
<212> TYPE: DNA
<213> ORGANISM: Solanum okadae

<400> SEQUENCE: 7

| | | | | | |
|---|---|---|---|---|---|
| atggctgaaa | ttcttctcac | agcagtcatc | aataaatcaa | tagaaatagc | tggaaatgta | 60 |
| ctctttcaag | aaggtacgcg | tttatattgg | ttgaaagagg | acatcgattg | gctccagaga | 120 |
| gaaatgagac | acattcgatc | atatgtagac | aatgcaaagg | caaggaagt | tggaggcgat | 180 |
| tcaagggtga | aaaacttatt | aaaagatatt | caacaactgg | caggtgatgt | ggaggatcta | 240 |
| ttagatgagt | tccttccaaa | aattcaacaa | tccataagt | tcatttgttg | ccttaagacg | 300 |
| gtttcttttg | ccgatgagtt | tgctatggag | attgagaaga | taaaaagaag | agttgctgat | 360 |
| attgaccgtg | taaggacaac | ttacagcatc | acagatacaa | gtaacaataa | tgatgattgc | 420 |
| attccattgg | accggagaag | attgttcctt | catgctgatg | aaacagaggt | catcggtctg | 480 |
| gaagatgact | tcaatacact | acaagccaaa | ttacttgatc | atgatttgcc | ttatggagtt | 540 |
| gtttcaatag | ttggcatgcc | cggtttggga | aaaacaactc | ttgccaagaa | actttatagg | 600 |
| catgtctgtc | atcaatttga | gtgttcggga | ctggtctatg | tttcacaaca | gccaagggcg | 660 |
| ggagaaatct | tacatgacat | agccaaacaa | gttggactga | cggaagagga | aaggaaagaa | 720 |
| aacttggaga | caacctacg | atcactcttg | aaaataaaaa | ggtatgttat | tctcttagat | 780 |
| gacatttggg | atgttgaaat | tgggatgat | ctaaaacttg | tccttcctga | atgtgattca | 840 |
| aaaattggca | gtaggataat | tataaccctct | cgaaatagta | atgtaggcag | atacatagga | 900 |
| ggggatttct | caatccacgt | gttgcaaccc | ctagattcag | agaaaagctt | tgaactcttt | 960 |
| accaagaaaa | tctttaattt | tgttaatgat | aattgggcca | atgcttcacc | agacttggta | 1020 |
| aatattggta | gatgtatagt | tgagagatgt | ggaggtatac | cgctagcaat | tgtggtgact | 1080 |
| gcaggcatgt | taagggcaag | aggaagaaca | gaacatgcat | ggaacagagt | acttgagagt | 1140 |
| atggctcata | aaattcaaga | tggatgtggt | aaggtattgg | ctctgagtta | caatgatttg | 1200 |
| cccattgcat | taaggccatg | tttcttgtac | tttggtcttt | accccgagga | ccatgaaatt | 1260 |
| cgtgctttg | atttgacaaa | tatgtggatt | gctgagaagc | tgatagttgt | aaatactggc | 1320 |
| aatgggcgag | aggctgaaag | tttggcggat | gatgtcctaa | atgatttggt | ttcaagaaac | 1380 |
| ttgattcaag | ttgccaaaag | gacatatgat | ggaagaattt | caagttgtcg | catacatgac | 1440 |
| tgttacata | gtttgtgtgt | ggacttggct | aaggaaagta | acttctttca | cacggagcac | 1500 |
| tatgcatttg | gtgatcctag | caatgttgct | agggtgcgaa | ggattacatt | ctactctgat | 1560 |
| gataatgcca | tgaatgagtt | cttccattta | aatcctaagc | ctatgaagct | tcgttcactt | 1620 |
| ttctgtttca | caaaagaccg | ttgcatattt | tctcaaatgg | ctcatcttaa | cttcaaatta | 1680 |
| ttgcaagtgt | tggttgtagt | catgtctcaa | aagggttatc | agcatgttac | tttccccaaa | 1740 |
| aaaattggga | acatgagttg | cctacgctat | gtgcgattgg | aggggcaat | tagagtaaaa | 1800 |
| ttgccaaata | gtattgtcaa | gctcaaatgt | ctagagaccc | tggatatatt | tcatagctct | 1860 |
| agtaaacttc | cttttggtgt | tgggagtct | aaaatattga | acatctttg | ttacacagaa | 1920 |
| gaatgttact | gtgtctcttt | tgcaagtcca | ttttgccgaa | tcatgcctcc | taataatcta | 1980 |

```
caaactttga tgtgggtgga tgataaattt tgtgaaccaa gattgttgca ccgattgata   2040
aatttaagaa cattgtgtat aatggatgta tccggttcta ccattaagat attatcagca   2100
ttgagccctg tgcctaaagc gttggaggtt ctgaagctca gattttcaa gaacacgagt    2160 gagcaaataa acttgtcgtc ccatccaaat attgtcgagt tgggtttggt tggtttctca   2220
gcaatgctct tgaacattga agcattccct ccaaatcttg tcaagcttaa tcttgtcggc   2280
ttgatggtag acggtcatct attggcagtg cttaagaaat tgcccaaatt aaggatactt   2340
atattgcttt ggtgcagaca tgatgcagaa aaaatggatc tctctggtga tagctttccg   2400
caacttgaag ttttgtatat tgaggatgca caagggttgt ctgaagtaac gtgcatggat   2460
gatatgagta tgcctaaatt gaaaaagcta tttcttgtac aaggcccaaa catttcccca   2520
attagtctca gggtctcgga acggcttgca aagttgagaa tatcacaggt actataa     2577
```

<210> SEQ ID NO 8
<211> LENGTH: 2571
<212> TYPE: DNA
<213> ORGANISM: Solanum mochiquense

<400> SEQUENCE: 8

```
atggctgaaa ttcttcttac aacagtcatc aataaatctg taggaatagc tgcaaatgta   60
ctctttcaag aaggaacgcg tttatattgg ttgaaagagg acatagattg gctccacaga   120
gaaatgagac acattcgatc atatgtagac gatgcaaagg ccaaggaagt tggaggcgat   180
tcaagggtca gaaacttatt aaaagatatt caacaactgg caggtgatgt ggaggatcta   240
ttagatgagt ttcttccaaa aattcaacaa tccataagt tcatttgttg ccttaagaca    300 gtttctttg ccgatgagtt tgccatggag attgagaaga taaaaagaag agttgctgat    360
attacccgtg taaggacaac ttacaacatc acagatacaa gtaacaataa tgatgattgc   420
attccattgg accggagaag attgttcctt catgctgatg aaacagaggt catcggtctg   480
gaagatgact tcaatacact aaaagccaaa ttacttgatc aagatttgcc ttatggagtt   540
gtttcaatag ttggcatgcc cggtctagga aaaacaactc ttgccaagaa actttatagg   600
catgtccgtg atcaatttga gagctcggga ctggtctacg tgtcccaaca gccaagagcg   660
ggagaaatct tacgtgacat agccaaacaa gttggactgc caaaagagga aaggaaagaa   720
aacttggagg gcaacctacg atcactcttg aaaacaaaaa ggtatgttat cctcctagat   780
gacatttggg atgttgaaat tgggatgat ctaaaactcg tccttcctga atgtgattca    840
gaaattggca gtaggataat tataacctct cgaaatagta atgtaggcag atacatagga   900
ggggatttct caattcacat gttgcaacct ctagattcgg agaacagttt tgaactcttt   960
accaagaaaa tctttacttt tgataacaat aataattggg ccaatgcttc accagacttg   1020
gtagatattg gtagaagtat agttggtaga tgcggaggta tacctctagc cattgtggtc   1080
actgcaggca tgtaagggc aagagaaaga acagaacatg catggaacag gtacttgag    1140 agtatgggcc ataaagttca agatggatgt gctaaggtat tggctttgag ttacaatgat   1200
ttgcccattg cattaaggcc atgtttcttg taccttggcc ttttccccga ggaccatgaa   1260
attcgtgcct ttgatttgac aaatatgtgg attgctgaga gctgatagt tgtaaatagt    1320 ggcaatgggc gagaggctga agtttggcg gaggatgttc taaatgattt tgtttctaga    1380
aacttgattc aagtttccca agaaaatgt aatggaagaa tttcaagtta tcgcatacat    1440
gacttgttac atagtttgtg cgtcgaattg ggcaaggaaa gtaactttt tcacactgaa    1500
```

-continued

```
cacaatgcat tggtgatcc agacaatgtt gctagggtgc aaggattac attctactct   1560 gataataatg ccatgagtaa gttcttccgt tcaaatccta agcctaagaa acttcgtgca   1620
cttttctgtt tcacaaattt agactcttgc atattttctc atttggctca tcatgacttc   1680
aaattattac aagtgttggt tgtagttatc tcttataatt ggttgagtgt cagtatctca   1740
aacaaatttg ggaagatgag ttgcttgcgc tatttgagat tggaggggcc aattgtggga   1800
gaactgtcaa atagtattgt gaagctcaaa cgtgtagaga ccatagatat tgcaggggat   1860
aacattaaaa ttccttgtgg tgtttgggag tctaaacaat tgagacatct ccgtaataga   1920
gaagaacgtc gctatttctt ttctgtaagc ccattttgcc taaacatgta cccattgcct   1980
cctaataatc tacaaacttt ggtgtggatg gatgataaat ttttttgaacc gagattgttg   2040 caccgattga tcaatttaag aaaattgggt atatggggca catctgattc tacaattaag   2100
atattatcag cattgagccc tgtgccaaca gcgttggagg ttctgaagct ctacttttg    2160 agggacctga gtgagcaaat aaacttgtca acctatccaa atattgttaa gttgaatttg   2220
caaggattcg taagagtgcg cttgaactct gaagcattcc ctccaaatct tgtcaagctt   2280
attcttgaca aaattgaggt agagggtcat gtagtggcag ttcttaagaa attgcccaca   2340
ttaaggatac ttaaaatgta tgggtgcaaa cataatgaag aaaagatgga tctctctggt   2400
gatggtgatg gtgatagctt tccgcaactt gaagttttgc atattgagag accattcttc   2460
ttgtttgaaa taacgtgcac agatgatgac agtatgccta aattgaaaaa gctattactt   2520
accacttcga acgttaggct ctcggaaaga cttgcaaaac tgagagtatg a            2571
```

<210> SEQ ID NO 9
<211> LENGTH: 858
<212> TYPE: PRT
<213> ORGANISM: Solanum okadae

<400> SEQUENCE: 9

```
Met Ala Glu Ile Leu Leu Thr Ala Val Ile Asn Lys Ser Ile Glu Ile
1               5                   10                  15

Ala Gly Asn Val Leu Phe Gln Glu Gly Thr Arg Leu Tyr Trp Leu Lys
            20                  25                  30

Glu Asp Ile Asp Trp Leu Gln Arg Glu Met Arg His Ile Arg Ser Tyr
        35                  40                  45

Val Asp Asn Ala Lys Ala Lys Glu Val Gly Gly Asp Ser Arg Val Lys
    50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Asn Lys Phe Ile Cys
                85                  90                  95

Cys Leu Lys Thr Val Ser Phe Ala Asp Glu Phe Ala Met Glu Ile Glu
            100                 105                 110

Lys Ile Lys Arg Arg Val Ala Asp Ile Asp Arg Val Arg Thr Thr Tyr
        115                 120                 125

Ser Ile Thr Asp Thr Ser Asn Asn Asn Asp Asp Cys Ile Pro Leu Asp
    130                 135                 140

Arg Arg Arg Leu Phe Leu His Ala Asp Glu Thr Glu Val Ile Gly Leu
145                 150                 155                 160

Glu Asp Asp Phe Asn Thr Leu Gln Ala Lys Leu Leu Asp His Asp Leu
                165                 170                 175

Pro Tyr Gly Val Val Ser Ile Val Gly Met Pro Gly Leu Gly Lys Thr
            180                 185                 190
```

```
Thr Leu Ala Lys Lys Leu Tyr Arg His Val Cys His Gln Phe Glu Cys
            195                 200                 205

Ser Gly Leu Val Tyr Val Ser Gln Gln Pro Arg Ala Gly Glu Ile Leu
    210                 215                 220

His Asp Ile Ala Lys Gln Val Gly Leu Thr Glu Glu Arg Lys Glu
225                 230                 235                 240

Asn Leu Glu Asn Asn Leu Arg Ser Leu Lys Ile Lys Arg Tyr Val
            245                 250                 255

Ile Leu Leu Asp Asp Ile Trp Asp Val Glu Ile Trp Asp Asp Leu Lys
            260                 265                 270

Leu Val Leu Pro Glu Cys Asp Ser Lys Ile Gly Ser Arg Ile Ile Ile
            275                 280                 285

Thr Ser Arg Asn Ser Asn Val Gly Arg Tyr Ile Gly Gly Asp Phe Ser
            290                 295                 300

Ile His Val Leu Gln Pro Leu Asp Ser Glu Lys Ser Phe Glu Leu Phe
305                 310                 315                 320

Thr Lys Lys Ile Phe Asn Phe Val Asn Asp Asn Trp Ala Asn Ala Ser
                325                 330                 335

Pro Asp Leu Val Asn Ile Gly Arg Cys Ile Val Glu Arg Cys Gly Gly
            340                 345                 350

Ile Pro Leu Ala Ile Val Val Thr Ala Gly Met Leu Arg Ala Arg Gly
            355                 360                 365

Arg Thr Glu His Ala Trp Asn Arg Val Leu Glu Ser Met Ala His Lys
    370                 375                 380

Ile Gln Asp Gly Cys Gly Lys Val Leu Ala Leu Ser Tyr Asn Asp Leu
385                 390                 395                 400

Pro Ile Ala Leu Arg Pro Cys Phe Leu Tyr Phe Gly Leu Tyr Pro Glu
                405                 410                 415

Asp His Glu Ile Arg Ala Phe Asp Leu Thr Asn Met Trp Ile Ala Glu
            420                 425                 430

Lys Leu Ile Val Val Asn Thr Gly Asn Gly Arg Glu Ala Glu Ser Leu
    435                 440                 445

Ala Asp Asp Val Leu Asn Asp Leu Val Ser Arg Asn Leu Ile Gln Val
450                 455                 460

Ala Lys Arg Thr Tyr Asp Gly Arg Ile Ser Ser Cys Arg Ile His Asp
465                 470                 475                 480

Leu Leu His Ser Leu Cys Val Asp Leu Ala Lys Glu Ser Asn Phe Phe
            485                 490                 495

His Thr Glu His Tyr Ala Phe Gly Asp Pro Ser Asn Val Ala Arg Val
                500                 505                 510

Arg Arg Ile Thr Phe Tyr Ser Asp Asp Asn Ala Met Asn Glu Phe Phe
            515                 520                 525

His Leu Asn Pro Lys Pro Met Lys Leu Arg Ser Leu Phe Cys Phe Thr
            530                 535                 540

Lys Asp Arg Cys Ile Phe Ser Gln Met Ala His Leu Asn Phe Lys Leu
545                 550                 555                 560

Leu Gln Val Leu Val Val Met Ser Gln Lys Gly Tyr Gln His Val
                565                 570                 575

Thr Phe Pro Lys Lys Ile Gly Asn Met Ser Cys Leu Arg Tyr Val Arg
            580                 585                 590

Leu Glu Gly Ala Ile Arg Val Lys Leu Pro Asn Ser Ile Val Lys Leu
            595                 600                 605
```

```
Lys Cys Leu Glu Thr Leu Asp Ile Phe His Ser Ser Lys Leu Pro
    610                 615                 620

Phe Gly Val Trp Glu Ser Lys Ile Leu Arg His Leu Cys Tyr Thr Glu
625                 630                 635                 640

Glu Cys Tyr Cys Val Ser Phe Ala Ser Pro Phe Cys Arg Ile Met Pro
                645                 650                 655

Pro Asn Asn Leu Gln Thr Leu Met Trp Val Asp Asp Lys Phe Cys Glu
            660                 665                 670

Pro Arg Leu Leu His Arg Leu Ile Asn Leu Arg Thr Leu Cys Ile Met
        675                 680                 685

Asp Val Ser Gly Ser Thr Ile Lys Ile Leu Ser Ala Leu Ser Pro Val
    690                 695                 700

Pro Lys Ala Leu Glu Val Leu Lys Leu Arg Phe Phe Lys Asn Thr Ser
705                 710                 715                 720

Glu Gln Ile Asn Leu Ser Ser His Pro Asn Ile Val Glu Leu Gly Leu
                725                 730                 735

Val Gly Phe Ser Ala Met Leu Leu Asn Ile Glu Ala Phe Pro Pro Asn
            740                 745                 750

Leu Val Lys Leu Asn Leu Val Gly Leu Met Val Asp Gly His Leu Leu
        755                 760                 765

Ala Val Leu Lys Lys Leu Pro Lys Leu Arg Ile Leu Ile Leu Leu Trp
    770                 775                 780

Cys Arg His Asp Ala Glu Lys Met Asp Leu Ser Gly Asp Ser Phe Pro
785                 790                 795                 800

Gln Leu Glu Val Leu Tyr Ile Glu Asp Ala Gln Gly Leu Ser Glu Val
                805                 810                 815

Thr Cys Met Asp Asp Met Ser Met Pro Lys Leu Lys Lys Leu Phe Leu
            820                 825                 830

Val Gln Gly Pro Asn Ile Ser Pro Ile Ser Leu Arg Val Ser Glu Arg
        835                 840                 845

Leu Ala Lys Leu Arg Ile Ser Gln Val Leu
    850                 855

<210> SEQ ID NO 10
<211> LENGTH: 856
<212> TYPE: PRT
<213> ORGANISM: Solanum mochiquense

<400> SEQUENCE: 10

Met Ala Glu Ile Leu Leu Thr Thr Val Ile Asn Lys Ser Val Gly Ile
1               5                   10                  15

Ala Ala Asn Val Leu Phe Gln Glu Gly Thr Arg Leu Tyr Trp Leu Lys
            20                  25                  30

Glu Asp Ile Asp Trp Leu His Arg Glu Met Arg His Ile Arg Ser Tyr
        35                  40                  45

Val Asp Asp Ala Lys Ala Lys Glu Val Gly Gly Asp Ser Arg Val Arg
    50                  55                  60

Asn Leu Leu Lys Asp Ile Gln Gln Leu Ala Gly Asp Val Glu Asp Leu
65                  70                  75                  80

Leu Asp Glu Phe Leu Pro Lys Ile Gln Gln Ser Asn Lys Phe Ile Cys
                85                  90                  95

Cys Leu Lys Thr Val Ser Phe Ala Asp Glu Phe Ala Met Glu Ile Glu
            100                 105                 110

Lys Ile Lys Arg Arg Val Ala Asp Ile Thr Arg Val Arg Thr Thr Tyr
        115                 120                 125
```

```
Asn Ile Thr Asp Thr Ser Asn Asn Asp Asp Cys Ile Pro Leu Asp
        130                 135                 140

Arg Arg Arg Leu Phe Leu His Ala Asp Glu Thr Glu Val Ile Gly Leu
145                 150                 155                 160

Glu Asp Asp Phe Asn Thr Leu Lys Ala Lys Leu Leu Asp Gln Asp Leu
                165                 170                 175

Pro Tyr Gly Val Val Ser Ile Val Gly Met Pro Gly Leu Gly Lys Thr
                180                 185                 190

Thr Leu Ala Lys Lys Leu Tyr Arg His Val Arg Asp Gln Phe Glu Ser
            195                 200                 205

Ser Gly Leu Val Tyr Val Ser Gln Gln Pro Arg Ala Gly Glu Ile Leu
        210                 215                 220

Arg Asp Ile Ala Lys Gln Val Gly Leu Pro Lys Glu Glu Arg Lys Glu
225                 230                 235                 240

Asn Leu Glu Gly Asn Leu Arg Ser Leu Leu Lys Thr Lys Arg Tyr Val
                245                 250                 255

Ile Leu Leu Asp Asp Ile Trp Asp Val Glu Ile Trp Asp Asp Leu Lys
                260                 265                 270

Leu Val Leu Pro Glu Cys Asp Ser Glu Ile Gly Ser Arg Ile Ile Ile
            275                 280                 285

Thr Ser Arg Asn Ser Asn Val Gly Arg Tyr Ile Gly Gly Asp Phe Ser
290                 295                 300

Ile His Met Leu Gln Pro Leu Asp Ser Glu Asn Ser Phe Glu Leu Phe
305                 310                 315                 320

Thr Lys Lys Ile Phe Thr Phe Asp Asn Asn Asn Trp Ala Asn Ala
                325                 330                 335

Ser Pro Asp Leu Val Asp Ile Gly Arg Ser Ile Val Gly Arg Cys Gly
                340                 345                 350

Gly Ile Pro Leu Ala Ile Val Val Thr Ala Gly Met Leu Arg Ala Arg
            355                 360                 365

Glu Arg Thr Glu His Ala Trp Asn Arg Val Leu Glu Ser Met Gly His
370                 375                 380

Lys Val Gln Asp Gly Cys Ala Lys Val Leu Ala Leu Ser Tyr Asn Asp
385                 390                 395                 400

Leu Pro Ile Ala Leu Arg Pro Cys Phe Leu Tyr Leu Gly Leu Phe Pro
                405                 410                 415

Glu Asp His Glu Ile Arg Ala Phe Asp Leu Thr Asn Met Trp Ile Ala
            420                 425                 430

Glu Lys Leu Ile Val Val Asn Ser Gly Asn Gly Arg Glu Ala Glu Ser
        435                 440                 445

Leu Ala Glu Asp Val Leu Asn Asp Phe Val Ser Arg Asn Leu Ile Gln
    450                 455                 460

Val Ser Gln Arg Lys Cys Asn Gly Arg Ile Ser Ser Tyr Arg Ile His
465                 470                 475                 480

Asp Leu Leu His Ser Leu Cys Val Glu Leu Gly Lys Glu Ser Asn Phe
                485                 490                 495

Phe His Thr Glu His Asn Ala Phe Gly Asp Pro Asp Asn Val Ala Arg
            500                 505                 510

Val Arg Arg Ile Thr Phe Tyr Ser Asp Asn Asn Ala Met Ser Lys Phe
        515                 520                 525

Phe Arg Ser Asn Pro Lys Pro Lys Lys Leu Arg Ala Leu Phe Cys Phe
530                 535                 540
```

Thr Asn Leu Asp Ser Cys Ile Phe Ser His Leu Ala His His Asp Phe
545                 550                 555                 560

Lys Leu Leu Gln Val Leu Val Val Val Ile Ser Tyr Asn Trp Leu Ser
            565                 570                 575

Val Ser Ile Ser Asn Lys Phe Gly Lys Met Ser Cys Leu Arg Tyr Leu
        580                 585                 590

Arg Leu Glu Gly Pro Ile Val Gly Glu Leu Ser Asn Ser Ile Val Lys
    595                 600                 605

Leu Lys Arg Val Glu Thr Ile Asp Ile Ala Gly Asp Asn Ile Lys Ile
610                 615                 620

Pro Cys Gly Val Trp Glu Ser Lys Gln Leu Arg His Leu Arg Asn Arg
625                 630                 635                 640

Glu Glu Arg Arg Tyr Phe Phe Ser Val Ser Pro Phe Cys Leu Asn Met
                645                 650                 655

Tyr Pro Leu Pro Pro Asn Asn Leu Gln Thr Leu Val Trp Met Asp Asp
            660                 665                 670

Lys Phe Phe Glu Pro Arg Leu Leu His Arg Leu Ile Asn Leu Arg Lys
        675                 680                 685

Leu Gly Ile Trp Gly Thr Ser Asp Ser Thr Ile Lys Ile Leu Ser Ala
    690                 695                 700

Leu Ser Pro Val Pro Thr Ala Leu Glu Val Leu Lys Leu Tyr Phe Leu
705                 710                 715                 720

Arg Asp Leu Ser Glu Gln Ile Asn Leu Ser Thr Tyr Pro Asn Ile Val
                725                 730                 735

Lys Leu Asn Leu Gln Gly Phe Val Arg Val Arg Leu Asn Ser Glu Ala
            740                 745                 750

Phe Pro Pro Asn Leu Val Lys Leu Ile Leu Asp Lys Ile Glu Val Glu
        755                 760                 765

Gly His Val Ala Val Leu Lys Lys Leu Pro Thr Leu Arg Ile Leu
    770                 775                 780

Lys Met Tyr Gly Cys Lys His Asn Glu Lys Met Asp Leu Ser Gly
785                 790                 795                 800

Asp Gly Asp Gly Asp Ser Phe Pro Gln Leu Glu Val Leu His Ile Glu
                805                 810                 815

Arg Pro Phe Phe Leu Phe Glu Ile Thr Cys Thr Asp Asp Ser Met
            820                 825                 830

Pro Lys Leu Lys Lys Leu Leu Thr Thr Ser Asn Val Arg Leu Ser
        835                 840                 845

Glu Arg Leu Ala Lys Leu Arg Val
    850                 855

<210> SEQ ID NO 11
<211> LENGTH: 1248
<212> TYPE: DNA
<213> ORGANISM: Solanum lycopersicum

<400> SEQUENCE: 11
atgggaagaa caccttgttg tgaaaaagtg ggcatcaaga gaggcagatg gactgcagaa     60
gaagatcaaa ttctcactaa ttatattatt tctaatggag aaggctcttg gaggtcgtta    120
cctaaaaatg ccggattatt gagatgcgga aagagttgta gactacgatg gattaattat    180
ttgaggtctg atctcaagag agggaacatt acttctcaag ggaagatat aattataaag    240 ttacatgcaa ctttgggtaa cagatggtct cttatagcag acatttatc aggtagaaca    300 gacaatgaga taaaaaacta ttggaactct catctaagtc gaaaagttga tagcttaagg    360

-continued

```
ataccaagcg atgagaagtt acctaaagcc gtagttgatt tggctaaaaa aggtataccg    420
aagccaatta aaaaatcatc gattagtcga ccaaaaaata aaaagtcaaa cttattagaa    480
aaagaagcat tgtgttgtac aaatatgcca gcttgtgata gtgccatgga attaatgcaa    540
gaagatctag caaagataga ggtgccaaat tcttgggcag gacctataga ggccaaggga    600
agccttagtt cagatagtga tatcgaatgg ccaagactcg aggagattat gccagacgtg    660
gtgattgatg atgaagataa gaacacaaat ttcatattga attgtttcag agaagaagta    720
acgagcaata atgtagggaa tagttattca tgtatcgagg aaggtaataa aaagatatca    780
agcgacgatg aaaaaatcaa attattaatg gattggcaag ataatgatga gttagtatgg    840
ccaacgttac catgggaatt agaaacggat atagttccca gttggccaca atgggacgat    900
actgacacta acttacttca aaattgcacc aatgataata ataattatga agaagcaaca    960
acaatggaaa ttaataacca aaatcatagt accattgtat cttggctttt gtcttagaaa   1020
tataataata tgacattata tattgctttt gaatatatta ctcaactctt tttgtttcgt   1080
tttatatttg gaatgtggga attagaatga ctagtttatg tacatatttt aagtttcgtt   1140
agaaatatcg tcaagtcaga ttaaaatatg tatgagttga tgtagtaata aatgttattg   1200
ttattacttt ttttgatgta aaaaaaaaaa aaaaaaaaaa aaaaaaaa                1248
```

<210> SEQ ID NO 12
<211> LENGTH: 338
<212> TYPE: PRT
<213> ORGANISM: Solanum lycopersicum

<400> SEQUENCE: 12

```
Met Gly Arg Thr Pro Cys Cys Glu Lys Val Gly Ile Lys Arg Gly
1               5                   10                  15

Trp Thr Ala Glu Glu Asp Gln Ile Leu Thr Asn Tyr Ile Ile Ser Asn
                20                  25                  30

Gly Glu Gly Ser Trp Arg Ser Leu Pro Lys Asn Ala Gly Leu Leu Arg
            35                  40                  45

Cys Gly Lys Ser Cys Arg Leu Arg Trp Ile Asn Tyr Leu Arg Ser Asp
        50                  55                  60

Leu Lys Arg Gly Asn Ile Thr Ser Gln Glu Glu Asp Ile Ile Ile Lys
65                  70                  75                  80

Leu His Ala Thr Leu Gly Asn Arg Trp Ser Leu Ile Ala Glu His Leu
                85                  90                  95

Ser Gly Arg Thr Asp Asn Glu Ile Lys Asn Tyr Trp Asn Ser His Leu
            100                 105                 110

Ser Arg Lys Val Asp Ser Leu Arg Ile Pro Ser Asp Glu Lys Leu Pro
        115                 120                 125

Lys Ala Val Val Asp Leu Ala Lys Lys Gly Ile Pro Lys Pro Ile Lys
    130                 135                 140

Lys Ser Ser Ile Ser Arg Pro Lys Asn Lys Ser Asn Leu Leu Glu
145                 150                 155                 160

Lys Glu Ala Leu Cys Cys Thr Asn Met Pro Ala Cys Asp Ser Ala Met
                165                 170                 175

Glu Leu Met Gln Glu Asp Leu Ala Lys Ile Glu Val Pro Asn Ser Trp
            180                 185                 190

Ala Gly Pro Ile Glu Ala Lys Gly Ser Leu Ser Ser Asp Ser Asp Ile
        195                 200                 205

Glu Trp Pro Arg Leu Glu Glu Ile Met Pro Asp Val Val Ile Asp Asp
```

```
                  210               215                   220
Glu Asp Lys Asn Thr Asn Phe Ile Leu Asn Cys Phe Arg Glu Glu Val
225                 230                 235                 240

Thr Ser Asn Asn Val Gly Asn Ser Tyr Ser Cys Ile Glu Glu Gly Asn
                245                 250                 255

Lys Lys Ile Ser Ser Asp Asp Glu Lys Ile Lys Leu Leu Met Asp Trp
                260                 265                 270

Gln Asp Asn Asp Glu Leu Val Trp Pro Thr Leu Pro Trp Leu Glu
            275                 280                 285

Thr Asp Ile Val Pro Ser Trp Pro Gln Trp Asp Asp Thr Asp Thr Asn
290                 295                 300

Leu Leu Gln Asn Cys Thr Asn Asp Asn Asn Asn Tyr Glu Glu Ala Thr
305                 310                 315                 320

Thr Met Glu Ile Asn Asn Gln Asn His Ser Thr Ile Val Ser Trp Leu
                325                 330                 335

Leu Ser

<210> SEQ ID NO 13
<211> LENGTH: 1089
<212> TYPE: DNA
<213> ORGANISM: Solanum tuberosum

<400> SEQUENCE: 13
atgggaagaa caccttgttg tgaaaaagtg ggtatcaaga gaggcagatg gactgcagaa    60
gaagatcaaa ttctcactaa ttatattctt tctaatggag aaggctcttg gaggtcatta   120
cccaaaaatg ccggattact gagatgtgga aagagttgta gactaagatg gattaattat   180
ttgaggtctg acctcaagag agggaacatt acttctcaag aggaagatat aatcataaag   240
ttacatgcaa ctttgggtaa caggtggtct ctaatagcgg acatttatc aggtagaaca    300
gacaatgaga ttaaaaatta ttggaactct catctaagtc gaaagttga tagcttaagg    360
ataccaagcg atgagaagtt gcctaaagct gtagttgatt tggctaaaaa gggtacattg   420
aagccaatta acattgtag aaaatcattg attagtcgat cgaaaaataa aaatcaaac     480
ttattagaag ctaaagaaaa tagtactagt ggggctttga ttggaattgt tcctatgcct   540
tcaacaccaa acatagaaaa agaagcattg tgttgtacaa atatgccagc ttgtgatagt   600
gccatggcat taatgcaaga gatgtagca aggtagagg tgccaaattc ttgggcaggg    660
tctatagagg ccaagggaag ccttagttca gatagtggta tggaatggcc aaggctcgag   720
gagattatgc cagacgtggt gattgatgat gaagatatga acccaaattt cattttgaat   780
ggtttagaag aagaagtaat gagcaataat gcagggaata attattcatg tatcgacgaa   840
ggaaataaaa acgtatcaag cgatgatgaa aaaagcaaat tattaatgga ttggcaagat   900
gatgatgaat tagtatggcc aacgccacca tgggaattag aaacagacat aattcctagt   960
tggccacaat gggacgatac tgacactgat ttacttcaaa attgcaccaa taataattat  1020
gaagaagcaa caacaatgga aattaataac caaaatcata gtgccattgt atcttggctt  1080
ttgtcttag                                                          1089

<210> SEQ ID NO 14
<211> LENGTH: 362
<212> TYPE: PRT
<213> ORGANISM: Solanum tuberosum

<400> SEQUENCE: 14
```

-continued

```
Met Gly Arg Thr Pro Cys Cys Glu Lys Val Gly Ile Lys Arg Gly Arg
1               5                   10                  15

Trp Thr Ala Glu Glu Asp Gln Ile Leu Thr Asn Tyr Ile Leu Ser Asn
            20                  25                  30

Gly Glu Gly Ser Trp Arg Ser Leu Pro Lys Asn Ala Gly Leu Leu Arg
        35                  40                  45

Cys Gly Lys Ser Cys Arg Leu Arg Trp Ile Asn Tyr Leu Arg Ser Asp
    50                  55                  60

Leu Lys Arg Gly Asn Ile Thr Ser Gln Glu Glu Asp Ile Ile Ile Lys
65                  70                  75                  80

Leu His Ala Thr Leu Gly Asn Arg Trp Ser Leu Ile Ala Gly His Leu
                85                  90                  95

Ser Gly Arg Thr Asp Asn Glu Ile Lys Asn Tyr Trp Asn Ser His Leu
            100                 105                 110

Ser Arg Lys Val Asp Ser Leu Arg Ile Pro Ser Asp Glu Lys Leu Pro
        115                 120                 125

Lys Ala Val Val Asp Leu Ala Lys Lys Gly Thr Leu Lys Pro Ile Lys
    130                 135                 140

His Cys Arg Lys Ser Leu Ile Ser Arg Ser Lys Asn Lys Lys Ser Asn
145                 150                 155                 160

Leu Leu Glu Ala Lys Glu Asn Ser Thr Ser Gly Ala Leu Ile Gly Ile
                165                 170                 175

Val Pro Met Pro Ser Thr Pro Asn Ile Glu Lys Glu Ala Leu Cys Cys
            180                 185                 190

Thr Asn Met Pro Ala Cys Asp Ser Ala Met Ala Leu Met Gln Glu Asp
        195                 200                 205

Val Ala Lys Val Glu Val Pro Asn Ser Trp Ala Gly Ser Ile Glu Ala
    210                 215                 220

Lys Gly Ser Leu Ser Ser Asp Ser Gly Met Glu Trp Pro Arg Leu Glu
225                 230                 235                 240

Glu Ile Met Pro Asp Val Ile Asp Asp Gly Asp Met Asn Pro Asn
                245                 250                 255

Phe Ile Leu Asn Gly Leu Glu Glu Glu Val Met Ser Asn Asn Ala Gly
            260                 265                 270

Asn Asn Tyr Ser Cys Ile Asp Glu Gly Asn Lys Asn Val Ser Ser Asp
        275                 280                 285

Asp Glu Lys Ser Lys Leu Leu Met Asp Trp Gln Asp Asp Glu Leu
    290                 295                 300

Val Trp Pro Thr Pro Trp Glu Leu Glu Thr Asp Ile Ile Pro Ser
305                 310                 315                 320

Trp Pro Gln Trp Asp Asp Thr Asp Thr Asp Leu Leu Gln Asn Cys Thr
                325                 330                 335

Asn Asn Asn Tyr Glu Glu Ala Thr Thr Met Glu Ile Asn Asn Gln Asn
            340                 345                 350

His Ser Ala Ile Val Ser Trp Leu Leu Ser
        355                 360
```

<210> SEQ ID NO 15
<211> LENGTH: 1751
<212> TYPE: DNA
<213> ORGANISM: Solanum lycopersicum
<220> FEATURE:
<221> NAME/KEY: misc_feature
<222> LOCATION: 664, 738
<223> OTHER INFORMATION: n is a or g or c or t

<400> SEQUENCE: 15

```
taaagcttcg ttttattaa aaaacgttaa taagaaatta tttgatataa atttaaattg      60
aattgtattt caaatacat atcgaattga atgaaaaatc caaagaaaa aattatatca     120
gattagactt tttttgtgt ttgttttaaa tttatacact aaaaattgta ataaatattt     180
tttccatttt aatttattta tcttatttta acttgacata taatttaaa aatgaagatt     240
ttgtaaaata atttaaatga ataagaaaat attctttta aaactattac aaaaagtag     300
aacagctata tcaaaacaaa attagcagta aatttaaact tatatctcta ataatagca     360
aagacttaaa attaagaatc gatctaaaaa gacatatttc ttatttaata ctatacttaa     420
tgactttatt tatttattat tcatgttaat ctcacttagt tatttgacaa tgttcacaat     480
aatataatct ctgtatttga aatttcattt atattaaaaa taattttaaa cattaaacgt     540
cttctgttat gaacaaaatt tacgcatgta atcacggccg tgttaaatgt ttttatgttt     600
acatacatct gtatcttatt tacaaaaaaa aaaatatat atccttataa tcgcgtcagt     660
tccnacttcc atgtaacgta acgttaattc ttccctccat ttcgtcaaac taactcatca     720
ttatcagtgt cggagtcnaa aaatttatta aaaagtcaaa aatacgaaga atagaaatac     780
gagaaatgca agaggtctta tatataatat cggaaaatct ttctggccag aagaatttag     840
ataaaattta taaatgatat tttacgttac ctttttgaac attttcattt taactttagt     900
atattttgat taaaaatag gaaaagagc tgtttattt aattctttg aatttctgaa     960
cactttttt gaccatttag cactaccctt taaaccatat atatatatat atatgttcga    1020
cctttgctag ctccaccctc gatcaagggt ggagctagct tatggtcagc ggttcatcta    1080
ctatttatta atagttaaat ttactttata tatatactct attttgttct tacttgtcta    1140
ttttgacaaa taaaaaattc ttacctatta tactcttaat tgattactgt gaaaaatata    1200
gaattttgc taaatcttaa atttttaatt tatccacgtc ataattaata tgagtaaaat    1260
gataaactcg ctaaatcaaa taattatttt cttaatagat gtgttaattc aagagtagac    1320
aaataactag ggatagagaa agtatactgt agatgttgaa ctctcttgat taattagtct    1380
gtatatttat tctttcacct aataaaaatc tgtcgatttt cggtagcaaa ggcattgaat    1440
actagcgtgt ggagtgtccc tcttgtgttc cctcattgcc ggttatgtga gggacaccat    1500
tccctgttgc atcaaatttg tgttccaaaa ctaacgtaac ttccgtgcaa aaatcgcacc    1560
caacgtgcgt ctgtttacct ggctgcaagc aagcgcgtat tgacaacgaa tcgtaggcga    1620
gttgttttct ccgtgttatt atttatgaga ttcatgcaca cacaaagaat aactcgccta    1680
catattgtct ttttcctata taacaatcct cacaattcac agcaattcaa atcaatcatt    1740
ctttctaaat c                                                        1751
```

<210> SEQ ID NO 16
<211> LENGTH: 11252
<212> TYPE: DNA
<213> ORGANISM: Artificial sequence
<220> FEATURE:
<223> OTHER INFORMATION: Synthetic sequence: Vector pSIM108

<400> SEQUENCE: 16

```
agctttggca ggatatatac cggtgtaaac gaagtgtgtg tggttgatcc aaaatctatc      60
gtacctttag aaagtgtagc tatgaaggat agtctcactt atgaagaact acctattgag     120
attcttgatc gtcaggtccg aaggttgaga aaaatagaag tcgcttcagt tacggctttg     180
tggaggagta agggtacccg gggatcaatt cccgatctag taacatagat gacaccgcgc     240
```

-continued

```
gcgataattt atcctagttt gcgcgctata ttttgttttc tatcgcgtat taaatgtata      300
attgcgggac tctaatcata aaacccatc tcataaataa cgtcatgcat tacatgttaa      360
ttattacatg cttaacgtaa ttcaacagaa attatatgat aatcatcgca agaccggcaa     420
caggattcaa tcttaagaaa ctttattgcc aaatgtttga acgatcgggg aaattcgagc     480
tctcagaaga actcgtcaag aaggcgatag aaggcgatgc gctgcgaatc gggagcggcg     540
ataccgtaaa gcacgaggaa gcggtcagcc cattcgccgc caagctcttc agcaatatca     600
cgggtagcca acgctatgtc ctgatagcgg tccgccacac ccagccggcc acagtcgatg     660
aatccagaaa agcggccatt ttccaccatg atattcggca agcaggcatc gccatgggtc     720
acgacgagat catcgccgtc gggcatgcgc gccttgagcc tggcgaacag ttcggctggc     780
gcgagcccct gatgctcttc gtccagatca tcctgatcga caagaccggc ttccatccga     840
gtacgtgctc gctcgatgcg atgtttcgct tggtggtcga atgggcaggt agccggatca     900
agcgtatgca gccgccgcat tgcatcagcc atgatggata cttttctcggc aggagcaagg     960 tgagatgaca ggagatcctg ccccggcact tcgcccaata gcagccagtc ccttcccgct    1020
tcagtgacaa cgtcgagcac agctgcgcaa ggaacgcccg tcgtggccag ccacgatagc    1080
cgcgctgcct cgtcctgcag ttcattcagg gcaccggaca ggtcggtctt gacaaaaaga    1140
accgggcgcc cctgcgctga cagccggaac acggcggcat cagagcagcc gattgtctgt    1200
tgtgcccagt catagccgaa tagcctctcc acccaagcgg ccggagaacc tgcgtgcaat    1260
ccatcttgtt caatcatacc cggggatcct ctagagtccc ccgtgttctc tccaaatgaa    1320
atgaacttcc ttatatagag gaagggtctt gcgaaggata gtgggattgt gcgtcatccc    1380
ttacgtcagt ggagatatca catcaatcca cttgctttga agacgtggtt ggaacgtctt    1440 cttttccac gatgctcctc gtgggtgggg gtccatcttt gggaccactg tcggcagagg    1500
catcttcaac gatggccttt cctttatcgc aatgatggca tttgtaggag ccaccttcct    1560
tttccactat cttcacaata aagtgacaga tagctgggca atggaatccg aggaggtttc    1620
cggatattac cctttgttga aaagtctcaa ttgcccttg tcttctgag actgtatctt     1680 tgatattttt ggagtagaca agtgtgtcgt gctccaccat gttgacgaag attttcttct    1740
tgtcattgag tcgtaagaga ctctgtatga actgttcgcc agtctttacg gcgagttctg    1800
ttaggtcctc tatttgaatc tttgactcca tggcctttga ttcagtggga actacctttt    1860
tagagactcc aatctctatt acttgccttg gtttgtgaag caagccttga atcgtccata    1920
ctggaatagt acttctgatc ttgagaaata tatctttctc tgtgttcttg atgcagttag    1980
tcctgaatct tttgactgca tctttaacct tcttgggaag gtatttgatt tcctggagat    2040
tattgctcgg gtagatcgtc ttgatgagac ctgctgcgta agcctctcta accatctgtg    2100
ggttagcatt ctttctgaaa ttggaaaagg ctaatctggg gacctgcagt tatgctataa    2160
atttcatata tttagttggg agtaggcttt ataccgagtt ggactacggt cagtcacttt    2220
caagtcctag aactacgtgc ccctgtaggt tataagtctc ctctgtgggc atcaatttag    2280
tgatcatgcc agtcatgcct ctatacctct gacaggatat atggtactgt aaacactagt    2340
tgtgaataag tcgctgtgta tgtttgtttg agatctctaa gagaaaagag cgtttattag    2400
aataacggat atttaaaagg gcgtgaaaag gtttatccgt tcgtccattt gtatgtggtc    2460
acctatctcg agcatgccaa ccacagggtt cccctcggga tcaaagtact ttgatccaac    2520
ccctccgctg ctatagtgca gtcggcttct gacgttcagt gcagccgtct tctgaaaacg    2580
```

```
acatgtcgca caagtcctaa gttacgcgac aggctgccgc cctgccctt tcctggcgtt    2640
ttcttgtcgc gtgttttagt cgcataaagt agaatacttg cgactagaac cggagacatt    2700
acgccatgaa caagagcgcc gccgctggcc tgctgggcta tgcccgcgtc agcaccgacg    2760
accaggactt gaccaaccaa cggggccgaac tgcacgcggc cggctgcacc aagctgtttt    2820
ccgagaagat caccggcacc aggcgcgacc gcccggagct ggccaggatg cttgaccacc    2880
tacgccctgg cgacgttgtg acagtgacca ggctagaccg cctggcccgc agcacccgcg    2940
acctactgga cattgccgag cgcatccagg aggccggcgc gggcctgcgt agcctggcag    3000
agccgtgggc cgacaccacc acgcggccg gccgcatggt gttgaccgtg ttcgccggca    3060
ttgccgagtt cgagcgttcc ctaatcatcg accgcacccg gagcgggcgc gaggccgcca    3120
aggcccgagg cgtgaagttt ggcccccgcc ctaccctcac cccggcacag atcgcgcacg    3180
cccgcgagct gatcgaccag gaaggccgca ccgtgaaaga ggcggctgca ctgcttggcg    3240
tgcatcgctc gaccctgtac cgcgcacttg agcgcagcga ggaagtgacg cccaccgagg    3300
ccaggcggcg cggtgccttc cgtgaggacg cattgaccga ggccgacgcc ctggcggccg    3360
ccgagaatga acgccaagag gaacaagcat gaaaccgcac caggacggcc aggacgaacc    3420
gttttcatt accgaagaga tcgaggcgga gatgatcgcg gccgggtacg tgttcgagcc    3480
gcccgcgcac gtctcaaccg tgcggctgca tgaaatcctg gccggtttgt ctgatgccaa    3540
gctggcggcc tggccggcca gcttggccgc tgaagaaacc gagcgccgcc gtctaaaaag    3600
gtgatgtgta tttgagtaaa acagcttgcg tcatgcggtc gctgcgtata tgatgcgatg    3660
agtaaataaa caaatacgca aggggaacgc atgaaggtta tcgctgtact taaccagaaa    3720
ggcgggtcag gcaagacgac catcgcaacc catctagccc gcgccctgca actcgccggg    3780
gccgatgttc tgttagtcga ttccgatccc cagggcagtg cccgcgattg gcggccgtg    3840
cgggaagatc aaccgctaac cgttgtcggc atcgaccgcc cgacgattga ccgcgacgtg    3900
aaggccatcg gccggcgcga cttcgtagtg atcgacggag cgcccaggc ggcggacttg    3960
gctgtgtccg cgatcaaggc agccgacttc gtgctgattc cggtgcagcc aagcccttac    4020
gacatatggg ccaccgccga cctggtggag ctggttaagc agcgcattga ggtcacggat    4080
ggaaggctac aagcggcctt tgtcgtgtcg cgggcgatca aaggcacgcg catcggcggt    4140
gaggttgccg aggcgctggc cgggtacgag ctgcccattc ttgagtcccg tatcacgcag    4200
cgcgtgagct acccaggcac tgccgccgcc ggcacaaccg ttcttgaatc agaacccgag    4260
ggcgacgctg cccgcgaggt ccaggcgctg ccgctgaaa ttaaatcaaa actcatttga    4320
gttaatgagg taaagagaaa atgagcaaaa gcacaaacac gctaagtgcc ggccgtccga    4380
gcgcacgcag cagcaaggct gcaacgttgg ccagcctggc agacacgcca gccatgaagc    4440
gggtcaactt tcagttgccg gcggaggatc acaccaagct gaagatgtac gcggtacgcc    4500
aaggcaagac cattaccgag ctgctatctg aatacatcgc gcagctacca gagtaaatga    4560
gcaaatgaat aaatgagtag atgaattta gcggctaaag gaggcggcat ggaaaatcaa    4620
gaacaaccag gcaccgacgc cgtggaatgc cccatgtgtg gaggaacggg cggttggcca    4680
ggcgtaagcg gctgggttgt ctgccggccc tgcaatggca ctggaacccc caagcccgag    4740
gaatcggcgt gacggtcgca aaccatccgg cccggtacaa atcggcgcgg cgctgggtga    4800
tgacctggtg gagaagttga aggccgcgca ggccgcccag cggcaacgca tcgaggcaga    4860
agcacgcccc ggtgaatcgt ggcaagcggc cgctgatcga atccgcaaag aatcccggca    4920
accgccggca gccggtgcgc cgtcgattag gaagccgccc aagggcgacg agcaaccaga    4980
```

-continued

| | |
|---|---|
| ttttttcgtt ccgatgctct atgacgtggg cacccgcgat agtcgcagca tcatggacgt | 5040 |
| ggccgttttc cgtctgtcga agcgtgaccg acgagctggc gaggtgatcc gctacgagct | 5100 |
| tccagacggg cacgtagagg tttccgcagg gccggccggc atggccagtg tgtgggatta | 5160 |
| cgacctggta ctgatggcgg tttcccatct aaccgaatcc atgaaccgat accgggaagg | 5220 |
| gaagggagac aagcccggcc gcgtgttccg tccacacgtt gcggacgtac tcaagttctg | 5280 |
| ccggcgagcc gatggcggaa agcagaaaga cgacctggta gaaacctgca ttcggttaaa | 5340 |
| caccacgcac gttgccatgc agcgtacgaa gaaggccaag aacggccgcc tggtgacggt | 5400 |
| atccgagggt gaagccttga ttagccgcta caagatcgta aagagcgaaa ccgggcggcc | 5460 |
| ggagtacatc gagatcgagc tagctgattg gatgtaccgc gagatcacag aaggcaagaa | 5520 |
| cccgacgtg ctgacggttc accccgatta cttttttgatc gatcccggca tcggccgttt | 5580 |
| tctctaccgc ctggcacgcc gcgccgcagg caaggcagaa gccagatggt tgttcaagac | 5640 |
| gatctacgaa cgcagtggca gcgccggaga gttcaagaag ttctgttttca ccgtgcgcaa | 5700 |
| gctgatcggg tcaaatgacc tgccggagta cgatttgaag gaggaggcgg ggcaggctgg | 5760 |
| cccgatccta gtcatgcgct accgcaacct gatcgagggc gaagcatccg ccggttccta | 5820 |
| atgtacggag cagatgctag ggcaaattgc cctagcaggg gaaaaaggtc gaaaaggtct | 5880 |
| cttttcctgtg gatagcacgt acattgggaa cccaaagccg tacattggga accggaaccc | 5940 |
| gtacattggg aacccaaagc cgtacattgg gaaccggtca cacatgtaag tgactgatat | 6000 |
| aaaagagaaa aaaggcgatt tttccgccta aaactcttta aaacttatta aaactcttaa | 6060 |
| aacccgcctg gcctgtgcat aactgtctgg ccagcgcaca gccgaagagc tgcaaaaagc | 6120 |
| gcctacccctt cggtcgctgc gctccctacg ccccgccgct tcgcgtcggc ctatcgcggc | 6180 |
| cgctggccgc tcaaaaatgg ctggcctacg gccaggcaat ctaccagggc gcggacaagc | 6240 |
| cgcgccgtcg ccactcgacc gccggcgccc acatcaaggc accctgcctc gcgcgttttcg | 6300 |
| gtgatgacgg tgaaaacctc tgacacatgc agctcccgga gacggtcaca gcttgtctgt | 6360 |
| aagcggatgc cggagcagaa caagcccgtc agggcgcgtc agcgggtgtt ggcgggtgtc | 6420 |
| ggggcgcagc catgacccag tcacgtagcg atagcggagt gtatactggc ttaactatgc | 6480 |
| ggcatcagag cagattgtac tgagagtgca ccatatgcgg tgtgaaatac cgcacagatg | 6540 |
| cgtaaggaga aaataccgca tcaggcgctc ttccgcttcc tcgctcactg actcgctgcg | 6600 |
| ctcggtcgtt cggctgcggc gagcggtatc agctcactca aaggcggtaa tacggttatc | 6660 |
| cacagaatca ggggataacg caggaaagaa catgtgagca aaaggccagc aaaaggccag | 6720 |
| gaaccgtaaa aaggccgcgt tgctggcgtt tttccatagg ctccgccccc ctgacgagca | 6780 |
| tcacaaaaat cgacgctcaa gtcagaggtg gcgaaacccg acaggactat aaagatacca | 6840 |
| ggcgtttccc cctggaagct ccctcgtgcg ctctcctgtt ccgaccctgc cgcttaccgg | 6900 |
| atacctgtcc gcctttctcc cttcgggaag cgtggcgctt tctcatagct cacgctgtag | 6960 |
| gtatctcagt tcggtgtagg tcgttcgctc caagctgggc tgtgtgcacg aaccccccgt | 7020 |
| tcagcccgac cgctgcgcct tatccggtaa ctatcgtctt gagtccaacc cggtaagaca | 7080 |
| cgacttatcg ccactggcag cagccactgg taacaggatt agcagagcga ggtatgtagg | 7140 |
| cggtgctaca gagttcttga agtggtggcc taactacggc tacactagaa ggacagtatt | 7200 |
| tggtatctgc gctctgctga agccagttac cttcggaaaa agagttggta gctcttgatc | 7260 |
| cggcaaacaa accaccgctg gtagcggtgg tttttttgtt tgcaagcagc agattacgcg | 7320 |

```
cagaaaaaaa ggatctcaag aagatccttt gatcttttct acggggtctg acgctcagtg   7380
gaacgaaaac tcacgttaag ggattttggt catgcattct aggtactaaa acaattcatc   7440
cagtaaaata taatatttta ttttctccca atcaggcttg atcccagta agtcaaaaaa    7500 tagctcgaca tactgttctt ccccgatatc ctccctgatc gaccggacgc agaaggcaat   7560
gtcataccac ttgtccgccc tgccgcttct cccaagatca ataaagccac ttactttgcc   7620
atctttcaca aagatgttgc tgtctcccag gtcgccgtgg aaaagacaa gttcctcttc    7680 gggcttttcc gtctttaaaa aatcatacag ctcgcgcgga tctttaaatg gagtgtcttc   7740
ttcccagttt tcgcaatcca catcggccag atcgttattc agtaagtaat ccaattcggc   7800
taagcggctg tctaagctat tcgtataggg acaatccgat atgtcgatgg agtgaaagag   7860
cctgatgcac tccgcataca gctcgataat cttttcaggg ctttgttcat cttcatactc   7920
ttccgagcaa aggacgccat cggcctcact catgagcaga ttgctccagc catcatgccg   7980
ttcaaagtgc aggacctttg gaacaggcag ctttccttcc agccatagca tcatgtcctt   8040
ttcccgttcc acatcatagg tggtcccttt ataccggctg tccgtcattt ttaaatatag   8100
gttttcattt tctcccacca gcttatatac cttagcagga cattccctt ccgtatcttt    8160 tacgcagcgg tattttttcga tcagtttttt caattccggt gatattctca ttttagccat   8220
ttattatttc cttcctcttt tctacagtat ttaaagatac cccaagaagc taattataac   8280
aagacgaact ccaattcact gttccttgca ttctaaaacc ttaaatacca gaaacagct    8340 ttttcaaagt tgttttcaaa gttggcgtat aacatagtat cgacggagcc gattttgaaa   8400
ccgcggatcc tgcagccaaa gcacatactt atcgatttaa atttcatcga agagattaat   8460
atcgaataat catatacata ctttaaatac ataacaaatt ttaaatacat atatctggta   8520
tataattaat tttttaaagt catgaagtat gtatcaaata cacatatgga aaaaattaac   8580
tattcataat ttaaaaaata gaaaagatac atctagtgaa attaggtgca tgtatcaaat   8640
acattaggaa aagggcatat atcttgatct agataattaa cgattttgat ttatgtataa   8700
tttccaaatg aaggtttata tctacttcag aaataacaat atacttttat cagaacattc   8760
aacaaagtaa caaccaacta gagtgaaaaa tacacattgt tctctaaaca tacaaaattg   8820
agaaaagaat ctcaaaattt agagaaacaa atctgaattt ctagaagaaa aaaataatta   8880
tgcactttgc tattgctcga aaaataaatg aaagaaatta gacttttta aaagatgtta    8940 gactagatat actcaaaagc tatcaaagga gtaatattct tcttacatta agtattttag   9000
ttacagtcct gtaattaaag acacatttta gattgtatct aaacttaaat gtatctagaa   9060
tacatatatt tgaatgcatc atatacatgt atccgacaca ccaattctca taaaaagcgt   9120
aatatcctaa actaatttat ccttcaagtc aacttaagcc caatatacat tttcatctct   9180
aaaggcccaa gtggcacaaa atgtcaggcc caattacgaa gaaaagggct tgtaaaaccc   9240
taataaagtg gcactggcag agcttacact ctcattccat caacaaagaa accctaaaag   9300
ccgcagcgcc actgatttct ctcctccagg cgaagatgca gatcttcgtg aagaccctaa   9360
cggggaagac gatcacccta gaggttgagt cttccgacac catcgacaat gtcaaagcca   9420
agatccagga caaggaaggg attccccag accagcagcg tttgattttc gccggaaagc    9480
agcttgagga tggtcgtact cttgccgact acaacatcca gaaggagtca actctccatc   9540
tcgtgctccg tctccgtggt ggtggatcca tggacctgca tctaattttc ggtccaactt   9600
gcacaggaaa gacgacgacc gcgatagctc ttgcccagca gacagggctt ccagtccttt   9660
cgcttgatcg ggtccaatgc tgtcctcaac tatcaaccgg aagcggacga ccaacagtgg   9720
```

```
aagaactgaa aggaacgacg cgtctctacc ttgatgatcg gcctctggtg gagggtatca   9780
tcgcagccaa gcaagctcat cataggctga tcgaggaggt gtataatcat gaggccaacg   9840
gcgggcttat tcttgaggga ggatccacct cgttgctcaa ctgcatggcg cgaaacagct   9900
attggagtgc agattttcgt tggcatatta ttcgccacaa gttacccgac caagagacct   9960
tcatgaaagc ggccaaggcc agagttaagc agatgttgca ccccgctgca ggccattcta  10020
ttattcaaga gttggtttat ctttggaatg aacctcggct gaggcccatt ctgaaagaga  10080
tcgatggata tcgatatgcc atgttgtttg ctagccagaa ccagatcacg gcagatatgc  10140
tattgcagct tgacgcaaat atggaaggta agttgattaa tgggatcgct caggagtatt  10200
tcatccatgc gcgccaacag gaacagaaat tcccccaagt taacgcagcc gctttcgacg  10260
gattcgaagg tcatccgttc ggaatgtatt aggttacgcc agccctgcgt cgcacctgtc  10320
ttcatctgga taagatgttc gtaattgttt ttggctttgt cctgttgtgg cagggcggca  10380
aatacttccg acaatccatc gtgtcttcaa actttatgct ggtgaacaag tcttagtttc  10440
cacgaaagta ttatgttaaa ttttaaaatt tcgatgtata atgtggctat aattgtaaaa  10500
ataaactatc gtaagtgtgc gtgttatgta taatttgtct aaatgtttaa tatatatcat  10560
agaacgcaat aaatattaaa tatagcgctt ttatgaaata taaatacatc attacaagtt  10620
gtttatattt cgggtggact agttttaat gtttagcaaa tgtcctatca gttttctctt  10680
tttgtcgaac ggtaatttag agttttttt gctatatgga ttttcgtttt tgatgtatgt  10740
gacaaccctc gggattgttg atttatttca aaactaagag ttttgctta ttgttctcgt  10800 ctattttgga tatcaatctt agtttatat cttttctagt tctctacgtg ttaaatgttc  10860
aacacactag caatttggct gcagcgtatg gattatggaa ctatcaagtc tgtgggatcg  10920
ataaatatgc ttctcaggaa tttgagattt tacagtcttt atgctcattg ggttgagtat  10980
aatatagtaa aaaaatagga attctatccg cggtgatcac aggcagcaac gctctgtcat  11040
cgttacaatc aacatgctac cctccgcgag atcatccgtg tttcaaaccc ggcagcttag  11100
ttgccgttct tccgaatagc atcggtaaca tgagcaaagt ctgccgcctt acaacggctc  11160
tcccgctgac gccgtcccgg actgatgggc tgcctgtatc gagtggtgat tttgtgccga  11220
gctgccggtc ggggagctgt tggctggctg ga                                11252
```

<210> SEQ ID NO 17
<211> LENGTH: 777
<212> TYPE: DNA
<213> ORGANISM: Solanum lycopersicum

<400> SEQUENCE: 17

```
atgagtactc ctatgatgtg tacatttttg ggagtaataa ggaaaggttc atggactgaa    60
gaagaagata ttcttttgag gaaatgtatt gataagtatg gagaaggaaa gtggcatctt   120
gttccaacta gagctggatt aaacagatgc agaaaaagtt gtagactgag gtggctaaat   180
tatctaaggc cacatatcaa gagaggtgac tttgaaccag atgaagtgga tctcatcttg   240
agacttcata agctcttagg caaccgatgg tcacttattg ctggtagact tccaggaagg   300
acagctaacg atgtgaaaaa ctattggaac actaaccttc taaggaagct aaatactagt   360
actaaatttg ctccctcaacc acaagaagga attaatacta gtactattgc tcctcaacca   420
caagaaggaa ttaagtatgg gcaagccaat gccataataa gacctcaacc tcagaaattc   480
acaagctcca tgaagattaa tgtctcttgg tgcaacaaca atagtatggt aaataatgaa   540
```

```
gaagcatcga aagacaacaa cgatatgcaa tggtgggcaa atatactgga aaactgcaat      600
gacattggag aaggagaagc tgaaagaaca ctaccttcat gtaaggaaat taattgcaat      660
gaaattgata aagcaccaag tttgttacat gagggaggca actccatgca acaaggacaa      720
ggtgatggtg gttgggatga atttgctcta gatgatatat ggaatctact taattag        777
```

```
<210> SEQ ID NO 18
<211> LENGTH: 258
<212> TYPE: PRT
<213> ORGANISM: Solanum lycopersicum

<400> SEQUENCE: 18
```

Met Ser Thr Pro Met Met Cys Thr Phe Leu Gly Val Ile Arg Lys Gly
1               5                   10                  15

Ser Trp Thr Glu Glu Asp Ile Leu Leu Arg Lys Cys Ile Asp Lys
            20                  25                  30

Tyr Gly Glu Gly Lys Trp His Leu Val Pro Thr Arg Ala Gly Leu Asn
        35                  40                  45

Arg Cys Arg Lys Ser Cys Arg Leu Arg Trp Leu Asn Tyr Leu Arg Pro
    50                  55                  60

His Ile Lys Arg Gly Asp Phe Glu Pro Asp Glu Val Asp Leu Ile Leu
65                  70                  75                  80

Arg Leu His Lys Leu Leu Gly Asn Arg Trp Ser Leu Ile Ala Gly Arg
                85                  90                  95

Leu Pro Gly Arg Thr Ala Asn Asp Val Lys Asn Tyr Trp Asn Thr Asn
            100                 105                 110

Leu Leu Arg Lys Leu Asn Thr Ser Thr Lys Phe Ala Pro Gln Pro Gln
        115                 120                 125

Glu Gly Ile Asn Thr Ser Thr Ile Ala Pro Gln Pro Gln Glu Gly Ile
    130                 135                 140

Lys Tyr Gly Gln Ala Asn Ala Ile Ile Arg Pro Gln Pro Gln Lys Phe
145                 150                 155                 160

Thr Ser Ser Met Lys Ile Asn Val Ser Trp Cys Asn Asn Asn Ser Met
                165                 170                 175

Val Asn Asn Glu Glu Ala Ser Lys Asp Asn Asn Asp Met Gln Trp Trp
            180                 185                 190

Ala Asn Ile Leu Glu Asn Cys Asn Asp Ile Gly Glu Gly Glu Ala Glu
        195                 200                 205

Arg Thr Leu Pro Ser Cys Lys Glu Ile Asn Cys Asn Glu Ile Asp Lys
    210                 215                 220

Ala Pro Ser Leu Leu His Glu Gly Gly Asn Ser Met Gln Gln Gly Gln
225                 230                 235                 240

Gly Asp Gly Gly Trp Asp Glu Phe Ala Leu Asp Asp Ile Trp Asn Leu
                245                 250                 255

Leu Asn

```
<210> SEQ ID NO 19
<211> LENGTH: 777
<212> TYPE: DNA
<213> ORGANISM: Solanum tuberosum

<400> SEQUENCE: 19
atgagtactc ctatgatgtg tacatttttg ggagtaataa ggaaaggttc atgactgaa       60 gaagaagata ttcttttgag gaaatgtatt gataagtatg gagaaggaaa gtggcatctt      120
gttccaacta gagctggatt aaacagatgc agaaaaagtt gtagactgag gtggctaaat      180
```

```
tatctaaggc cacatatcaa gagaggtgac tttgaaccag atgaagtgga tctcatcttg    240
agacttcata agctcttagg caaccgatgg tcacttattg ctggtagact tccaggaagg    300
acagctaacg atgtgaaaaa ctattggaac actaaccttc taaggaagct aaatactagt    360
actaaatttg ctcctcaacc acaagaagga attaatacta gtactattgc tcctcaacca    420
caagaaggaa ttaagtatgg gcaagccaat gccataataa gacctcaacc tcagaaattc    480
acaagctcca tgaagattaa tgtctcttgg tgcaacaaca atagtatggt aaataatgaa    540
gaagcatcga agacaacaa cgatatgcaa tggtgggcaa atatactgga aaactgcaat    600
gacattggag aaggagaagc tgaaagaaca ctaccttcat gtaaggaaat taattgcaat    660
gaaattgata aagcaccaag tttgttacat gagggaggca actccatgca acaaggacaa    720
ggtgatggtg gttgggatga atttgctcta gatgatatat ggaatctact taattag      777
```

<210> SEQ ID NO 20
<211> LENGTH: 258
<212> TYPE: PRT
<213> ORGANISM: Solanum tuberosum

<400> SEQUENCE: 20

```
Met Ser Thr Pro Met Met Cys Thr Phe Leu Gly Val Ile Arg Lys Gly
1               5                   10                  15

Ser Trp Thr Glu Glu Asp Ile Leu Leu Arg Lys Cys Ile Asp Lys
            20                  25                  30

Tyr Gly Glu Gly Lys Trp His Leu Val Pro Thr Arg Ala Gly Leu Asn
            35                  40                  45

Arg Cys Arg Lys Ser Cys Arg Leu Arg Trp Leu Asn Tyr Leu Arg Pro
    50                  55                  60

His Ile Lys Arg Gly Asp Phe Glu Pro Asp Val Asp Leu Ile Leu
65                  70                  75                  80

Arg Leu His Lys Leu Leu Gly Asn Arg Trp Ser Leu Ile Ala Gly Arg
                85                  90                  95

Leu Pro Gly Arg Thr Ala Asn Asp Val Lys Asn Tyr Trp Asn Thr Asn
            100                 105                 110

Leu Leu Arg Lys Leu Asn Thr Ser Thr Lys Phe Ala Pro Gln Pro Gln
        115                 120                 125

Glu Gly Ile Asn Thr Ser Thr Ile Ala Pro Gln Pro Gln Glu Gly Ile
    130                 135                 140

Lys Tyr Gly Gln Ala Asn Ala Ile Ile Arg Pro Gln Pro Gln Lys Phe
145                 150                 155                 160

Thr Ser Ser Met Lys Ile Asn Val Ser Trp Cys Asn Asn Ser Met
                165                 170                 175

Val Asn Asn Glu Glu Ala Ser Lys Asp Asn Asn Asp Met Gln Trp Trp
            180                 185                 190

Ala Asn Ile Leu Glu Asn Cys Asn Asp Ile Gly Glu Gly Ala Glu
        195                 200                 205

Arg Thr Leu Pro Ser Cys Lys Glu Ile Asn Cys Asn Glu Ile Asp Lys
    210                 215                 220

Ala Pro Ser Leu Leu His Glu Gly Gly Asn Ser Met Gln Gln Gly Gln
225                 230                 235                 240

Gly Asp Gly Gly Trp Asp Glu Phe Ala Leu Asp Asp Ile Trp Asn Leu
                245                 250                 255

Leu Asn
```

<210> SEQ ID NO 21
<211> LENGTH: 339
<212> TYPE: PRT
<213> ORGANISM: Solanum lycopersicum

<400> SEQUENCE: 21

```
Met Gly Arg Thr Pro Cys Cys Glu Lys Val Gly Ile Lys Arg Gly Arg
1               5                   10                  15

Trp Thr Ala Glu Glu Asp Gln Ile Leu Thr Asn Tyr Ile Ile Ser Asn
            20                  25                  30

Gly Glu Gly Ser Trp Arg Ser Leu Pro Lys Asn Ala Gly Leu Leu Arg
        35                  40                  45

Cys Gly Lys Ser Cys Arg Leu Arg Trp Ile Asn Tyr Leu Arg Ser Asp
    50                  55                  60

Leu Lys Arg Gly Asn Ile Thr Ser Gln Glu Asp Ile Ile Ile Lys
65                  70                  75                  80

Leu His Ala Thr Leu Gly Asn Arg Trp Ser Leu Ile Ala Glu His Leu
                85                  90                  95

Ser Gly Arg Thr Asp Asn Glu Ile Lys Asn Tyr Trp Asn Ser His Leu
            100                 105                 110

Ser Arg Lys Val Asp Ser Leu Arg Ile Pro Ser Asp Glu Lys Leu Pro
        115                 120                 125

Lys Ala Val Val Asp Leu Ala Lys Lys Gly Ile Pro Lys Pro Ile Lys
    130                 135                 140

Lys Ser Ser Ile Ser Arg Pro Lys Asn Lys Lys Ser Asn Leu Leu Glu
145                 150                 155                 160

Lys Glu Ala Leu Cys Cys Thr Asn Met Pro Ala Cys Asp Ser Ala Met
                165                 170                 175

Glu Leu Met Gln Glu Asp Leu Ala Lys Ile Glu Val Pro Asn Ser Trp
            180                 185                 190

Gly Arg Thr Tyr Arg Gly Gln Gly Lys Pro Leu Val Gln Ile Val Ile
        195                 200                 205

Ser Asn Gly Pro Arg Leu Glu Glu Ile Met Pro Asp Val Val Ile Asp
    210                 215                 220

Asp Glu Asp Lys Asn Thr Asn Phe Ile Leu Asn Cys Phe Arg Glu Glu
225                 230                 235                 240

Val Thr Ser Asn Asn Val Gly Asn Ser Tyr Ser Cys Ile Glu Glu Gly
                245                 250                 255

Asn Lys Lys Ile Ser Ser Asp Asp Glu Lys Ile Lys Leu Leu Met Asp
            260                 265                 270

Trp Gln Asp Asn Asp Glu Leu Val Trp Pro Thr Leu Pro Trp Glu Leu
        275                 280                 285

Glu Thr Asp Ile Val Pro Ser Trp Pro Gln Trp Asp Asp Thr Asp Thr
    290                 295                 300

Asn Leu Leu Gln Asn Cys Thr Asn Asp Asn Asn Tyr Glu Glu Ala
305                 310                 315                 320

Thr Thr Met Glu Ile Asn Asn Gln Asn His Ser Thr Ile Val Ser Trp
                325                 330                 335

Leu Leu Ser
```

<210> SEQ ID NO 22
<211> LENGTH: 371
<212> TYPE: PRT
<213> ORGANISM: Arabidopsis thaliana

<400> SEQUENCE: 22

```
Met Gly Arg Ala Pro Cys Cys Glu Lys Val Gly Ile Lys Arg Gly Arg
1               5                   10                  15

Trp Thr Ala Glu Glu Asp Gln Ile Leu Ser Asn Tyr Ile Gln Ser Asn
            20                  25                  30

Gly Glu Gly Ser Trp Arg Ser Leu Pro Lys Asn Ala Gly Leu Lys Arg
        35                  40                  45

Cys Gly Lys Ser Cys Arg Leu Arg Trp Ile Asn Tyr Leu Arg Ser Asp
    50                  55                  60

Leu Lys Arg Gly Asn Ile Thr Pro Glu Glu Glu Leu Val Val Lys
65                  70                  75                  80

Leu His Ser Thr Leu Gly Asn Arg Trp Ser Leu Ile Ala Gly His Leu
                85                  90                  95

Pro Gly Arg Thr Asp Asn Glu Ile Lys Asn Tyr Trp Asn Ser His Leu
            100                 105                 110

Ser Arg Lys Leu His Asn Phe Ile Arg Lys Pro Ser Ile Ser Gln Asp
        115                 120                 125

Val Ser Ala Val Ile Met Thr Asn Ala Ser Ser Ala Pro Pro Pro Pro
    130                 135                 140

Gln Ala Lys Arg Arg Leu Gly Arg Thr Ser Arg Ser Ala Met Lys Pro
145                 150                 155                 160

Lys Ile His Arg Thr Lys Thr Arg Lys Thr Lys Thr Ser Ala Pro
                165                 170                 175

Pro Glu Pro Asn Ala Asp Val Ala Gly Ala Asp Lys Glu Ala Leu Met
            180                 185                 190

Val Glu Ser Ser Gly Ala Glu Ala Glu Leu Gly Arg Pro Cys Asp Tyr
        195                 200                 205

Tyr Gly Asp Asp Cys Asn Lys Asn Leu Met Ser Ile Asn Gly Asp Asn
    210                 215                 220

Gly Val Leu Thr Phe Asp Asp Ile Ile Asp Leu Leu Asp Glu
225                 230                 235                 240

Ser Asp Pro Gly His Leu Tyr Thr Asn Thr Thr Cys Gly Gly Asp Gly
                245                 250                 255

Glu Leu His Asn Ile Arg Asp Ser Glu Gly Ala Arg Gly Phe Ser Asp
            260                 265                 270

Thr Trp Asn Gln Gly Asn Leu Asp Cys Leu Leu Gln Ser Cys Pro Ser
        275                 280                 285

Val Glu Ser Phe Leu Asn Tyr Asp His Gln Val Asn Asp Ala Ser Thr
    290                 295                 300

Asp Glu Phe Ile Asp Trp Asp Cys Val Trp Gln Gly Ser Asp Asn
305                 310                 315                 320

Asn Leu Trp His Glu Lys Glu Asn Pro Asp Ser Met Val Ser Trp Leu
                325                 330                 335

Leu Asp Gly Asp Asp Glu Ala Thr Ile Gly Asn Ser Asn Cys Glu Asn
            340                 345                 350

Phe Gly Glu Pro Leu Asp His Asp Asp Glu Ser Ala Leu Val Ala Trp
        355                 360                 365

Leu Leu Ser
    370
```

<210> SEQ ID NO 23
<211> LENGTH: 21
<212> TYPE: DNA
<213> ORGANISM: Artificial sequence

```
<220> FEATURE:
<223> OTHER INFORMATION: Synthetic sequence: Primer

<400> SEQUENCE: 23
cttcagtctt gtccatcggt g                                              21

<210> SEQ ID NO 24
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 24
ctaacggttc tccaaagttc tcac                                           24

<210> SEQ ID NO 25
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 25
cctgttccac cacaaggaca a                                              21

<210> SEQ ID NO 26
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 26
gtgccaagtt taccgatttg c                                              21

<210> SEQ ID NO 27
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 27
cctgttccac cacaaggaca a                                              21

<210> SEQ ID NO 28
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 28
gtgccaagtt taccgatttg c                                              21

<210> SEQ ID NO 29
<211> LENGTH: 20
<212> TYPE: DNA
<213> ORGANISM: Artificial sequence
<220> FEATURE:
<223> OTHER INFORMATION: Synthetic sequence: Oligonucleotide

<400> SEQUENCE: 29
atgggaagaa caccttgttg                                                20
```

```
<210> SEQ ID NO 30
<211> LENGTH: 17
<212> TYPE: DNA
<213> ORGANISM: Artificial sequence
<220> FEATURE:
<223> OTHER INFORMATION: Synthetic sequence: Oligonucleotide

<400> SEQUENCE: 30
gactcgagtc gacatcg                                                    17

<210> SEQ ID NO 31
<211> LENGTH: 20
<212> TYPE: DNA
<213> ORGANISM: Artificial sequence
<220> FEATURE:
<223> OTHER INFORMATION: Synthetic sequence: Oligonucleotide

<400> SEQUENCE: 31
atgggaagaa caccttgttg                                                 20

<210> SEQ ID NO 32
<211> LENGTH: 23
<212> TYPE: DNA
<213> ORGANISM: Artificial sequence
<220> FEATURE:
<223> OTHER INFORMATION: Synthetic sequence: Oligonucleotide

<400> SEQUENCE: 32
ctaagacaaa agccaagata caa                                             23

<210> SEQ ID NO 33
<211> LENGTH: 21
<212> TYPE: DNA
<213> ORGANISM: Artificial sequence
<220> FEATURE:
<223> OTHER INFORMATION: Synthetic sequence: Oligonucleotide

<400> SEQUENCE: 33
gagcaataat gtagggaata g                                               21

<210> SEQ ID NO 34
<211> LENGTH: 23
<212> TYPE: DNA
<213> ORGANISM: Artificial sequence
<220> FEATURE:
<223> OTHER INFORMATION: Synthetic sequence: Oligonucleotide

<400> SEQUENCE: 34
ttgaagtaag ttagtgtcag tat                                             23

<210> SEQ ID NO 35
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 35
aacctatctc gtggctcttt                                                 20

<210> SEQ ID NO 36
<211> LENGTH: 20
<212> TYPE: DNA
<213> ORGANISM: Artificial sequence
<220> FEATURE:
<223> OTHER INFORMATION: Synthetic sequence: Primer
```

<400> SEQUENCE: 36 tcttttttcgc tgaatcttgc					20

<210> SEQ ID NO 37
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 37
caacagaaag gagagatcaa cgag					24

<210> SEQ ID NO 38
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 38
cacagcctga aggtatggaa gc					22

<210> SEQ ID NO 39
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 39
acacacaaag gcttagtcac ga					22

<210> SEQ ID NO 40
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 40
aacagaggca acacacacat ca					22

<210> SEQ ID NO 41
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 41
tggtcaccgt ggaggagtat c					21

<210> SEQ ID NO 42
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 42
gatcgtagct ggaccctctg c					21

<210> SEQ ID NO 43

```
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 43
gtttttcaca aaccaacagt tctgat                                          26

<210> SEQ ID NO 44
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 44
gaagcagtgc tcgattccat aat                                             23

<210> SEQ ID NO 45
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 45
cacaccgatc caggaaccat                                                 20

<210> SEQ ID NO 46
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 46
gcccaccaac ttggtcttgt a                                               21

<210> SEQ ID NO 47
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 47
gcaccacgaa tgcacttgc                                                  19

<210> SEQ ID NO 48
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 48
cgttagtacc gtcggcgaat                                                 20

<210> SEQ ID NO 49
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 49
```
ggcaattgga cgagatcctg                                              20

<210> SEQ ID NO 50
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 50
aaggaacctc tcgggagtga a                                            21

<210> SEQ ID NO 51
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 51
gagcatgaag ttgggccaat                                              20

<210> SEQ ID NO 52
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 52
tggtgggttg gcctcattaa                                              20

<210> SEQ ID NO 53
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 53
tccgaagacg acaacggttt                                              20

<210> SEQ ID NO 54
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 54
tgacaagcca agagccgata a                                            21

<210> SEQ ID NO 55
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 55
gaactagcac ttggcgtcga a                                            21

<210> SEQ ID NO 56
<211> LENGTH: 19
<212> TYPE: DNA

```
<213> ORGANISM: Artificial sequence
<220> FEATURE:
<223> OTHER INFORMATION: Synthetic sequence: Primer

<400> SEQUENCE: 56
ttgcaagcca ggcaccata                                                   19

<210> SEQ ID NO 57
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 57
cgaacgacga aacactgttg a                                                21

<210> SEQ ID NO 58
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 58
tgcagcatag atggcattgg                                                  20

<210> SEQ ID NO 59
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 59
ctggcaatgc aaacagagtg a                                                21

<210> SEQ ID NO 60
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 60
tcgacttgcg gaagagtgag a                                                21

<210> SEQ ID NO 61
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 61
cataaactct accaccgtct cc                                               22

<210> SEQ ID NO 62
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 62
aatccatccc atttctactc aa                                               22
```

<210> SEQ ID NO 63
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 63
aggtgaaaaa ctcaacgatg gt                                              22

<210> SEQ ID NO 64
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 64
acactaggcg tgtggaaatt ag                                              22

<210> SEQ ID NO 65
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 65
gtgttttgtt tgttgaggct ga                                              22

<210> SEQ ID NO 66
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 66
tgatgaagtg gatggatgag ag                                              22

<210> SEQ ID NO 67
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 67
cctgttccac cacaaggaca a                                               21

<210> SEQ ID NO 68
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 68
gtgccaagtt taccgatttg c                                               21

<210> SEQ ID NO 69
<211> LENGTH: 34
<212> TYPE: DNA
<213> ORGANISM: Artificial sequence
<220> FEATURE:

<223> OTHER INFORMATION: Synthetic sequence: Primer

<400> SEQUENCE: 69
ggggtaccca tccctaatga tattgttcac gtaa     34

<210> SEQ ID NO 70
<211> LENGTH: 36
<212> TYPE: DNA
<213> ORGANISM: Artificial sequence
<220> FEATURE:
<223> OTHER INFORMATION: Synthetic sequence: Primer

<400> SEQUENCE: 70
cggggatccg cactgtgaat gattagaata atttct     36

<210> SEQ ID NO 71
<211> LENGTH: 59
<212> TYPE: DNA
<213> ORGANISM: Artificial sequence
<220> FEATURE:
<223> OTHER INFORMATION: Synthetic sequence: Primer

<400> SEQUENCE: 71
ggggacaagt ttgtacaaaa aagcaggcta ccatggctac tggtatccaa aaccaaaag     59

<210> SEQ ID NO 72
<211> LENGTH: 63
<212> TYPE: DNA
<213> ORGANISM: Artificial sequence
<220> FEATURE:
<223> OTHER INFORMATION: Synthetic sequence: Primer

<400> SEQUENCE: 72
ggggaccact ttgtacaaga aagctgggtg gatccaactt caagacttca tagtaacttt     60
ctg     63

<210> SEQ ID NO 73
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 73
cggggatcca tggaaaagaa ttgtcgtgga gt     32

<210> SEQ ID NO 74
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 74
tcccccgggt taatttccaa tttgttgggc ct     32

<210> SEQ ID NO 75
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 75
atgagttaga agtgaagcgg     20

<210> SEQ ID NO 76
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 76
atccccagag ccaaagcagc a                                              21

<210> SEQ ID NO 77
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 77
gtgtccacgg gccatctgac ca                                             22

<210> SEQ ID NO 78
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 78
gctcaggcac accgatggca                                                20

<210> SEQ ID NO 79
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 79
atgggaagaa caccttgttg tg                                             22

<210> SEQ ID NO 80
<211> LENGTH: 22
<212> TYPE: DNA
<213> ORGANISM: Artificial sequence
<220> FEATURE:
<223> OTHER INFORMATION: Synthetic sequence: Oligonucleotide

<400> SEQUENCE: 80
atgagtactc ctatgatgtg ta                                             22

<210> SEQ ID NO 81
<211> LENGTH: 24
<212> TYPE: DNA
<213> ORGANISM: Artificial sequence
<220> FEATURE:
<223> OTHER INFORMATION: Synthetic sequence: Oligonucleotide

<400> SEQUENCE: 81
ctaattaagt agattccata tatc                                           24

<210> SEQ ID NO 82
<211> LENGTH: 345
<212> TYPE: DNA
<213> ORGANISM: Solanum sp.

-continued

<400> SEQUENCE: 82

```
atagtaattt cttttttttga ttttttcgtga tgtccggtac ttatattaga atctgactga    60
attcagattc acgcgactcc ttatctaggg ggactcgaac ccaacacctc tgattaagaa   120
tgaatgagta cttattactc cgacatatgg ttggtattaa agaaatatgt aatggtaatt   180
aatattattg taaacttgta atagggatcc aatcgtcctt tatactttgt atcctaatta   240
caagttgtta ggaatgtaat ttaagaatt attgtaagtg catgcactct atttttatat    300
ttgatgtgaa tttaaggatt gagcataaat atgaaaaatc aaaat                   345
```

<210> SEQ ID NO 83
<211> LENGTH: 663
<212> TYPE: DNA
<213> ORGANISM: Antirrhinum majus
<220> FEATURE:
<221> NAME/KEY: CDS
<222> LOCATION: (1)...(663)

<400> SEQUENCE: 83

| | | |
|---|---|---|
| atg gaa aag aat tgt cgt gga gtg aga aaa ggt act tgg acc aaa gaa<br>Met Glu Lys Asn Cys Arg Gly Val Arg Lys Gly Thr Trp Thr Lys Glu<br>1               5                   10                  15 | | 48 |
| gaa gac act ctc ttg agg caa tgt ata gaa gag tat ggt gaa ggg aaa<br>Glu Asp Thr Leu Leu Arg Gln Cys Ile Glu Glu Tyr Gly Glu Gly Lys<br>            20                  25                  30 | | 96 |
| tgg cat caa gtt cca cac aga gca ggg ttg aac cgg tgt agg aag agt<br>Trp His Gln Val Pro His Arg Ala Gly Leu Asn Arg Cys Arg Lys Ser<br>        35                  40                  45 | | 144 |
| tgc agg ctg agg tgg ttg aat tat ctg agg cca aat atc aaa aga ggt<br>Cys Arg Leu Arg Trp Leu Asn Tyr Leu Arg Pro Asn Ile Lys Arg Gly<br>    50                  55                  60 | | 192 |
| cgg ttt tcg aga gat gaa gtg gac cta att gtg agg ctt cat aag ctg<br>Arg Phe Ser Arg Asp Glu Val Asp Leu Ile Val Arg Leu His Lys Leu<br>65                  70                  75                  80 | | 240 |
| ttg ggt aac aaa tgg tcg ctg att gct ggt aga att cct gga agg aca<br>Leu Gly Asn Lys Trp Ser Leu Ile Ala Gly Arg Ile Pro Gly Arg Thr<br>                85                  90                  95 | | 288 |
| gct aat gac gtg aag aac ttt tgg aat act cat gtg ggg aag aat tta<br>Ala Asn Asp Val Lys Asn Phe Trp Asn Thr His Val Gly Lys Asn Leu<br>            100                 105                 110 | | 336 |
| ggc gag gat gga gaa cga tgc cgg aaa aat gtt atg aac aca aaa acc<br>Gly Glu Asp Gly Glu Arg Cys Arg Lys Asn Val Met Asn Thr Lys Thr<br>        115                 120                 125 | | 384 |
| att aag ctg act aat atc gta aga ccc cga gct cgg acc ttc acc gga<br>Ile Lys Leu Thr Asn Ile Val Arg Pro Arg Ala Arg Thr Phe Thr Gly<br>    130                 135                 140 | | 432 |
| ttg cac gtt act tgg ccg aga gaa gtc gga aaa acc gat gaa ttt tca<br>Leu His Val Thr Trp Pro Arg Glu Val Gly Lys Thr Asp Glu Phe Ser<br>145                 150                 155                 160 | | 480 |
| aat gtc cgg tta aca act gat gag att cca gat tgt gag aag caa acg<br>Asn Val Arg Leu Thr Thr Asp Glu Ile Pro Asp Cys Glu Lys Gln Thr<br>                165                 170                 175 | | 528 |
| caa ttt tac aat gat gtt gcg tcg cca caa gat gaa gtt gaa gac tgc<br>Gln Phe Tyr Asn Asp Val Ala Ser Pro Gln Asp Glu Val Glu Asp Cys<br>            180                 185                 190 | | 576 |
| att cag tgg tgg agt aag ttg cta gaa aca acg gag gat ggg gaa tta<br>Ile Gln Trp Trp Ser Lys Leu Leu Glu Thr Thr Glu Asp Gly Glu Leu<br>        195                 200                 205 | | 624 |
| gga aac cta ttc gag gag gcc caa caa att gga aat taa<br>Gly Asn Leu Phe Glu Glu Ala Gln Gln Ile Gly Asn *<br>    210                 215 | | 663 |

<210> SEQ ID NO 84
<211> LENGTH: 220
<212> TYPE: PRT
<213> ORGANISM: Antirrhinum majus

<400> SEQUENCE: 84

```
Met Glu Lys Asn Cys Arg Gly Val Arg Lys Gly Thr Trp Thr Lys Glu
 1               5                  10                  15

Glu Asp Thr Leu Leu Arg Gln Cys Ile Glu Glu Tyr Gly Glu Gly Lys
             20                  25                  30

Trp His Gln Val Pro His Arg Ala Gly Leu Asn Arg Cys Arg Lys Ser
         35                  40                  45

Cys Arg Leu Arg Trp Leu Asn Tyr Leu Arg Pro Asn Ile Lys Arg Gly
 50                  55                  60

Arg Phe Ser Arg Asp Glu Val Asp Leu Ile Val Arg Leu His Lys Leu
 65                  70                  75                  80

Leu Gly Asn Lys Trp Ser Leu Ile Ala Gly Arg Ile Pro Gly Arg Thr
                 85                  90                  95

Ala Asn Asp Val Lys Asn Phe Trp Asn Thr His Val Gly Lys Asn Leu
            100                 105                 110

Gly Glu Asp Gly Glu Arg Cys Arg Lys Asn Val Met Asn Thr Lys Thr
        115                 120                 125

Ile Lys Leu Thr Asn Ile Val Arg Pro Arg Ala Arg Thr Phe Thr Gly
130                 135                 140

Leu His Val Thr Trp Pro Arg Glu Val Gly Lys Thr Asp Glu Phe Ser
145                 150                 155                 160

Asn Val Arg Leu Thr Thr Asp Glu Ile Pro Asp Cys Glu Lys Gln Thr
                165                 170                 175

Gln Phe Tyr Asn Asp Val Ala Ser Pro Gln Asp Glu Val Glu Asp Cys
            180                 185                 190

Ile Gln Trp Trp Ser Lys Leu Leu Glu Thr Thr Glu Asp Gly Glu Leu
        195                 200                 205

Gly Asn Leu Phe Glu Glu Ala Gln Gln Ile Gly Asn
    210                 215                 220
```

<210> SEQ ID NO 85
<211> LENGTH: 2075
<212> TYPE: DNA
<213> ORGANISM: Antirrhinum majus
<220> FEATURE:
<221> NAME/KEY: CDS
<222> LOCATION: (25)...(1959)

<400> SEQUENCE: 85

```
gtagagagga gagaggattc aaga atg gct act ggt atc caa aac caa aag        51
                        Met Ala Thr Gly Ile Gln Asn Gln Lys
                         1               5 ata gtg cct gag aat ttg agg aag caa ctt gct att gct gtg aga agt       99
Ile Val Pro Glu Asn Leu Arg Lys Gln Leu Ala Ile Ala Val Arg Ser
 10                  15                  20                  25 atc caa tgg agt tat gca att ttc tgg tcc aat tca gtt gca caa cca      147
Ile Gln Trp Ser Tyr Ala Ile Phe Trp Ser Asn Ser Val Ala Gln Pro
                 30                  35                  40 ggg gtc ttg gag tgg ggt gat ggg ttc tac aat gga gat att aaa act      195
Gly Val Leu Glu Trp Gly Asp Gly Phe Tyr Asn Gly Asp Ile Lys Thr
             45                  50                  55
```

-continued

| | | |
|---|---|---|
| cga aaa act gta caa tct gtc gaa ttg aat caa gat cag ctg gga ttg<br>Arg Lys Thr Val Gln Ser Val Glu Leu Asn Gln Asp Gln Leu Gly Leu<br>        60                       65                    70 | 243 |
| cag aga agt gat caa ttg aga gaa ctt tat gag tct ctt tca ctt ggt<br>Gln Arg Ser Asp Gln Leu Arg Glu Leu Tyr Glu Ser Leu Ser Leu Gly<br>75                    80                    85 | 291 |
| gaa acc aac aca caa gct aaa agg cct act gct gca tta tca cca gaa<br>Glu Thr Asn Thr Gln Ala Lys Arg Pro Thr Ala Ala Leu Ser Pro Glu<br>90                    95                    100         105 | 339 |
| gac ctc act gat gct gag tgg ttt ttc ttg gtt tgc atg tct ttc ata<br>Asp Leu Thr Asp Ala Glu Trp Phe Phe Leu Val Cys Met Ser Phe Ile<br>              110                    115                   120 | 387 |
| ttc aat att ggc caa ggg ttg cct gga aga aca tta gca cga aat caa<br>Phe Asn Ile Gly Gln Gly Leu Pro Gly Arg Thr Leu Ala Arg Asn Gln<br>                 125                   130                  135 | 435 |
| gca gta tgg cta tgc aac gct cat cgt gcg gac acc aaa gtt ttc tcg<br>Ala Val Trp Leu Cys Asn Ala His Arg Ala Asp Thr Lys Val Phe Ser<br>              140                    145                   150 | 483 |
| cgt tct ttg ctt gca aag agt gcg tca att cag aca gtt gtg tgc ttt<br>Arg Ser Leu Leu Ala Lys Ser Ala Ser Ile Gln Thr Val Val Cys Phe<br>155                    160                    165 | 531 |
| cca tat tca gaa ggt gta gtt gag ctg gga gca aca gag cta gta ccg<br>Pro Tyr Ser Glu Gly Val Val Glu Leu Gly Ala Thr Glu Leu Val Pro<br>170                    175                    180                   185 | 579 |
| gag gat ttg aat cta atc cag cat ata aaa act tca ttc ttg gac agt<br>Glu Asp Leu Asn Leu Ile Gln His Ile Lys Thr Ser Phe Leu Asp Ser<br>              190                    195                   200 | 627 |
| cct gcc acc gtt ccc aag att ccc aac tat gtc tcc aac agt att aca<br>Pro Ala Thr Val Pro Lys Ile Pro Asn Tyr Val Ser Asn Ser Ile Thr<br>               205                    210                  215 | 675 |
| aac aac aat gac ctc att tgt gaa gcg ctt gaa cat gct aat ata cca<br>Asn Asn Asn Asp Leu Ile Cys Glu Ala Leu Glu His Ala Asn Ile Pro<br>220                    225                    230 | 723 |
| gaa aac gat ctt gat cag ctt ttg aat tgt cca gac acg aac ata tgt<br>Glu Asn Asp Leu Asp Gln Leu Leu Asn Cys Pro Asp Thr Asn Ile Cys<br>        235                    240                    245 | 771 |
| tct cct gat aac agt ttg gat gac ttt gca gac aat tta ctc ata gac<br>Ser Pro Asp Asn Ser Leu Asp Asp Phe Ala Asp Asn Leu Leu Ile Asp<br>250                    255                    260                   265 | 819 |
| gaa tcg aat ttg gca gaa ggc atc aat ggg gag gtt cct caa aca caa<br>Glu Ser Asn Leu Ala Glu Gly Ile Asn Gly Glu Val Pro Gln Thr Gln<br>              270                    275                   280 | 867 |
| agc tgg cct ttc atg gat gat gca atc agc aat tgt ctc aat agt tct<br>Ser Trp Pro Phe Met Asp Asp Ala Ile Ser Asn Cys Leu Asn Ser Ser<br>               285                    290                  295 | 915 |
| atg aat tct agt gac tgt ata tct caa act cat gaa aat cta gag tct<br>Met Asn Ser Ser Asp Cys Ile Ser Gln Thr His Glu Asn Leu Glu Ser<br>300                    305                    310 | 963 |
| ttt gct cca ctt tct gat gga aaa ggg cca ccg gag acg aat aat tgt<br>Phe Ala Pro Leu Ser Asp Gly Lys Gly Pro Pro Glu Thr Asn Asn Cys<br>        315                    320                    325 | 1011 |
| atg cac agc act caa aaa tgc aat cag cag ata gaa aac acg ggt gtc<br>Met His Ser Thr Gln Lys Cys Asn Gln Gln Ile Glu Asn Thr Gly Val<br>330                    335                    340                   345 | 1059 |
| caa ggc gat gag gtc cat tat caa ggg gta ctt tcc aat ctt ttg aag<br>Gln Gly Asp Glu Val His Tyr Gln Gly Val Leu Ser Asn Leu Leu Lys<br>              350                    355                   360 | 1107 |
| agt tcc cat cag ttg gtt ctt ggt ccc tac ttc aga aat ggg aat aga<br>Ser Ser His Gln Leu Val Leu Gly Pro Tyr Phe Arg Asn Gly Asn Arg<br>               365                    370                  375 | 1155 |

```
gaa tca agc ttc gtt agt tgg aac aag gat gga tcg tcg ggt act cat       1203
Glu Ser Ser Phe Val Ser Trp Asn Lys Asp Gly Ser Ser Gly Thr His
        380                 385                 390 gtt ccc cga agc gga acc tca caa aga ttt ctg aag aaa gta ctt ttt       1251
Val Pro Arg Ser Gly Thr Ser Gln Arg Phe Leu Lys Lys Val Leu Phe
    395                 400                 405 gaa gta gct aga atg cat gaa aac tcc agg ctt gat gct ggt aaa caa       1299
Glu Val Ala Arg Met His Glu Asn Ser Arg Leu Asp Ala Gly Lys Gln
410                 415                 420                 425 aag ggc aac agt gac tgc ctt gca aag cca acg gct gat gaa att gat       1347
Lys Gly Asn Ser Asp Cys Leu Ala Lys Pro Thr Ala Asp Glu Ile Asp
                430                 435                 440 aga aac cac gtc ttg tca gag aga aaa cgc aga gag aaa ata aac gaa       1395
Arg Asn His Val Leu Ser Glu Arg Lys Arg Arg Glu Lys Ile Asn Glu
            445                 450                 455 cgg ttt atg att ctt gca tcc cta gtc cca tcc ggt ggc aag gtt gac       1443
Arg Phe Met Ile Leu Ala Ser Leu Val Pro Ser Gly Gly Lys Val Asp
        460                 465                 470 aaa gta tca ata cta gac cat aca ata gat tac ttg aga ggg ctt gag       1491
Lys Val Ser Ile Leu Asp His Thr Ile Asp Tyr Leu Arg Gly Leu Glu
    475                 480                 485 agg aaa gtc gac gag ctg gaa tct aac aaa atg gta aag ggc cgg ggg       1539
Arg Lys Val Asp Glu Leu Glu Ser Asn Lys Met Val Lys Gly Arg Gly
490                 495                 500                 505 cgg gaa tca act aca aaa act aaa cta cac gat gcc att gag agg acc       1587
Arg Glu Ser Thr Thr Lys Thr Lys Leu His Asp Ala Ile Glu Arg Thr
                510                 515                 520 tct gat aat tat ggc gca aca agg aca agt aac gtc aag aaa ccg ttg       1635
Ser Asp Asn Tyr Gly Ala Thr Arg Thr Ser Asn Val Lys Lys Pro Leu
            525                 530                 535 aca aac aag aga aag gct tct gat acg gac aag att gga gcc gta aat       1683
Thr Asn Lys Arg Lys Ala Ser Asp Thr Asp Lys Ile Gly Ala Val Asn
        540                 545                 550 agc aga ggt cga ttg aaa gat tcc tta aca gat aat ata act gtg aac       1731
Ser Arg Gly Arg Leu Lys Asp Ser Leu Thr Asp Asn Ile Thr Val Asn
    555                 560                 565 att aca aac aag gat gtg ttg att gtc gtg act tgt tct tcc aag gag       1779
Ile Thr Asn Lys Asp Val Leu Ile Val Val Thr Cys Ser Ser Lys Glu
570                 575                 580                 585 ttt gta ttg ctt gaa gtg atg gaa gcc gta aga cga cta agt ttg gat       1827
Phe Val Leu Leu Glu Val Met Glu Ala Val Arg Arg Leu Ser Leu Asp
                590                 595                 600 tcc gaa act gtt caa tct tcc aac aga gat gga atg ata tct att acc       1875
Ser Glu Thr Val Gln Ser Ser Asn Arg Asp Gly Met Ile Ser Ile Thr
            605                 610                 615 ata aaa gcc aag tgc aag gga ttg aag gtt gca tca gca agt gtg atc       1923
Ile Lys Ala Lys Cys Lys Gly Leu Lys Val Ala Ser Ala Ser Val Ile
        620                 625                 630 aaa caa gct ctt cag aaa gtt act atg aag tct tga agttgattta            1969
Lys Gln Ala Leu Gln Lys Val Thr Met Lys Ser *
    635                 640 tgctcactat ctatagctag cttttgtgta aaaaatttgt attcataact tttgctaagt     2029
aatttgcagg gcttttccaa gtagttcaga tcaataaaaa aaaaaa                    2075

<210> SEQ ID NO 86
<211> LENGTH: 644
<212> TYPE: PRT
<213> ORGANISM: Antirrhinum majus
```

```
<400> SEQUENCE: 86

Met Ala Thr Gly Ile Gln Asn Gln Lys Ile Val Pro Glu Asn Leu Arg
  1               5                  10                  15

Lys Gln Leu Ala Ile Ala Val Arg Ser Ile Gln Trp Ser Tyr Ala Ile
             20                  25                  30

Phe Trp Ser Asn Ser Val Ala Gln Pro Gly Val Leu Glu Trp Gly Asp
         35                  40                  45

Gly Phe Tyr Asn Gly Asp Ile Lys Thr Arg Lys Thr Val Gln Ser Val
     50                  55                  60

Glu Leu Asn Gln Asp Gln Leu Gly Leu Gln Arg Ser Asp Gln Leu Arg
 65                  70                  75                  80

Glu Leu Tyr Glu Ser Leu Ser Leu Gly Glu Thr Asn Thr Gln Ala Lys
                 85                  90                  95

Arg Pro Thr Ala Ala Leu Ser Pro Glu Asp Leu Thr Asp Ala Glu Trp
            100                 105                 110

Phe Phe Leu Val Cys Met Ser Phe Ile Phe Asn Ile Gly Gln Gly Leu
        115                 120                 125

Pro Gly Arg Thr Leu Ala Arg Asn Gln Ala Val Trp Leu Cys Asn Ala
    130                 135                 140

His Arg Ala Asp Thr Lys Val Phe Ser Arg Ser Leu Leu Ala Lys Ser
145                 150                 155                 160

Ala Ser Ile Gln Thr Val Val Cys Phe Pro Tyr Ser Glu Gly Val Val
                165                 170                 175

Glu Leu Gly Ala Thr Glu Leu Val Pro Glu Asp Leu Asn Leu Ile Gln
            180                 185                 190

His Ile Lys Thr Ser Phe Leu Asp Ser Pro Ala Thr Val Pro Lys Ile
        195                 200                 205

Pro Asn Tyr Val Ser Asn Ser Ile Thr Asn Asn Asp Leu Ile Cys
    210                 215                 220

Glu Ala Leu Glu His Ala Asn Ile Pro Glu Asn Asp Leu Asp Gln Leu
225                 230                 235                 240

Leu Asn Cys Pro Asp Thr Asn Ile Cys Ser Pro Asp Asn Ser Leu Asp
                245                 250                 255

Asp Phe Ala Asp Asn Leu Leu Ile Asp Glu Ser Asn Leu Ala Glu Gly
            260                 265                 270

Ile Asn Gly Glu Val Pro Gln Thr Gln Ser Trp Pro Phe Met Asp Asp
        275                 280                 285

Ala Ile Ser Asn Cys Leu Asn Ser Ser Met Asn Ser Ser Asp Cys Ile
    290                 295                 300

Ser Gln Thr His Glu Asn Leu Glu Ser Phe Ala Pro Leu Ser Asp Gly
305                 310                 315                 320

Lys Gly Pro Pro Glu Thr Asn Asn Cys Met His Ser Thr Gln Lys Cys
                325                 330                 335

Asn Gln Gln Ile Glu Asn Thr Gly Val Gln Gly Asp Glu Val His Tyr
            340                 345                 350

Gln Gly Val Leu Ser Asn Leu Leu Lys Ser Ser His Gln Leu Val Leu
        355                 360                 365

Gly Pro Tyr Phe Arg Asn Gly Asn Arg Glu Ser Phe Val Ser Trp
    370                 375                 380

Asn Lys Asp Gly Ser Ser Gly Thr His Val Pro Arg Ser Gly Thr Ser
385                 390                 395                 400

Gln Arg Phe Leu Lys Lys Val Leu Phe Glu Val Ala Arg Met His Glu
                405                 410                 415
```

-continued

```
Asn Ser Arg Leu Asp Ala Gly Lys Gln Lys Gly Asn Ser Asp Cys Leu
            420                 425                 430

Ala Lys Pro Thr Ala Asp Glu Ile Asp Arg Asn His Val Leu Ser Glu
        435                 440                 445

Arg Lys Arg Arg Glu Lys Ile Asn Glu Arg Phe Met Ile Leu Ala Ser
        450                 455                 460

Leu Val Pro Ser Gly Gly Lys Val Asp Lys Val Ser Ile Leu Asp His
465                 470                 475                 480

Thr Ile Asp Tyr Leu Arg Gly Leu Glu Arg Lys Val Asp Glu Leu Glu
                485                 490                 495

Ser Asn Lys Met Val Lys Gly Arg Gly Arg Glu Ser Thr Thr Lys Thr
            500                 505                 510

Lys Leu His Asp Ala Ile Glu Arg Thr Ser Asp Asn Tyr Gly Ala Thr
            515                 520                 525

Arg Thr Ser Asn Val Lys Lys Pro Leu Thr Asn Lys Arg Lys Ala Ser
    530                 535                 540

Asp Thr Asp Lys Ile Gly Ala Val Asn Ser Arg Gly Arg Leu Lys Asp
545                 550                 555                 560

Ser Leu Thr Asp Asn Ile Thr Val Asn Ile Thr Asn Lys Asp Val Leu
                565                 570                 575

Ile Val Val Thr Cys Ser Ser Lys Glu Phe Val Leu Leu Glu Val Met
                580                 585                 590

Glu Ala Val Arg Arg Leu Ser Leu Asp Ser Glu Thr Val Gln Ser Ser
            595                 600                 605

Asn Arg Asp Gly Met Ile Ser Ile Thr Ile Lys Ala Lys Cys Lys Gly
        610                 615                 620

Leu Lys Val Ala Ser Ala Ser Val Ile Lys Gln Ala Leu Gln Lys Val
625                 630                 635                 640

Thr Met Lys Ser
```

METHODS AND COMPOSITIONS FOR MODIFYING PLANT FLAVONOID COMPOSITION AND DISEASE RESISTANCE

CROSS-REFERENCE TO RELATED APPLICATIONS

This application is a divisional of U.S. application Ser. No. 12/918,248, filed Aug. 18, 2010, which has a 35 U.S.C. 371 (c) date of Dec. 20, 2010, which is the U.S. National Stage of International Patent Application No. PCT/GB2009/000431, filed Feb. 18, 2009, which designates the U.S. and was published by the International Bureau in English on Aug. 27, 2009, and which claims the benefit of U.S. Provisional Patent Application No. 61/029,416, filed Feb. 18, 2008; all of which are hereby incorporated herein in their entirety by reference.

TECHNICAL FIELD

The present invention relates generally to methods and compositions for modifying the levels of transcription factors in plants, and introducing disease resistance genes into plants, to produce products with elevated levels of antioxidant compounds, including but not limited to flavonols and chlorogenic acid, as well as exhibiting enhanced disease resistance, and optionally altered appearance.

BACKGROUND ART

There is a growing literature, some of which is discussed below, which provides insights into the structure and function of certain plant genes, including transcription factors in the MYB superfamily. There is also a growing literature providing insights into the structure and function of certain plant disease resistance genes.

This invention provides novel compositions and methods for producing a novel class of plants, including but not limited to crop plants such as potato, exhibiting enhanced levels of antioxidant compounds, including but not limited to flavonols, chlorogenic acid, anthocyanins, and the like, as well as enhanced disease resistance.

In "The *Arabidopsis* Transcription Factor MYB12 is a Flavonol-Specific Regulator of Phenylpropanoid Biosynthesis", *Plant Phisiology*. Vol. 138, pp. 1083-1096, June 2005, Mehrtens et al., provided evidence that the *Arabidopsis thaliana* R2R3-MYB transcription factor MYB12 acts as a flavonol-specific activator of flavonoid biosynthesis.

In "A Small Family of MYB-Regulatory Genes Controls Floral Pigmentation Intensity and Patterning in the Genus *Antirrhinum*", *The Plant Cell Vol.* 18, pp. 831-851 (2006), Schwinn et al., disclosed that Rosea1, Rosea2, and *Venosa* genes encode MYB-related transcription factors, active in the flowers of *Antirrhinum majus*, differentially control the level of expression of magenta anthocyanin pigmentation in flowers.

In "High-Flavonol Tomatoes Resulting from the Heterologous Expression of the Maize Transcription Factor Genes LC and C1", *The Plant Cell*, Vol. 14, 2509-2526, October 2002, Bovy et al., showed that the flavonoids kaempferol and naringenin, but not anthocyanins nor quercetin, accumulated in the fruit flesh of transgenic tomato expressing the maize LC and C1 transcription factor genes.

In WO2006/062698, researchers at Cornell reported on "Genes That Determine Plant Color and Uses Thereof", including identification and cloning of a potato gene, referred to as pan1 (potato anthocyanin 1), the gene product of which was shown to share extensive homology with the gene product of the Petunia R2R3 MYB domain gene An2, the tomato anti, and pepper A. The expression pattern of the pan1 gene correlated tightly with the production of colored potato progeny, reflecting the role of the pan1 gene in control of coloured anthocyanin production.

WO2007027105 relates to polynucleotides encoding transcription factors and to the encoded transcription factors, that are capable of regulating anthocyanin production in plants. These are mainly derived from apple species.

There remains a need in the art for improved plant and crop species, either transgenic or cisgenic in composition, exhibiting not only enhanced disease resistance, but improved content of beneficial compounds, such as flavonols. This invention provides compositions, methods and plants which significantly advance the art with respect to meeting these needs.

SUMMARY OF THE INVENTION

The present inventors have provided genes encoding MYB12 homologs from *Solanum* species and these form the basis for various aspects of the invention.

They have further demonstrated that a gene encoding MYB12 can be expressed in *Solanum* species and lead to increased levels of flavonols.

They have further demonstrated that other MYB transcription factors (e.g. Rosea1) can be expressed in *Solanum* species and lead to elevated levels of coloured anthocyanins, as well as providing useful markers during transformation, without the necessity for 'foreign' genes. Homologs of these MYB transcription factors from *Solanum* species are already available in the art.

The inventors have further demonstrated that functional homologs of these MYB transcription factors from *solanum* species can induce the production of colored anthocyanins when expressed ectopically in other *solanum* species.

Other aspects of the invention thus include materials (e.g. vectors), methods, and systems utilising these findings in modifying multiple traits in *Solanum* species. Preferably these employ other *Solanum*-derived genes (e.g. pathogen resistance genes), promoters, and other functional sequences (e.g. border sequences for genomic integration).

Various aspects of the invention are set out below, and hereinafter.

In a first aspect, this invention provides genetic constructs useful in the production of plants exhibiting some or all of the following features: elevated levels of colourless antioxidant flavonoids and/or chlorogenic acid; elevated levels of disease resistance; colour-specific identification of successful plants or plant cells transformed with the genetic construct by means of tissue-specific expression of coloured anthocyanins.

While adapted for transgenic plant production, in a preferred aspect of this invention, the genetic construct transfers only genetic material from the same species into the plant, i.e. cis-genic material is used. This aspect of the invention is provided in exemplary embodiments of this aspect of the invention, in which a genetic construct comprising the following elements is utilized to produce a high-flavonoid potato with enhanced disease resistance: (a) an inducible promoter, (for example a promoter responsive to indole acetic acid), driving expression of (b) at least one MYB related gene, expression of which results in enhanced production of coloured anthocyanin secondary metabolites; (c) a plant tissue specific promoter (e.g. a potato tuber specific promoter such as pB33), operatively linked to (d) a AtMYB12 gene or a specific homolog, e.g. the potato homolog, of the AtMYB12 gene and (e) at least one disease resistance gene. In a preferred embodiment of this aspect of the invention, elements (a)-(e) are disposed between left and right P-DNA sequences (which resemble or mimic the T-DNA border sequences of *Agrobacterium tumifaciens*) to facilitate integration of these elements into a target plant genome. Specifics of this aspect of the invention are provided in the detailed disclosure of the preferred embodiments of the invention below.

In a second aspect, this invention provides a plant comprising or transformed with the genetic construct according to the first aspect of this invention, or progeny of the same.

In a third aspect, this invention provides a genetic construct comprising variants on elements (a)-(e) according to the first aspect of the invention. Thus, for example, in one embodiment according to this aspect of the invention, the construct is adapted for optimal expression in a *solanceous* plant other than potato. According to this embodiment of the invention, for example, the promoters and/or encoded genes operatively linked to said promoters are chosen to be tomato-specific. In another embodiment according to this aspect of the invention, the promoters and/or encoded genes operatively linked to said promoters are chosen for optimal operation in a *brassica* plant.

In a fourth aspect, this invention provides a plant comprising or transformed with the genetic construct according to the third aspect of this invention, or progeny of the same.

In a fifth aspect, this invention provides a genetic construct wherein one or more of the elements (a)-(e) is eliminated to achieve a particular desired result. Thus, for example, in one embodiment according to this aspect of the invention, the genetic construct comprises only elements (a) an inducible promoter, (for example indole acetic acid induced), driving expression of (b) at least one MYB related gene, expression of which results in enhanced production of coloured anthocyanin secondary metabolites.

In one exemplary embodiment according to this aspect of the invention, a novel tomato having a flesh with high-anthocyanin content is produced by means of coordinate expression of the Rosea1 (Ros1) and Delila (Del) genes of *Antirrhinum*, contrary to the result expected from Bovy et al. 2005. In another embodiment, according to this aspect of the invention, only elements (c) a plant tissue specific promoter, (e.g. a potato tuber specific promoter such as pB33), operatively linked to (d) the AtMYB12 gene or a specific homolog, e.g. the potato homolog, of the AtMYB12 gene, are included in the construct. In such an embodiment of this aspect of the invention, we anticipate production of high levels of flavonoids in the specific tissue of the plant in which the promoter is activated.

In a sixth aspect, this invention provides a plant comprising or transformed with the genetic construct according to the fifth aspect of this invention, or progeny of the same.

In a seventh aspect, this invention provides a method whereby a coloured anthocyanin product produced in a plant or a plant cell transformed with a genetic construct according to the fifth aspect which according to this invention provides a maker for a successful transformation event for any gene linked to said genetic construct.

Further aspects, embodiments and advantages of the invention disclosed herein will be apparent to one of skill in the art upon reading of the entire disclosure provided herein and the appended claims.

Any sub-titles herein are included for convenience only, and are not to be construed as limiting the disclosure in any way.

BRIEF DESCRIPTION OF THE DRAWINGS

FIG. 9 Amino acid sequence of SlMYB12 (A) (SEQ ID NO: 21) and phylogenetic comparison of SlMYB12 with other members of the R2R3MYB subgroup 7; transcription factors which regulate flavonol or phlobaphene production in plants (B).

FIG. 10.1 Fruit-specific phenotypes of T1 generation tomatoes expressing both Delila (Del) and Rosea1 (Ros1) under the control of the E8 promoter. (A) Map of T-DNA region of the binary vector used for transformation. (B) Phenotypic analysis of wild type (upper row), Del/Ros1C (middle) and Del/Ros1N (lower) tomato fruit harvested at the green (left column), breaker (middle) and red (right) ripening stages. (C) Del/Ros1N tomato plant showing fruit at different stages of ripening. (D) Whole and cross-section of ripe wild type and Del/Ros1N tomato fruit.

FIG. 10.2 Comparative analysis of phenylpropanoid content and composition. HPLC chromatogram of methanol extracts from Del/Ros1N (purple line) and wild type (red line) tomato fruit. HPLC analysis, recorded at 535 nm (A and B) or 280 nm (D and E) of extracts from peel (A and D) or flesh (B and E) of ripe fruit. Peaks marked with numbers represent anthocyanins and peaks marked with letters represent other flavonoids. Classification and identification of methanol soluble compounds was performed based on PDA absorbance and ESI-Q-TOF mass spectrometry (Tables C and F). The purified compounds were analyzed by HPLC and ESI-MS/MS. Spectral characteristics, molecular ions and fragments obtained are tabulated. Identification was confirmed by hydrolysis and HPLC analysis of the respective acyl and sugar moieties (data not shown).

FIG. 10.3 Expression of Del and Ros1 causes the upregulation of genes required for anthocyanin biosynthesis and results in increased PAL activity and higher total antioxidant capacity.

Figure 1:
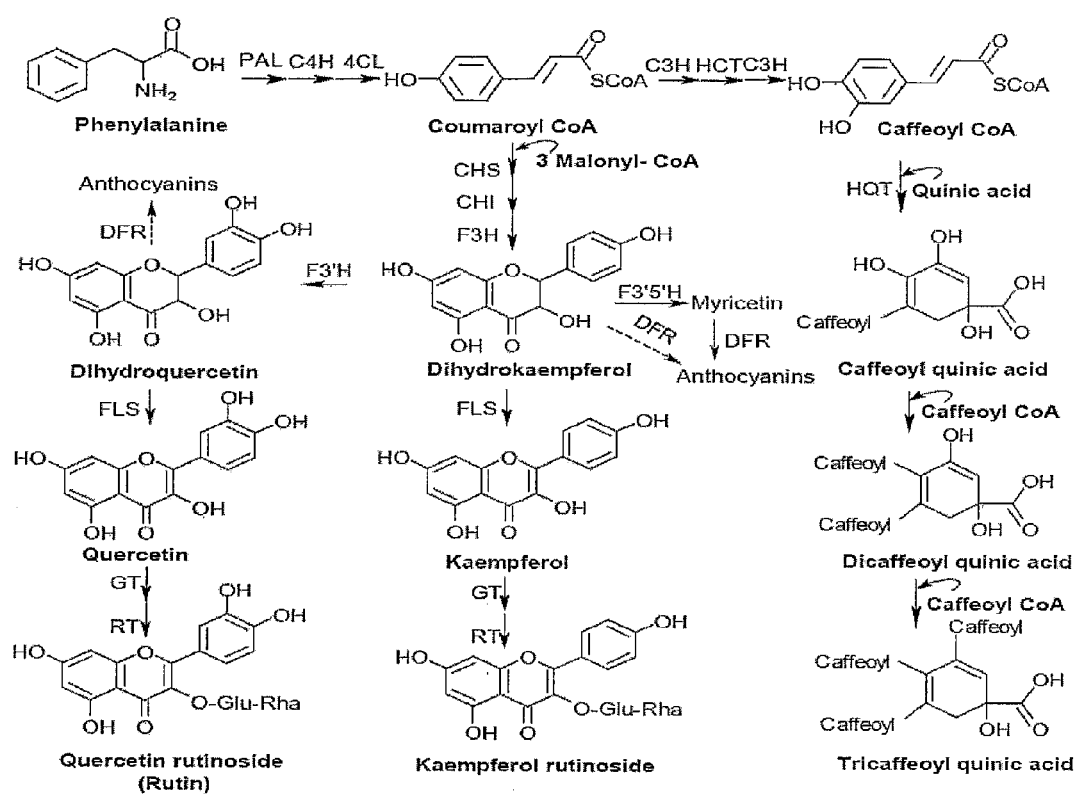
FIG. 1 Scheme of the phenylpropanoid biosynthesis pathway. PAL, phenylalanine ammonia lyase; C4H, cinnamate 4-hydroxylase; 4CL, 4-hydroxycinnamoyl-CoA ligase; CHS, chalcone synthase; CHI, chalcone isomerase; F3H, flavanone-3-hydroxylase; F3'H, flavanone-3'-hydroxylase; F3'5'H, flavanone-3'5'-hydroxylase; FLS, flavonol synthase; DFR, dihydroflavonol reductase; GT, UDPglucose flavonoid-3-glucosyltransferase; RT, UDPrhamnoseflavonoid-3-glucoside-rhamnosyltransferase; C3H, p-coumaroyl ester 3-hydroxylase; HCT, cinnamoyl-CoA shikimate/quinate hydroxycinnamoyl transferase; HQT, hydroxycinnamoyl-CoA quinate hydroxycinnamoyl transferase.

(A) Northern blot showing the differential expression of several anthocyanin biosynthetic genes identified by Suppression Subtractive Hybridization. With the exception of PAL, the transcripts that were upregulated in Del/Ros1N fruit were undetectable in the untransformed control. (B) Schematic representation of the anthocyanin biosynthetic pathway. Enzymes are PAL, phenylalanine ammonia lyase; 4CL, 4-coumarate:coenzyme A ligase; C4H, cinnamic acid 4-hydroxylase; C3H, p-coumaroyl ester 3-hydroxylase; CHS, chalcone synthase; CHI, chalcone isomerase; F3H, flavanone-3-hydroxylase; F3'H, flavanone-3'-hydroxylase; F3'5'H, flavanone-3'5'-hydroxylase; FLS, flavonol synthase; DFR, dihydroflavonol reductase; ANS, anthocyanidin synthase; 3-GT, flavonoid 3-O-glucosyltransferase; RT, flavonoid 3-O-glucoside-rhamnosyltransferase; AAC, anthocyanin acyltransferase; 5-GT, flavonol-5-glucosyltransferase; GST, glutathione S-transferase; PAT, anthocyanin transporter. (C) Analysis of specific PAL activity in ripe tomato fruit from wild type and transgenic lines Del/Ros1C and Del/Ros1N. Histograms represent mean values±se of n=3 separate measurements. Results were confirmed in two independent experiments. (D) Analysis of hydrophilic and lipophilic antioxidant activity in ripe tomato fruit from wild type and transgenic lines Del/Ros1C and Del/Ros1N. Data represent mean values±se and are derived from at least seven tomatoes per plant.

FIG. 10.4 Expression of Del and Ros1 extends the shelf life of tomato fruit. (A) Wild type (upper panel) and transgenic lines Del/Ros1N (lower panel) tomato fruit tagged during the first stages of development and harvested and photographed at the end of the green stage (left). The same fruit, stored at room temperature, were re-photographed after three months (right). (B) Severe symptoms of opportunistic infection normally associated with over-ripe wild type tomato fruit (left) are not observed in Del/Ros1N tomato fruit of the same age grown under identical greenhouse conditions (right). (C) Visual phenotypes of F2 tomato fruit obtained crossing Del/Ros1N 'Micro-Tom' plants with aw (dfr-) 'Ailsa Craig' mutant. (bottom panel) compared to tomato fruit obtained crossing wild type 'Micro-Tom' plants with aw (dfr-) 'Ailsa Craig' mutant (top panel). The picture shows the difference in pigmentation and texture in fruit harvested three weeks after the breaker stage. (D) Comparative analysis of hydrophilic and lipophilic antioxidant activity of aw (dfr-) fruit and of fruit obtained by crossing Del/Ros1N 'Micro-Tom' with aw (dfr-) mutants in the background of 'Ailsa Craig' or 'VF36'.

FIG. 10.5 Fruit-specific purple phenotype induced by the expression of Del and Ros1 can be transferred to other genetic backgrounds. Visual phenotypes of F1 tomato fruit obtained crossing Del/Ros1N 'Micro-Tom' plants with 'Money maker' (A), 'VF36' (B) or 'Ailsa Craig' (C and D) tomato varieties. (E) Wild type 'Ailsa Craig' fruit shown as control. (F) Del/Ros1 N tomato fruit from a 'Micro-Tom' plant of the T2 generation.

FIG. 10.6 Measurement of anthocyanin levels and HPLC analysis of flavonoids in tomatoes from independent transgenic lines compared to wild type controls. (A) Anthocyanins were extracted and measured from fruit of the four independent transgenic lines and two wild type control lines as described in the methods section. (B) Anthocyanin profiles in whole fruit extracts of the four transgenic lines and one wild type control determined by absorption at 512 nm. (C) Flavonoid profiles in the whole fruit extracts of four transgenic lines and one wild type control determined by absorption at 360 nm.

FIG. 10.7 Identification of major anthocyanins. UV chromatograms of absorption at 535 nm wavelength are presented for the purified fraction of peak 3 (A) and peak 6 (B). The UV spectra of the purified anthocyanins are depicted in the embedded graph, respectively. MS/MS fragmentation patterns of the purified anthocyanins are shown for the purified fraction of peak 3 (C) and peak 6 (D). The purified substances were analysed by ESI-MS/MS (Q-TOF Premier, Waters) as described in the Materials and Methods section. Peaks were identified based on mass fragmentation patterns and PDA absorbance: peak 3, delphindin 3-(p-coumaroyl) rutinoside-5-glucoside; peak 6, petunidin 3-(p-coumaroyl) rutinoside-5-glucoside. Identification was confirmed by hydrolysis and HPLC analysis of the respective acyl and sugar moieties (data not shown).

FIG. 10.8 Expression of Del and Ros1 results in a transient increase in chalcone isomerase (CHI) activity in tomato fruit. Analysis of CHI activity in tomato fruit harvested at the end of the mature green stages (late green) or at later stages of ripening (turn/ripe) from wild type (white histograms) and Del/RosiN lines (grey histograms). Data represent mean values±se of n=3 (WT late green), n=6 (VVT turn/ripe), n=5 (Del/Ros1N late green) and n=9 (Del/Ros1N turn/ripe) separate measurements.

FIG. 10.9 High levels of flavonols are accumulated in F2 tomato fruit obtained by crossing Del/Ros1 N MicroTom with aw (dfr-) mutants. Comparative HPLC analysis of tomato fruit methanol extracts recorded at 325 nm showing the accumulation of several new phenolic compounds when the Del/Ros1N transgene had been introduced in the aw (dfr-) background of Ailsa Craig (A) or VF36 (B) varieties. The same analyses for wild type Micro-Tom (C) and for the parental lines aw VF36 (D) and aw Ailsa Craig (E) are shown as controls. Peaks marked with numbers represent the six most abundant compounds identified as flavonols after HPLC-ESI-MS/MS analysis (F).

FIG. 10.10 FT-IR (Fourier Transform Infrared) spectra of wild type (A and B) and Del/Ros1N (C and D) tomato peel. The analysis of the outer (A and C) and inner side (B and D) of the peel is shown. (E) Analysis of lignin in wild type, Del/Ros1C and Del/Ros1N tomato fruit.

FIG. 10.11 Expression of Del and Ros1 delays tomato fruit ripening. (A) Expression analysis of the ripening-regulated genes encoding S-adenosyl-L-methionine synthase1 (SAM1) and phytoene synthase (PSY) in fruit of wild type (WT) and Del/Ros1N (N) tomato lines harvested 5, 12, an 19 days after the breaker stage. (B) Ethylene production in wild type (o) and Del/Ros1N (●) tomato fruit during ripening. Data represent mean values±se of at least ten individual fruit of each genotype. (C) Schematic representation of the ripening process in wild type and transgenic lines Del/Ros1N tomato fruit.

FIG. 10.12 Phenotype of AtMYB12/Del/Ros1 tomatoes. The color of the anthocyanins that accumulate in the fruit due to del/ros1 activity is changed by the presence of flavonols accumulating as a result of AtMYB12 activity. The color is more intense and much bluer than in Del/Ros1 fruit (indigo compared to purple). Tomatoes are clockwise from top left: control (WT), Del/Ros1, AtMYB12/Del/Ros1, AtMYB12.

FIG. 11.1 Photograph showing the utility of Ros1 as an early visual marker of transformation.

FIG. 11.2 Effectiveness of promIAA:pan1:Sopan2 3'UTR for use as a screenable marker for transformation in tobacco. Transformed cells are colored red. A. callus on edge of leaf discs, arrows indicate red foci. B. close up of pigmented cells C. regenerating tobacco shoot.

Figure 12:
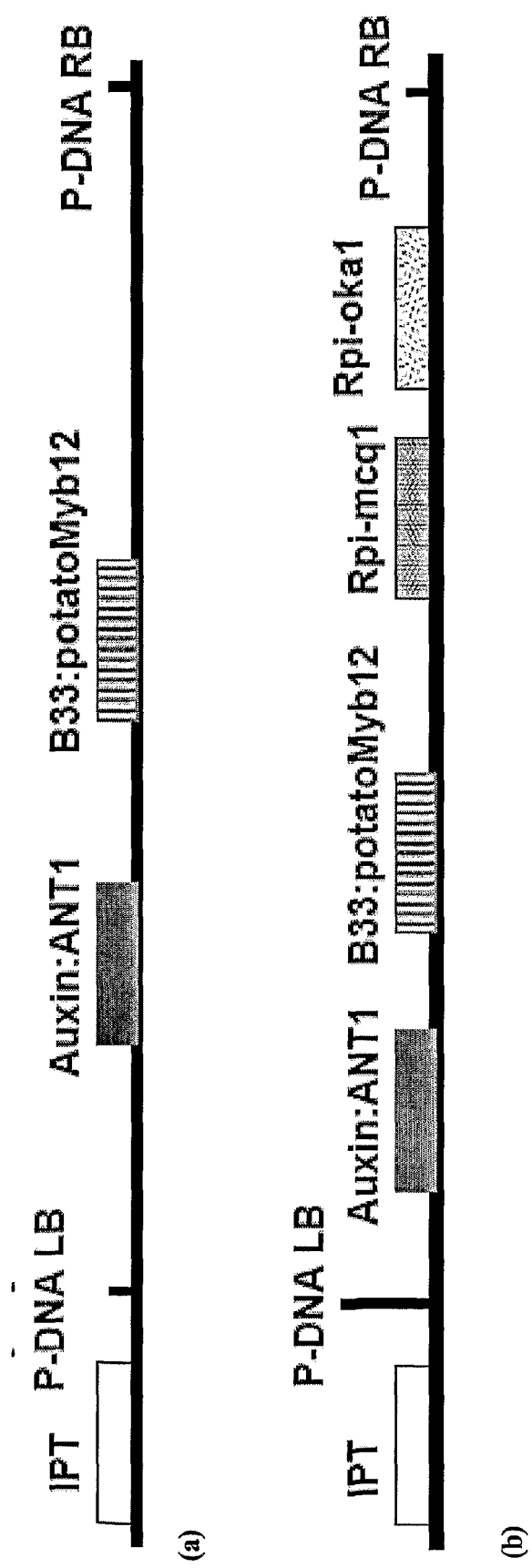

FIG. 12a) Schematic illustration of a vector suitable for engineering flavonol accumulation and other traits into potato tuber by a cis-genic strategy. In this illustration the orthologue of AtMYB12 from tomato (ANT1) is shown, although Pan1 may be preferred.

FIG. 12b) Schematic illustration of a vector suitable for additionally engineering late blight resistance. The constructs show 2 Rpi genes (Rpi-mcq1 and Rpi-oka1) in pIPDNA vectors that confer anthocyanin pigmentation and tuber flavonol elevation

DETAILED DISCLOSURE OF THE PREFERRED EMBODIMENTS OF THE INVENTION

Increase of Flavonols and Other Compounds in Plants

The biosynthetic pathway leading to the synthesis of anthocyanins (the main pigments in flowers), flavones and flavonols (co-pigments) and proanthocyanidins is generally well established (see FIG. 1, plus also e.g. Heller, W. and Forkmann, G. (1988) In: The Flavonoids (Harborne, J. B. ed), Chapman and Hall, London, pp 399-425; Stafford, H. A. (1990) Flavonoid Metabolism, CRC Press Inc., Boca Raton, USA).

In support of aspects of this invention wherein the AtMYB12 gene or a plant specific homologue thereof is included, we demonstrate that overexpression of AtMYB12 in both tomato and tobacco results in increased levels of flavonols (quercetin rutinoside [rutin] and kaempferol diglycoside) and the major hydroxycinnamate of Solanaceous plants, chlorogenic acid. The increases in the levels of flavonols are very high (at least 4 mg per gram fresh weight in tomato fruit) which is an increase of at least 200-fold over wild type and 20 fold more than that achieved by Bovy et al. utilizing LC/C1. The increases in chlorogenic acid in tobacco are smaller, but chlorogenic acid is, in any event, present in large amounts in tobacco. In tomato fruit the increases in chlorogenic acid are more significant (20-fold) and we have evidence that AtMYB12 induces the expression of the key enzyme for chlorogenic acid biosynthesis (HQT) in tomato. Both flavonols and chlorogenic acid are important dietary bioactives, and, without wishing to be bound by mechanism, it is thought that this is mainly through their activities as antioxidants or as inducers of endogenous antioxidant defence mechanisms. There is evidence for flavonols and chorogenic acid in protection against cardio-vascular disease and cancers. We present evidence for the changes in antioxidant capacity of the tomatoes as a result of AtMYB12 expression. We have transformed two tomato varieties with AtMYB12, MicroTom and Money Maker, a commercial variety. We have also shown the stability of inheritance of the high flavonol trait in subsequent generations of tomato. In one example provided herein, we have used the E8 promoter to drive the expression of AtMYB12 in tomato. With this limited expression pattern, AtMYB12 has no noticeable effects on growth or productivity of tomatoes. We did not quantitify such effects in tobacco where the gene was driven by the 35S promoter, reduced growth in AtMYB12 tobacco was not sufficiently noticeable to have been casually observed.

In summary, as exemplified above, and without limitation, the invention provides in various aspects:

Use of AtMYB12 or a variant thereof to increase the levels of flavonols or flavonol derivatives and/or chlorogenic acid (CGA) in a plant;

Methods, materials and processes for achieving the same, optionally in conjunction with the modificiation of other traits described herein;

Isogenic or transgenic plants obtained by said processes, particularly those also isogenic or transgenic for other traits described below;

Some of these aspects and embodiments are described in more detail below.

The plant will be one other than *Arabidopsis*—preferably it will be of the family Solanaceae, more preferably genus *Solanum*. Optionally the plant may be *S. tuberosum* or *S. lycopersicum*, and AtMYB12 homologs from these plants are described in more detail below.

For example the invention provides a method for increasing the levels of flavonols or flavonol derivatives and/or chlorogenic acid (CGA) in such plants, through flavonoid biosynthesis, such as to enhance the nutritional or nutraceutical properties thereof, by causing or allowing expression of a heterologous MYB12 nucleic acid sequence as discussed above within the cells of the plants. The step may be preceded by the earlier step of introduction of the nucleic acid into a cell of the plant or an ancestor thereof i.e. transforming at least one plant cell with a recombinant DNA construct comprising a nucleic acid sequence encoding the MYB12 transcription factor and regenerating a transgenic plant from the transformed cell, wherein the expression of the MYB12 gene encoding the MYB12 transcription factor is increased relative to a nontransformed plant and whereby the increased expression of the MYB12 transcription factor for increases the levels of flavonols or flavonol derivatives and/or chlorogenic acid (CGA) in the plant.

As demonstrated herein, the method may be used to increase flavonols preferentially to anthocyanins. Levels of rutin and kaempferol rutinoside may be particularly increased—indeed results described herein demonstrate unexpectedly, and unprecedentedly, high levels of flavonol accumulation in tomatoes (up to about 10% of the dry weight in whole tomato fruit). In preferred embodiments of the invention at least 10, 20, 30, 40, 50, 60, 70-fold increases of total flavonols, and greater than 5, 10 or and 20-fold higher levels of CQAs such as CGA may be achieved.

Such plants producing elevated levels of flavonols reduce the growth of adipocytes and reduce the tendency for obesity on a high fat diet, and methods of treatment of the human body (to reduce the tendency for obesity using the MYB12-based methods and products described herein) forms one aspect of the present invention.

Those skilled in the art will appreciate that nucleic acid can be transformed into plant cells, which can be regenerated, using any suitable technology. In a typical transformation strategy useful with potato *Agrobacterium tumefaciens* culture(s) with the appropriate antibiotic selection regime are set up and grown for 24 hours with shaking at 28° C. Stem internode sections (without nodes) are harvested from 4-6 week old potato cv. Desiree plants grown in aseptic culture on MS medium (2% sucrose). The internodes are sliced into 1 cm sections and placed into 20 ml of LSR broth. 100 ul of overnight *Agrobacterium tumefaciens* culture is added to stem sections and incubated for 20 minutes at 40 rpm in the dark at 24° C. The stem sections are removed from the *Agrobacterium tumefaciens* suspension, blotted dry and incubated under low light conditions at 18 C for 3 days on LSR1 solid media (around 15-20 explants are plated per dish). Co-cultivated stem sections are then transferred to LSR1 medium with selection antibiotics at around 10 explants per dish. Stem explants are subcultured onto fresh LSR1 media every 7-10 days for around 3-6 weeks or until the appearance of the first small calli. Once the calli have sufficiently developed the stem sections are transferred onto LSR2 media with selection antibiotics. Stem sections are subcultured every 7-10 days until shoots start to develop. Shoots appear within 2 months from the start of transformation. Shoots are removed with a sharp scalpel and planted into MS2R solid media with selection antibiotics. Transgenic plants harbouring appropriate antibiotic or herbicide resistance genes start to root normally within 2 weeks and are weaned out of tissue culture into sterile peat blocks before being transplanted to the glasshouse.

Transformation of tomato is demonstrated in more detail in the Examples hereinafter.

Other strategies, particularly those applicable to the genus *Solanum*, are well known to those skilled in the art (see e.g. Mansure and Magioli, Acta Botanica Brasilica, 2005 (Vol. 19) (No. 1) 139-148). The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

To engineer flavonol accumulation in potato tuber by a cis-genic strategy, the appropriate genes and promoters from potato itself are isolated. For example a construct using the tuber specific B33 patatin gene promoter to drive expression of the potato cDNA encoding the homolog\ortholog of AtMYB12 is utilized to confer on potato plants high-level flavonol production in tubers. Preferred "cis-genic" vectors are described in detail hereinbelow.

AtMYB12 Homologs from Tomato and Potato

As described in the Examples below, in furtherance of the present invention, the present inventors have isolated a *Solanum* homolog of AtMYB12 from tomato termed herein SlMYB12 (*Solanum lycopersicum* MYB12; see SEQUENCE ANNEX I—unpublished GenBank accession EU419748; SEQ ID NO: 12 and 11). The inventors provided this full length cDNA sequence by extension of a cDNA EST.

Despite significant technical difficulties, the inventors have further isolated the sequence encoding the *Solanum* homolog of AtMYB12 from potato termed herein StMYB12 (*Solanum tuberosum* MYB12; see SEQUENCE ANNEX II describing the amino acid and nucleotide sequences respectively; SEQ ID NO: 14 and 13, respectively).

SEQUENCE ANNEX VIII shows a comparison of the encoded polypeptides with that encoded by the AtMYB12 sequence.

Using LALIGN available on the world wide web at ch.embnet.org/software/LALIGN_form.html) with default settings the sequences showed the following levels of identity with AtMyb12: 39.7% (SlMyb12) and 40.2% (StMyb12).

Isolated or recombinant nucleic acids including either of these AtMYB12 gene homologs from tomato and potato form aspects of the present invention.

For example the invention provides an isolated nucleic acid molecule which nucleic acid comprises a *Solanum*-derived MYB12 nucleotide sequence encoding a transcriptional regulator of a biosynthetic gene encoding a polypeptide with flavonoid-biosynthetic or transport activity.

A nucleic acid of the present invention may include one of the nucleotide sequences described above in SEQUENCE ANNEX I or II (SEQ ID NO: 11 and 13, respectively).

Nucleic acid molecules according to the present invention may be provided, isolated and/or purified from their natural environment, in substantially pure or homogeneous form, or free, or substantially free, of other nucleic acids of the species of origin. Where used herein, the term "isolated" encompasses all of these possibilities.

The nucleic acid molecules may be wholly or partially synthetic. In particular they may be recombinant in that nucleic acid sequences which are not found together in nature (do not run contiguously) have been ligated or otherwise combined artificially.

Preferred nucleic acids consist essentially of the gene in question, optionally in an expression vector as described in more detail below.

Nucleic acid according to the present invention may include cDNA, RNA, genomic DNA and modified nucleic acids or nucleic acid analogs. Where a DNA sequence is specified, e.g. with reference to a figure, unless context requires otherwise the RNA equivalent, with U substituted for T where it occurs, is encompassed. Where a nucleic acid of the invention is referred to herein, the complement of that nucleic acid will also be embraced by the invention. The 'complement' of a given nucleic acid (sequence) is the same length as that nucleic acid (sequence), but is 100% complementary thereto.

Where genomic nucleic acid sequences of the invention are disclosed, nucleic acids comprising any one or more (e.g. 2) introns or exons from any of those sequences are also embraced.

A nucleic acid of the present invention may encode one of the amino acid sequences described above in SEQUENCE ANNEX I or II (SEQ ID NO: 12 and 14, respectively) e.g. be degeneratively equivalent to the corresponding nucleotide sequences.

In a further aspect of the present invention there are disclosed nucleic acids which are variants of the sequences of this aspect.

A variant nucleic acid molecule shares homology with, or is identical to, all or part of the coding sequence discussed above. Variants encode MYB12 transcriptional regulators capable of up-regulating expression of genes involved in flavonoid biosynthesis in a plant into which they are introducted, and in particular genes involved in flavonol synthesis e.g. PAL, CHS, and GT genes.

"Transcriptional regulator" is a term well understood by those skilled in the art to mean a polypeptide or protein that binds to regulatory regions of a gene and controls (increases or reduces) gene expression, here, in respect of flavonoid biosynthetic flux.

Variants of the present invention can be artificial nucleic acids (i.e. containing sequences which have not originated naturally) which can be prepared by the skilled person in the light of the present disclosure. Alternatively they may be novel, naturally occurring, nucleic acids from *Solanum* species, which may be isolatable using the sequences of the present invention.

Thus a variant may be a distinctive part or fragment (however produced) corresponding to a portion of the sequence provided. The fragments may encode particular functional parts of the polypeptide.

Also included are nucleic acids which have been extended at the 3' or 5' terminus.

Sequence variants which occur naturally may include alleles or other *Solanum* homologues.

Artificial variants (derivatives) may be prepared by those skilled in the art, for instance by site-directed or random mutagenesis, or by direct synthesis. Preferably the variant nucleic acid is generated either directly or indirectly (e.g. via one or amplification or replication steps) from an original nucleic acid having all or part of the sequences of the first aspect.

The term "variant" nucleic acid as used herein encompasses all of these possibilities. When used in the context of polypeptides or proteins it indicates the encoded expression product of the variant nucleic acid.

Some of the aspects of the present invention relating to variants will now be discussed in more detail.

Homology (i.e. similarity or identity) may be as defined above using the LALIGN. Homology may be at the nucleotide sequence and/or encoded amino acid sequence level. Preferably, the nucleic acid and/or amino acid sequence shares at least about 50%, or 60%, or 70%, or 80% homology, most preferably at least about 90%, 95%, 96%, 97%, 98% or 99% homology with a sequence of SEQUENCE ANNEX I or II (SEQ ID NO: 11-14).

It further provides an isolated protein having an amino acid sequence which is at least 50, 60, 70, 80, 90 or 100% identical to the amino acid sequence provided herein in SEQUENCE ANNEX I or II (SEQ ID NO: 12 and 14, respectively), or encoded by a nucleic acid described therein.

In a further aspect of this part of the invention there is disclosed a method of producing a derivative nucleic acid comprising the step of modifying the coding sequence of a nucleic acid of the present invention described above.

Changes to a sequence, to produce a derivative, may be by one or more of addition, insertion, deletion or substitution of one or more nucleotides in the nucleic acid, leading to the addition, insertion, deletion or substitution of one or more amino acids in the encoded polypeptide. Changes may be desirable for a number of reasons, including introducing or removing the following features: restriction endonuclease sequences; codon usage; other sites which are required for post translation modification; cleavage sites in the encoded polypeptide; motifs in the encoded polypeptide (e.g. binding sites). Leader or other targeting sequences may be added or removed from the expressed protein to determine its location following expression. All of these may assist in efficiently cloning and expressing an active polypeptide in recombinant form (as described below).

Other desirable mutations may be generated by random or site directed mutagenesis in order to alter the activity (e.g. specificity) or stability of the encoded polypeptide. Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation.

Also included are variants having non-conservative substitutions. As is well known to those skilled in the art, substitutions to regions of a peptide which are not critical in determining its conformation may not greatly affect its activity because they do not greatly alter the peptide's three dimensional structure.

In a further aspect of the present invention there is provided a method of identifying and/or cloning a nucleic acid variant from a plant which method employs a distinctive MYB12 sequence of SEQUENCE ANNEX I or II (SEQ ID NO: 11 and 13, respectively).

An oligonucleotide for use in probing or amplification reactions comprise or consist of about 30 or fewer nucleotides in length (e.g. 18, 21 or 24). Generally specific primers are upwards of 14 nucleotides in length. For optimum specificity and cost effectiveness, primers of 16-24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

Preferably the probe/primer is distinctive in the sense that it is present in the *Solanum* MYB12 sequences disclosed herein, but not in AtMYB12.

Suitable conditions include, e.g. for detection of sequences that are about 80-90% identical, hybridization overnight at 42° C. in 0.25M Na$_2$HPO$_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M Na$_2$HPO$_4$, pH 7.2, 6.5% SDS, 10% dextran sulfate and a final wash at 60° C. in 0.1×SSC, 0.1% SDS.

It is well known in the art to increase stringency of hybridisation gradually until only a few positive clones remain. Suitable conditions would be achieved when a large number of hybridising fragments were obtained while the background hybridisation was low.

Thus one embodiment of this aspect of the present invention is nucleic acid including or consisting essentially of a sequence of nucleotides complementary to a nucleotide sequence hybridisable with any encoding sequence provided herein. Another way of looking at this would be for nucleic acid according to this aspect to be hybridisable with a nucleotide sequence complementary to any encoding sequence provided herein.

The methods described above may also be used to determine the presence of one of the nucleotide sequences of the present invention within the genetic context of an individual plant. This may be useful in plant breeding programmes e.g. to directly select plants containing alleles which are responsible for desirable traits in that plant species, either in parent plants or in progeny (e.g. hybrids, F1, F2 etc.), or for assessing expression of genes. For example, the present inventors used the sequences described herein to monitor expression of SIMYB12 in tomato fruit using quantative RT-PCR.

Thus it will be appreciated that, unless context demands otherwise, where the present invention refers to AtMYB12 (for example in discussion of an Example, or aspect or embodiment) this is to be understood as relating likewise to AtMYB12 homolgoues or orthologs e.g. obtainable from potato or other *Solanum* species, such as the sequences above, or variants thereof.

In one aspect of the present invention, the MYB12-encoding nucleic acid described above is in the form of a recombinant and preferably replicable vector. "Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic hosts either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eucaryotic (e.g. higher plant, yeast or fungal cells).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

By "promoter" is meant a sequence of nucleotides from which transcription may be initiated of DNA operably linked downstream (i.e. in the 3' direction on the sense strand of double-stranded DNA). "Operably linked" means joined as part of the same nucleic acid molecule, suitably positioned and oriented for transcription to be initiated from the promoter. DNA operably linked to a promoter is "under transcriptional initiation regulation" of the promoter.

Thus this aspect of the invention provides a gene construct, preferably a replicable vector, comprising a promoter operatively linked to a nucleotide sequence provided by the present invention, such as one shown in SEQUENCE ANNEX I or II (SEQ ID NO: 11 and 13, respectively) or a variant thereof.

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press (or later editions of this work).

Many known techniques and protocols for manipulation of nucleic acid, for example in preparation of nucleic acid constructs, mutagenesis (see above discussion in respect of variants), sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

In one embodiment of this aspect of the present invention, there is provided a gene construct, preferably a replicable vector, comprising an inducible promoter operatively linked to a nucleotide sequence provided by the present invention. The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Of particular interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148).

Suitable promoters which operate in plants include the Cauliflower Mosaic Virus 35S (CaMV 35S). Other examples are disclosed at pg. 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177-180.

It may be desirable to use a strong constitutive promoter. If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate).

The present invention also provides methods comprising introduction of such a construct into a host cell, particularly a plant cell.

In a further aspect of the invention, there is disclosed a host cell containing a heterologous construct according to the present invention, especially a plant or a microbial cell. The term "heterologous" is used broadly in this aspect to indicate that the gene/sequence of nucleotides in question (e.g. the MYB12 encoding gene in this aspect) have been introduced into said cells of the plant or an ancestor thereof, using genetic engineering, i.e. by human intervention. A heterologous gene may replace an endogenous equivalent gene, i.e. one which normally performs the same or a similar function, or the inserted sequence may be additional to the endogenous gene or other sequence.

Nucleic acid heterologous to a plant cell may be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant. A further possibility is for a nucleic acid sequence to be placed within a cell in which it or a homolog is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

The host cell (e.g. plant cell) is preferably transformed by the construct, which is to say that the construct becomes established within the cell, altering one or more of the cell's characteristics and hence phenotype e.g. with respect flavonol synthesis.

Thus a further aspect of the present invention provides a method of transforming a plant cell involving introduction of a construct as described above into a plant cell and causing or allowing recombination between the vector and the plant cell genome to introduce a nucleic acid according to the present invention into the genome.

The invention further encompasses a host cell transformed with nucleic acid or a vector according to the present invention especially a plant or a microbial cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

Plants which include a plant cell according to the inventions described above are also provided.

In addition to the regenerated plant, the present invention embraces all of the following: a clone of such a plant, selfed or hybrid progeny and descendants (e.g. F1 and F2 descendants) and any part of any of these. The invention also provides parts of such plants e.g. any part which may be used in reproduction or propagation, sexual or asexual, including cuttings, seed and so on, or which may be a commodity per se e.g. tuber.

The present invention also encompasses the expression product of the nucleic acid sequences disclosed above, plus also methods of making the expression product by expression from encoding nucleic acid therefore under suitable conditions, which may be in suitable host cells. Such proteins of the invention may be used to raise antibodies employing techniques which are standard in the art. Specific binding members such as antibodies and polypeptides including antigen binding domains of antibodies that bind and are preferably specific for polypeptides of the invention, and represent further aspects of the present invention, as do their use and methods which employ them.

Decreased Chlorogenic Acid Production by Gene Silencing or Suppression

In specific enhancements to aspects of this invention, we also disclose further increases in flavonol levels by inhibiting chlorogenic acid production in conjunction with AtMYB12 overexpression.

This is achieved, for example, by gene knockout or silencing of chlorogenic acid production, for example by use of RNAi specific for the HQT gene which catalyses production of caffeoyl quinic acid (see FIG. 1). The sequence of the HQT gene is described by Niggeweg, R., Michael, A. J., & Martin, C. (2004) Nat Biotechnol 22, 746-754 (see also WO 2004/001028).

In summary, as exemplified above, and without limitation, the invention provides in various aspects:

A method of inhibiting chlorogenic acid production in a plant in which AtMYB12 or a variant thereof is used to increase the levels of flavonols e.g. in a plant of the family Solanaceae, more preferably genus *Solanum*. Optionally the plant may be *S. tuberosum* or *S. lycopersicum*. This may be achieved by use of a nucleic acid sequence capable of silencing or downregulating a gene which encodes an enzyme present in the chlorogenic acid production pathway e.g. the HQT gene.

Methods, materials and processes for achieving the same, optionally in conjunction with the modificiation of yet other traits described herein.

Isogenic or transgenic plants obtained by said processes, particularly those also isogenic or transgenic for other traits described herein.

The nucleic acid sequence capable of silencing or down-regulating a gene which encodes an enzyme present in the chlorogenic acid production pathway e.g. the HQT gene, may be as follows.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724-726; Zhang et al, (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell, (1994) *PNAS USA* 91, 3490-3496.

An alternative to anti-sense is to use a copy of all or part of the target gene inserted in sense, that is the same, orientation as the target gene, to achieve reduction in expression of the target gene by co-suppression. See, for example, van der Krol at al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of the gene silencing or co-suppression technology may be found in WO95/34668 (Biosource); Angell & Baulcombe (1997) The EMBO Journal 16, 12:3675-3684; and Voinnet & Baulcombe (1997) Nature 389: pg 553.

Anti-sense or sense regulation may itself be regulated by employing an inducible promoter in an appropriate construct.

Double stranded RNA (dsRNA) has been found to be even more effective in gene silencing than both sense or antisense strands alone (Fire A. et al Nature, Vol 391, (1998)). dsRNA mediated silencing is gene specific and is often termed RNA interference (RNAi) (See also Fire (1999) *Trends Genet.* 15: 358-363, Sharp (2001) *Genes Dev.* 15: 485-490, Hammond et al. (2001) *Nature Rev. Genes* 2: 1110-1119 and Tuschl (2001) *Chem. Biochem.* 2: 239-245).

RNA interference is a two step process. First, dsRNA is cleaved within the cell to yield short interfering RNAs (siRNAs) of about 21-23nt length with 5' terminal phosphate and 3' short overhangs (~2nt) The siRNAs target the corresponding mRNA sequence specifically for destruction (Zamore P. D. Nature Structural Biology, 8, 9, 746-750, (2001)

Thus one embodiment of the invention utilises double stranded RNA comprising a sequence from part of the HQT gene, which may for example be a "long" double stranded RNA (which will be processed to siRNA, e.g., as described above). These RNA products may be synthesised in vitro, e.g., by conventional chemical synthesis methods.

RNAi may be also be efficiently induced using chemically synthesized siRNA duplexes of the same structure with 3'-overhang ends (Zamore P D et al Cell, 101, 25-33, (2000)). Synthetic siRNA duplexes have been shown to specifically suppress expression of endogenous and heterologous genes in a wide range of mammalian cell lines (Elbashir S M. et al., Nature, 411, 494-498, (2001)).

In one embodiment, the vector may comprise a nucleic acid sequence according to the invention in both the sense and antisense orientation, such that when expressed as RNA the sense and antisense sections will associate to form a double stranded RNA. This may for example be a long double stranded RNA (e.g., more than 23nts) which may be processed in the cell to produce siRNAs (see for example Myers (2003) *Nature Biotechnology* 21:324-328).

Alternatively, the double stranded RNA may directly encode the sequences which form the siRNA duplex, as described above. In another embodiment, the sense and antisense sequences are provided on different vectors.

Another methodology known in the art for down-regulation of target sequences is the use of "microRNA" (miRNA) e.g. as described by Schwab et al 2006, Plant Cell 18, 1121-1133. This technology employs artificial miRNAs, which may be encoded by stem loop precursors incorporating suitable oligonucleotide sequences, which sequences can be generated using well defined rules in the light of the disclosure herein. Thus, for example, in one aspect there is provided a nucleic acid encoding a stem loop structure including a sequence portion of the target HQT gene of around 20-25 nucleotides, optionally including one or more mismatches such as to generate miRNAs (see e.g. http://wmd.weigelworld.orgibin/mirnatools.pl). Such constructs may be used to generate transgenic plants using conventional techniques.

These vectors and RNA products may be useful for example to inhibit de novo production of the HQT polypeptide. They may be used analogously to the expression vectors in the various embodiments of the invention discussed herein.

Notwithstanding the above, it should nevertheless be noted that where increased chlorogenic acid levels are produced according to this invention, we have observed this to limit infection by pathogens and increase innate immunity. It is likely that increasing anthocyanin and flavonol levels also contribute to this effect, thereby providing extended shelf life as a result of reduced opportunistic infection.

Increase of Anthocyanins in Plants

In support of embodiments according to various aspects of this invention in which elevated levels of coloured anthocyanins are required, we present evidence of successful production of purple tomatoes containing high levels of anthocyanins as a result of fruit-specific expression of two transcription factors (Rosea1 and Delila) from *Antirrhinum majus*, under the control of the E8 promoter. These tomatoes have extended shelf life. Shelf life is also extended if anthocyanin synthesis is blocked (using a mutant of tomato called aw) and flavonols accumulate instead. This effect was also observed in the AtMYB12 high flavonol tomatoes.

In summary, as exemplified above, and without limitation, the invention provides in various aspects:

Use of a gene encoding a MYB transcription factor (e.g. Rosea1, or a variant thereof such as Ant1 or pan1) to increase the levels of anthocyanins in a plant e.g. of the family Solanaceae, more preferably genus *Solanum*. Optionally the plant may be *S. tuberosum* or *S. lycopersicum*.

Methods, materials and processes for achieving the same, including for extending shelf-life, optionally in conjunction with the modification of yet other traits described herein.

Isogenic or transgenic plants obtained by said processes, particularly those also isogenic or transgenic for other traits described herein.

The sequence of Ant1 (nucleotide and encoded protein) is shown in Sequence annex VI (SEQ ID NO: 17 and 18, respectively).

The sequence of pan1 (nucleotide and encoded protein) is shown in Sequence annex VII (SEQ ID NO: 19 and 20, respectively).

For example the invention provides a method for increasing the levels of one or more anthocyanins in plants, through flavonoid biosynthesis, such as to enhance the appearance, nutritional or nutraceutical properties, or shelf-life thereof, by causing or allowing expression of a heterologous MYB-encoding nucleic acid sequence as discussed above within the cells of the plants. The step may be preceded by the earlier step of introduction of the nucleic acid into a cell of the plant or an ancestor thereof.

As demonstrated herein, the method may be used to increase highly coloured anthocyanins such as 3,5-diglucosides acylated with cinnamic acids—indeed results described herein demonstrate a 3-fold increase in antioxidant activity in the water-soluble fraction.

The methods may also be used to increase the expression levels of any of the cloned genes shown in Table 2.S1. of Example 2 (especially those marked ++ or +++).

Vectors, constructs, plants and so on may be prepared and utilised in these methods by those skilled in the art in analogous manner to the methods and materials described above in respect of MYB12.

Plants carrying a combination of Delila, Rosea1 and AtMYB12 genes expressed in tomato fruit that accumulate indigo pigment of high intensity as a result of accumulation of both anthocyanins and flavonols in skin and flesh of the fruit Novel Transformation Markers in *Solanum* and Other Plants For aspects of this invention wherein coloured products indicative of transformation are desired, we provide herein evidence that in transformation experiments with tobacco, expression of just the MYB transcription factor (Rosea1) on its own (under the control of a suitable promoter) gives rise to coloured callus tissue and can be used for selection of transformed tissue (see example herein providing a tobacco callus expressing Rosea1). Accordingly, accumulation of anthocyanins in transformed callus may be used as a selectable marker in the cis-genic transformation of potato and other plants or plant cells.

As described in more detail below in relation to "cisgenic" transformation systems, desirably, the appropriate MYB gene from the particular plant of interest is used. Thus, for potato transformation, the pant gene according to this aspect of the invention, used, preferably under the control of an auxin-inducible promoter (e.g. an IAA promoter) to ensure that it is operational during callusing and regeneration of potato tissue.

In summary, as exemplified above, and without limitation, the invention provides in various aspects:
- Use of a *Solanum*-derived MYB transcription factor (e.g. Rosea1 homolog, or a variant thereof such as pan1) which increases the levels of anthocyanins in a plant as a visual screen e.g. for identification of transformed cells in *Solanum* species, by virtue of the pigment that they produce. Preferably the transformation is performed in media which ensures transcription of the promoter controlling the anthoxcyanin marker e.g. in high levels of auxin.
- Vectors and other transformation constructs employing the same.
- Methods of use comprising the step of introducing such a construct into host cells, particularly a plant cell, and selecting host cells containing or transformed with the construct according to their colour or appearance.

Preferred vectors and constructs utilising this system are described in more detail below.

Preferred *Solanum* Plants in which the Invention has Utility

Potato (*Solanum tuberosum* L.) is the fourth most important crop, and the most important non-cereal food crop, in the world.

Basic foodstuffs such as potatoes, with elevated levels of anti-oxidant flavonoids (as described above) could benefit prosperous Westerners and subsistence farmers alike. Potatoes are a globally important crop, with 300 million tonnes being harvested from over 17 million hectares. As well as being widely eaten in industrialised countries, they form an increasingly important staple crop in much of the developing world.

For example, 320 million tonnes of potatoes were harvested across the world in 2004. The biggest growers (2004 figures) are: China (23%), EU (14%), USA (6%, 20.4 million tonnes), India (8%). The great majority of the crop is used for human food, either sold fresh for home preparation, or else processed into chips, crisps etc. The value of the US market alone was estimated at $2.6 billion (Best Food Nation; 2006). Two thirds of the crop is processed, and Russet Burbank is the dominant variety, particularly for French fries.

In preferred aspects of the invention, the plants having multiple improved traits, obtained by the processes described herein, are potato plants.

However it will be appreciated that other crops—in particular other *Solanum* species such as tomatoes, aubergines and also peppers—could also be transformed to confer both disease resistance and high levels of natural antioxidants. Using the methods and techniques disclosed herein with specific reference to potato are utilized in a straightforward way to create other high antioxidant crops, such as broccoli, calabrese, maize, barley, soy.

Enhanced Disease Resistance in Plants of the Invention

Genes conferring resistance to plant disease of economic importance are combined in certain select embodiments according to this invention.

In preferred aspects of the invention—when applied within potato—the invention incorporates the use of at least one heterologous gene encoding resistance to at least one late potato blight (*Phytophthora infestans*).

Late blight is a virulent disease which occurs in all growing areas and can lead to major crop losses. To counteract this, even partially resistant varieties are usually sprayed with fungicides many times a season, which is costly in terms of agrochemicals, tractor fuel, $CO_2$ emissions and soil compaction. The disease is responsible for global losses of £3 billion and can have devastating effects in places where they are a subsistence crop; the 19th Century Irish potato famine is the best known example in Europe.

Late blight was estimated in 2000 to cost US growers $77 million in fungicides, plus an additional $210 million in lost revenues: an average of $507 per acre, not including additional control practices or associated spraying costs (Potato Research; Volume 44, Number 2/June, 2001; Guenthner, Michael and Nolte). In the UK alone, which grows only 10% of the European total crop of 60 million tonnes, fungicide application costs £200 per hectare, a total of £20 million.

The area planted to potatoes in the US and much of Europe has varied little in recent years, but the crop is becoming increasingly important in many developing countries. In India, it is grown as a cash crop and has replaced a number of traditional crops such as buckwheat and millet. 1.4 million hectares were sown in 2003, and there is heavy use of fungicide to control blight. In Indonesia, where potatoes have become an increasingly popular crop for small-scale farmers, late blight can cause yield losses in the range of 12 to 31%, even destroying whole crops in some instances. Fungicides account for 13.5% of the total cost of production.

The International Potato Center in Lima, Peru, estimates late blight losses at $3-5 billion annually worldwide. In China, the world's largest potato producer (with more than 4 million hectares grown), it was estimated that 56% of the total planting area was infected by blight in 1996, giving a total loss of 2.5 million tonnes, worth $170 million at local prices.

Specific resistance to late blight in gene can be introduced by way of major dominant resistance (R) genes. 11 R genes (R1-R11) derived from *S. demissum* have been previously identified.

Prior filed, unpublished, UK priority patent application number 0714241.7 (and corresponding PCT publication WO2009013468) disclose several different late blight R genes derived from the potato wild species *S. okadae* plus also from *S. mochiquense* and *S. neorossii*. The disclosure of said patent applications, and in particular the sequences of Rpi-mcq1 and Rpi-oka1, and the manner in which they were provided and may be generally utilised is specifically incorporated herein by reference.

The following sequences are provided herein in SEQUENCE ANNEX III.

| Seq ID | Rpi Sequence |
|---|---|
| 1a | oka1 nt (SEQ ID NO: 1) |
| 1b | oka2 nt (SEQ ID NO: 7) |
| 2a | magi (candidate 1) nt (SEQ ID NO: 2) |
| 2b | magi (candidate 2) nt (SEQ ID NO: 8) |
| 3 | nrs1 nt (SEQ ID NO: 3) |

It will be appreciated that these sequences, or active variants (within the meaning discussed in GB0714241.7 or WO2009013468 and above) of them, or other RPI genes, can be combined with the other genes discussed herein to provide potatoes expressing novel combinations of traits, and that such is a useful addition to the art.

Preferred Combinations of Traits in Plants of the Present Invention

It has been realised for some time that effective metabolic engineering to improve the content of important bioactives is dependent on securing sufficiently large increases to ensure that the engineered changes are nutritionally, and therefore economically, significant. Engineering large changes in target bioactives requires the use of proteins that regulate the activity of all of the enzyme steps in a metabolic pathway. Genes encoding such transcription factors have been identified from various plant species; of particular relevance to the present invention are two MYB-related genes, one of which is responsible for up-regulating flavonol biosynthesis in *Arabidopsis* (AtMYB12) and the other that up-regulates anthocyanin biosynthesis in *Antirrhinum majus* (Rosea1).

Using fruit-specific expression of AtMYB12 in tomato, we demonstrate increased flavonol levels up to about 4 mg per g fresh weight, and, using Rosea1 we demonstrate the ability to switch on anthocyanin production in tomato fruit, achieving accumulation to levels of 3 mg per g fresh weight. Both increases are highly significant: the fruit of the Rosea1 lines are deep purple in colour and the antioxidant level is comparable to that in red wine, moderate consumption of which has a demonstrable protective effect against cardiovascular disease. Thus these genes have been shown to effectively redirect secondary metabolism, and increase antioxidant activity in particular target tissues of a crop plant. Fruit-specific expression ensured that these engineering steps had no deleterious effects on yield.

The high anthocyanin tomatoes already developed represent a registered food source for extraction of high levels of purple anthocyanins. Crude extraction can be achieved very easily by squeezing the tomatoes. The crude extracts of the purple tomatoes have a good color (stronger and more blue than that of purple sweet potato) but they are less stable than the sweet potato anthocyanins.

In terms of improving the color of the anthocyanins and giving stronger blues, a high flavonol, high anthocyanin tomato has been developed (AtMYB12/Del/Ros1) which is more intensely colored with a pigment that is far bluer than with anthocyanins on their own (indigo as compared to purple). This is due to the copigmentation effect of the flavonols in combination with the anthocyanins. These tomatoes represent an excellent source of this new color which would be easy to extract for preparation of food colorants. Alternatively the anthocyanins and flavonols could be prepared separately from the lines producing high levels of each, and then mixed, post extraction, to develop the color required.

It will be understood that the this paradigmatic demonstration in *solanum* species likewise provides for the analogous use in in potato tubers (to give health-promoting potatoes) and also for selection of transformed lines using anthocyanin production. Herein disclosed and enabled appropriate constructs for cis-genic engineering of high level of flavonols. This is accomplished in a range of potato varieties, suitable for different markets, each having both blight resistance and elevated flavonol levels.

Via introduction of appropriate genes and promoters, beneficial flavonols are induced to accumulate in the crop, e.g. potato tuber, thereby enhancing the nutritional quality.

The proven constructs according to this invention may be used to transform appropriate germplasm to give varieties of high commercial value. For most crops, it is sufficient to select one successful transformant and transfer traits to a range of other varieties using conventional back-crossing. In the case of potato, this is not a viable option. Instead, the germplasm transformed must have all the necessary agronomic and culinary traits other than blight resistance: it must be an existing high volume cultivar. Accordingly, for this particular crop, one or more varieties for each market are selected. A range of cultivars appropriate for particular markets (geographical, plus also fresh vs. processing markets) is transformed. These may optionally be selected from: Maris Piper, Wilja or other major northern European variety; A further European variety for the processing market; An appropriate variety for Eastern Europe; Russet Burbank, for US processing market; A further appropriate variety (Russet or Red) for US fresh market; An appropriate variety for India; An appropriate variety for China; and so on.

Additionally, for example, blight resistance genes (e.g. late blight) are combined with anthocyanin and flavonol inducing genes in a construct to achieve a single-stage, multi-gene transformation. Thus, in one specific embodiment according to this invention, Rpi-mcq1, Rpi-oka1, or both genes are combined into, for example, pIPDNA vectors that confer anthocyanin pigmentation, tuber flavonol elevation. Use of more than one Rpi-gene enhances the likelihood that resistance will not be rapidly broken down by new races of *P. infestans* that can overcome resistance. A potato variety of choice, (e.g. Desiree), is selected based in part on experience with transformation of several varieties, and cis-genic transformants transformants are selected for subsequent screening and evaluation for tuber flavonol content and blight resistance In summary, as exemplified herein, and without limitation, the invention provides in various aspects:

A transgenic-, or more preferably cis-genic, potato comprising within its genome the following heterologous nucleic acid encoding for the following traits:
(i) a gene encoding AtMYB12 or a variant thereof to increase the levels of flavonols and/or chlorogenic acid in the plant. Preferably this is the orthologue of AtMYB12 from tomato or potato. Optionally this is under the control of the tuber specific B33 patatin gene promoter;

(ii) a gene encoding at least one MYB transcription factor (e.g. Rosea1, or a variant thereof such as pan1 or Anti) to increase the levels of anthocyanins in the plant. Optionally this is under the control of an auxin specific promoter (e.g. the IAA4 promoter shown in Sequence Annex IV; SEQ ID NO: 15);

(iii) a gene encoding resistance to at least one late potato blight. Optionally this is under the control of its native promoter;

(iv) optionally, nucleic acid capable of inhibiting chlorogenic acid production in the plant e.g. by encoding a sequence capable of silencing or downregulating a gene which encodes an enzyme present in the chlorogenic acid production pathway e.g. the HQT gene.

Methods, materials (e.g. vectors) and processes for achieving the same, optionally in conjunction with the modificiation of yet other traits described herein.

Cis-genic or transgenic plants obtained by said processes, particularly those also cis-genic or transgenic for other traits described herein.

Cis-Genic Transformation Systems of the Invention

It is an unfortunate fact that in many territories, public acceptance of plants obtained utilising recombinant DNA (r-DNA) technology has been cautious to date, irrespective of their nutritional or other benefits.

In one embodiment according to this invention, we provide new high-flavonol, blight-resistant potato germplasm using new "cis-genic" technology involving the transfer of only *Solanum* DNA into potato. Cis-genic gene transfer technology involves the transfer of only same-genus or same species DNA and is based on serendipitous homology between plant sequences and the T-DNA borders in *Agrobacterium*-mediated transformation.

While it is understood "cis-genic" transformation may require the same regulatory oversight as inter-species transformation, and under current legislation will also have the same labelling requirements, the present inventors believe that it nevertheless confers significant potential advantages. One criticism regularly leveled at the products of r-DNA technology is that they contain DNA combinations which could not be brought about by conventional breeding. Indeed, for many species, it would be irrational to produce by genetic modification something which could be done by breeding without encountering such high regulatory hurdles.

In the case of potatoes, incorporating individual new traits via conventional breeding is all but impossible, so rDNA technology represents the only effective route to providing blight resistance without accompanying undesirable changes to other traits. The cis-genic approach removes one potential barrier to commercialisation. In time, it may also be recognised legislatively as different from trans-genesis.

We disclose a system for crop, including potato, transformation using only genetic material from that crop, e.g. potato itself and related *Solanum* species. Selection is visual, using colour generated by expressing anthocyanins in the plant tissue. This is also, optionally, used to give a distinctive colour to the crop, e.g. potato skin or veins of leaves, making it both distinctive as a variety and easily identifiable by consumers.

Rommens et al (Plant Physiology, May 2004, Vol. 135, pp. 421-431; herein incorporated by reference) report using two T-DNA constructs on compatible plasm ids, one of which carries NPT and also a codA counterselectable marker (conferring 5-fluorouracil sensitivity), the other of which carries the gene of interest. This latter construct carries "P-DNA", comprising functional T-DNA borders based on serendipitous homology to T-DNA found in potato genomic DNA. This also carries a counterselectable marker (ipt—isopentenyltransferase) which enables screening out transformants in which T-DNA transfer extends beyond the left border (LB). Corresponding vectors are also disclosed in U.S. Pat. No. 7,250,554.

In one embodiment according to this invention, an NPT and codA construct is used as a "life support" vector alongside an ipt-, P-DNA construct, pIPDNA, into which is cloned a MYB gene construct that enables cis-genic plant material to be detected by pigmentation. This construct is used in transformation of several varieties, focusing initially on Desiree because of its amenability for *Agrobacterium* transformation.

Disclosed above is the use of anthocyanin, and in particular genes affecting (enhancing) the biosynthesis of anthocyanins, as transformation markers.

To develop a cis-genic marker for potato transformation, a functional potato ortholog of the Rosea 1 gene is obtained using oligonucleotides designed from the pan1 sequence and function is verified in transient and/or stable assays in tobacco. Pan1 is expressed from an auxin-inducible promoter from tomato (e.g. IAA4 as shown in Sequence Annex IV (SEQ ID NO: 15), or the auxin inducible AUX/IAA protein IAA2 Genbank NP000208), to allow production of high levels of anthocyanin in cells which are transformed and express the cis-genic construct in response to the high levels of auxin present in regeneration media during transformation, as demonstrated herein as a simple visual screen in tobacco, where transformed single cells or clumps of cells were identified by the red pigment they produce (FIG. 11.2). Placing the anthocyanin-inducing regulatory gene under an auxin-inducible promoter ensures that the gene does not stay switched on in the majority of mature and differentiated tissues or in apical meristems so that the gene can be used specifically for selection of transformed groups of cells prior to regeneration. Any pigmentation conferred in regenerated plants by the gene, such as pigment of the epidermal cells overlying the vascular tissues, supports distinctness (results now shown).

In summary, as exemplified herein, and without limitation, the invention provides in various aspects:

A transformation vector, or system of vectors for simultaneous transformation, comprising (i) a gene encoding at least one MYB transcription factor (e.g. Rosea1, or a variant thereof such as ANT1 or pan1) to increase the levels of anthocyanins in the plant. Optionally this is under the control of an auxin-inducible promoter from tomato as described above, (ii) preferably left and right P-DNA borders as described herein, (iii) preferably a counter selectable marker situated outside of the the P-DNA borders;

The vector above further comprising one, two, or three of the following between the P-DNA borders:

(i) a gene encoding AtMYB12 or a variant thereof to increase the levels of flavonols and/or chlorogenic acid in the plant. Optionally this is under the control of the B33 promoter, (ii) a gene encoding resistance to at least one potato blight (*Phytophthora infestans*), optionally under the control of its native promoter, (iii) optionally, nucleic acid capable of inhibiting chlorogenic acid production in the plant e.g. by encoding a sequence capable of silencing or downregulating a gene which encodes an enzyme present in the chlorogenic acid production pathway e.g. the HQT gene.

Methods, materials and processes for using the same—e.g. for transformation and a simple visual screen for transformed single cells, by virtue of the pigment that they produce. Preferably the transformation is performed in media which ensures transcription of the promoter controlling the anthoxcyanin marker e.g. in high levels of auxin.

Isogenic plants obtained by said processes, particularly those isogenic for the traits described herein.

Those skilled in the art will appreciate that the construct may also include e.g. terminators, and other sequences as appropriate Non-limiting illustrations of vectors of the invention include those shown in FIGS. 12(a) and (b).

Any sub-titles herein are included for convenience only, and are not to be construed as limiting the disclosure in any way.

Having generally described this invention, with respect to various aspects and preferred embodiments thereof, the following examples are provided to extend the written description and to ensure that those skilled in the art are enabled to practice all aspects of this invention, including its best mode. However, those skilled in the art should not take the specifics of the examples which follow as limiting on the scope of this invention, for which reference rather should be made to the appended claims and equivalents thereof.

The disclosure of all references cited herein, inasmuch as it may be used by those skilled in the art to carry out the invention, is hereby specifically incorporated herein by cross-reference.

EXAMPLES

Example 1

High Flavonol and Hydroxycinnamic Acid Tomatoes and Tobacco Plants

Many food products from plants are rich in protective compounds with health benefits. Among these, metabolites derived from the phenylpropanoid pathway—polyphenols—have gained considerable attention recently.

One subclass of plant polyphenols, flavonoids, exhibits a broad spectrum of biological effects including antioxidant, antitumor (Braganhol et al., 2006), antiinflammatory, antiviral, antibacterial (Rigano et al., 2007), and antifungal activities. There is robust evidence to suggest that dietary flavonoids inhibit low density lipid (LDL) oxidation once absorbed, so reducing the primary risk factor for artherosclerosis and related diseases. Longer term administration of dietary flavonoids offers cardioprotection in both ex vivo and in vivo ischaemia-reperfusion assays in rats (Toufektsian et al., 2008) and improves the levels of risk factors in mouse models of cardiovascular disease (Rein et al., 2006), although it is likely that they protect indirectly by inducing reactive oxygen species (ROS)-scavenging mechanisms. In cell-based assays not all flavonoids are equally efficacious at inhibiting LDL peroxidation; the flavonols quercetin and kaempferol are particularly effective against chemically-induced lipid peroxidation. Quercetin is more active than kaempferol, possibly because it has an ortho-dihydroxyl functionality which confers higher antioxidant activity (Zhou et al., 2004; FIG. 1). Dietary flavonoids may confer protection against other diseases. For example, continuous administration of quercetin can reduce blood glucose levels and oxidative stress in STZ-induced diabetic rats, suggesting a protective role against diabetes (Asian et al., 2007).

Flavonols also protect by mechanisms beyond their activities as antioxidants or as inducers of ROS-scavenging mechanisms. For example, flavonols are effective inhibitors of platelet aggregation and hence factors contributing to stroke and thrombosis (Nijveldt et al., 2001).

Supporting the results of cell-based assays and feeding trials with animals, several epidemiological studies have established a strong inverse correlation between the occurrence of cardiovascular disease, certain cancers and age-related degenerative diseases, and consumption of flavonol-rich diets (Hertog et al., 1993, Renaud and de Lorgeril, 1992, Joseph et al., 1999, Seeram et al., 2004, Hou et al., 2004). Based on such studies, it has been suggested that a systemic increase in the daily intake of certain flavonoids could lead to between 7 and 31% reduction in the incidence of all cancers and between 30 and 40% reduction in death from coronary heart diseases (Hertog et al, 1993, Soobrattee et al., 2005).

Another important group of plant-based bioactive polyphenols are the caffeoyl quinic acids (CQAs) of which chlorogenic acid (CGA) is the major soluble phenolic in *solanaceous* species such as potato, tomato and eggplant, and in coffee. Consequently, CGA forms one of the most abundant polyphenols in the human diet, and is the major antioxidant in the average US diet. CQAs have strong antioxidant activity and can limit low-density lipid (LDL) oxidation. CGA protects against environmentally-induced carcinogenesis through its up-regulation of cellular ROS-scavenging enzymes and suppression of ROS-mediated NFκβ, AP-1, and MAPK activation (Feng et al., 2005). Other caffeoyl quinic acids with multiple caffeoyl groups, such as dicaffeoylquinic acid (diCQA) and tricaffeoylquinic acid (triCQA), offer even greater protection than mono-caffeoyl quinic acid (CGA), when included in the diet (Islam, 2006). High antioxidant capacity may be the explanation for the efficacy of these compounds because they have additional ortho dihydroxyl functionalities (Zhou et al., 2004, Cheng et al., 2007). Dietary CQAs are also beneficial in specific ways. For example, oral administration of triCQA to diabetic model rats reduces significantly their blood glucose content. Caffeoylquinic acid derivatives are neuroprotective against retinal damage (Nakajima et al., 2007), 3,4,5-triCQA inhibits HIV/AIDS (18), and diCQA has anti-hepatotoxic activity (Choi et al., 2005), suggesting that CQAs protect humans (Matsui et al., 2004, Kim et al., 2005) by a range of different mechanisms (Islam, 2003).

In addition to their individual health-promoting effects, synergistic effects of plant phenolics have also been reported. For example, the antibacterial activities of flavonoids are enhanced when they are administered in combination. The antibacterial activities of quercetin can be enhanced by the presence of rutin (Arima et al., 2002). Synergistic antiproliferative effects of quercetin and kaempferol on cancer cell proliferation have been reported (Ackland et al., 2005), suggesting that combinations of flavonoids, which are naturally present in whole fruits and vegetables, are more effective in inhibiting growth of malignant cells than individual flavonoids.

Several different strategies have been used to increase the production of polyphenolic compounds such as CQAs and flavonol glycosides in food plants (FIG. 1). Over-expression of genes encoding individual biosynthetic enzymes such as hydroxycinnamoyl CoA quinate transferase (HQT), a key enzyme of CGA synthesis, leads to nearly a doubling of CGA levels in tomato leaves (Niggeweg et al., 2004) and over-expression of the gene encoding chalcone isomerase (CHI) results in a more than 70-fold increase of rutin levels in tomato fruit peel (Muir et al., 2001). The problem with this type of strategy is that the whole biosynthetic pathway is not activated, and the overall increase in end products is usually not high enough for practical application purposes. Even in the case of CHI overexpression, because peel accounts for less than 10% of the fruit mass, the overall content of flavonols was increased to no more than 200 ug/g fresh weight. An alternative engineering strategy involves the overexpression of regulatory genes that induce these pathways. For example, increases of up to 20-fold in flavonols were obtained by simultaneous expression of maize transcription factors Lc and C1 (which induce anthocyanin biosynthesis in maize) in tomato fruit (Bovy et al., 2002). When the endogenous photomorphogenesis regulatory gene DET1 was suppressed in a fruit-specific manner in tomato, modest increases in carotenoid and flavonoid contents of fruits were achieved (Davuluri et al., 2005). Although this type of strategy provides a more effective means of engineering metabolism to achieve significant enhancements in the levels of end products, care is needed when choosing the transcription factor(s) to use, to ensure they have the appropriate specificity in target crop species. For example, because Lc and C1 transcription factors did not induce both general phenylpropanoid and flavonol biosynthetic pathways in tomato, the overall levels of flavonol derivatives (20 times more than in the control) were not great enough for application purposes.

Here, we show that it is possible to engineer massive increases of multiple health-promoting polyphenolic compounds from the phenylpropanoid pathway by tissue-specific expression of a single gene encoding a transcription factor, AtMYB12, from *Arabidopsis thaliana*. We show that even though identified as a flavonol-specific transcriptional activator in *arabidopsis*, AtMYB12 can activate additional pathways when over-expressed in a tissue-specific manner in tomato, and can be used to produce fruit with extremely high levels of several health-promoting hydrophilic polyphenolic antioxidants. Tomatoes with improved antioxidant activities of this order of magnitude should offer significant protection against heart disease, cancers and age-related degenerative diseases, if included in the diet.

Materials and Methods

Plasmid Construction, Plant Transformation and Confirmation of Transgenic Lines

For tobacco transformation: The binary vector pBin-35S-AtMYB12 was produced by cloning the cDNA of AtMYB12 between the double 35S promoter from CaMV and the CaMV Terminator in pBin19 (Bevan, 1984). The T-DNA region of pBin-35S-AtMYB12 was transformed using *A. tumefaciens* (LBA4404) into *N. tabaccum* var. Samsun using the leaf disc transformation method (Horsch et al., 1985). Insertion of the T-DNA was confirmed by PCR of genomic DNA extracted from the kanamycin-resistant plants. AtMYB12 transcript levels were measured by RNA gel blots using the tobacco ubiquitin gene as a control.

For tomato transformation: The binary vector pSLJ-E8-MYB12 was constructed by replacing the double 355 promoter in pJIT160 (Gerineau and Mullineaux, 1993) by the E8 promoter between the KpnI site and BamHI site to make pJ1T160-E8. The full length sequence of the AtMYB12 cDNA was amplified and inserted between BamHI and EcoRI cloning sites of pJIT160-E8 to make NIT160-E8-MYB12. The fragment between SstI and XhoI in pJIT I 60-E8-MYB12 was inserted into the same sites in pSLJ7291 to make pSLJ-E8-MYB12. The binary plasmid pSLJ E8-MYB12 was then transferred to *Agrobacterium* strain GV3101 by the triparental mating (Ditta et al., 1980). Tomato varieties Micro-Tom and Money Maker were transformed by *Agrobacterium*-mediated transformation of cotyledons (Fillatti, 1987). Insertion of the AtMYB12-containing T-DNA was confirmed by PCR of genomic DNA extracted from the kanamycin-resistant plants. Transcript levels of AtMYB12 were measured by real-time RT-PCR by the following procedure; RNA was extracted from the fruit of kanamycin-resistant plants, cDNA was prepared, and real-time RT-PCR was carried out using the primers 5'-CTTCAGTCTTGTCCATCGGTG-3' (SEQ ID NO: 23) and 5'-CTAACGGTTCTCCAAAGTTCTCAC-3' (SEQ ID NO: 24). The tomato ASR1 gene was amplified as a control using primers CCTGTTCCACCACAAGGACAA-3' (SEQ ID NO: 25) and 5'-GTGCCAAGTTTACCGATTTGC-3' (SEQ ID NO: 26).

Analysis of Total Anthocyanin

Anthocyanin was extracted from the petals of the flowers by acidified MeOH (3% HCl) and was quantified as previously described (Martin et al., 1985).

Analysis and Identification of Phenylpropanoids by LC-MS/MS

Phenylpropanoids were extracted either from fresh samples with 100% methanol or from freeze-dried samples with 70% methanol. HPLC analysis of the phenylpropanoids and the identification of peaks have been described elsewhere (Luo et al., 2007). Quantification of phenylpropanoids was achieved by calculating the area of each individual peak and comparing this to the standard curves obtained from the pure compounds. Pure flavonoids, kaempferol rutinoside, naringenin, naringenin chalcone were purchased from Apin Chemicals Ltd available on the world wide web at apin.co.uk/new) or Extrasynthese available on the world wide web at extrasynthase.com). Quercetin rutinoside (rutin), chlorogenic acid (CGA), and lycopene were purchased from Sigma available on the world wide web at sigmaaldrich.com).

Quantitative RT-PCR

Total RNA was obtained using an RNeasy Plant Mini Kit (Qiagen) First-strand cDNA was synthesized using the adaptor oligoDT17 primer (Frohman et al., 1988) (Sigma) and SuperScript III (Invitrogen) from 5 ug of total RNA. Quantitative real-time RT-PCR was carried out using gene specific primers as shown in supplementary Table S3. All quantifications were normalized to abscisic stress ripening gene 1 (ASR1) amplified under the same conditions using primers 5'-CCTGTTCCACCACAAGGACAA-3' (SEQ ID NO: 27) and 5'-GTGCCAAGTTTACCGATTTGC-3' (SEQ ID NO: 28).

RNA Gel Blot Analysis

Total RNA was purified from tobacco leaves using TRI-REAGENT (Sigma Chemical Co.; available on the world wide web at sigmaaldrich.com/) according to procedures provided by the manufacturer. Total RNA (20 pg) was then separated on denaturing agarose and transferred onto nylon membranes (GE Healthcare, available on the world wide web at gelifesciences.com) and hybridized to radioactive DNA probes.

Cloning of SIMYB12 and Assaying its Expression in Tomato Fruit

The tomato EST database was searched for sequences homologous to AtMY.B12 and the EST with the highest sequence similarity to AtMYB12 (TC172990) was used to identify a fall-length cDNA from tomato fruit using 3'RACE PCR (Frohmann et al., 1988). Total RNA was isolated and first-strand cDNA was synthesized as described previously (Luo et al., 2007). The 3' end of the cDNA was amplified using oligonucleotides: ATGGGAAGAACACCTTGTTG- 3' (SEQ ID NO: 29) and the 3' adaptor sequence, 5' GACTC-GAGTCGACATCG-3' (SEQ ID NO: 30) (Frohmann et al., 1988). The amplified sequence was cloned into pGEM-T easy and sequenced. The full-length cDNA was then reamplified using the forward oligo 5'-ATGGGAAGAACACCT-TGTTG-3' (SEQ ID NO: 31) and the reverse oligo 5'-CTAAGACAAAAGCCAAGATACAA-3' (SEQ ID NO: 32) based on the 3' sequence amplified by 3'-RACE. The sequence for SlMYB12 has been submitted to the EMBL database with the accession number EU419748.

The expression of SlMYB12 in Micro Tom tomato fruit was assayed by quantitative RT-PCR (Luo et al., 2007) using oligonucleotides 5'-GAGCAATAATGTAGGGAATAG-3' (SEQ ID NO: 33) and 5' TTGAAGTAAGTTAGTGTCAG-TAT-3' (SEQ ID NO: 34).

Phylogenetic Analysis

Amino acid sequences were aligned using the CLUSTALW program (Thompson et al, 1994). Phylogenetic analysis was performed with PHYLIP programs (version 3.67) using the region of the alignment corresponding to the MYB DNA binding domain (indicated by '=' characters). A distance matrix method employing the Jones-Taylor-Thornton model was used to compare the sequences and a tree was derived using the Neighbour-joining clustering method (Saitou and Nei, 1987). 1000 bootstapped data sets were used to indicate the confidence of each tree Glade.

Total Antioxidant Activity

Wild type and transgenic tomatoes were washed, deprived of seeds, homogenized in liquid nitrogen in a mortar, and then freeze-dried. For the total antioxidant activity assay, 50 mg of the freeze-dried sample was extracted with 4 mL of water by vortexing for 20 min at room temperature, centrifugation at 10,000×g for 10 min and the supernatant was collected. The extraction was repeated with 2 mL of water and the two supernatants were combined. The pulp residue was re-extracted by the addition of 4 mL of acetone and vortexing for 20 min at room temperature, centrifugation at 10,000×g for 10 min and then the supernatant was collected. The extraction was repeated with 2 mL of acetone and the two supernatants were combined. Tomato extracts were immediately analyzed for their antioxidant capacity. The trolox equivalent antioxidant capacity (TEAC), based on the ability of antioxidant molecules to quench the long-lived ABTS [2,2'-azinobis(3-ethylbenzthiazoline-6-sulfonate), Sigma-Aldrich, UK] radical cation, a blue-green chromophore with characteristic absorption at 734 nm, compared with that of trolox (6-hydroxy-2.5,7,8-tetramethylchroman-2-carboxylic acid, Fluka, Germany), a water-soluble vitamin E analog, was determined (Pellegrini, 1999). Results were expressed as TEAC in mmol of trolox per kg of dry weight.

Analysis of Total Carotenoids

Total carotenoids were extracted from freeze-dried tomato fruit samples and extracted twice in the dark with tetrafuroran for 20 min followed by centrifugation (10,000 g) at room temperature for 10 min. The supernatants were combined and absorbance was measured at 472 nm. Quantification of total carotenoid levels was done using a calibration curve obtained for the pure compound, lycopene.

Results

Figure 2:
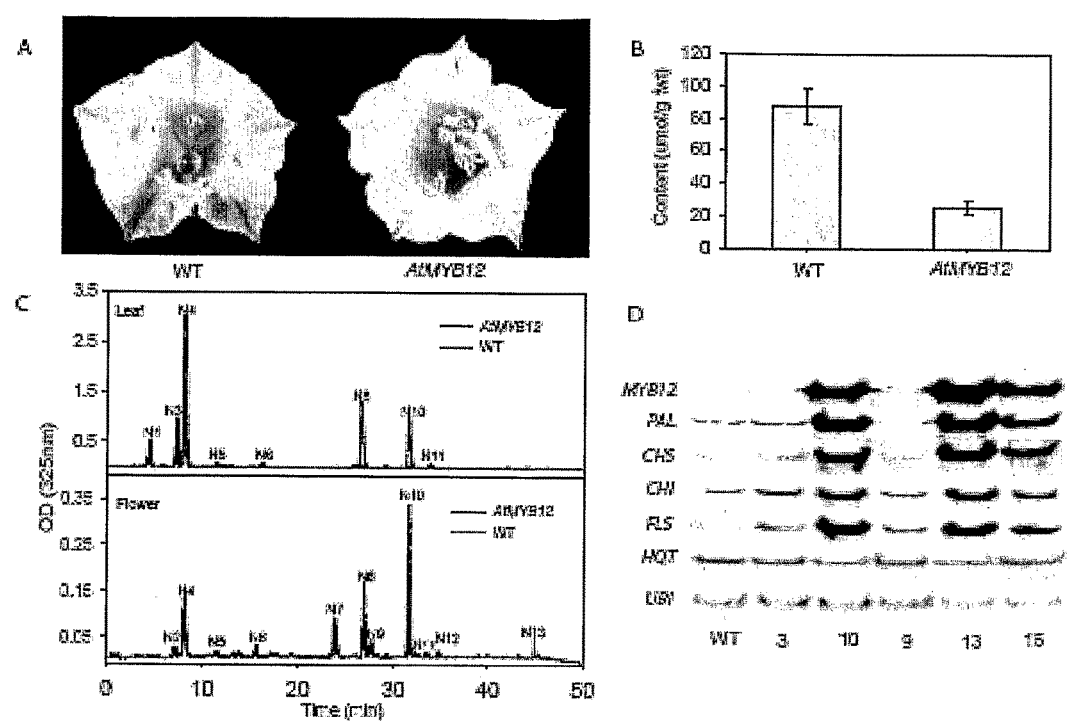
FIG. 2. Expression of AtMYB12 in tobacco. (A) Flowers of wild type (left) and an AtMYB12 expressing line (right). (B) Total anthocyanin contents in wild type and AtMYB12 flower petals. (C) HPLC analysis of methanol extracts from leaf and flowers of wild type and AtMYB12-expressing tobacco plants. N1, 3-caffeoyl quinic acid; N2, caffeoyl-spermidnine; N3, 4-caffeoyl quinic acid; N4, 5-Caffeoyl quinic acid N5, quercetin glucosyl-glucoside rhamnoside; N6, kaempferol glucosyl-glucoside rhamnoside; N7, N-caffeoyl-N'-dihydrocaffeoyl spermidine; N8, quercetin rutinoside (rutin); N9, dicaffeoyl spermidine; N10, kaempferol rutinoside; N11, kaempferol malonylglucoside; N12, unknown; N13, tricoumaroyl spermidine. Identification of peaks is described in Table 1. (D) RNA gel blot of some structural genes involved in phenylpropanoid biosynthesis in tobacco. Genes that have been analyzed are described in FIG. 1, except the transgene AtMYB12, and the tobacco ubiquitin gene (UBI) which was used as a control. FW, fresh weight.

AtMYB12 has been identified as a transcription factor that specifically activates flavonol accumulation in *arabidopsis* (29). To determine whether AtMYB12 could work the same way in other species, we first introduced the AtMYB12 cDNA into tobacco (*Nicotiana tabaccum*) under the control of the strong, constitutive CaMV35S promoter. From more than 15 independent transformants, three lines (lines 10, 13, and 15) with different levels of transgene expression were investigated further. The transgenic lines grew normally compared to controls; the only visible difference was that the flowers of the transgenic plants were more palely coloured than their wild type counterparts (FIG. 2A). This phenotype was correlated with the expression level of the AtMYB12 transgene (FIG. 2B). The levels of phenolics in leaves and flowers of transgenic plants were compared to those in wild type plants (FIG. 2C, Table S1). CQAs (specifically the three isomers of chlorogenic acid; 3-caffeoyl quinic acid, 4-caffeoyl quinic acid and 5-caffeoyl quinic acid) were, by far, the most abundant phenolics in wild type leaves, although low levels of quercetin glycosides (mainly rutin) were identified, but kaempferol glycosides were barely detectable. Expression of AtMYB12 resulted in 46-fold and 83-fold increases of rutin (quercetin rutinoside) and kaempferol rutinoside in leaves, respectively. An acylated kaempferol derivative, kaempferol malonylglucoside was detected from AtMYB12 leaves but not in extracts from control leaves. In addition, a 2-fold increase in CGA levels was detected in leaves of the transgenic lines.

Flowers of tobacco expressing AtMYB12 also had increased rutin, kaempferol rutinoside, CGA and kaempferol malonylglucoside contents compared to wild type flowers, and lower levels of anthocyanins (FIG. 2B). The polyamine conjugates, remained unchanged in abundance in flowers of transgenic plants.

The expression of the genes encoding enzymes involved in flavonol and CGA biosynthesis were compared between control plants and lines expressing AtMYB12, by RNA gel blots (FIG. 2D). Among the genes that were tested, those encoding phenylalanine ammonia lyase (PAL), chalcone synthase (CHS), chalcone isomerase (CHI) and flavonol synthase (FLS) were induced by AtMYB12 expression in tobacco. HQT, which is involved in CGA biosynthesis (Niggeweg et al., 2004), was not induced, and dihydroflavonol 4-reductase (DFR), which is required specifically for anthocyanin biosynthesis, could not be detected in either the control or the AtMYB12-expressing plants.

These results showed that AtMYB12 can act as a positive regulator of the flavonol biosynthetic pathway in tobacco. To exploit the potential of AtMYB12 for metabolic engineering, the gene was then introduced into tomato driven by the fruit-specific E8 promoter, which is most active in developing fruit after the breaker stage. Two varieties of tomato (*Solanum lycopersicum* cv. Micro-Tom and cv Money Maker) were transformed with SLJ-E8-MYB12 and more than 30 independent kanamycin resistant plants (T0) were obtained for each variety.

Figure 3:
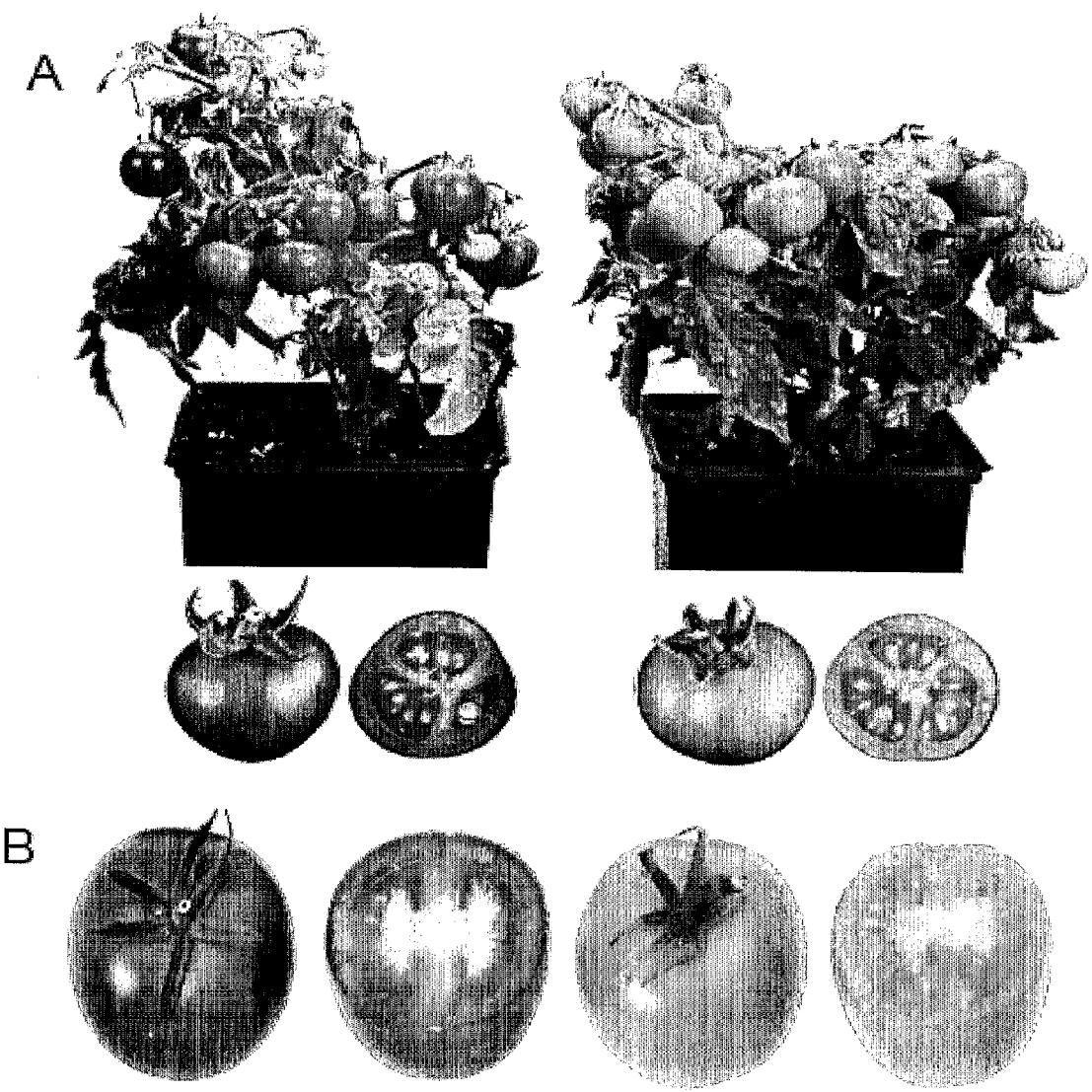
FIG. 3. Phenotypes of wild type and AtMYB12-expressing tomato fruit. (A) Phenotype of AtMYB12 expression in 'Micro Tom' tomato. Pictures show whole plants; wild type (upper left) and AtMYB12-expressing line (upper right), and fruit of wild type (lower left) and AtMYB12-expressing line (lower right) tomato. (B) Phenotype of AtMYB12 expression in 'Money Maker' tomato. Pictures show fruit of wild type (left) and an AtMYB12-expressing line (right).

AtMYB12 primary transformants developed normally during vegetative growth and were indistinguishable from controls. Transgenic fruit also developed normally and were indistinguishable from fruit from control plants until the turning stage. At maturity, instead of turning the pink-red colour of control fruit, the transgenic fruit were orange (FIG. 3A). This phenotype was correlated with the expression level of AtMYB12 and the content of flavonol derivatives in the transgenic fruit. The same orange fruit phenotype was observed in the fruit of the transformants in the Money Maker background (FIG. 3B)

Figure 4:
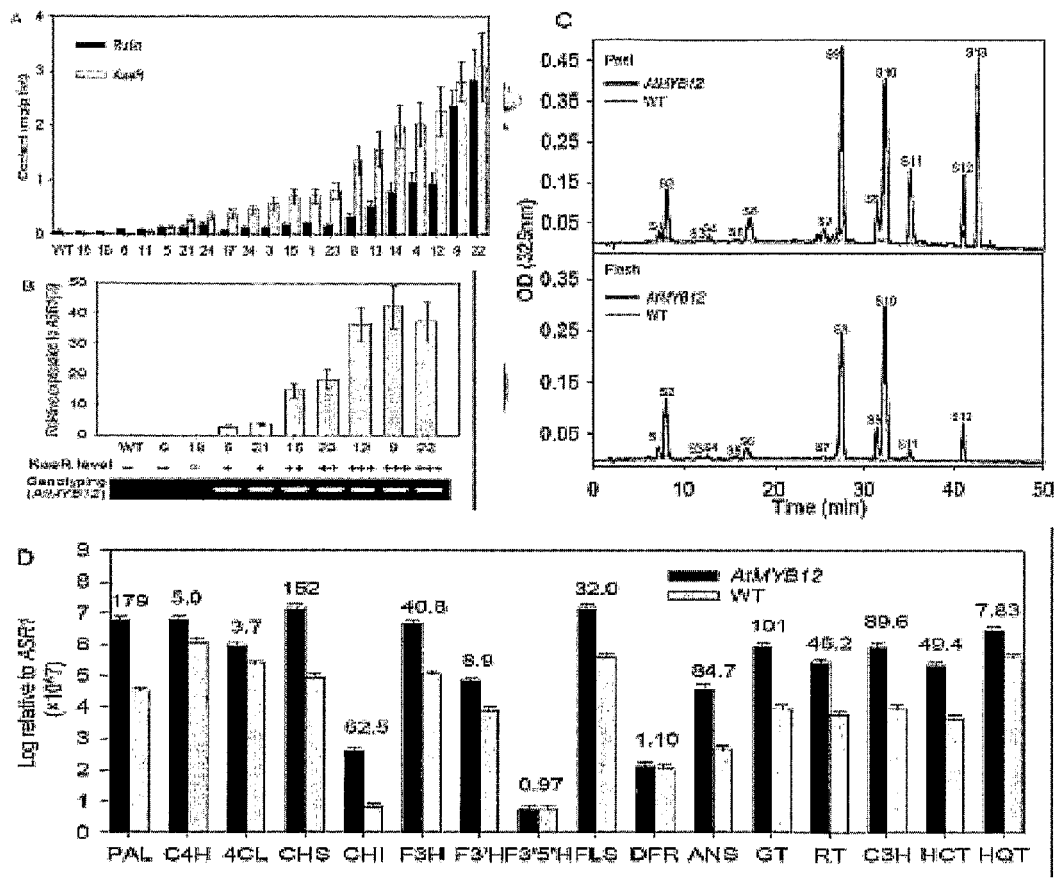
FIG. 4. Screening of T0 tomato transformants expressing AtMYB12, phenylpropanoid levels and structural gene expression in wild type and AtMYB12-expressing 'Micro Tom' tomato fruit. (A) Flavonoid levels in whole fruit of wild type and T0 transgenic 'Micro Tom' tomato fruit. (B) Transcription of AtMYB12 (upper), kaempferol rutinoside (KaeR) levels (middle) and AtMYB12 genotyping (lower) of wild type and selected T0 transgenic tomato fruit. FW, fresh weight. (C) HPLC analysis of methanol extracts from peel and flesh of wild type and AtMYB12-expressing tomato fruits. S1, coumaric acid glucoside; S2, 5-caffeoyl quinic acid; S3, quercetin diglucoside; S4, quercetin glucosyl-glucoside rhamnoside; S5, kaempferol diglucoside; S6, kaempferol glucosyl-glucoside rhamnoside; S7, naringenin; S8, quercetin rutinoside (rutin); S9, dicaffeoyl quinic acid; S10, kaempferol rutinoside; S11, naringenin chalcone glucoside; S12, tricaffeoyl quinic acid; S13, naringenin chalcone. Identification of peaks is described in Supplementary Table S2. (D) Analysis of transcript levels of structural genes of phyenylpropanoid metabolism by real-time RT PCR. Genes analyzed are described in FIG. 1. Transcript levels relative to abiotic stress responsive 1 (ASR) are presented using a Log 10 scale and the fold-increase in levels in AtMYB12-expressing fruit compared to wild type is given above the bars for each gene. The data represent the mean values (±SD) of triplicate experiments from two independent biological samples. CQA, caffeoyl quinic acid; diCQA, di caffeoyl quinic acid; triCQA, tricaffeoyl quinic acid; KaeR, kaempferol rutinoside; KGGR, kaempferol glucosyl-glucoside rhamnoside; NCG, Naringenin chalcone glucoside; NC, Naringenin chalcone.
Figure 8:
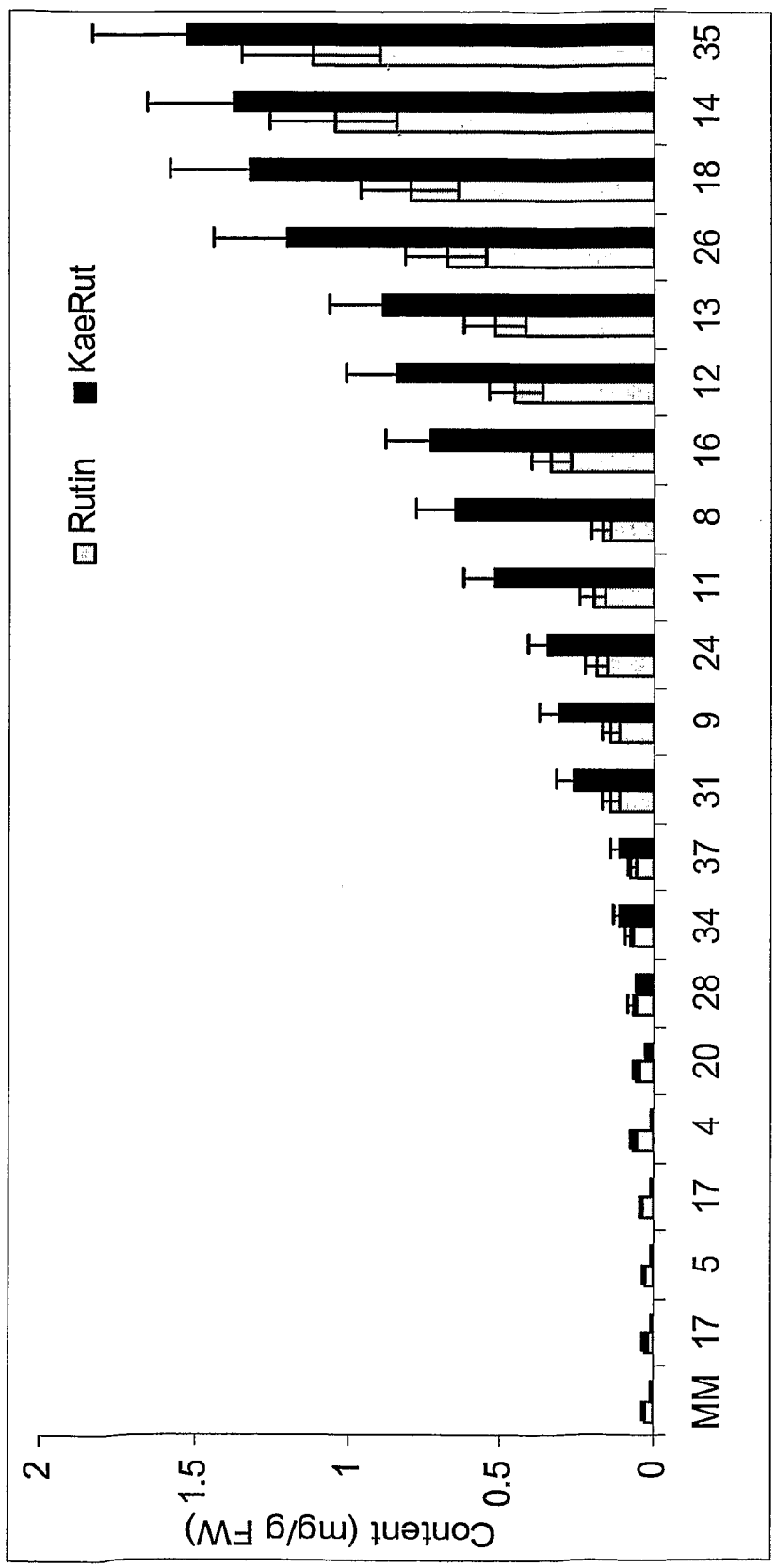
FIG. 8 Flavonoid levels in the whole fruit of wild type and T0 transgenic 'Money Maker' tomato fruit.

Mature T0 fruits of each variety were screened for their quercetin rutinoside (rutin) and kaempferol rutinoside contents (FIG. 4A and FIG. 8 for Micro Tom and Money Maker, respectively). Because of the shorter generation time and relative ease of cultivation of dwarf varieties, transgenic plants in the MicroTom background with different levels of flavonol derivatives were selected for further genotyping and the transcript levels of AtMYB12 in the fruit of these plants were analyzed by real-time qRT-PCR (FIG. 4B). Control fruit showed no AtMYB12 transcript, while all transgenic plants tested showed clear transcripts for the transgene in fruit. Furthermore, there was a good correlation between the transcript levels of the AtMYB12 gene and the kaempferol rutinoside contents of the fruit. Three of the transgenic plants (lines 9, 12, and 22) were then used for further analyses, on the basis of their high AtMYB12 transcript levels and their high levels of flavonol accumulation in fruit. For all three lines, the transgene was inherited in a 3:1 ratio by the $T_1$ progeny, as expected for single copy transgene insertions.

Ripe fruit from both transgenic and control lines were harvested and peel and flesh were analyzed separately for their polyphenol contents by LC/MS (FIG. 4C and Table S2). The main flavonoid in wild type peel extract was naringinin chalcone, accompanied by small amounts of rutin, kaempferol rutinoside, CGA, diCQA and triCQA, confirming results recently reported by Moco et al (2006). Wild type flesh produced only small amounts of CQAs, and other phenolics at detectable levels. In both the peel and the flesh of transgenic fruit, massive levels of flavonol derivatives (mainly rutin and kaempferol rutinoside) were detected. Kaempferol glucosyl-glucoside rhamnoside and chalcone glucose were among the flavonoids that also were elevated in the peel of transgenic fruit. Surprisingly, high levels of CQAs (CGA, diCQA, and triCQA) were also detected in the fruit of the lines expressing AtMYB12. The major phenolics in whole fruit were quantified using purified standards (FIG. 4D). On a whole-fruit basis, more than 15 mg/g DW of CQAs and 72 mg/g DW of flavonols (rutin and kaempferol rutinoside) were detected in the transgenic fruit in the MicroTom background, which is equivalent to 22, and 65-fold higher levels respectively compared to wild type fruit. In the Money Maker background AtMYB12 also increased the levels of both CQAs and flavonols (to more than 3 mg/g DW and 48 mg/g DW respectively). The total levels of these polyphenols were lower in the Money Maker than in the MicroTom background, but this was probably because the levels of these compounds are generally lower in this variety than in MicroTom; a feature shared by larger fruited varieties compared to cherry tomatoes (Raffo et al., 2002). However, the fold increases in polyphenols induced by AtMYB12 were higher in the Money Maker background than in the MicroTom back ground; more than 30-fold for CQAs and more than 125-fold for flavonols (FIG. 4D).

The high-polyphenol phenotype was maintained in mature fruit of hemizygous T1 and homozygous T2 individuals of three single-copy AtMYB12 lines (Supplemental Table S3), showing that the high-flavonol/high CQA phenotype is inherited stably in subsequent generations and is, in fact, somewhat enhanced as the AtMYB12 transgene is brought to homozygosity.

The effect of AtMYB12 on the expression of genes involved in flavonoid biosynthesis was examined by real-time qRT-PCR in fruit from the T1 generation of plants. RNA was extracted from fruit of AtMYB12 and control plants at the turning stage. Expression levels of phenylpropanoid pathway genes encoding PAL, cinnamate 4-hydroxylase (C4H), 4-hydroxycinnamoyl-CoA ligase (4CL), CHS, CHI, flavanone-3-hydroxylase (F3H), flavonoid-3'-hydroxylase (F3'H), flavonoid-3'5'-hydroxylase (F3'5'H), FLS, DFR, anthocyanidin synthase (ANS), flavonol-3-glucosyltransferase (GT), flavonol 3-glucoside-rhamnosyltransferase (RT), p-coumaroyl ester 3-hydroxylase (C3H), hydroxycinnamoyl-CoA shikimate/quinate transferase (HCT), and HQT were compared in control and transgenic fruit expressing AtMYB12. Expression of the abscisic stress ripening 1 (ASR1) gene (Iusem et al., 1993) was used as an internal control due to its high and stable mRNA expression levels in different ripening stages and different tissues of tomato fruit (Bovy et al., 2002).

As shown in FIG. 4E, transcripts of PAL, F3H, F3'H, FLS, GT, and RT genes were readily detectable in wild-type fruit. In AtMYB12 fruit, however, we observed more than 100-fold induction of the genes encoding PAL, CHS, and GT, between 50- and 100-fold induction of the genes encoding CHI, ANS, C3H, between 10- and 50-fold induction of genes encoding F3H, RT, and HCT, and between 3- and 10-fold induction of genes encoding F3'H, C4H, 4CL and HQT relative to the wild-type fruit. Neither F3'5'H nor DFR were up-regulated in AtMYB12 fruit. In conclusion, these results showed that fruit-specific expression of AtMYB12 in tomato leads to the induction of all of the biosynthetic genes required for the production of flavonols and their derivatives and, in addition, those required for the synthesis of CGA and its derivatives, while at least some of the genes involved in anthocyanin production remain uninduced. The exception was ANS which is involved in anthocyanin biosynthesis and was highly induced by AtMYB12 expression.

Figure 5:
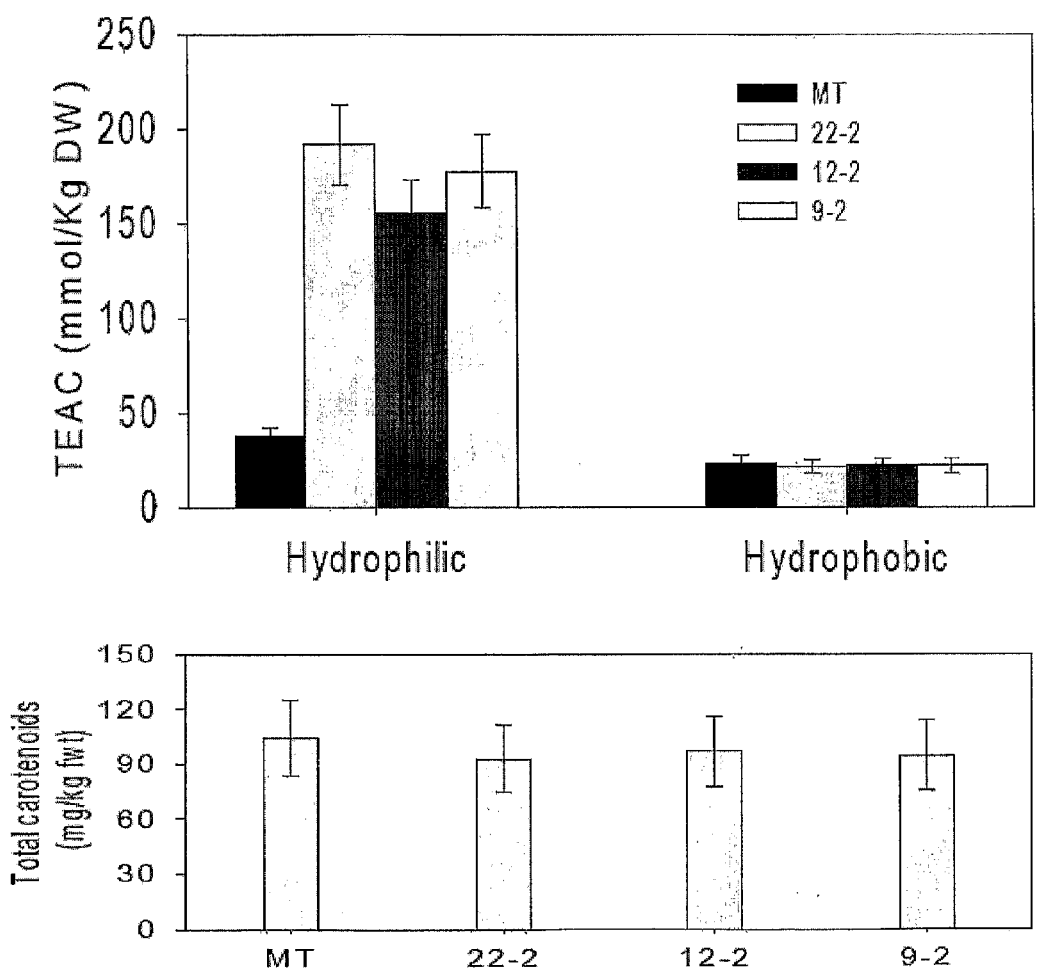
FIG. 5. Total antioxidant capacity and total carotenoids in wild type and T2 generation AtMYB12-expressing tomato fruit. Upper graph: Hydrophilic and lipophilic antioxidant activities in mature tomato fruit from wild type and AtMYB12-expressing lines. Lower graph: Total carotenoid levels in mature tomato fruit from wild type and AtMYB12-expressing lines.

Differences in the total antioxidant capacity between transgenic and control tomato fruit were measured using the Trolox Equivalent Antioxidant Capacity (TEAC) assay. In AtMYB12 fruit the TEAC activity of the water-soluble fraction (containing phenolics) was increased up to 5-fold compared to the control (FIG. 5A) whereas no significant difference could be detected for the TEAC activities of the lipophilic fraction between control and transgenic fruit. This suggested that the increase of the phenylpropanoids was not achieved at the expense of carotenoid accumulation in tomato fruit. No significant difference in total carotenoid content was detected between transgenic and wild type tomato fruit (FIG. 5B).

Figure 6:
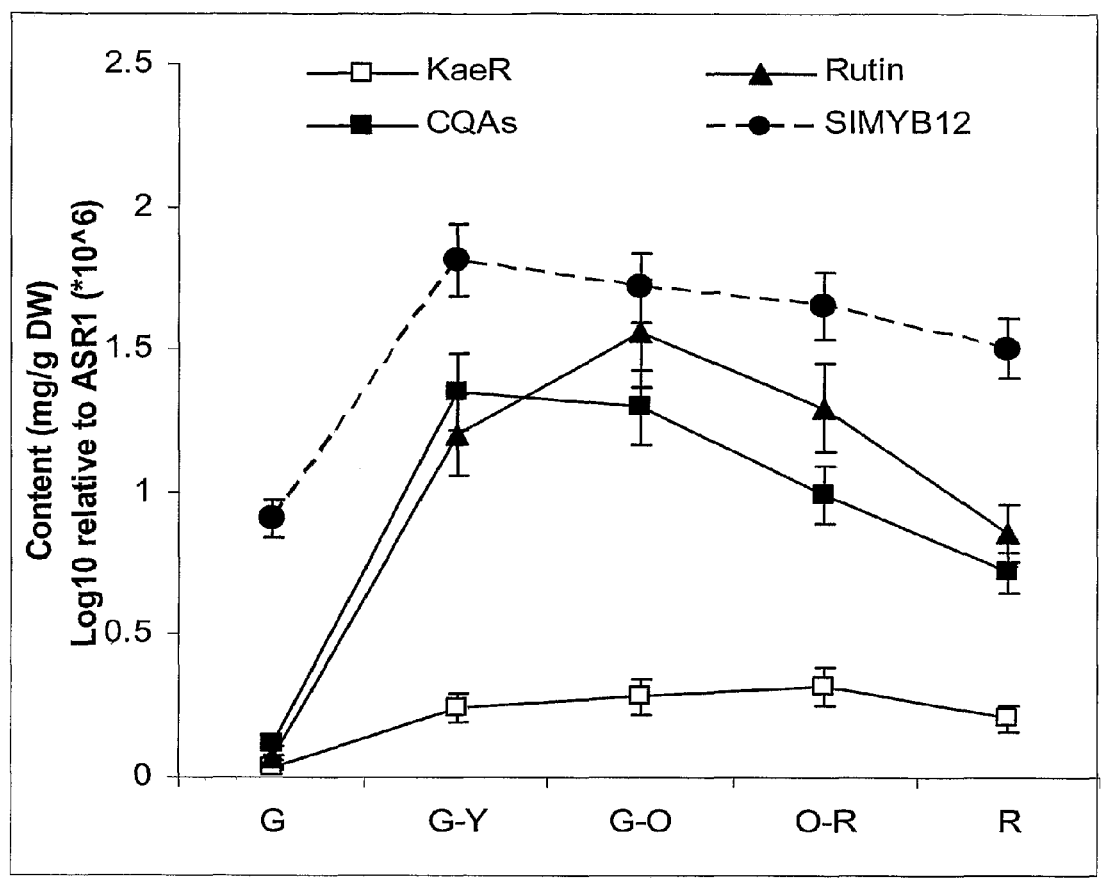
FIG. 6. Polyphenolic contents and SlMYB12 transcript levels in developing 'Micro Tom' tomato fruit. Levels of SlMYB12 transcript levels in tomato fruit at different ripening stages. Transcript levels determined by real time RT-PCR are expressed relative to ASR1 using a Log 10 scale. CQAs and flavonol rutinoside levels in 'Micro Tom' tomato fruit at different ripening stages. Results are averages±SD from three measurements of two independent biological replicates.

To investigate the role of AtMYB12-like transcription factors in tomato, the tomato EST data-base was searched and three ESTs encoding different MYB12-like proteins were identified. The sequence of one EST, which showed the greatest similarity to AtMYB12, was identified as being expressed early during fruit development. This EST sequence was used to identify a full-length cDNA clone which encodes a protein very similar to AtMYB12, and which we named SlMYB12 (*Solanum lycopersicum* MYB12; FIG. 9A,B). The expression of SlMYB12 was analysed by real-time qRT-PCR during tomato fruit development and compared to the levels of flavonols and CQAs at the same stages (FIG. 6A,B). SlMYB12 transcript levels increased markedly between the green and green-yellow stages of fruit development, a time at which the levels of both flavonols and CQAs also rose sharply. At later stages of ripening SlMYB12 transcript levels did not increase further (and in fact declined slightly). The levels of CQAs and flavonols also increased no further, but rather declined in red tomatoes. SlMYB12 was expressed most highly in the peel of developing fruit but was also expressed at a lower level in the flesh where lower amounts of CQAs and flavonols accumulate (FIG. 6C,D). Taken together, these data support the idea that regulation of CQA biosynthesis is a function of SlMYB12 in tomato fruit as well as regulation of flavonol biosynthesis. Our data show that MYB12-like transcription factors are powerful tools for engineering levels of both types of polyphenols, at least in some species that operate both metabolic pathways.

Discussion

Our study demonstrates that expression of the transcription factor, AtMYB12, results in unprecedentedly high levels of flavonol accumulation in both tobacco and tomato (up to about 10% of the dry weight in whole tomato fruit). In tomato fruit significantly higher levels of CQAs also accumulate as a result of expression of AtMYB12. In ripe fruit there were up to 70-fold higher levels of total flavonols and 20-fold higher levels of CQAs, compared to controls. Enhanced levels of both types of polyphenol were observed in MicroTom and Money Maker varieties, indicating that these increases were not variety-specific. The increases in soluble phenolics resulted in very significant increases in the hydrophilic antioxidant capacity of fruit; up to five-fold higher capacities in MicroTom. This is higher than previous attempts to elevate antioxidant capacity in tomato (Schijlen et al., 2006, Giovinazzo et al., 2005). Such elevated antioxidant capacities could contribute significantly to the dietary antioxidant capacity if such tomatoes were consumed as part of a regular diet.

When AtMYB12 was expressed at high levels in tobacco, significant increases in two flavonols only, rutin and kaempferol glycoside, were observed. This ability of AtMYB12 to stimulate flavonol accumulation was predicted from analysis of AtMYB12 function in *arabidopsis* (Mehrtens et al., 2005). The effect of AtMYB12 on CQA levels in tobacco leaves was relatively modest, especially in comparison to the effects of the transcription factor in tomato fruit. It is very likely that the 2-fold increase in CQA levels observed in tobacco expressing AtMYB12 resulted from the transcription factor stimulating the expression of the genes encoding PAL, rather than any direct effect on CQA biosynthesis—since we observed no stimulation of the transcript levels for the genes encoding HQT nor C3H (FIG. 2D and unpublished results) in tobacco. In fact increases of between 2 and 3-fold have been reported for overexpression of PAL in tobacco (Howles et al., 1996), which is the same order of magnitude of increase in CQA levels as observed in our experiments with AtMYB12 in tobacco.

However, AtMYB12 expression induced not only the production of flavonols (quercetin and kaempferol rutinosides), but also CQA levels: 20-fold increases in hydroxycinnamic acid derivatives (CQA, diCQA, and triCQA) were achieved in tomato fruit on whole fruit basis.

The very significant increases in levels of polyphenols from different branches of the phenylpropanoid pathway in tomato fruit was due to the increases in transcript levels of the genes encoding the enzymes of both flavonoid and CQA biosynthesis. Expression of the gene encoding PAL was induced more than 100-fold by AtMYB12. PAL has been suggested to be a major control point determining the flux into phenylpropanoid metabolism, and its induction is likely to be crucial to achieving high levels of accumulation of any polyphenolics. Induction of expression of the gene encoding PAL by AtMYB12 represents a significant difference between the effects of AtMYB12 and the effects of Lc and C1 transcription factors from maize which did not induce PAL expression in tomato (Bovy et al., 2002). Lc and C1 increased flavonol levels to about 0.13 mg per g fresh weight of tomato whereas AtMYB12 increased flavonol levels to over 90 mg per g dry weight (equivalent to 7.1 mg per g fresh weight) and enhanced the already high levels of CQAs by up to 20-fold (total 20 mg per g dry weight, equivalent to 1.6 mg per g fresh weight). In addition, AtMYB12 induced the production of both quercetin and kaempferol-type flavonols. This is in contrast to the activity of Lc and C1 in tomato which induced primarily the production of kaempferol derivatives (Bovy et al., 2002). This difference is attributable to the activation of the gene encoding F3'H, which is necessary for the production of quercetin (FIG. 1), by AtMYB12, which Lc and C1 did not induce. Our data emphasise the importance of the specificity of transcription factors for their target genes in heterologous hosts, for determining the efficacy of engineering strategies to improve metabolite accumulation and antioxidant capacity of crops.

Identified originally as a flavonol-specific transcription factor in *arabidopsis*, AtMYB12 has been shown to target flavonol-specific genes, and the general phenylpropanoid pathway gene encoding 4CL (38). Our results show that the overexpression of AtMYB12 in tomato results in the induction of not only the above mentioned genes but also all other genes that are involved in the biosynthesis of flavonol derivatives, including those encoding PAL, C4H and 4CL. In addition, AtMYB12 also induces the transcript levels of genes involved in CQA biosynthesis including HCT, C3H, and HQT in tomato. The increased accumulation of both diCQA and triCQA, which are the products of further steps in the CQA biosynthetic pathway, suggests that the additional gene(s) required for the biosynthesis of these compounds are probably also induced by the expression of AtMYB12, although these genes remain to be identified at the molecular level.

We do not have a ready explanation for why AtMYB12 might induce CQA and flavonol biosynthesis in tomato but only flavonol biosynthesis in tobacco. AtMYB12 does not induce CQA biosynthesis in *arabidopsis*, but *arabidopsis* lacks HQT, one of the genes required for CQA production (Arima et al., 2002; Niggeweg et al., 2004). Interestingly, however, the P gene of maize and a close homologue (IF35), which encode transcription factors closely related structurally to AtMYB12 (FIG. 9A), and which share some of its target genes, do appear to regulate the production of CGA in maize (Zhang et al., 2003). P lies at a major QTL determining CGA levels in silks of this crop (Szalma et al., 2005) and IF35 maps closely to a minor QTL for the same trait. These observations coupled to ours for the effects of AtMYB12 on CQA levels in tomato fruit suggest that regulation of the pathways for CQA biosynthesis may be an additional and perhaps an ancient function of AtMYB12-like transcription factors. In tobacco it would appear that MYB12-like proteins no longer have the capacity to activate transcription of the genes encoding C3H and HQT, and that alternative regulatory mechanisms have evolved to regulate CQA accumulation. However, the fact that, in tomato, AtMYB12 and likely the endogenous MYB12-like gene S1MYB12, regulate both flavonol and CQA production makes MYBs of the R2R3-MYB subgroup 7 powerful tools for metabolic engineering and improving the health promoting properties of foods, particularly in species that maintain both flavonol and CQA biosynthetic pathways.

Unlike natural foods which usually accumulate a mixture of bioactive compounds including a range of polyphenolics, functional foods produced by metabolic engineering usually have enhanced levels of a single bioactive. Considering the synergistic effects of combinations of different bioactives in the diet (quercetin, kaempferol, CGA and the particularly beneficial diCQA and triCQA; Arima et al., 2002, Ackland et al., 2005), functional foods with increases in several distinct bioacitves (as demonstrated here for tomato fruit-specific expression of AtMYB12) offer significant advantages for health promotion through improving the phytonutrient and hydrophilic antioxidant content of foods.

TABLE 1

Quantification of major phenolics in wild type (MicroTom [MT], Money Maker [MM]) and AtMYB12-expressing tomatoes[a].

| Compound | MT (mg/g DW) | MT-MYB12 (mg/g DW) | Fold increase | MM (mg/g DW) | MM-MYB12 (mg/g DW) | Fold increase |
|---|---|---|---|---|---|---|
| CGA | 0.25 ± 0.04 | 4.96 ± 0.72 | 19.8 | 0.04 ± 0.01 | 1.17 ± 0.25 | 27.2 |
| diCQA | 0.19 ± 0.04 | 4.21 ± 0.69 | 22.2 | 0.03 ± 0.01 | 0.85 ± 0.14 | 26.6 |
| triCQA | 0.28 ± 0.05 | 6.59 ± 1.09 | 23.5 | 0.04 ± 0.01 | 1.36 ± 0.28 | 42.5 |
| QueRut | 0.92 ± 0.20 | 30.90 ± 5.21 | 33.6 | 0.30 ± 0.05 | 20.20 ± 3.40 | 67.3 |
| KaeRut | 0.20 ± 0.04 | 41.70 ± 6.74 | 209.0 | 0.05 ± 0.01 | 28.50 ± 5.62 | 593.5 |
| KaeGRG | ND | 4.47 ± 0.64 | — | ND | 1.12 ± 0.21 | — |
| NCG | ND | 1.55 ± 0.27 | — | ND | 0.43 ± 0.08 | — |
| NC | 0.89 ± 0.24 | 0.85 ± 0.22 | 1.0 | 0.03 ± 0.01 | 0.03 ± 0.01 | 0.9 |

[a]MT, Micro Tom; MM, Monkey Maker; CGA, chlorogenic acid; diCQA, dicaffeoyl quinic acid; triCQA, tricaffeoyl quinic acid; QueRut, quercetin rutinoside; KaeRut, kaempferol rutinoside; KGRG, kaempferol glucosyl-rhamnosylglucoside; NCG, naringenin chalcone glucoside; NC, naringenin chalcone.

TABLE 2

Stability of the AtMYB12-expression phenotype in T1 and T2 generations of transgenic lines in Micro Tom[a].

| Line | Caffeoyl quinic acids (mg/g DW) | Quercetin rutinoside (mg/g DW) | Kaempferol derivatives[b] (mg/g DW) |
|---|---|---|---|
| T1 generation | | | |
| MT | 0.8 ± 0.1 | 1.0 ± 0.1 | 0.2 ± 0.1 |
| 22-1 | 20.3 ± 2.9 | 34.9 ± 4.4 | 46.0 ± 6.9 |
| 12-1 | 18.8 ± 2.6 | 21.9 ± 3.6 | 31.0 ± 4.1 |
| 9-1 | 16.1 ± 2.1 | 18.8 ± 2.7 | 35.1 ± 4.3 |
| T2 generation | | | |
| MT | 0.7 ± 0.1 | 1.0 ± 0.1 | 0.3 ± 0.1 |
| 22-2 | 16.8 ± 2.0 | 40.5 ± 5.0 | 50.4 ± 6.3 |
| 12-2 | 15.5 ± 1.7 | 35.4 ± 4.1 | 42.7 ± 5.1 |
| 9-2 | 20.8 ± 2.2 | 32.6 ± 4.0 | 46.9 ± 5.4 |

[a]Mature fruits were harvested from hemizygous T1 (A) and homozygous T2 (B) populations of three independent transgenic lines (line 22, 12 and 9). Eight plants from each independent line were analyzed. From each plant 2-3 fruits were pooled, methanol extracts were prepared, and phenylpropanoid levels were determined. DW, dry weight.
[b]Total amount of kaempferol rutinoside and kaempferol glucosyl-rhamnosylglucoside

TABLE S1

Identification of major phenylpropanoids in leaf and flower of wild type and AtMYB12-expressing tobacco plants.

| Peak | Putative Identification | UV/Vis λmax (nm) | [M − H]+ (m/z) | MS/MS Fragments |
|---|---|---|---|---|
| N1 | 3-Caffeoyl quinic acid | (298), 326 | 355 | 355 (163) |
| N2 | Caffeoyl-spermidnine | (295), 320 | 308 | 308 (163) |
| N3 | 4-Caffeoyl quinic acid | (298), 326 | 355 | 355 (163) |
| N4 | 5-Caffeoyl quinic acid | (298), 326 | 355 | 355 (163) |
| N5 | Quercetin glucosyl-glucoside rhamnoside | 258, 353 | 773 | 773 (627, 611, 465, 449, 303) |
| N6 | Kaempferol glucosyl-glucoside rhamnoside | 266, 347 | 757 | 757 (611, 595, 449, 433, 287) |
| N7 | N-Caffeoyl-N'-dihydrocaffeoyl spermidine | (290), 320 | 472 | 472 (310, 163) |
| N8 | Quercetin rutinoside (rutin) | 256, 353 | 611 | 611 (465, 303) |
| N9 | Dicaffeoyl spermidine | (294), 320 | 470 | 470 (308, 163) |
| N10 | Kaempferol rutinoside | 265, 348 | 595 | 595 (449, 433, 287) |
| N11 | Kaempferol malonylglucoside | 266, 345 | 535 | 535 (287) |
| N12 | unknown | 287, 328 | 273 | 273, 195 |
| N13 | tricoumaroyl spermidine | 297, 305 | 584 | 584 (438, 292, 147) |

TABLE S2

Identification of major phenylpropanoids in peel and flesh of wild type and AtMYB12-expressing tomato fruit.

| Peak | Putative Identification | UV/Vis λmax (nm) | [M − H]+ (m/z) | MS/MS Fragments |
|---|---|---|---|---|
| S1 | coumaric acid glucoside I | (295), 313 | 327 | 327(163) |
| S2 | 5-Caffeoyl quinic acid | (298), 326 | 355 | 355 (163) |
| S3 | Quercetin diglucoside | 258, 353 | 627 | 627 (465, 303) |
| S4 | Quercetin glucosyl-glucoside rhamnoside | 256, 353 | 773 | 773 (627, 611, 465, 449, 303) |
| S5 | Kaempferol diglucoside | 265, 346 | 611 | 611 (449, 287) |
| S6 | Kaempferol glucosyl-glucoside rhamnoside | 266, 347 | 757 | 757 (611, 595, 449, 433, 287) |
| S7 | Naringenin | 284, (329) | 273 | 273 (153, 147) |
| S8 | Quercetin rutinoside (rutin) | 256, 353 | 611 | 611 (465, 303) |
| S9 | Dicaffeoyl quinic acid | (300), 330 | 539 | 539 (377, 163) |
| S10 | Kaempferol rutinoside | 265, 345 | 595 | 595 (449, 287) |
| S11 | Naringenin chalcone glucoside | (315), 367 | 435 | 435 (273) |
| S12 | Tricaffeoyl quinic acid | (303), 329 | 701 | 701 (539, 377) |
| S13 | Naringenin chalcone | 369 | 273 | 273 (153, 147) |

TABLE S3

Primers used for real-time RT-PCR of structural genes in phenylpropanoid biosynthetic pathway in tomato.

| Primer | Gene | Sequence (5' to 3') |
|---|---|---|
| PAL_TOM_F | PAL | AACCTATCTCGTGGCTCTTT (SEQ ID NO: 35) |
| PAL_TOM_R | PAL | TCTTTTTCGCTGAATCTTGC (SEQ ID NO: 36) |
| C4H_TOM_F | C4H | CAACAGAAAGGAGAGATCAACGAG (SEQ ID NO: 37) |
| C4H_TOM_R | C4H | CACAGCCTGAAGGTATGGAAGC (SEQ ID NO: 38) |
| 4CL_TOM_F | 4CL | ACACACAAAGGCTTAGTCACGA (SEQ ID NO: 39) |
| 4CL_TOM_R | 4CL | AACAGAGGCAACACACACATCA (SEQ ID NO: 40) |
| CHSTOM_F | CHS | TGGTCACCGTGGAGGAGTATC (SEQ ID NO: 41) |

TABLE S3-continued

Primers used for real-time RT-PCR of structural genes in phenylpropanoid biosynthetic pathway in tomato.

| Primer | Gene | Sequence (5' to 3') |
| --- | --- | --- |
| CHS_TOM_R | CHS | GATCGTAGCTGGACCCTCTGC (SEQ ID NO: 42) |
| CHI_TOM_F | CHI | GTTTTTCACAAACCAACAGTTCTGAT (SEQ ID NO: 43) |
| CHI_TOM_R | CHI | GAAGCAGTGCTCGATTCCATAAT (SEQ ID NO: 44) |
| F3H_TOM_F | F3H | CACACCGATCCAGGAACCAT (SEQ ID NO: 45) |
| F3H_TOM_R | F3H | GCCCACCAACTTGGTCTTGTA (SEQ ID NO: 46) |
| F3'H_TOM_F | F3'H | GCACCACGAATGCACTTGC (SEQ ID NO: 47) |
| F3'H_TOM_R | F3'H | CGTTAGTACCGTCGGCGAAT (SEQ ID NO: 48) |
| F3'5'H_TOM_F | F3'5'H | GGCAATTGGACGAGATCCTG (SEQ ID NO: 49) |
| F3'5'H_TOM_R | F3'5'H | AAGGAACCTCTCGGGAGTGAA (SEQ ID NO: 50) |
| FLS_TOM_F | FLS | GAGCATGAAGTTGGGCCAAT (SEQ ID NO: 51) |
| FLS_TOM_R | FLS | TGGTGGGTTGGCCTCATTAA (SEQ ID NO: 52) |
| DFR_TOM_F | DFR | TCCGAAGACGACAACGGTTT (SEQ ID NO: 53) |
| DFR_TOM_R | DFR | TGACAAGCCAAGAGCCGATAA (SEQ ID NO: 54) |
| ANS_TOM_F | ANS | GAACTAGCACTTGGCGTCGAA (SEQ ID NO: 55) |
| ANS_TOM_R | ANS | TTGCAAGCCAGGCACCATA (SEQ ID NO: 56) |
| GT_TOM_F | GT | CGAACGACGAAACACTGTTGA (SEQ ID NO: 57) |
| GT_TOM_R | GT | TGCAGCATAGATGGCATTGG (SEQ ID NO: 58) |
| RT_TOM_F | RT | CTGGCAATGCAAACAGAGTGA (SEQ ID NO: 59) |
| RT_TOM_R | RT | TCGACTTGCGGAAGAGTGAGA (SEQ ID NO: 60) |
| C3H_TOM_F | C3H | CATAAACTCTACCACCGTCTCC (SEQ ID NO: 61) |
| C3H_TOM_R | C3H | AATCCATCCCATTTCTACTCAA (SEQ ID NO: 62) |
| HCT_TOM_F | HCT | AGGTGAAAAACTCAACGATGGT (SEQ ID NO: 63) |
| HCT_TOM_R | HCT | ACACTAGGCGTGTGGAAATTAG (SEQ ID NO: 64) |
| HQT_TOM_F | HQT | GTGTTTTGTTTGTTGAGGCTGA (SEQ ID NO: 65) |
| HQT_TOM_R | HQT | TGATGAAGTGGATGGATGAGAG (SEQ ID NO: 66) |
| ASR1_TOM_F | ASR1 | CCTGTTCCACCACAAGGACAA (SEQ ID NO: 67) |
| ASR1_TOM_R | ASR1 | GTGCCAAGTTTACCGATTTGC (SEQ ID NO: 68) |

References Cited in this Example:

Ackland, M. L., van de Waarsenburg, S., & Jones, R. (2005) *In Vivo* 19, 69-76.

Arima, H., Ashida, H., & Danno, G. (2002) *Biosci Biotechnol Biochem* 66, 1009-1014.

Asian, M., Orhan, D. D., Orhan, N., Sezik, E., & Yesilada, E. (2007) *J Med Food* 10, 396-400.

Bevan, M. (1984) *Nucl Acids Res* 12, 8711-8721.

Bovy, A., de Vos, R., Kemper, M., Schijlen, E., Almenar Pertejo, M., Muir, S., Collins, G., Robinson, S., Verhoeyen, M., Hughes, S., et al. (2002) *Plant Cell* 14, 2509-2526.

Braganhol, E., Zamin, L. L., Canedo, A. D., Horn, F., Tamajusuku, A. S., Wink, M. R., Salbego, C., & Battastini, A. M. (2006) *Anticancer Drugs* 17, 663-671.

Cheng, J. C., Dai, F., Zhou, B., Yang, L., & Liu, Z. L. (2007) *Food Chem* 104, 132-139.

Choi, J., Park, J. K., Lee, K. T., Park, K. K., Kim, W. B., Lee, J. H., Jung, H. J., & Park, H. J. (2005) *J Med Food* 8, 348-352.

Davuluri, G. R., van Tuinen, A., Fraser, P. D., Manfredonia, A., Newman, R., Burgess, D., Brummell, D. A., King, S. R., Palys, J., Uhlig, J., et al. (2005) *Nat Biotechnol* 23, 890-895.

Ditta, G., Stanfield, S., Corbin, D., & Helinski, D. R. (1980) *Proc Natl Acad Sci USA* 77, 7347-7351

Feng, R., Lu, Y., Bowman, L. L., Qian, Y., Castranova, V., & Ding, M. (2005) *J Biol Chem* 280, 27888-27895.

Fillatti, J. J. (1987) Bio Technol 5, 726-730.

Frohman, M. A., Dush, M. K., & Martin, G. R. (1988) *Proc Natl Acad Sci USA* 85, 8998-9002.

Giovinazzo, G., D'Amico, L., Paradiso, A., Bollini, R., Sparvoli, F., & DeGara, L. (2005) *Plant Biotechnol J* 3, 57-69.

Guerineau, F. & Mullineaux, P. (1993) in *Plant Molecular Biology Labfax*, ed. Croy, R. R. D. (BIOS Scientific Publishers Ltd, Oxford), pp. 121-147.

Hertog, M. G., Feskens, E. J., Hollman, P. C., Katan, M. B., & Kromhout, D. (1993) *Lancet* 342, 1007-1011.

Horsch et al., (1985) *Science* 227, 1229-1231.

Hou, D. X., Fujii, M., Terahara, N., & Yoshimoto, M. (2004) *J Biomed Biotechnol* 2004, 321-325.

Howles, P. A., Sewalt, V., Paiva, N. L., Elkind, Y., Bate, N. J., Lamb, C., & Dixon, R. A. (1996) *Plant Physiol* 112, 1617-1624.

Islam, M. S. (2003) *J Am Soc Hortic Sci* 128, 182-187.

Islam, S. (2006) *J Food Sci* 71, R13-R21.

Iusem, N. D., Bartholomew, D. M., Hitz, W. D., & Scolnik, P. A. (1993) *Plant Physiol* 102, 1353-1354.

Jones, D. T., W. R. Taylor and J. M. Thornton. (1992). *Computer Applications in the Biosciences (CABIOS)* 8: 275-282.

Joseph, J. A., Shukitt-Hale, B., Denisova, N. A., Bielinski, D., Martin, A., McEwen, J. J., & Bickford, P. C. (1999) *J Neurosci* 19, 8114-8121.

Kim, S. S., Park, R. Y., Jeon, H. J., Kwon, Y. S., & Chun, W. (2005) *Phytother Res* 19, 243-245.

Knekt, P., Kumpulainen, J., Jarvinen, R., Rissanen, H., Heliovaara, M., Reunanen, A., Hakulinen, T., & Aromaa, A. (2002) *Am J Clin Nutr* 76, 560-568.

Luo, J., Nishiyama, Y., Fuell, C., Taguchi, G., Elliott, K., Hill, L., Tanaka, Y., Kitayama, M., Yamazaki, M., Bailey, P., et al. (2007) *Plant J* 50, 678-695.

Martin, C., Carpenter, R., Sommer, H., Saedler, H., & Coen, E. S. (1985) *Embo J* 4, 1625-1630.

Matsui, T., Ebuchi, S., Fujise, T., Abesundara, K. J., Doi, S., Yamada, H., & Matsumoto, K. (2004) *Biol Pharm Bull* 27, 1797-1803.

Mehrtens, F., Kranz, H., Bednarek, P., & Weisshaar, B. (2005) *Plant Physiol* 138, 1083-1096.

Moco, S., Bino, R. J., Vorst, O., Verhoeven, H. A., de Groot, J., van Beek, T. A., Vervoort, J., & de Vos, C. H. (2006) *Plant Physiol* 141, 1205-1218.

Muir, S. R., Collins, G. J., Robinson, S., Hughes, S., Bovy, A., Ric De Vos, C. H., van Tunen, A. J., & Verhoeyen, M. E. (2001) *Nat Biotechnol* 19, 470-474.

Nakajima, Y., Shimazawa, M., Mishima, S., & Hara, H. (2007) *Life Sci* 80, 370-377.

Niggeweg, R., Michael, A. J., & Martin, C. (2004) *Nat Biotechnol* 22, 746-754.

Nijveldt, R. J., van Nood, E., van Hoorn, D. E., Boelens, P. G., van Norren, K., & van Leeuwen, P. A. (2001) *Am J Clin Nutr* 74, 418-425.

Pellegrini, N. (1999) *Methods Enzymol* 299, 379-389.

Raffo, A., Leonardi, C., Fogliano, V., Ambrosino, P., Salucci, M., Gennaro, L., Bugianesi, R., Giuffrida, F., & Quaglia, G. (2002) *J Agric Food Chem* 50, 6550-6556.

Rein, D., Schijlen, E., Kooistra, T., Herbers, K., Verschuren, L., Hall, R., Sonnewald, U., Bovy, A., & Kleemann, R. (2006) *J Nutr* 136, 2331-2337.

Renaud, S. & de Lorgeril, M. (1992) *Lancet* 339, 1523-1526.

Rigano, D., Formisano, C., Basile, A., Lavitola, A., Senatore, F., Rosselli, S., & Bruno, M. (2007) *Phytother Res* 21, 395-397.

Saitou, N., and M. Nei. (1987). *Molecular Biology and Evolution* 4: 406-425. Schijlen, E., Ric de Vos, C. H., Jonker, H., van den Broeck, H., Molthoff, J., van Tunen, A., Martens, S., & Bovy, A. (2006) *Plant Biotechnol J* 4, 433-444

Seeram, N. P., Adams, L. S., Hardy, M. L., & Heber, D. (2004) *J Agric Food Chem* 52, 2512-2517.

Soobrattee, M. A., Bahorun, T., & Aruoma, O. I. (2006) *Biofactors* 27, 19-35.

Stracke, R., Ishihara, H., Huep, G., Barsch, A., Mehrtens, F., Niehaus, K., & Weisshaar, B. (2007) *Plant J* 50, 660-677.

Szalma, S. J., Buckler, E. S. t., Snook, M. E., & McMullen, M. D. (2005) *Theor Appl Genet* 110, 1324-1333.

Tamura, H., Akioka, T., Ueno, K., Chujyo, T., Okazaki, K., King, P. J., & Robinson, W. E., Jr. (2006) *Mol Nutr Food Res* 50, 396-400.

Thompson, J. D., Higgins, D. G. and Gibson, T. J. (1994) *Nucleic Acids Research,* 22:4673-4680.

Zhang, P. F., Wang, Y. B., Zhang, J. B., Maddock, S., Snook, M., & Peterson, T. (2003) *Plant Mol Biol* 52, 1-15.

Zhou, B., Yang, L., & Liu, Z. L. (2004) *Chem Phys Lipids* 131, 15-25.

Example 2

Ectopic Production of Anthocyanins Results in Purple Tomatoes with Increased Antioxidant Capacity and Extended Shelf Life As part of the human diet, flavonoids offer protection against a broad range of human diseases. Consumption of foods containing high levels of flavonoids is associated with a lower risk of cancer, cardiovascular and neurological diseases.

Anthocyanins represent a subset of flavonoids with particularly high antioxidant capacity, and concomitantly strong health-promoting effects. With the objective of producing fruit with high levels of anthocyanins, we expressed two transcription factors from snapdragon in tomato fruit. Expression of the two genes together caused an increase in the expression of all the genes committed to anthocyanin biosynthesis and resulted in fruit which displayed an intense purple coloration in both peel and flesh. Anthocyanins accumulated at levels significantly higher than anything previously reported and enhanced the antioxidant capacity three-fold. High flavonoid fruit were associated with delayed ripening, resistance to opportunistic infection and, consequently, a considerably longer shelf life.

In any attempt to improve crops through metabolic engineering, the amounts of target metabolites induced are of primary importance. For applications, changes in flux need to be large, meaning that much of the metabolic engineering that has been reported for crop plants has not yet been applied successfully. Anthocyanins are pigments produced by most higher plants. As part of the human diet they offer protection against cardiovascular disease, certain cancers and age-related degenerative diseases (1-4). There is evidence that anthocyanins also have anti-inflammatory activity (5), promote visual acuity (6), and hinder obesity and diabetes (7). The health-promoting role of anthocyanins has been linked to their high antioxidant activities (8) although recent reports suggest that some of the biological effects of anthocyanins and flavonoids are actually related to their ability to modulate mammalian cell signalling pathways (9, 10). However all these effects are dependent on relatively high levels of dietary flavonoids.

Figures from the National Cancer Institute of America (11) argue strongly for the development of strategies to increase the levels of health-promoting bioactive compounds such as anthocyanins in the fruits and vegetables that people actually consume in significant amounts.

Tomato is an excellent candidate for enhancement of its flavonoid content. It is an important food crop worldwide and its levels of flavonoids are considered sub-optimal, with only small amounts of naringenin chalcone and rutin accumulating in tomato peel (12). Flavonoids represent an important source of hydrophilic dietary antioxidants, whereas the most abundant antioxidant in tomato fruit is lycopene, a lipophilic antioxidant. Generally, foods rich in both soluble and membrane-associated antioxidants are considered to offer the best protection against disease.

Although most tomato cultivars do not produce anthocyanins in fruit, low and light-dependent accumulation of anthocyanins in sectors of the skin has been achieved by introgression of a trait from a wild relative of tomato (13). Genetic engineering strategies have also provided modest success. Silencing of the tomato DET1 gene which represses photomorphogenesis, resulted in increases in flavonoid levels of up to 3.5-fold (14). Constitutive, high-level activity of chalcone isomerase (CHI) in tomato resulted in up to 78-fold increases in the levels of flavonols in fruit peel (12). However, because peel accounts for only about 5% of fruit mass, the total levels were no more than 300 µg per g fresh weight.

Generally, transcription factors that regulate the expression of the genes involved in entire metabolic pathways provide the most effective tools for engineering metabolic flux (15, 16). Consequently, overexpression of a gene encoding a transcription factor that regulates anthocyanin production in tomato resulted in limited purple spotting on the skin and pericarp (17). However, overexpression of Lc and C1, two regulatory genes that encode transcription factors that control anthocyanin biosynthesis in maize, resulted in tomato fruit containing increased levels of flavonols (130 µg per g fresh weight) but no anthocyanins (18).

While regulatory proteins offer the greatest potential to enhance anthocyanin biosynthesis, their specificity may differ in different plant species. Differences in their efficacy in inducing anthocyanin production and in their target gene specificity have been reported (19-22), and may explain the lack of anthocyanin production following expression of Lc and C1 in tomato fruit (18).

With the objective of producing tomato fruit with significantly elevated levels of anthocyanins by harnessing the broad target specificity of selected transcription factors, we have expressed the Delile (Del) and Rosea1 (Ros1) genes from *A. majus* in the fruit of transgenic tomatoes. Del encodes a basic helix-loop-helix transcription factor and Ros1, encodes a MYB-related transcription factor (20, 23). See materials and methods section at the end of this example.

A binary vector was constructed containing the Del and Ros1 cDNAs each under the control of the fruit-specific E8 promoter (FIG. 10.1A). Tomato leaf discs (*Solanum lycopersicum* cv. Micro-Tom) were transformed with the construct and four primary transformants were investigated in detail; designated Del/Ros1 lines C, N, Y and Z. The presence of the transgenes was confirmed by both DNA gel blots and PCR analysis of genomic DNA. The transgenes were inherited stably in later generations and could be transferred to other genetic backgrounds with no loss of phenotype (Money Maker, Ailsa Craig and VF36) by cross-pollination (FIG. 10.5).

Del/Ros1 primary transformants developed normally during vegetative growth and were indistinguishable from controls. Stems and leaves showed no abnormal anthocyanin accumulation. Transgenic fruit developed normally and started to show visible signs of purple pigmentation at the end of the mature green stage (FIG. 10.1B). Pigmentation matched the expression pattern of the E8 gene (24) and intensified rapidly in the few days after its onset, initially associated with the vascular tissue but quickly extending to peel, pericarp and inner flesh (FIG. 10.1, C and D). At maturity, the different transgenic tomato lines showed a range of phenotypes, with medium (Del/Ros1Z), strong (Del/Ros1C and Del/Ros1Y) or very strong accumulation of anthocyanin (Del/Ros1N). Fruit from plants of the $T_1$ and $T_2$ generations showed more intense pigmentation than those from the $T_0$ generation. For line Del/Ros1N, the highest pigment accumulator, fruit from plants of the $T_1$, $T_2$ and $T_3$ generations were almost black.

The total anthocyanin content was determined in the fruit of the $T_o$ Del/Ros1 lines and compared to those in wild type Micro-Tom fruit (FIG. 10.6A). The highest concentrations were found in the fruit of line N, which averaged 2.83±0.46 mg of anthocyanin per g fresh weight. Anthocyanins were virtually undetectable in wild type fruit. Ripe tomatoes from both transgenic Del/Ros1N and wild type lines were harvested and peel and flesh were analyzed separately by HPLC for their phenylpropanoid contents (FIG. 10.2). High levels of anthocyanins were detected in both peel and flesh of purple fruit (FIG. 10.2, A and B). The major anthocyanins were 3,5-diglucosides acylated with cinnamic acids (FIG. 10.2C and 10.7). In peel of purple fruit several methanol-soluble phenolic compounds were detected that were barely detectable in peel of wild type tomatoes (FIG. 10.2D) including the main natural flavonol, rutin, and other flavonol derivatives (FIG. 10.2, D and F). There were no increases in flavonols in the flesh of transgenic tomatoes (FIG. 10.2E).

Comparative HPLC data showed that the same anthocyanins and flavonols accumulated in all four independent lines (FIG. 10.6, B and C).

The alterations in gene expression induced by Del and Ros1 in fruit from line N were determined by comparison to control fruit by suppression subtractive hybridization (SSH). Differentially expressed genes in tomato fruit are listed in table 2.S1. Expression of Del and Ros1 increased the transcript levels of almost all of the genes encoding anthocyanin biosynthetic enzymes and genes encoding enzymes required for side-chain modification; a putative anthocyanin acyltransferase and two genes likely involved in the transport of anthocyanins into the vacuole including a putative anthocyanin transporter.

The differential expression of the genes identified by SSH was validated by RNA gel blot hybridization (FIG. 10.3A), which was also used to verify the expression of Del and Ros1 and to demonstrate the induction of expression of the gene encoding flavanone 3-hydroxylase (F3H) by Del and Ros1, since this gene was not isolated by SSH. With the exception of PAL, there was no detectable expression of any of these genes in wild type tomato fruit. The induction of expression of these anthocyanin biosynthetic genes was confirmed by micro-array analysis for all the independent transformed lines (table 2.S2). The induction of PAL expression by Del and Ros1 significantly enhanced PAL enzyme activity, increasing it 200-fold in Del/Ros1 line N (FIG. 10.3C). The transcription factors also increased chalcone isomerase (CHI) activity three-fold, but only transiently during fruit development (FIG. 10.8)

Changes in total antioxidant activity between transgenic and wild type tomato fruit was measured using the trolox equivalent antioxidant capacity (TEAC). In Del/Ros1N fruit the activity of the water-soluble fraction (containing anthocyanins) was increased 3-fold compared to the control (FIG. 10.3D) and was not obtained at the expense of the lipo-soluble antioxidants (extracted with acetone). The increase in antioxidant activity in line C was less pronounced, but still significantly higher than controls (FIG. 10.3D).

Fruit from Del/Ros1 line N had normal size, shape and number of seeds. However, fruit from this line exhibited delayed softening when compared to control fruit. This was apparent from the appearance of the fruit both on the vine and during post-harvest storage (FIG. 10.4A) and the reduced level of opportunistic fungal infection of fruit under either condition (FIG. 10.4B). To confirm these striking visual observations, purple and red fruit in two genetic backgrounds—Micro-Tom and fruit obtained by crossing Del/Ros1N with tomato cv. Money Maker—were compared in a series of mechanical property tests. Tensile tests revealed significant differences in strength and stiffness between purple and red tomatoes for skin (Table 2.S3). Tomato lines expressing Del and Ros1 had significantly stiffer and stronger fruit skin than control fruit (p<0.01). Cutting and compression tests on cut halves of the same tomatoes, for which the flesh is the major component, were less conclusive, although purple Micro-Tom tomatoes were significantly firmer than red Micro-Tom tomatoes, at p<0.01 and <0.04 respectively.

To test whether the extended shelf life was specific to tomatoes accumulating anthocyanins, Del/Ros1N was crossed to aw mutants in two different genetic backgrounds (Ailsa Craig and VF36). aw mutants lack DFR activity and can not make anthocyanins (25). In the $F_2$ generation of both crosses plants, harbouring the transgene and lacking DFR activity were selected. These plants produced orange fruit which accumulated high levels of kaempferol, quercetin and myricetin glycosides (FIG. 10.9). Measurement of antioxidant capacities showed that the orange fruit had antioxidant capacities that were two-fold higher than for the parental aw lines although TEAC values were never as high as for purple fruit segregating in the same population (FIG. 10.4E). The lower antioxidant capacities of the orange fruit compared to the purple fruit probably reflect the lower intrinsic antioxidant capacities of dihydroflavonols compared to anthocyanins. Most strikingly, orange, high flavonol tomatoes also had markedly extended shelf lives compared to parental lines (FIG. 10.4D).

Longer shelf life, associated with slower fruit softening, integrity of stored fruit, ease of transportation and resistance to post-harvest pathogens, is probably the most important trait for commercially-grown tomatoes. Since neither cell wall phenolics nor lignin composition were significantly increased in purple fruit (FIG. 10.10), it is possible that slower fruit softening is the result of delayed ripening from the breaker stage in transgenic fruit. To test this possibility, expression of two genes that are markers for different stages of fruit development (26) was compared in purple and red fruit aged by date of reaching the breaker stage. For the genes encoding phytoene synthase (PSY) and S-adenosyl-L methionine synthase 1 (SAM1), ripening related expression changes were slowed relative to controls (FIG. 10.11A).

Production of ethylene, required for full ripening in climacteric fruit such as tomato, was transiently increased 2-fold in purple transgenic fruit compared to controls (FIG. 10.11), suggesting that the effects of elevated flavonoids on fruit ripening were not due to reduced ethylene production. Confirming this, application of exogenous ethylene to detached fruits was unable to restore the normal rate of softening to Del/Ros1 fruit.

As an alternative explanation, we suggest an ethylene-independent mechanism where ripening is slower in high flavonoid fruit because of their increased antioxidant capacity. The levels of reactive oxygen species (ROS) do increase markedly in the later stages of tomato ripening and are needed to facilitate many of the metabolic changes associated with maturation of tomato fruit (27). Accordingly, cultivars with short shelf life show reduced scavenging ability and associated increases in oxidative stress (28). We suggest that the significant elevation in the antioxidant capacities achieved by increasing flavonoid biosynthesis (with the accumulation of either dihydroflavonols or anthocyanins) reduces the tissue-damaging activity of ROS and delays the final stages of ripening, resulting in the marked extension in shelf life of the transgenic tomatoes. Increases in polyamines have also been reported to extend shelf life of tomatoes (29), and may achieve their effects through their activities as antioxidants. The increased production of antimicrobial phenolic intermediates in Del/Ros1 tomatoes, may explain the reduced levels of opportunistic infection of these fruit (30).

Our study demonstrates that expression of the specific anthocyanin-regulating transcription factors, Del and Ros1, induces the accumulation of unprecedentedly high levels of anthocyanins. The reasons underlying the success of this regulatory combination are multifold. Firstly, expression of both the MYB and the bHLH transcription factors gives rise to much higher levels of gene induction throughout all the tissues of the fruit, in contrast to expression of either the MYB or the bHLH protein on its own (17, 31). Secondly, Del and Ros1 activate a broader spectrum of genes in the phenylpropanoid/flavonoid pathway than Lc and C1 in tomato. PAL transcript levels and enzyme activity were increased very significantly by Del and Ros1 in contrast to the effects of Lc and C1 (18). There are several reports that PAL activity determines flux through phenylpropanoid metabolism in *Solanaceous* species (32,33) and the effects of Del and Rost on PAL activity may explain the very high levels of anthocyanins that accumulated in Del/Rost tomato fruit. Thirdly, Del and Ros1 induced CHI activity which Lc and C1 did not (18). Since CHI activity may limit the flux through flavonoid metabolism in tomato skin (12), the ability of Del and Ros1 to induce the activity of this enzyme may also have contributed to the high levels of anthocyanin or dihydroflavonol accumulation achieved. Fourthly, Del/Ros1 activated F3'5'H whereas Lc/C1 failed to activate the expression of this gene meaning that dihydrokaempferol rather than dihydromyricetin would have been formed as an intermediate in flavonoid biosynthesis. In *Solanaceous* species, DFR is specific for dihydromyricetin and will not accept dihydrokaempferol as a substrate, which may explain why Lc and C1 failed to induce anthocyanin accumulation in tomato fruit (18).

The high anthocyanin tomatoes already developed represent a registered food source for extraction of high levels of purple anthocyanins. Crude extraction can be achieved very easily by squeezing the tomatoes. The crude extracts of the purple tomatoes have a good color (stronger and more blue than that of purple sweet potato) but they are less stable than the sweet potato anthocyanins.

In terms of improving the color of the anthocyanins and giving stronger blues, a high flavonol, high anthocyanin tomato has been developed (AtMYB12/Del/Ros1) which is more intensely colored with a pigment that is far bluer than with anthocyanins on their own (indigo as compared to purple; FIG. 10.12). This is due to the copigmentation effect of the flavonols in combination with the anthocyanins. These tomatoes represent an excellent source of this new color which would be easy to extract for preparation of food colorants. Alternatively the anthocyanins and flavonols could be prepared separately from the lines producing high levels of each, and then mixed, post extraction, to develop the color required.

Our results show that selective use of transcription factors with broad target specificity can achieve very significant increases in flux along secondary metabolic pathways in plants. They also shed new light on the processes involved in the later stages of fruit ripening in tomato and, unexpectedly, positively impact an important quality trait as well as providing health-promoting fruit in this important crop.

TABLE 2.S1

Genes upregulated in Del/Ros1N tomato fruit. cDNA fragments identified by SSH were cloned and sequenced. The putative identity of the corresponding genes was assigned based on a BLASTX search against the nonredundant protein database in GenBank. Accession numbers and e-values of the best hits are shown. Number of total clones isolated corresponding to individual genes and level of expression in Del/Ros1N tomato fruit, determined by dot blot analysis, are also reported.

| Clone | Clone ID (first hit blast X) | accession | E-value | total clones | expression level |
|---|---|---|---|---|---|
| PAL | Phenylalanine ammonia-lyase *Lycopersicon esculentum* | P26600 | 8e-134 | 39 | +++ |
| C3H | Putative p-coumaroyl 3'-hydroxylase CYP98A-C1 *Coffea canephora* | ABB83676.1 | 7e-51 | 1 | ++ |
| CHI (like) | Putative chalcone isomerase 4 *Glycine max* | AAT94362.1 | 4e-48 | 2 | + |
| F3'5'H | Flavonoid 3',5'-hydroxylase *Solanum tuberosum* | AAV85472.1 | 5e-113 | 3 | ++ |
| DFR | Dihydroflavonol reductase *Solanum tuberosum* | AAZ57436.1 | 7e-39 | 2 | + |
| ANS | Leucoanthocyanidin dioxygenase (LDOX) *Petunia x hybrida* | P51092 | 8e-82 | 9 | +++ |
| 3-GT | Flavonoid 3-glucosyl transferase *Solanum tuberosum* | AAX63403.1 | 5e-62 | 6 | ++ |
| 5-GT | Anthocyanin 5-O-glucosyltransferase *Petunia x hybrida* | BAA89009.1 | 5e-39 | 5 | ++ |
| RT | UDP rhamnose: anthocyanidin-3-glucoside rhamnosyltransferase *Petunia x hybrida* | CAA81057.1 | 1e-18 | 1 | ++ |
| AAC | Transferase *Arabidopsis thaliana* | NP_173852.1 | 8e-12 | 2 | ++ |
| GST | Glutathione S-transferase *Petunia x hybrida* | CAA68993.1 | 5e-36 | 10 | ++ |
| PAT | Putative anthocyanin permease *Lycopersicon esculentum* | AAQ55183.1 | 3e-59 | 3 | ++ |
| Defensin | Gamma-thionin *Lycopersicon esculentum* | CAB42006.1 | 3e-37 | 5 | +++ |
| Del | Delila *Antirrhinum majus* | AAA32663.1 | 0.14 | 1 | + |

TABLE 2.S2

Expression of anthocyanin biosynthetic genes in independent Del/Ros1 lines compared to untransformed controls. Fold-changes in flavonoid gene expression of non-transgenic and Del/Ros1 overexpressing tomato lines from DNA microarray data are given in relation to a common reference which comprised equal amounts of RNA from all sample types. A negative value indicates a down regulation relative to the common reference and a positive value an up regulation. Controls are untransformed wild type Micro Tom.

| EST ID | Control 1 | Control 2 | Del/Ros1 Z | Del/Ros1 C | Del/Ros1 Y | Del/Ros1 N | gene |
|---|---|---|---|---|---|---|---|
| (TC84666) phenylalanine ammonia-lyase | -3.92 | -9.32 | -2.19 | 1.48 | 1.57 | 1.75 | PAL |
| (TC93956) cinnamic acid 4-hydroxylase | -1.73 | -2.55 | -1.54 | -1.22 | -1.04 | 1.57 | C4H |
| (TC89693) 4-coumarate—CoA ligase 1 | -1.59 | -1.22 | -1.06 | 1.09 | 1.23 | -1.09 | 4CL |
| (TC86565) chalcone synthase 1 | -2.73 | -4.79 | -1.27 | 2.17 | 1.16 | -1.04 | CHS1 |
| (TC90271) chalcone synthase 2 | -1.60 | -3.07 | 1.16 | 1.01 | 1.06 | 1.01 | CHS2 |
| (TC86916) flavanone 3-hydroxylase | -2.20 | -2.36 | 2.01 | 1.33 | -1.37 | -1.01 | F3H |
| c32-TOM_f3p5ph_ flavonoid 3'5' hydroxylase (tomato) | -1.51 | -1.78 | 2.50 | 1.66 | -1.71 | 4.92 | F3'5'H |

TABLE 2.S2-continued

Expression of anthocyanin biosynthetic genes in independent Del/Ros1 lines compared to untransformed controls. Fold-changes in flavonoid gene expression of non-transgenic and Del/Ros1 overexpressing tomato lines from DNA microarray data are given in relation to a common reference which comprised equal amounts of RNA from all sample types. A negative value indicates a down regulation relative to the common reference and a positive value an up regulation. Controls are untransformed wild type Micro Tom.

| EST ID | Control 1 | Control 2 | Del/Ros1 Z | Del/Ros1 C | Del/Ros1 Y | Del/Ros1 N | gene |
|---|---|---|---|---|---|---|---|
| (c32-TOM_ANS_cont) anthocyanidin synthase (tomato) | −1.53 | −1.14 | −1.22 | 2.06 | −1.24 | 2.08 | ANS |
| (TC90395) flavonol 3-O-glucosyltransferase | −3.20 | −2.89 | −2.36 | 1.61 | 1.39 | −1.84 | F-3-GT |
| (TC91185) anthocyanidin 3-O-glucosyltransferase | −2.23 | −2.10 | 1.27 | 2.85 | −1.46 | 3.34 | A-3-GT |
| (TC89444) anthocyanin 5-O-glucosyltransferase (Petunia) | −3.71 | −4.11 | −1.13 | 1.10 | −1.04 | 1.04 | A-5-GT |

TABLE 2.S3

Expression of Del and Ros1 delays softening of tomato fruit. Young's modulus, E, and tensile strength, σ, for red and purple tomatoes, averaged over n fruit. Significance levels, p, between red and purple tomatoes are shown in each case. For the larger tomatoes in the Money Maker background, the average value of E was 70.9 Pa for purple fruit compared to 50.3 Pa for red fruit. Likewise, σ for purple tomatoes (5.3 Pa) was significantly greater than for red ones (2.9 Pa). Similar significant differences were observed for red and purple tomatoes in the Micro-Tom background.

| a | E (MPa) | p | n = | σ(MPa) | p | n = |
|---|---|---|---|---|---|---|
| Average purple big (MM × MT) | 70.9 | 0.009 | 15 | 5.3 | 0.000 | 15 |
| Average red big (MM × MT) | 50.3 |  | 15 | 2.9 |  | 15 |
| Average purple cherry (MT) | 60.5 | 0.003 | 12 | 4.2 | 0.008 | 12 |
| Average red cherry (MT) | 29.7 |  | 12 | 2.6 |  | 12 |

References and Notes Cited in this Example
1. S. Renaud, M. de Lorgeril, *Lancet* 339, 1523 (1992).
2. J. A. Joseph et al., *J. Neurosci.* 19, 8114 (1999).
3. N. P. Seeram, L. S. Adams, M. L. Hardy, D. Heber, *J. Agric. Food Chem.* 52, 2512 (2004).
4. D. X. Hou, M. Fujii, N. Terahara, M. Yoshimoto, *J. Biomed. Biotechnol.* 5, 321
5. W. H. Shin, S. J. Park, E. J. Kim, *Life Sci.* 79, 130 (2006).
6. H. Matsumoto, Y. Nakamura, S. Tachibanaki, S. Kawamura, M. Hirayama, *J. Agric. Food Chem.* 51, 3560 (2003).
7. T. Tsuda, F. Horio, K. Uchida, H. Aoki, T. Osawa, *J. Nutr.* 133, 2125 (2003).
8. O. K. Chun, D. O. Kim, C. Y. Lee, *J. Agric. Food Chem.* 51, 8067 (2003).
9. S. Meiers et al., *J. Agric. Food Chem.* 49, 958 (2001).
10. R. J. Williams, J. P. Spencer J P, C. Rice-Evans, *Free Radical Biol. Med.* 36, 838 (2004).
11. Data available on the world wide web at 5aday.gov.
12. S. R. Muir et al., *Nat. Biotechnol.* 19, 470 (2001).
13. C. M. Jones, P. Mes, J. R. Myers, *J. Hered.* 94, 449 (2003).
14. G. R. Davuluri et al., *Nat. Biotechnol.* 23, 890 (2005).
15. P. Broun, C. Somerville, *Proc. Natl. Acad. Sci. USA*, 98, 8925-8927 (2001)
16. C. Martin, *Curr. Opin. Biotech.* 7, 130-138 (1996).
17. H. Mathews et al., *Plant Cell* 15, 1689 (2003).
18. A. Bovy et al., *Plant Cell* 14, 2509 (2002).
19. C. Martin, A. Prescott, S. Mackay, J. Bartlett, E. Vrijlandt, *Plant J.* 1, 37 (1991).
20. K. Schwinn et al., *Plant Cell* 18, 831-851 (2006).
21. H. K. Dooner, *Mol. Gen. Genet.* 67, 345 (1983).
22. F. Quattrocchio, J. F. Wing, H. Leppen, J. Mol, R. E. Koes, *Plant Cell* 5, 1497 (1993).
23. J. Goodrich, R. Carpenter, E. S. Coen, *Cell* 68, 955 (1992).
24. M. L. Kneissl, J. Deikman, *Plant Physiol.* 112, 537 (1996).
25. A. Goldsborough, F. Belzile, J. I. Yoder, *Plant Physiol.* 105, 491-496 (1994)
26. R. Alba R. et al., *Plant Cell* 17, 2954 (2005).
27. A. Jimenez et al., *Planta* 214, 751 (2002).
28. K. Mondal, N. S. Sharma, S. P. Malhotra, K. Dhawan, R. Singh, *Biol Plantarum* 48, 49 (2004).
29. R. A. Mehta et al., *Nat Biotechnol.* 20, 613 (2002).
30. E. J. Smid, L. Hendriks, H. A. M. Boerrigter, L. G. M. Garris, *Postharvest Biol. Tech.* 9, 343-350 (1996).
31. M. Mooney et al., *Plant J.* 7, 333 (1995).
32. N. J. Bate et al., *Proc. Natl. Acad. Sci. USA* 91, 7608-7612 (1994).
33. P. A. Howles et al., *Plant Physiol.* 112, 1617-1624 (1996).

Materials and Methods Used for Example 2
Plasmid Construction and Plant Transformation
A binary vector was constructed containing both the Del and Ros1 cDNAs under the control of the fruit-specific E8 promoter from tomato. The E8 promoter was amplified from tomato genomic DNA by PCR with the following primers: E8FK, 5'-GGGGTACCCATCCCTAATGATATTGT-TCACGTAA-3' (SEQ ID NO: 69) and E8RB 5'-CGGGGATCCGCACTGTGAATGATTA-GAATAATTTCT-3' (SEQ ID NO: 70). A DNA fragment was obtained which included 2175 bp upstream of the transcriptional start of the E8 gene and 27 nucleotides of 5' untranslated region. The promoter was cloned using KpnI and BamHI restriction enzyme sites in pET60 (S1) to replace the CaMV 35S promoter and in pJAM1500, (pJIT60 containing a Gateway cassette, Invitrogen, Carlsbad, Calif., USA) between the CaMV35S promoter and the CaMVpolyA polyadenylation signal again by replacing the 35S promoter. This resulted in plasmids pE8.60 and pE8.1500 respectively. The region containing E8-Gateway-CaMVpolyA from pE8.1500 was cloned in pSLJ7291, a binary vector containing the nopaline synthase promoter, the neomycin phosphotransferase gene and the octopine synthase polyadenylation sequence (S2). This resulted in plasmid pSLIE8.1500. The full-length Del cDNA was amplified by PCR using primers: DELF, 5'-GGGGACAAGTTTGTA-CAAAAAAGCAGGCTACCATGGCTACTGGTATCCA-AAACCAAAAG-3' (SEQ ID NO: 71) and DELR, 5'-GGGGACCACTTTGTACAAGAAAGCTGGGTG-GATCCAACTTCAAGACTTCATAGTAA CTTTCTG-3' (SEQ ID NO: 72) inserted in this plasmid using Gateway recombination technology, resulting in the binary construct pSLJ.E8.DEL. The full-length Ros1 cDNA was amplified with the following primers: ROSEF, 5'-CGGGGATCCATG-GAAAAGAATTGTCGTGGAGT-3' (SEQ ID NO: 73) and ROSR, 5'-TCCCCCGGGGTTAATTTCCAATTTGT-TGGGCCT-3' (SEQ ID NO: 74) and inserted in the plasmid pE8.60 as a BamHI-SmaI fragment, resulting in plasmid pE8.ROS. After the introduction of a double strand oligonucleotide containing a SalI restriction site in this plasmid, the region containing E8-Rost cDNA-CaMVpolyA was cloned as a SalI-XhoI fragment in XhoI-digested and dephosphorylated pSLJ.E8.DEL resulting in the binary construct pDEL.ROS. The binary plasmid pDEL.ROS was transferred to *Agrobacterium* strain LBA4404 by the triparental mating method (S3) Tomato variety Micro-Tom was transformed by *Agrobacterium*-mediated transformation of cotyledons (S4). Four independent transformed lines that showed accumulation of anthocyanin in fruit were generated, and called Del/Ros1 lines C, N, Y and Z. Southern blots and segregation analysis of the T1 generation of each line suggested that line N had 4 copies of the T-DNA inserted at 2 unlinked loci, line C had 3 copies of the T-DNA inserted at 2 unlinked loci, line Y had 2 copies of the T-DNA inserted at 1 locus and line Z had 1 copy of the T-DNA inserted at 1 locus.

Analysis and Identification of Anthocyanins and Phenylpropanoids

To estimate the total concentration of anthocyanins in tomato fruit, anthocyanins were extracted from chopped fruit with 5 ml of acidified (0.3% HCl, v/v) methanol in darkness for 24 h at 4° C. The extraction was repeated three times with 5 ml of acidified methanol shaking the samples for 20 min at room temperature. At the end of the extraction, samples were vortexed and centrifuged for 20 min at 5000× g. The samples were diluted in acidified methanol and the concentration was determined spectrophotometrically at 535 nm. The total amount of anthocyanins was expressed as mg of petunidin-3-(p-coumaroyl rutinoside)-5-glucoside (the main compound identified in Del/Ros1 tomatoes) per g fresh weight, based on an extinction coefficient of 17,000 and a molecular mass of 934 (S5).

For the extraction and HPLC analysis of phenylpropanoid compounds in wild type and Del/Ros1 N tomato fruit, all chemicals were obtained from Fluka (Neu-Ulm, Germany), Roth (Karlsruhe, Germany), Sigma-Aldrich (Munich, Germany), Serva (Heidelberg, Germany) and Merck (Darmstadt, Germany) and were of the highest quality available.

Powdered plant material (100 mg) was extracted with 400 µl of 50% MeOH and 400 µl of 100% MeOH. Phenylpropanoids in the cleared extracts were analysed by HPLC (Alliance, Waters, Eschborn, Germany) combined with a photodiode array detector (996, Waters). Separation was performed by reverse-phase chromatography on an Aqua C18, 5 µm, 4.6×250 mm column (Phenomenex, Aschaffenburg, Germany), maintained at 25° C. The mobile phase was composed of 87% water, 3% ACN and 10% acetic acid (solvent A) as well as 40% water, 50% ACN and 10% acetic acid (solvent B) at a flow rate of 1 ml/min. The gradient was as follows: initial 6% B; 20 min, 20% B; 35 min, 40% B; 40 min, 60% B; 45 min, 90% B; 60 min, 6% B. Absorbance spectra were recorded every 1 s, between 210 and 600 nm, with a bandwidth of 1.2 nm, and chromatograms were acquired at 280 and 535 nm. Data were analyzed using Waters Empower software.

For the identification of the major anthocyanins in Del/Ros1 N tomato fruit, extracts were prepared from 5 g powdered tomato fruit with 50 ml of 50% MeOH and 25 ml of 100% MeOH. The respective extracts were cleared by filtration through paper, combined and finally cleared by filtration through a membrane filter (0.22 µm, Millipore, Schwalbach, Germany). The cleared extract was then concentrated in a rotary evaporator to a final volume of 20 ml. A W600 pump system (Waters) with a preparative HPLC column (X-Bridge MS C18, 5 µm, 10×150 mm, Waters), maintained at 24° C. was used for separation. The mobile phase was composed as described above at a flow rate of 2 ml/min. For elution the following gradient was used: initial 5% B; 80 min, 40% B; 85-90 min, 100% B; 98 min, 5% B. Detection of eluted compounds was as mentioned above. Separated anthocyanins were collected and the fractions were subjected to analytical HPLC analysis as described above for confirmation. For identification the purified substances were subjected to ESI-MS/MS. Samples were injected by a syringe pump in 50% MeOH with 1% formic acid. The nanoscale effluent from the syringe pump was directed to the NanoLockSpray source of a Q/Tof Premier hybrid orthogonal accelerated Time-of-Flight (oa-ToF) mass spectrometer (Waters Corporation, MS Technologies Centre, Manchester, UK). The mass spectrometer operated in a positive ion mode with a source temperature of 80° C. and a cone gas flow of 30 l/h. A voltage of approximately 2 kV was applied to the nano flow sample tip. The mass spectra were acquired with the TOF mass analyzer in V-mode of operation and spectra were integrated over 1 s intervals. MS and MS/MS data were acquired in a continuum mode using MassLynx 4.0 software (Waters Corporation, Technologies Centre). The instrument was calibrated with a multi-point calibration using selected fragment ions of the CID of Glu-Fibrinopeptide B (Sigma-Aldrich).

For comparison of individual flavonoids, tomatoes were extracted in 75% aqueous methanol with 10 minutes of sonication. HPLC analysis was performed on a C18 reverse phase HPLC column (Phenomenex Luna, 3 µm, 150×40 mm, 40° C.) with photodiode array detection (type 996, Waters, The Netherlands). A gradient of 5 to 50% acetonitrile in 0.1% tri-fluoro acetic acid was used as the mobile phase. Absorbance spectra (240-600 nm) and retention times of eluting peaks were used for identification by comparison with authentic flavonoid standards (Apin chemicals, Abingdon, UK).

For the identification of acyl moieties, 20 μl of pure anthocyanin fractions were subjected to alkaline hydrolysis with 250 μl 10% KOH for 30 min at room temperature, respectively. The lysate was acidified to pH 1.0 with 250 μl 2 N HCl and the decomposition products were extracted with three volume ethyl acetate. The organic phase was evaporated to dryness and the phenylpropanoids were resuspended in 100 μl of solvent A for HPLC-analysis as described above.

For identification of sugar moieties, 20 μl of pure anthocyanin fractions were subjected to acid hydrolysis with 120 μl 2 M HCL for 30 min at 95° C. in a sealed vial. After cooling of the lysate in an ice bath the aglycones were extracted with 1 ml 1-pentanol. The organic and the water phase were evaporated to dryness. The phenylpropanoids were resuspended in 100 μl of solvent A for HPLC analysis as described above. The sugar moieties were resuspended in 100 μl of water for HPLC-analysis as recommended by DIONEX (S6).

Gene Expression Analysis

Total RNA was extracted from tomato fruit by an established procedure (S7). Samples to be used in SSH were obtained from fruit harvested at the turning, pink and red stages. To minimize the effect of ripening-related genes, minor RNA amounts (11%) extracted from fruit at the breaker and over-ripe stages were also included in the wild type, control RNA pool. PolyA+ mRNA was purified from total RNA using mRNA purification kit (Amersham Biosciences, UK) according to the manufacturer's instructions. Approximately 2 μg each of Del/Ros1 N and wild type polyA+ mRNA were reverse transcribed into cDNA and further processed according to the protocol supplied with the Clontech PCR-Select cDNA Subtraction Kit. PCR products were cloned using T/A cloning vector (Invitrogen) and used to transform E. Coli cells (DH5α). Two hundred colonies were randomly selected for colony PCR amplification and the reaction products were spotted on four nylon membranes according to the protocol supplied with the Clontech PCR-Select Differential Screening Kit and probed in duplicate with radiolabeled cDNA obtained from either wild type or Del/Ros1 N transgenic Micro-Tom fruit. Clones showing changes in expression between the wild type and transgenic samples were selected for DNA sequencing and validated by Northern blot hybridization. Four identical 1.2% agarose formaldehyde gels where prepared, each containing 15 μg of total RNA extracted from wild type and Del/Ros1 N tomato fruit. The RNA was transferred to nylon membranes and equal RNA loading and transfer were confirmed by methylene blue staining. The membranes were hybridized (S8) with labeled cDNA fragments corresponding to regulated transcripts isolated by SSH and obtained from EcoRI-digested plasmids. The radioactivity on the membranes was detected with a PhosphorImager (Fuji BAS 1000) or with Kodak Biomax film (Kodak, New Haven, Conn.). The membranes were stripped after each round of hybridization and exposed to a PhosphorImager to verify complete removal of the probe.

To investigate the expression of ripening-related genes, tomato fruit were tagged at the breaker stage. For Del/Ros1 N tomatoes, only fruit showing a visible break in color from green to tannish-yellow (despite the developing purple pigmentation) were selected. Total RNA was extracted from fruit harvested at 5, 12 and 19 days after tagging using the RNeasy Plant Mini Kit (Qiagen, Stanford, Calif.). For each sample, 4 pg of total RNA were used for Northern blot analysis as described above. Probes corresponding to phytoene synthase (PSY) and S-adenosyl-L-methionine synthase1 (SAM1) were obtained by PCR amplification of wild type double strand cDNA using the following primers: PSYF, 5'-ATGAGTTAGAAGTGAAGCGG-3' (SEQ ID NO: 75) and PSYR, 5'-ATCCCCAGAGCCAAAGCAGCA-3' (SEQ ID NO: 76) for PSY, and SAMF, 5'-GTGTC-CACGG-GCCATCTGACCA-3' (SEQ ID NO: 77) and SAMR, 5'-GCTCAGGCACACCGATGGCA-3' (SEQ ID NO: 78) for SAM1.

DNA Micro-Arrays: Preparation

The PROFOOD oligonucleotide microarray was constructed using 1034 70-mer oligonucleotides (Qiagen Operon), each representing a tomato EST selected by bioinformatic analysis. The 1034 selected ESTs represented genes involved in metabolic and regulatory pathways related to fruit quality and nutritional value. Control oligo's were included for background subtraction and normalisation. Each oligonucleotide was printed four times on amino-silane coated glass slides (Corning BV) by a capillary spotting device (Cartesian Technologies). After printing the slides were air-dried for several days, rehydrated and the DNA was cross-linked using an UV-cross linker at 150 m Joules. The slides were soaked twice in 0.2% SDS for 2 minutes, twice in MQ water for 2 minutes and once in boiling MQ water for 2 minutes. After drying, the slides were rinsed three times in 0.2% SDS for 1 min and once in MQ water for 1 min. Finally the slides were submerged in boiling MQ water for 2 sec.

DNA Micro-Arrays: cDNA Labelling and Hybridisation

Cy3- and CY5-labelled cDNA probes were prepared using 5 μg total RNA with a kit from Genisphere Inc. Hybridsations were performed with CY3-labelled cDNA from duplicate biological samples of each individual Del/Ros1 line, and two control lines compared to a common CY5-labelled reference (i.e. pooled cDNA composed of equal amounts from each individual line).

All micro-arrays were pre-hybridised for 3 hours at 45° C. prior to overnight hybridisation in a 120 μl hybridisation volume. All hybridisation and washing steps were carried out using an automatic hybridisation station (HybArray 12, Perkin Elmer). The slides were dried by centrifugation prior to scanning. Detection of the CY3 and CY5 signals was performed (ScanArray Express HT, Perkin Elmer). Spot identification and signal quantification was performed using Analytical Imaging Station AIS 4.0 software (IMAGING Research inc.)

DNA Micro-Arrays: Data Analysis:

The background levels of signal in the micro-array experiments were calculated from the raw data signals from oligo spots of non-plant origin. The mean values of these were subtracted from all others. Normalisation was carried out against the median for each experiment. For statistical analysis of micro-array data from the different tomato lines, mean values for genes from the biological replicates were used for pair-wise comparison between all values.

Determination of PAL Activity

Samples (300 mg) of frozen tomato fruit were finely ground and homogenized 1:1 (mg/μl) in 100 mM sodium borate buffer, pH 8.8 containing protease inhibitors (Protease Inhibitor Mix HP, Serra, Heidelberg, Germany) and 5 mM 2-mercaptoethanol. Insoluble PVP was added (10% w/w) to minimize oxidative protein loss. After 30 min incubation on ice, the extracts were sonicated (2×30 s) and then centrifuged at 13000×g for 5 min. Protein was quantified using the Bradford protein assay (Sigma-Aldrich, UK) following desalting the extracts by gel filtration on Nap5 columns (GE Healthcare/Amersham Biosciences, Freiburg, Germany). PAL assays were performed (S9) using 100 µl of desalted enzyme extract from the transgenic lines. For the PAL determination from wild type line Micro-Tom, desalted protein extracts were concentrated ten-fold by Ultrafiltration on Microcon Centrifugal Filter Units with cut-off of 10 kDa (Millipore, Schwalbach, Germany). PAL activity was calculated from intervals of linear product formation. The enzymic product was quantified using authentic t-cinnamic acid as a standard.

Determination of CHI Activity

Naringenin chalcone was chemically prepared from naringenin (Sigma-Aldrich) as described (S10). Samples (1 g) of fresh tomato fruit were finely ground at 4° C. in 3 ml 0.1 M potassium phosphate buffer, pH 7.4 containing 50 mM 2-mercaptoethanol 0.5 g quartz sand and 0.5 g insoluble PVPP. Each extract was centrifuged at 13000×g for 5 min and the supernatant was used in the assay. Protein was quantified using the Bradford protein assay (Sigma-Aldrich, UK). CHI activity was measured spectrophotometrically at 375 nm, a decrease in absorbance indicating a conversion of naringenin chalcone to naringenin. Assays were carried out at 25° C. The reaction mixture contained 1 ml 0.1 M potassium phosphate buffer, pH 7.4, 1 µg/ml BSA and a final concentration of naringenin chalcone of 16 µM. The reaction was started by adding 20-50 µl of the appropriate enzyme preparation. The background rate of spontaneous conversion was subtracted from the enzyme-mediated rate of conversion in all experiments.

Total Antioxidant Activity

Wild type and transgenic tomatoes were washed, deprived of seeds and homogenized in liquid nitrogen in a mortar. One g of the homogenized sample was extracted with 4 ml of water under agitation for 20 min at room temperature, centrifuged at 1000×g for 10 min and the supernatant collected. The extraction was repeated with 2 ml of water and the two supernatants were combined. The pulp residue was reextracted by the addition of 4 ml of acetone under agitation for 20 min at room temperature, centrifuged at 1000×g for 10 min and the supernatant collected. The extraction was repeated with 2 ml of acetone and the two supernatants were combined. Tomato extracts were immediately analyzed for their antioxidant capacity. The trolox equivalent antioxidant capacity (TEAC), based on the ability of antioxidant molecules to quench the long-lived ABTS [2,2'-azinobis(3-ethylbenzthiazoline-6-sulfonate), Sigma-Aldrich, UK] radical cation, a blue-green chromophore with characteristic absorption at 734 nm, compared with that of trolox (6-hydroxy-2.5,7,8-tetramethylchroman-2-carboxylic acid, Fluka, Germany), a water-soluble vitamin E analog, was determined (Sib). Results were expressed as TEAC in mmol of trolox per kg of fresh weight.

Mechanical Properties

For the analysis of tomato skin, a rectangular piece of skin (width, 3 mm) was removed horizontally from the equatorial area of the tomato. Each extremity of the piece was glued (Cyanoacrylate) on a stainless steel tab to give a sample length of 35 mm and the two tabs were positioned in the tensile grips of a universal test machine (Stable Microsystems, Godalming, Surrey, TAXT2) using a transfer jig. Care was taken so as not to tear and to damage the skin whilst excising and preparing the sample. The test-speed was 0.3 mm/sec. The Youngs modulus, E, and strength, σ, were approximated from the formulae for uniaxial specimens:

$$E = \frac{dF}{dx} * \frac{length}{thickness * width}$$

$$\sigma = \frac{F\,max}{thickness * width}$$

where dF/dx is the slope of the initial linear force (F)—displacement (x) curve and $F_{max}$ is the sample breaking force.

For the analysis of whole tomato fruit, a razor blade was attached to a vice on the crosshead of the test machine. Cutting was carried out with a test speed of 0.1 mm/sec on halved tomatoes with the cut surface in contact with the base plate. The other half of tomato from the cutting test was compressed, again with cut surface in contact with the base plate, at a crosshead speed of 0.1 mm/sec between parallel plates (diameter, 100 mm).

Ethylene Measurements and Treatment

Ethylene was measured from fruit harvested at or just before the breaker stage. Fruit were sealed in airtight tubes for 20 h after which a 1 mL sample of the headspace was taken and injected into a gas chromatograph (Shimadzu model GC-14B, Kyoto, Japan) equipped with a flame ionization detector. Samples were compared to a standard of known concentration and normalized for fruit mass. For ethylene treatment, wild type and Del/Ros1 N ripe tomato fruit were placed together in a sealed chamber and gassed with 25 µL/L ethylene or air. After two and four weeks, fruit were manually inspected for firmness.

Determination of Lignin

The content of lignin was determined as the thioglycolate derivative according to the protocol described (S12). Recovery rates for each individual experiment were determined by analyzing parallel samples with appropriate amounts of authentic lignin (Sigma).

References Cited in Materials and Methods Section of this Example

1 F. Guerineau, P. Mullineaux, Plant transformation and expression vectors. In Croy, R. R. D. (ed.), *Plant Molecular Biology Labfax*. BIOS Scientific Publishers Ltd, Oxford, UK, pp. 121-147 (1993).
2 K. E. Hammond-Kosack, S. Tang, K. Harrison, J. D. Jones, *Plant Cell* 10, 1251 (1998).
3 G. Ditta, S. Stanfield, D. Corbin, D. R. Helinski, *Proc. Natl. Acad. Sci. USA.* 77, 7347 (1980).
4 J. J. Fillatti, J. Kiser, R. Rose, L. Comai, *Bio. Technol.* 5, 726 (1987).
5 C. L. Price, R. E. Wrolstad, *J. Food Sci.* 60, 369 (1995).
6 Application Note 82: Analysis of fruit juice adulterated with medium invert sugar from beets, Method B, DIONEX.
7 S. Chang, J. Puryear, J. Cairney, *Plant Mol. Biol. Rep.* 11, 113 (1993).
8 Current Protocols in Molecular Biology, John Wiley & Sons, Inc. 4.9.1-4.9.8 (1997).
9 A. Matros et al., *Plant, Cell Environ.* 29, 126 (2006).
10 E. Moustafa, E. Wong, *Phytochemistry* 6, 625 (1967).
11 N. Pellegrini, R. Re, M. Yang, C. A. Rice-Evans, *Methods. Enzymol.* 299, 379 (1999).
12 M. M. Campbell, B. E. Ellis, *Planta* 196, 409 (1992).

Example 3

Tobacco Transformation with ROSEA1

This example provides a variation of the work disclosed above in which tomato fruit with significantly elevated levels of anthocyanins was produced by harnessing the broad target specificity of selected transcription factors, via expression of the Della (Del) and Rosea1 (Ros1) genes from *A. majus* in the fruit of transgenic tomatoes. In this example, Ros1 was cloned and transformed alone into tobacco. The Ros 1 cDNA (Schwinn et al, 2006, *The Plant Cell*, 18, 831-851) was inserted between the double 35S promoter from CaMV and the CaMV Terminator in pJIT 60 (Gerineau and Mullineaux, 1993, in *Plant Molecular Biology Labfax*, ed. Croy, R. R. D. (BIOS Scientific Publishers Ltd, Oxford), pp. 121-147.). This gene construct was inserted as a KpnI/XhoI fragment into the KpnI and SalI sites of pBin19 (Bevan, 1984, *Nucl Acids Res.* 12, 8711-8721). The T-DNA of this binary vector was transformed into tobacco using *Agrobacterium tumifaciens*, LBA4404.

In FIG. 11.1, we show that utilizing this strategy, it was possible to generate and identify transformed tobacco material due to induction of anthocyanin production only in the transformed tissue.

Example 4

Provision of Tomato Homologue of AtMYB12

The tomato EST database was searched for sequences homologous to AtMYB12 and the EST (TC172990) with the highest sequence similarity to AtMYB12 was used to identify a full-length eDNA from tomato fruit using 3'RACE PCR[5]. Total RNA was isolated and first-strand eDNA was synthesized. The 3' end of the eDNA was amplified using oligonucleotides: 5'-ATGGGAAGAACACCTTGTTG-3' (SEQ ID NO: 29) and the 3' adaptor sequence, 5' GACTC-GAGTCGACATCG-3' (SEQ ID NO: 30). The amplified sequence was cloned into pGEM-T easy and sequenced. The full-length eDNA was then reamplified using the forward oligo 5'-ATGGGAAGAACACCTTGTTG-3' (SEQ ID NO: 31) and the reverse oligo 5'-CTAAGACAAAAGCCAAGA-TACAA-3' (SEQ ID NO: 32) based on the 3' sequence amplified by 3'-RACE. The sequence for SlMYB12 has been submitted to the EMBL database with the accession number EU419748 (embargoed).

The sequence of the cDNA and expressed polypeptide are shown in SEQUENCE ANNEX I (SEQ ID NO: 11 and 12, respectively).

Figure 7:
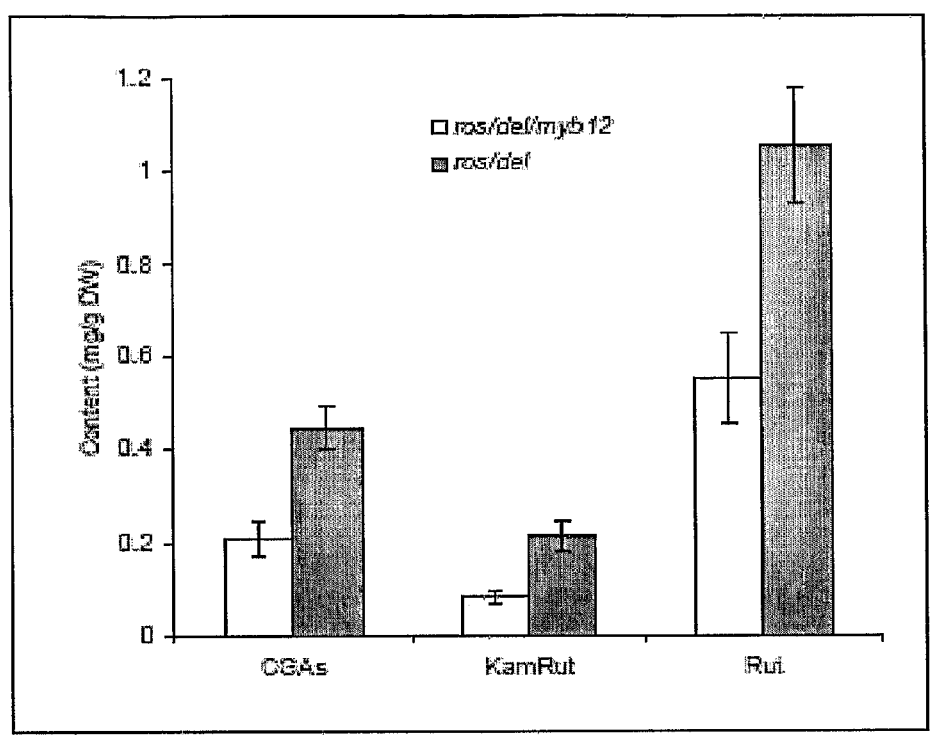
FIG. 7 Effect of SlMYB12 silencing by Agro-injection of tomato fruit on the production of CQAs (caffeoyl Quinic Acids) and flavonols. CGA is chlorogenic acid; KanRut is kaempferol rutinoside; Rut is rutin (quercetin rutinoside); DW is dry weight. The data represent the mean values (+/−SD) of two, independent biological samples. Ros/del indicates tissues from fruit silenced for the marker genes only, ros/del/myb12 indicates tissues from fruit silenced for the markers and SlMYB12, together.

We inserted a fragment of the tomato MYB12 gene (SIMYB12; see FIG. 9; SEQUENCE ANNEX I) into the sequences of the PVX virus along with sequences of other genes that mark the silenced tissues in agro-injected tomato fruit. The silenced tissue was dissected from the fruit and compared by metabolic profiling to tissue silenced for the markers genes but without the SIMYB12 sequences. The results showed that silencing of SIMYB12 reduces the levels of flavonols and of chlorogenic acid (FIG. 7) confirming its functional equivalence to AtMYB12 (Luo et al., 2008).

Example 5

Provision of Potato Homologue of AtMYB12

A blast search using SlMyb12 (see Example 4) against solanaceae database revealed one EST annotated as SGN U282939. An oligonucleotide was designed (LB6OF 5'-ATGGGAAGAACACCTTGTTGTG3'; SEQ ID NO: 79) and used with the oligo dT to amplify the whole fragment.

RNA was extracted from *solanum tuberosum* flowers using RNeasy plant RNA mini kit (Qiagen®) and 3μ was used to reverse transcribe the messenger into cDNA (Super-script® II, Invitrogen). The full length transcript (1089nt) was obtained by PCR (Turbo Pfu® polymerase, Stratagene) using LB 60F and oligo dT. The resulting fragment was sub-cloned into pGEM-T® vector (Promega) and then sequenced.

The sequence of the cDNA and expressed polypeptide are shown in SEQUENCE ANNEX II.

The SIMYB12 cDNA sequence (see SEQUENCE ANNEX II) was tested for its functionality in regulating expression of the genes involved in flavonol biosynthesis using a transient assay system in *Nicotiana benthamiana*. In this system we expressed the SIMYB12 cDNA under the control of a strong promoter (2×35S) in a binary vector. We also prepared reporter gene constructs from the F3H and DFR genes linked to GUS in separate binary vectors. promF3H should be activated by functional homologues of AtMYB12, whereas promDFR should not. We used AtMYB12 as a positive control. All binary vectors were transferred to *Agrobacterium tumefaciens* and combinations of the vectors expressing the transcription factors and the different reporter genes were agro-infiltrated into *N. benthamiana* leaves. Assays of GUS activity by histochemical staining showed the potato MYB12 gene (StMYB12) could activate the promF3H but not the promDFR in the same way as the positive control (AtMYB12).

Example 6

Cis-Genic Production of Potato Utilising Genetic Constructs Comprising a Cis-Genic Marker Linked to an Auxin Inducible Promoter The 'T-DNA mimic' sequences for potato, termed 'P-DNA' are available from Simplot (Boise, Id., USA) for example, supplied in a vector such as pSIM108 (see SEQUENCE ANNEX V) together with sequence information detailing restriction sites that are used for cloning. The 35S promoter: nptII: nos terminator sequences that lie between the P-DNA border sequences are removed and replaced by a series of gene constructs in which 1) colour-based selection/screening system are enabled, 2) the tuber-expressed MYB12 gene (StMYB12) from potato is included, 3) late blight resistance genes, or other desirable disease resistance genes, are included. Incorporated by reference herein for this purpose are the details of late blight resistance genes which have been cloned, sequenced and, as disclosed and claimed in UK priority patent application number 0714241.7. Other genes of value in this regard include, but are not limited to, for example, a gene encoding plant resistance protein to the tomato mosaic tobamovirus or related viruses, as disclosed in EP1247867 and references cited therein. See also Smilde et al, Theor. Appl. Genet (2005) 110: 252-258, which describes chromosomal location of a novel late blight resistance gene, Rpi-moc1.

The pan1 gene was isolated as follows and is included for implementing colour selection. Pan1 cDNA has been amplified from *Solanum tuberosum* cultivar salad blue with the following oligonucleotides LB3F 5'-ATGAGTACTCCTAT-GATGTGTA-3' (SEQ ID NO: 80) and LB4R 5'-CTAAT-TAAGTAGATTCCATATATC-3' SEQ ID NO: 81).

The sequence of the cDNA and expressed polypeptide are shown in SEQUENCE ANNEX VII (SEQ ID NO: 19 and 20, respectively).

The isolated potato MYB12 gene (StMYB12; see SEQUENCE ANNEX II; SEQ ID NO: 13) is also included This was obtained by using the SlMYB12 sequence to search a potato EST collection, and identifying a single EST from a mixed tissue RNA preparation.

A first colour-selection construct, pNPS1, comprises the pan1 gene (coding sequences plus optionally a stabilising 3'UTR) driven by the IAA4 promoter (see SEQUENCE ANNEX IV; SEQ ID NO: 15) inserted between the P-DNA borders in pSIM108 (see SEQUENCE ANNEX V; SEQ ID NO: 16).

A preferred 3'UTR for stabilisation and localisation of the mRNA in the cell is the 3'UTR region from Slpan2. The 3'UTR has the following sequence (SEQ ID NO: 82):

```
Atagtaatttctttttttgatttttcgtgatgtccggtacttatattaga atctgactgaattcagattcacgcgactccttatctaggggactcgaac ccaacacctctgattaagaatgaatgagtacttattactccgacatatgg ttggtattaaagaaatatgtaatggtaattaatattattgtaaacttgta atagggatccaatcgtcctttatactttgtatcctaattacaagttgtta ggaatgtaattttaagaattattgtaagtgcatgcactctatttttatat ttgatgtgaatttaaggattgagcataaatatgaaaaatcaaaat
```

An IAA4:Stpan1 gene fusion is constructed in pBluescript, for transfer as a KpnI/PstI fragment into KpnI/PstI digested pSIM108, thus replacing the 35S: nptII gene construct between the P-DNA borders. The IAA4:Stpan1 gene fusion is also directly inserted into pSIM108 without intermediate passage through pBluescript. pNPS1 is transferred to *Agrobacterium tumifaciens* (strain GV3101) by electroporation. The construct is used to transform tobacco to test the functionality of the IAA4:pan1 construct by transient assays, as well as by stable transformation of tobacco callus, which we anticipate will be just as quick a means of verifying functionality, and which also confirms the effectiveness of the construct for screening for transformed cells, mirroring the potato transformation protocol.

The frequency of recovering colour+plants is compared with the frequency of obtaining explants using a system utilizing the 35S:codA counter selection for transient expression of kanamycin resistance on a separate plasmid in *Agrobacterium* (see U.S. Pat. No. 7,250,554 which describes example vectors for this purpose). The colour selection system is anticipated to provide a higher transformation frequency, permitting the discontinuance of the transient kanamycin resistance system, which has negative regulatory implications for production of crops for human or animal consumption.

pNPS1 is used to transform potato (for example, cv. Desireé, although, of course, other varieties may be used analogously) tuber discs, and. due to the action of the IAA4:Stpan1 construct, colour is used to select transformed potato cells. Foci of coloured cells are transferred onto shooting medium for regeneration of shoots.

Shoots from red calli are transferred to hormone-free medium for the induction of roots, and plants that have grown to a suitable size are subsequently transferred to soil. The phenotypes of these primary transformants are recorded compared to controls, especially with respect to colouring of vegetative tissues by anthocyanins. The fidelity of P-DNA transfer and the copy number of inserted P-DNAs is confirmed by Southern blots and PCR analysis.

A second construct, pNPS2, is produced as a refinement of the first construct by inclusion of the StMYB12 gene with its 3' UTR fused to the B33 promoter of the patatin 1 gene from potato. This gene construct is combined with the IAA4: Stpan1 sequences in pBluescript and then reassembled as a KpnI/PstI fragment in pSIM108. pNPS2 is trialled using stable transformation of tobacco in which high levels of flavonol production is induced by growing plantlets on 7% sucrose to induce the B33 promoter. This construct is also transferred to potato (as described above), and the tubers of mature T0 plants exhibiting high flavonoid and hydroxycinnamate content by LC/MS are selected for further use.

Thus we inserted the Pan1 cDNA driven by the auxin-inducible promoter from the tomato IAA4 gene and used the pant terminator 3'UTR sequence, derived from the *S. okadae* BAC library, in pSim108 in recombination deficient *E. coli* and then transferred this binary vector to *Agrobacterium tumefaciens* strains GV3101 and LBA4404 by electroporation. To test the functionality of this screenable marker for transformation, we transformed tobacco (var Samsun) which never makes anthocyanins in vegetative tissues. We used the leaf disc method of transformation but omitted any antibiotics to select for transformed cells or plantlets. Callus developed in abundance on the cut edges of the leaf discs. Amongst these calli were foci coloured red, due to the production of anthocyanin as a result of pan1 activity (FIG. 11.2). These foci were dissected away from the uncoloured callus and placed onto shoot regeneration medium, with high auxin levels. The explants remained coloured especially at their growing apices, and started to develop into shoots. This suggested that the promIAA:pan1:pan2 3'UTR construct in pSim108 was functional and worked efficiently as a screenable marker for transformed shoots of tobacco.

The construct was also used to transform potato ('Desireé' and 'Maris Piper') using stem explants. This system does not involve production of large amounts of callus as an intermediary in the procedure. Rather, shoots are produced from the callus at the cut ends of the explants. When the promIAA:pan1:Sopan2 3'UTR construct in pSim108 was used for the transformation, shoots were produced which were coloured red, particularly around the edges of the leaf-lets (results not shown).

This was not observed with other constructs used to transform potato, although potato explants of the cv. Desiree do produce some anthocyanin when stressed, which can occur during the transformation and selection procedures. The transformed shoots were identified by screening for the production of anthocyanin, in the absence of any selection requiring antibiotics.

Selected shoots (colored) of both tobacco and potato were rooted and then grown on in soil. Normally vegetative tissues lack anthocyanins completely. However adult tobacco plants carrying promIAA:pan1:Sopan2 3'UTR showed anthocyanin in the epidermal tissues overlying veins in the leaves and anthocyanin production in the stems and petioles. Anthocyanin production in flowers was enhanced, particularly in the regions of epidermis overlying the main veins in the petals (results not shown)

One, two or more disease resistance genes, including but not limited to, for example, late blight resistance genes Rpi-mcq, Rpi-oka1, or both, are incorporated into the pNPS2 vector in stages 3 and 4. These genes are driven by their own promoters. These genes are incorporated into the IAA4:Stpan1+B33: SoMYB12 sequences in pBluescript and are then transferred to pSIM108 to attach the P-DNA sequences, thereby providing pNPS3 and pNPS4. Transformation of potato is conducted following the protocols described above.

SEQUENCE ANNEX I
(SEQ ID NO: 12, amino acid sequence;
SEQ ID NO: 11, nucleotide sequence):

```
LOCUS       bankit1056867 1248 bp mRNA linear
PLN
22-JAN-2008
DEFINITION  solanum lycopersicum (tomato) MYB12
            mRNA, complete cds.
ACCESSION   1056867
VERSION
KEYWORDS    .
SOURCE      Solanum lycopersicum
            (Lycopersicon esculentum)
ORGANISM    Solanum lycopersicum
            Eukaryota; Viridiplantae; Streptophyta;
            Embryophyta; Tracheophyta;
            Spermatophyta; Magnoliophyta;
            eudicotyledons; core eudicotyledons;
            asterids; lamiids; Solanales;
            Solanaceae; Solanoideae; Solaneae;
            Solanum; Lycopersicon.
REFERENCE   1 (bases 1 to 1248)
AUTHORS     Luo, J. and Martin, C.
TITLE       Metabolic engineering to enhance levels
            of both flavonols and hydroxycinnamic
            acids in tomato fruit
JOURNAL     Unpublished
REFERENCE   2 (bases 1 to 1248)
AUTHORS     Luo, J. and Martin, C.
TITLE       Direct Submission
JOURNAL     Submitted (22-JAN-2008) Metabolic
            Biology, John Innes Centre,
            Norwich Research Park, Colney,
            Norwich, Norfolk NR4
            7UH, UK
FEATURES    Location/Qualifiers
source      1..1248
            /organism="Solanum lycopersicum"
            /mol_type="mRNA"
            /db_xref="taxon:4081"
gene        1..1248
            /gene="MYB12"
CDS         1..1017
            /gene="MYB12"
            /codonstart=1
            /product="MYB12"
/translation="MGRTPCCEKVGIKRGRWTAEEDQILTNYIISNGEGS
WRSLPKNAGLLRCGKSCRLRWINYLRSDLKRGNITSQEEDIIIKLHATLG
NRWSLIAEHLSGRTDNEIKNYWNSHLSRKVDSLRIPSDEKLPKAVVDLAK
KGIPKPIKKSSISRPKNKKSNLLEKEALCCTNMPACDSAMELMQEDLAKI
EVPNSWAGPIEAKGSLSSDSDIEWPRLEEIMPDVVIDDEDKNTNFILNCF
REEVTSNNVGNSYSCIEEGNKKISSDDEKIKLLMDWQDNDELVWPTLPWE
LETDIVPSWPQWDDTDTNLLQNCTNDNNNYEEATTMEINNQNHSTIVSWL
LS"
BASE COUNT  481 a 156 c 257 g 354 t
ORIGIN
    1 atgggaagaa caccttgttg tgaaaaagtg
      ggcatcaaga gaggcagatg gactgcagaa
   61 gaagatcaaa ttctcactaa ttatattatt
      tctaatggag aaggctcttg gaggtcgtta
  121 cctaaaaatg ccggattatt gagatgcgga
      aagagttgta gactacgatg gattaattat
  181 ttgaggtctg atctcaagag agggaacatt
      acttctcaag aggaagatat aattataaag
  241 ttacatgcaa ctttgggtaa cagatggtct
      cttatagcag aacatttatc aggtagaaca
  301 gacaatgaga taaaaactaa ttggaactct
      catctaagtc gaaaagttga tagcttaagg
  361 ataccaagcg atgagaagtt acctaaagcc
      gtagttgatt tggctaaaaa aggtataccg
  421 aagccaatta aaaaatcatc gattagtcga
      ccaaaaaata aaaagtcaaa cttattagaa
  481 aaagaagcat tgtgttgtac aaatatgcca
      gcttgtgata gtgccatgga attaatgcaa
  541 gaagatctag caaagataga ggtgccaaat
      tcttgggcag gacctataga ggccaaggga
  601 agccttagtt cagatagtga tatcgaatgg
      ccaagactcg aggagattat gccagacgtg
  661 gtgattgatg atgaagataa gaacacaaat
      ttcatattga attgtttcag agaagaagta
  721 acgagcaata atgtagggaa tagttattca
      tgtatcgagg aaggtaataa aaagatatca
  781 agcgacgatg aaaaaatcaa attattaatg
      gattggcaag ataatgatga gttagtatgg
  841 ccaacgttac catgggaatt agaaacggat
      atagttccca gttggccaca atgggacgat
  901 actgacacta acttacttca aaattgcacc
      aatgataata ataattatga agaagcaaca
  961 acaatggaaa ttaataacca aaatcatagt
      accattgtat cttggctttt gtcttagaaa
 1021 tataataata tgacattata tattgctttt
      gaatatatta ctcaactctt tttgtttcgt
 1081 tttatatttg aatgtgggaa attagaatga
      ctagtttatg tacatatttt aagtttcgtt
 1141 agaaatatcg tcaagtcaga ttaaaatatg
      tatgagttga tgtagtaata aatgttattg
 1201 ttattacttt ttttgatgta aaaaaaaaaa
      aaaaaaaaaa aaaaaaaa
```

SEQUENCE ANNEX II
(SEQ ID NO: 14, amino acid sequence;
SEQ ID NO: 13, nucleotide sequence):

>StMyb12
MGRTPCCEKVGIKRGRWTAEEDQILTNYILSNGEGSWRSLPKNAG

LLRCGKSCRLRWINYLRSDLKRGNITSQEEDIIIKLHATLGNRWS

LIAGHLSGRTDNEIKNYWNSHLSRKVDSLRIPSDEKLPKAVVDLA

KKGTLKPIKHCRKSLISRSKNKKSNLLEAKENSTSGALIGIVPMP

STPNIEKEALCCTNMPACDSAMALMQEDVAKVEVPNSWAGSIEAK

GSLSSDSGMEWPRLEEIMPDVVIDDEDMNPNFILNGLEEEVMSNN

AGNNYSCIDEGNKNVSSDDEKSKLLMDWQDDDELVWPTPPWELET

DIIPSWPQWDDTDTDLLQNCTNNNYEEATTMEINNQNHSAIVSWL

LS

>StMyb12
atgggaagaacaccttgttgtgaaaaagtgggtatcaagagaggc agatggactgcagaagaagatcaaattctcactaattatattctt tctaatggagaaggctcttggaggtcattacccaaaaatgccgga ttactgagatgtgaaagagttgtagactaagatggattaattat ttgaggtctgacctcaagagagggaacattacttctcaagaggaa gatataatcataaagttacatgcaactttgggtaacaggtggtct ctaatagcgggacatttatcaggtagaacagacaatgagattaaa aattattggaactctcatctaagtcgaaaagttgatagcttaagg ataccaagcgatgagaagttgcctaaagctgtagttgatttggct aaaaagggtacattgaagccaattaaacattgtagaaaatcattg attagtcgatcgaaaaataaaaaatcaaacttattagaagctaaa gaaaatagtactagtggggctttgattggaattgttcctatgcct tcaacaccaaacatagaaaaagaagcattgtgttgtacaaatatg ccagcttgtgatagtgccatggcattaatgcaagaagatgtagca aaggtagaggtgccaaattcttgggcagggtctatagaggccaag ggaagccttagttcagatagtggtatggaatggccaaggctcgag gagattatgccagacgtggtgattgatgatgaagatatgaaccca aatttcattttgaatggtttagaagaagaagtaatgagcaataat gcagggaataattattcatgtatcgacgaaggaaataaaaacgta tcaagcgatgatgaaaaaagcaaattattaatggattggcaagat gatgatgaattagtatggccaacgccaccatgggaattagaaaca gacataattcctagttggccacaatgggacgatactgacactgat ttacttcaaaattgcaccaataataattatgaagaagcaacaaca atggaaattaataaccaaaatcatagtgccattgtatcttggctt ttgtcttag

SEQUENCE ANNEX III:

SEQ ID NO: 1 = NUCLEIC ACID SEQUENCE OF Rpi-oka1
   1 atggctgaaa ttcttctcac agcagtcatc aataaatcaa
     tagaaatagc tggaaatgta 61 ctctttcaag aaggtacgcg tttatattgg ttgaaagagg
     acatcgattg gctccagaga 121 gaaatgagac acattcgatc atatgtagac aatgcaaagg
     caaaggaagt tggaggcgat 181 tcaagggtga aaaacttatt aaaagatatt caacaactgg
     caggtgatgt ggaggatcta 241 ttagatgagt ttccttccaaa aattcaacaa tccaataagt
     tcatttgttg ccttaagacg 301 gtttcttttg ccgatgagtt tgctatggag attgagaaga
     taaaaagaag agttgctgat 361 attgaccgtg taaggacaac ttacagcatc acagatacaa
     gtaacaataa tgatgattgc 421 attccattgg accggagaag attgttcctt catgctgatg
     aaacagaggt catcggtctg 481 gaagatgact caatacact acaagccaaa ttacttgatc
     atgatttgcc ttatggagtt 541 gtttcaatag ttggcatgcc cggtttggga aaaacaactc
     ttgccaagaa actttatagg 601 catgtctgtc atcaatttga gtgttcggga ctggtctatg
     tttcacaaca gccaagggcg 661 ggagaaatct tacatgacat agccaaacaa gttggactga
     cggaagagga aggaaagaa 721 aacttggaga caaacctacg atcactcttg aaaataaaaa
     ggtatgttat tctcttagat 781 gacatttggg atgttgaaat ttgggatgat ctaaaacttg
     tccttcctga atgtgattca 841 aaaattggca gtaggataat tataacctct cgaaatagta
     atgtaggcag atacatagga 901 ggggatttct caatccacgt gttgcaaccc ctagattcag
     agaaaagctt tgaactcttt 961 accaagaaaa tctttaattt tgttaatgat aattgggcca
     atgcttcacc agacttggta 1021 aatattggta gatgtatagt tgagagatgt ggaggtatac
     cgctagcaat tgtggtgact 1081 gcaggcatgt taagggcaag aggaagaaca gaacatgcat
     ggaacagagt acttgagagt 1141 atggctcata aaattcaaga tggatgtggt aaggtattgg
     ctctgagtta caatgattg 1201 cccattgcat taaggccatg tttcttgtac tttggtcttt
     accccgagga ccatgaaatt 1261 cgtgcttttg atttgacaaa tatgtggatt gctgagaagc
     tgatagttgt aaatactggc 1321 aatgggcgag aggctgaaag tttggcggat gatgtcctaa
     atgatttggt ttcaagaaac 1381 ttgattcaag ttgccaaaag gacatatgat ggaagaattt
     caagttgtcg catacatgac 1441 ttgttacata gtttgtgtgt ggacttggct aaggaaagta
     acttctttca cacggagcac 1501 aatgcatttg gtgatcctag caatgttgct agggtgcgaa
     ggattacatt ctactctgat

SEQUENCE ANNEX III:

```
1561 gataatgcca tgaatgagtt cttccattta aatcctaagc
     ctatgaagct tcgttcactt 1621 ttctgtttca caaaagaccg ttgcatattt tctcaaatgg
     ctcatcttaa cttcaaatta 1681 ttgcaagtgt tggttgtagt catgtctcaa aagggttatc
     agcatgttac tttccccaaa 1741 aaaattggga acatgagttg cctacgttat gtgcgattgg
     aggggggcaat tagagtaaaa 1801 ttgccaaata gtattgtcaa gctcaaatgt ctagagaccc
     tggatatatt tcatagctct 1861 agtaaacttc cttttggtgt ttgggagtct aaaatattga
     gacatctttg ttacacagaa 1921 gaatgttact gtgtctcttt tgcaagtcca ttttgccgaa
     tcatgcctcc taataatcta 1981 caaactttga tgtgggtgga tgataaattt tgtgaaccaa
     gattgttgca ccgattgata 2041 aatttaagaa cattgtgtat aatggatgta tccggttcta
     ccattaagat attatcagca 2101 ttgagccctg tgcctagagc gttggaggtt ctgaagctca
     gattttttcaa gaacacgagt 2161 gagcaaataa acttgtcgtc ccatccaaat attgtcgagt
     tgggttttggt tggtttctca 2221 gcaatgctct tgaacattga agcattccct ccaaatcttg
     tcaagcttaa tcttgtcggc 2281 ttgatggtag acggtcatct attggcagtg cttaagaaat
     tgcccaaatt aaggatactt 2341 atattgcttt ggtgcagaca tgatgcagaa aaaatggatc
     tctctggtga tagcttccg 2401 caacttgaag ttttgtatat tgaggatgca caagggttgt
     ctgaagtaac gtgcatggat 2461 gatatgagta tgcctaaatt gaaaaagcta tttcttgtac
     aaggcccaaa catttcccca 2521 attagtctca gggtctcgga acggcttgca aagttgagaa
     tatcacaggt actataa
```

SEQ ID NO: 7 = NUCLEIC ACID SEQUENCE OF Rpi-oka2

```
   1 atggctgaaa ttcttctcac agcagtcatc aataaatcaa
     tagaaatagc tggaaatgta 61 ctctttcaag aaggtacgcg tttatattgg ttgaaagagg
     acatcgattg gctccagaga 121 gaaatgagac acattcgatc atatgtagac aatgcaaagg
     caaaggaagt tggaggcgat 181 tcaagggtga aaaacttatt aaaagatatt caacaactgg
     caggtgatgt ggaggatcta 241 ttagatgagt ttccttccaaa aattcaacaa tccaataagt
     tcatttgttg ccttaagacg 301 gtttcttttg ccgatgagtt tgctatggag attgagaaga
     taaaaagaag agttgctgat 361 attgaccgtg taaggacaac ttacagcatc acagataaa
     gtaacaataa tgatgattgc 421 attccattgg accggagaag attgttcctt catgctgatg
     aaacagaggt catcggtctg
```

SEQUENCE ANNEX III:

```
 481 gaagatgact tcaatacact acaagccaaa ttacttgatc
     atgatttgcc ttatggagtt 541 gtttcaatag ttggcatgcc cggtttggga aaaacaactc
     ttgccaagaa actttatagg 601 catgtctgtc atcaatttga gtgttcggga ctggtctatg
     tttcacaaca gccaagggcg 661 ggagaaatct tacatgacat agccaaacaa gttggactga
     cggaagagga aaggaaagaa 721 aacttggaga acaacctacg atcactcttg aaaataaaaa
     ggtatgttat tctcttagat 781 gacatttggg atgttgaaat tgggatgat ctaaaacttg
     tccttcctga atgtgattca 841 aaaattggca gtaggataat tataacctct cgaaatagta
     atgtaggcag atacatagga 901 ggggatttct caatccacgt gttgcaaccc ctagattcag
     agaaaagctt tgaactcttt 961 accaagaaaa tctttaattt tgttaatgat aattgggcca
     atgcttcacc agacttggta 1021 aatattggta gatgtatagt tgagagatgt ggaggtatac
     cgctagcaat tgtggtgact 1081 gcaggcatgt taagggcaag aggaagaaca gaacatgcat
     ggaacagagt acttgagagt 1141 atggctcata aaattcaaga tggatgtggt aaggtattgg
     ctctgagtta caatgatttg 1201 cccattgcat taaggccatg tttcttgtac tttggtctttt
     accccgagga ccatgaaatt 1261 cgtgcttttg atttgacaaa tatgtggatt gctgagaagc
     tgatagttgt aaatactggc 1321 aatgggcgag aggctgaaag tttggcggat gatgtcctaa
     atgatttggt ttcaagaaac 1381 ttgattcaag ttgccaaaag gacatatgat ggaagaattt
     caagttgtcg catacatgac 1441 ttgttacata gtttgtgtgt ggacttggct aaggaaagta
     acttctttca cacggagcac 1501 tatgcatttg gtgatcctag caatgttgct agggtgcgaa
     ggattacatt ctactctgat 1561 gataatgcca tgaatgagtt cttccattta aatcctaagc
     ctatgaagct tcgttcactt 1621 ttctgtttca caaaagaccg ttgcatattt tctcaaatgg
     ctcatcttaa cttcaaatta 1681 ttgcaagtgt tggttgtagt catgtctcaa aagggttatc
     agcatgttac tttccccaaa 1741 aaaattggga acatgagttg cctacgctat gtgcgattgg
     aggggggcaat tagagtaaaa 1801 ttgccaaata gtattgtcaa gctcaaatgt ctagagaccc
     tggatatatt tcatagctct 1861 agtaaacttc cttttggtgt ttgggagtct aaaatattga
     gacatctttg ttacacagaa 1921 gaatgttact gtgtctcttt tgcaagtcca ttttgccgaa
     tcatgcctcc taataatcta 1981 caaactttga tgtgggtgga tgataaattt tgtgaaccaa
     gattgttgca ccgattgata
```

SEQUENCE ANNEX III:

```
2041  aatttaagaa cattgtgtat aatggatgta tccggttcta
      ccattaagat attatcagca 2101  ttgagccctg tgcctaaagc gttggaggtt ctgaagctca
      gattttttcaa gaacacgagt 2161  gagcaaataa acttgtcgtc ccatccaaat attgtcgagt
      tgggtttggt tggtttctca 2221  gcaatgctct tgaacattga agcattccct ccaaatcttg
      tcaagcttaa tcttgtcggc 2281  ttgatggtag acggtcatct attggcagtg cttaagaaat
      tgcccaaatt aaggatactt 2341  atattgcttt ggtgcagaca tgatgcagaa aaaatggatc
      tctctggtga tagcttccg 2401  caacttgaag ttttgtatat tgaggatgca caagggttgt
      ctgaagtaac gtgcatggat 2461  gatatgagta tgcctaaatt gaaaaagcta tttcttgtac
      aaggcccaaa catttcccca 2521  attagtctca gggtctcgga acggcttgca aagttgagaa
      tatcacaggt actataa SEQ ID NO: 2 = NUCLEIC ACID SEQUENCE OF Rpi-mcq1
If candidate 1 then:
   1  atggctgaaa ttcttcttac agcagtcatc aataaatctg
      tagaaatagc tggaaatgta 61  ctctttcaag aaggtacgcg tttatattgg ttgaaggagg
      atatagattg gctccaaaga 121  gaaatgagac acattcgatc atatgtagac aatgcaaagg
      ccaaggaagt tggaggtgat 181  tcaagggtga aaaacttatt aaaagatatt caacaactcg
      caggtgatgt ggaggatctc 241  ctagatgagt ttcttccaaa aattcaacaa tccagtaagt
      tcaaaggcgc aatttgttgc 301  cttaagaccg tttcttttgc ggatgagttt gctatggaga
      ttgagaagat aaaaagaagg 361  gttgtggaca ttgatcgtgt aaggacaact tacaacatca
      tggatacaaa taacaacaat 421  gattgcattc cattggacca gagaagattg ttccttcatg
      ttgatgaaac agaggtcatc 481  ggtttggatg atgacttcaa tacactacaa gccaaattac
      ttgaccaaga tttgccttat 541  ggagttgttt caatagttgg catgcccggt ctaggaaaaa
      caactcttgc caagaaactt 601  tataggcatg tccgtcataa atttgagtgt tcgggactgg
      tctatgtttc acaacagcca 661  agggcgggag aaatcttaat cgacatagcc aaacaagttg
      gactgacgga agacgaaagg 721  aaagaaaact tggagaacaa cctacggtca ctcttgaaaa
      gaaaaaggta tgttattctc 781  ttagatgaca tttgggatgt tgaaatttgg gatgatctaa
      aacttgtcct tcctgaatgt 841  gattcaaaaa ttggcagtag ataattata acctctcgaa
      atagtaatgt aggcagatac 901  ataggagggg atttctcaat tcacgtgttg caacctctaa
      attcggagaa cagttttgaa
```

```
 961  ctctttacca agaaaatctt tattttttgat aacaataata
      attggaccaa tgcttcacca 1021  aacttggtag atattggtag aagtatagtt ggtagatgtg
      gtggtatacc actagccatt 1081  gtggtgactg caggcatgtt aagggcaaga gaaagaacag
      aacgtgcatg gaacaggtta 1141  cttgagagta tgagccataa agttcaagat ggatgtgcta
      aggtattggc tctgagttac 1201  aatgatttgc caattgcatt aaggccatgt ttcttgtatt
      ttggccttta ccccgaggat 1261  catgaaattc gtgcttttga tttgacaaat atgtggattg
      ctgagaagtt gatagttgta 1321  aatagtggca atgggcgaga ggctgaaagt ttggcggatg
      atgtcctaaa tgatttggtt 1381  tcaagaaaca tgattcaagt tgccaaaagg acatatgatg
      gaagaatttc aagttgtcgc 1441  atacatgact tgttacatag tttgtgtgtt gacttggcta
      aggaaagcaa cttctttcac 1501  accgagcaca atgcattggg tgatcccgga aatgttgcta
      ggctgcgaag gattacattc 1561  tactctgata taatgccat gaatgagttc ttccgttcaa
      atcctaagct tgagaagctt 1621  cgtgcacttt tctgttttac agaagaccct tgcatatttt
      ctcaactggc tcatcttgat 1681  ttcaaattat tgcaagtgtt ggttgtagtc atctttgttg
      atgatatttg tggtgtcagt 1741  atcccaaaca catttgggaa catgaggtgc ttacgttatc
      tgcgattcca ggggcatttt 1801  tatgggaaac tgccaaattg tatggtgaag ctcaaacgtc
      tagagaccct cgatattggt 1861  tatagcttaa ttaaatttcc tactggtgtt tggaagtcta
      cacaattgaa acatcttcgt 1921  tatggaggtt ttaatcaagc atctaacagt tgcttttcta
      taagcccatt tttcccaaac 1981  ttgtactcat tgcctcataa taatgtacaa actttgatgt
      ggctggatga taaatttttt 2041  gaggcggat tgttgcaccg attgatcaat ttaagaaaac
      tgggtatagc aggagtatct 2101  gattctacag ttaagatatt atcagcattg agccctgtgc
      caacggcgct ggaggttctg 2161  aagctcaaaa tttacaggga catgagtgag caaataaact
      tgtcgtccta tccaaatatt 2221  gttaagttgc gtttgaatgt ttgcggaaga atgcgcttga
      actgtgaagc atttcctcca 2281  aatcttgtca agcttactct tgtcggcgat gaggtagacg
      gtcatgtagt ggcagagctt 2341  aagaaattgc ccaaattaag gatacttaaa atgtttgggt
      gcagtcataa tgaagaaaag 2401  atggatctct ctggtgatgg tgatagcttt ccgcaacttg
      aagttctgca tattgatgaa 2461  ccagatgggt tgtctgaagt aacgtgtagg gatgatgtca
      gtatgcctaa attgaaaaag
```

SEQUENCE ANNEX III:

```
2521 ttgttacttg tacaacgccg cccttctcca attagtctct
     cagaacgtct tgcaaagctc 2581 agaatatga SEQ ID NO: 8 = NUCLEIC ACID SEQUENCE OF Rpi-mcq1
If candidate 2 then:
   1 atggctgaaa ttcttcttac aacagtcatc aataaatctg
     taggaatagc tgcaaatgta 61 ctctttcaag aaggaacgcg tttatattgg ttgaaagagg
     acatagaatt gctccacaga 121 gaaatgagac acattcgatc atatgtagac gatgcaaagg
     ccaaggaagt tggaggcgat 181 tcaagggtca gaaacttatt aaaagatatt caacaactgg
     caggtgatgt ggaggatcta 241 ttagatgagt ttcttccaaa aattcaacaa tccaataagt
     tcatttgttg ccttaagaca 301 gtttcttttg ccgatgagtt tgccatggag attgagaaga
     taaaaagaag agttgctgat 361 attacccgtg taaggacaac ttacaacatc acagatacaa
     gtaacaataa tgatgattgc 421 attccattgg accggagaag attgttcctt catgctgatg
     aaacagaggt catcggtctg 481 gaagatgact tcaatacact aaaagccaaa ttacttgatc
     aagatttgcc ttatggagtt 541 gtttcaatag ttggcatgcc cggtctagga aaaacaactc
     ttgccaagaa actttatagg 601 catgtccgtg atcaatttga gagctcggga ctggtctacg
     tgtcccaaca gccaagagcg 661 ggagaaatct tacgtgacat agccaaacaa gttggactgc
     caaaagagga aaggaaagaa 721 aacttggagg gcaacctacg atcactcttg aaaacaaaaa
     ggtatgttat cctcctagat 781 gacatttggg atgttgaaat ttgggatgat ctaaaactcg
     tccttcctga atgtgattca 841 gaaattgca gtaggataat tataacctct cgaaatagta
     atgtaggcag atacatagga 901 ggggatttct caattcacat gttgcaacct ctagattcgg
     agaacagttt tgaactcttt 961 accaagaaaa tctttacttt tgataacaat aataattggg
     ccaatgcttc accagacttg 1021 gtagatattg gtagaagtat agttggtaga tgcggaggta
     tacctctagc cattgtggtc 1081 actgcaggca tgttaagggc aagagaaaga acagaacatg
     catggaacag agtacttgag 1141 agtatgggcc ataaagttca agatggatgt gctaaggtat
     tggctttgag ttacaatgat 1201 ttgcccattg cattaaggcc atgtttcttg taccttggcc
     ttttccccga ggaccatgaa 1261 attcgtgcct tgatttgac aaatatgtgg attgctgaga
     agctgatagt tgtaaatagt 1321 ggcaatgggc gagaggctga agtttggcg gaggatgttc
     taaatgattt tgtttctaga
```

```
1381 aacttgattc aagtttccca aagaaaatgt aatggaagaa
     tttcaagtta tcgcatacat 1441 gacttgttac atagtttgtg cgtcgaattg ggcaaggaaa
     gtaactttt tcacactgaa 1501 cacaatgcat ttggtgatcc agacaatgtt gctagggtgc
     gaaggattac attctactct 1561 gataataatg ccatgagtaa gttcttccgt tcaaatccta
     agcctaagaa acttcgtgca 1621 cttttctgtt tcacaaattt agactcttgc atattttctc
     atttggctca tcatgacttc 1681 aaattattac aagtgttggt tgtagttatc tcttataatt
     ggttgagtgt cagtatctca 1741 aacaaatttg ggaagatgag ttgcttgcgc tatttgagat
     tggaggggcc aattgtggga 1801 gaactgtcaa atagtattgt gaagctcaaa cgtgtagaga
     ccatagatat tgcaggggat 1861 aacattaaaa ttccttgtgg tgtttgggag tctaaacaat
     tgagacatct ccgtaataga 1921 gaagaacgtc gctatttctt ttctgtaagc ccattttgcc
     taaacatgta cccattgcct 1981 cctaataatc tacaaacttt ggtgtggatg gatgataaat
     ttttgaacc gagattgttg 2041 caccgattga tcaatttaag aaaattgggt atatggggca
     catctgattc tacaattaag 2101 atattatcag cattgagccc tgtgccaaca gcgttggagg
     ttctgaagct ctactttttg 2161 agggacctga gtgagcaaat aaacttgtca acctatccaa
     atattgttaa gttgaatttg 2221 caaggattcg taagagtgcg cttgaactct gaagcattcc
     ctccaaatct tgtcaagctt 2281 attcttgaca aaattgaggt agagggtcat gtagtggcag
     ttcttaagaa attgcccaca 2341 ttaaggatac ttaaaatgta tgggtgcaaa cataatgaag
     aaaagatgga tctctctggt 2401 gatggtgatg gtgatagctt tccgcaactt gaagttttgc
     atattgagag accattcttc 2461 ttgtttgaaa taacgtgcac agatgatgac agtatgccta
     aattgaaaaa gctattactt 2521 accacttcga acgttaggct ctcggaaaga cttgcaaaac
     tgagagtatg a SEQ ID NO: 3 = NUCLEIC ACID SEQUENCE OF Rpi-nrs1
   1 atggctgaaa ttcttctcac agcagtcatc aataaatcaa
     tagaaatagc tggaaatgta 61 ctctttcaag aaggtacgcg tttatattgg ttgaaagagg
     acatcgattg gctccagaga 121 gaaatgagac acattcgatc atatgtagac aatgcaaagg
     caaaggaagt tggaggcgat 181 tcaagggtca aaaacttatt aaaagatatt caacaactgg
     caggtgatgt ggaggatcta 241 ttagatgagt ttcttccaaa aattcaacaa tccaataagt
     tcatttgttg ccttaagacg
```

SEQUENCE ANNEX III:

```
 301 gtttcttttg ccgatgagtt tgctatggag attgagaaga
     taaaaagaag agttgctgat 361 attgaccgtg taaggacaac ttacagcatc acagatacaa
     gtaacaataa tgatgattgc 421 attccattgg accggagaag attgttcctt catgctgatg
     aaacagaggt catcggtctg 481 gaagatgact tcaatacact acaagccaaa ttacttgatc
     atgatttgcc ttatggagtt 541 gtttcaatag ttggcatgcc cggtttggga aaacaactc
     ttgccaagaa actttatagg 601 catgtctgtc atcaatttga gtgttcggga ctggtctatg
     tttcacaaca gccaagggcg 661 ggagaaatct tacatgacat agccaaacaa gttggactga
     cggaagagga aaggaaagaa 721 aacttggaga acaacctacg atcactcttg aaaataaaaa
     ggtatgttat tctcttagat 781 gacatttggg atgttgaaat tgggatgat ctaaaacttg
     tccttcctga atgtgattca 841 aaaattggca gtaggataat tataacctct cgaaatagta
     atgtaggcag atacatagga 901 ggggatttct caatccacgt gttgcaaccc ctagattcag
     agaaaagctt tgaactcttt 961 accaagaaaa tcttaatttt tgttaatgat aattgggcca
     atgcttcacc agacttggta 1021 aatattggta gatgtatagt tgagagatgt ggaggtatac
     cgctagcaat tgtggtgact 1081 gcaggcatgt taagggcaag aggaagaaca gaacatgcat
     ggaacagagt acttgagagt 1141 atggctcata aaattcaaga tggatgtggt aaggtattgg
     ctctgagtta caatgatttg 1201 cccattgcat taaggccatg tttcttgtac tttggtcttt
     accccgagga ccatgaaatt 1261 cgtgcttttg atttgacaaa tatgtggatt gctgagaagc
     tgatagttgt aaatactggc 1321 aatgggcgag aggctgaaag ttttggcggat gatgtcctaa
     atgatttggt ttcaagaaac 1381 ttgattcaag ttgccaaaag gacatatgat ggaagaattt
     caagttgtcg catacatgac 1441 ttgttacata gtttgtgtgt ggacttggct aaggaaagta
     acttctttca cacggagcac 1501 tatgcatttg gtgatcctag caatgttgct agggtgcgaa
     ggattacatt ctactctgat 1561 gataatgcca tgaatgagtt cttccattta aatcctaagc
     ctatgaagct tcgttcactt 1621 ttctgtttca caaaagaccg ttgcatattt tctcaaatgg
     ctcatcttaa cttcaaatta 1681 ttgcaagtgt tggttgtagt catgtctcaa agggttatc
     agcatgttac tttccccaaa 1741 aaaattggga acatgagttg cctacgctat gtgcgattgg
     aggggcaat tagagtaaaa
```

```
1801 ttgccaaata gtattgtcaa gctcaaatgt ctagagaccc
     tggatatatt tcatagctct 1861 agtaaacttc cttttggtgt ttgggagtct aaaatattga
     gacatctttg ttacacagaa 1921 gaatgttact gtgtctcttt tgcaagtcca ttttgccgaa
     tcatgcctcc taataatcta 1981 caaactttga tgtgggtgga tgataaattt tgtgaaccaa
     gattgttgca ccgattgata 2041 aatttaagaa cattgtgtat aatggatgta tccggttcta
     ccattaagat attatcagca 2101 ttgagccctg tgcctaaagc gttggaggtt ctgaagctca
     gatttttcaa gaacacgagt 2161 gagcaaataa acttgtcgtc ccatccaaat attgtcgagt
     tgggtttggt tggtttctca 2221 gcaatgctct tgaacattga agcattccct ccaaatcttg
     tcaagcttaa tcttgtcggc 2281 ttgatggtag acggtcatct attggcagtg cttaagaaat
     tgcccaaatt aaggatactt 2341 atattgcttt ggtgcagaca tgatgcagaa aaaatggatc
     tctctggtga tagctttccg 2401 caacttgaag ttttgtatat tgaggatgca caagggttgt
     ctgaagtaac gtgcatggat 2461 gatatgagta tgcctaaatt gaaaaagcta tttcttgtac
     aaggcccaaa catttcccca 2521 attagtctca gggtctcgga acggcttgca aagttgagaa
     tatcacaggt actataa
```

SEQ ID NO: 4 = AMINO ACID SEQUENCE OF Rpi-okal

```
   1 MAEILLTAVI NKSIEIAGNV LFQEGTRLYW LKEDIDWLQR
     EMRHIRSYVD NAEAKEVGGD

61 SRVKNLLKDI QQLAGDVEDL LDEFLPKIQQ SNKFICCLKT
     VSFADEFAME IEKIKRRVAD

121 IDRVRTTYSI TDTSNNNDDC IPLDRRRLFL HADETEVIGL
     EDDFNTLQAK LLDHDLPYGV

181 VSIVGMPGLG KTTLAKKLYR HVCHQFECSG LVYVSQQPRA
     GEILHDIAKQ VGLTEEERKE

241 NLENNLRSLL KIKRYVILLD DIWDVEIWDD LKLVLPECDS
     KIGSRIIITS RNSNVGRYIG

301 GDFSIHVLQP LDSEKSFELF TKKIFNFVND NWANASPDLV
     NIGRCIVERC GGIPLAIVVT

361 AGMLRARGRT EHAWNRVLES MAHKIQDGCG KVLALSYNDL
     PIALRPCFLY FGLYPEDHEI

421 RAFDLTNMWI AEKLIVVNTG NGREAESLAD DVLNDLVSRN
     LIQVAKRTYD GRISSCRIHD

481 LLHSLCVDLA KESNFFHTEH NAFGDPSNVA RVRRITFYSD
     DNAMNEFFHL NPKPMKLRSL

541 FCFTKDRCIF SQMAHLNFKL LQVLVVVMSQ KGYQHVTFPK
     KIGNMSCLRY VRLEGAIRVK

601 LPNSIVKLKC LETLDIFHSS SKLPFGVWES KILRHLCYTE
     ECYCVSFASP FCRIMPPNNL

661 QTLMWVDDKF CEPRLLHRLI NLRTLCIMDV SGSTIKILSA
     LSPVPRALEV LKLRFFKNTS
```

SEQUENCE ANNEX III:

```
721  EQINLSSHPN IVELGLVGFS AMLLNIEAFP PNLVKLNLVG
     LMVDGHLLAV LKKLPKLRIL

781  ILLWCRHDAE KMDLSGDSFP QLEVLYIEDA QGLSEVTCMD
     DMSMPKLKKL FLVQGPNISP

841  ISLRVSERLA KLRISQVL*

SEQ ID NO: 9 = AMINO ACID SEQUENCE OF Rpi-oka2
  1  MAEILLTAVI NKSIEIAGNV LFQEGTRLYW LKEDIDWLQR
     EMRHIRSYVD NAKAKEVGGD

61  SRVKNLLKDI QQLAGDVEDL LDEFLPKIQQ SNKFICCLKT
     VSFADEFAME IEKIKRRVAD

121  IDRVRTTYSI TDTSNNNDDC IPLDRRRLFL HADETEVIGL
     EDDFNTLQAK LLDHDLPYGV

181  VSIVGMPGLG KTTLAKKLYR HVCHQFECSG LVYVSQQPRA
     GEILHDIAKQ VGLTEEERKE

241  NLENNLRSLL KIKRYVILLD DIWDVEIWDD LKLVLPECDS
     KIGSRIIITS RNSNVGRYIG

301  GDFSIHVLQP LDSEKSFELF TKKIFNFVND NWANASPDLV
     NIGRCIVERC GGIPLAIVVT

361  AGMLRARGRT EHAWNRVLES MAHKIQDGCG KVLALSYNDL
     PIALRPCFLY FGLYPEDHEI

421  RAFDLTNMWI AEKLIVVNTG NGREAESLAD DVLNDLVSRN
     LIQVAKRTYD GRISSCRIHD

481  LLHSLCVDLA KESNFFHTEH YAFGDPSNVA RVRRITFYSD
     DNAMNEFFHL NPKPMKLRSL

541  FCFTKDRCIF SQMAHLNFKL LQVLVVVMSQ KGYQHVTFPK
     KIGNMSCLRY VRLEGAIRVK

601  LPNSIVKLKC LETLDIFHSS SKLPFGVWES KILRHLCYTE
     ECYCVSFASP FCRIMPPNNL

661  QTLMWVDDKF CEPRLLHRLI NLRTLCIMDV SGSTIKILSA
     LSPVPKALEV LKLRFFKNTS

721  EQINLSSHPN IVELGLVGFS AMLLNIEAFP PNLVKLNLVG
     LMVDGHLLAV LKKLPKLRIL

781  ILLWCRHDAE KMDLSGDSFP QLEVLYIEDA QGLSEVTCMD
     DMSMPKLKKL FLVQGPNISP

841  ISLRVSERLA KLRISQVL*

SEQ ID NO: 5 = AMINO ACID SEQUENCE OF Rpi-mcq1
If candidate 1 then:
  1  MAEILLTAVI NKSVEIAGNV LFQEGTRLYW LKEDIDWLQR
     EMRHIRSYVD NAKAKEVGGD

61  SRVKNLLKDI QQLAGDVEDL LDEFLPKIQQ SSKFKGAICC
     LKTVSFADEF AMEIEKIKRR

121  VVDIDRVRTT YNIMDTNNNN DCIPLDQRRL FLHVDETEVI
     GLDDDFNTLQ AKLLDQDLPY

181  GVVSIVGMPG LGKTTLAKKL YNHVRHKFEC SGLVYVSQQP
     RAGEILIDIA KQVGLTEDER

241  KENLENNLRS LLKRKRYVIL LDDIWDVEIW DDLKLVLPEC
     DSKIGSRIII TSRNSNVGRY

301  IGGDFSIHVL QPLNSENSFE LFTKKIFIFD NNNNWTNASP
     NLVDIGRSIV GRCGGIPLAI

361  VVTAGMLRAR ERTERAWNRL LESMSHKVQD GCARVLALSY
     NDLPIALRPC FLYFGLYPED
```

SEQUENCE ANNEX III:

```
421  HEIRAFDLTN MWIAEKLIVV NSGNGREAES LADDVLNDLV
     SRNMIQVAKR TYDGRISSCR

481  IHDLLHSLCV DLAKESNFFH TEHNALGDPG NVARLRRITF
     YSDNNAMNEF FRSNPKLEKL

541  RALFCFTEDP CIFSQLAHLD FKLLQVLVVV IFVDDICGVS
     IPNTFGNMRC LRYLRFQGHF

601  YGKLPNCMVK LKRLETLDIG YSLIKFPTGV WKSTQLKHLR
     YGGFNQASNS CFSISPFFPN

661  LYSLPHNNVQ TLMWLDDKFF EAGLLHRLIN LRKLGIAGVS
     DSTVKILSAL SPVPTALEVL

721  KLKIYRDMSE QINLSSYPNI VKLRLNVCGR MRLNCEAFPP
     NLVKLTLVGD EVDGHVVAEL

781  KKLPKLRILK MFGCSHNEEK MDLSGDGDSF PQLEVLHIDE
     PDGLSEVTCR DDVSMPKLKK

841  LLLVQRRPSP ISLSERLAKL RI*

SEQ ID NO: 10 = AMINO ACID SEQUENCE OF Rpi-mcq1
If candidate 2 then:
  1  MAEILLTTVI NKSVGIAANV LFQEGTRLYW LKEDIDWLQR
     EMRHIRSYVD DAKAKEVGGD

61  SRVRNLLKDI QQLAGDVEDL LDEFLPKIQQ SNKFICCLKT
     VSFADEFAME IEKIKRRVAD

121  ITRVRTTYNI TDTSNNNDDC IPLDRRRLFL HADETEVIGL
     EDDFNTLKAK LLDQDLPYGV

181  VSIVGMPGLG KTTLAKKLYR HVRDQFESSG LVYVSQQPRA
     GEILRDIAKQ VGLPKEERKE

241  NLEGNLRSLL KTKRYVILLD DIWDVEIWDD LKLVLPECDS
     EIGSRIIITS RNSNVGRYIG

301  GDFSIHMLQP LDSENSFELF TKKIFTFDNN NNWANASPDL
     VDIGRSIVGR CGGIPLAIVV

361  TAGMLRARER TEHAWNRVLE SMGHKVQDGC AKVLALSYND
     LPIALRPCFL YLGLFPEDHE

421  IRAFDLTNMW IAEKLIVVNS GNGREAESLA EDVLNDFVSR
     NLIQVSQRKC NGRISSYRIH

481  DLLHSLCVEL GKESNFFHTE HNAFGDPDNV ARVRRITFYS
     DNNAMSKFFR SNPKPKKLRA

541  LFCFTNLDSC IFSHLAHHDF KLLQVLVVVI SYNWLSVSIS
     NKFGKMSCLR YLRLEGPIVG

601  ELSNSIVKLK RVETIDIAGD NIKIPCGVWE SKQLRHLRNR
     EERRYFFSVS PFCLNMYPLP

661  PNNLQTLVWM DDKFFEPRLL HRLINLRKLG IWGTSDSTIK
     ILSALSPVPT ALEVLKLYFL

721  RDLSEQINLS TYPNIVKLNL QGFVRVRLNS EAFPPNLVKL
     ILDKIEVEGH VVAVLKKLPT

781  LRILKMYGCK HNEEKMDLSG DGDGDSFPQL EVLHIERPFF
     LFEITCTDDD SMPKLKKLLL

841  TTSNVRLSER LAKLRV*

SEQ ID NO: 6 = AMINO ACID SEQUENCE OF Rpi-nrs1
  1  MAEILLTAVI NKSIEIAGNV LFQEGTRLYW LKEDIDWLQR
     EMRHIRSYVD NAKAKEVGGD

61  SRVKNLLKDI QQLAGDVEDL LDEFLPKIQQ SNKFICCLKT
     VSFADEFAME IEKIKRRVAD
```

SEQUENCE ANNEX III:

```
121  IDRVRTTYSI TDTSNNNDDC IPLDRRRLFL HADETEVIGL
     EDDFNTLQAK LLDHDLPYGV

181  VSIVGMPGLG KTTLAKKLYR RVCHQFECSG LVYVSQQPRA
     GEILHDIAKQ VGLTEEERKE

241  NLENNLRSLL KTKRYVILLD DIRDVEIRDD LKLVLPECDS
     KIGSRIIITS RNSNVGRYIG

301  GDFSIHVLQP LDSEKSFELF TKKIFNFVND NWANASPDLV
     NIGRCIVERC GGIPLAIVVT

361  AGMLRARGRT EHAWNRVLES MAHKIQDGCG KVLALSYNDL
     PIALRPCFLY FGLYPEDHEI

421  RAFDLTNMWI AEKLIVVNTG NGREAESLAD DVLNDLVSRN
     LIQVAKRTYD GRISSCRIHD

481  LLHSLCVDLA KESNFFHTEH YAFGDPSNVA RVRRITFYSD
     DNAMNEFFHL NPKPMKLRSL

541  FCFTKDRCIF SQMAHLNFKL LQVLVVVMSQ KGYQHVTFPK
     KIGNMSCLRY VRLEGAIRVK

601  LPNSIVKLKC LETLDIFHSS SKLPFGVWES KILRHLCYTE
     ECYCVSFASP FCRIMPPNNL

661  QTLMWVDDKF CEPRLLHRLI NLRTLCIMDV SGSTIKILSA
     LSPVPKALEV LKLRFFKNTS

721  EQINLSSHPN IVELGLVGFS AMLLNIEAFP PNLVKLNLVG
     LMVDGHLLAV LKKLPKLRIL

781  ILLWCRHDAE KMDLSGDSFP QLEVLYIEDA QGLSEVTCMD
     DMSMPKLKKL FLVQGPNISP

841  ISLRVSERLA KLRISQVL*
```

SEQUENCE ANNEX IV
(SEQ ID NO: 15):

>S1 IAAp
taaagcttcgttttattaaaaaacgttaataagaaattatttgatata
aatttaaattgaattgtatttcaaaatacatatcgaattgaatgaaaaa
tccaaaagaaaaaattatatcagattagacttttttttgtgtttgtttt
aaatttatacactaaaaattgtaataaaatatttttttccatttaattta
tttatcttatttttaacttgacatataattttaaaaatgaagattttgta
aaataatttaaatgaataagaaaatattcttttttaaaactattacaaaa
aagtagaacagctatatcaaaacaaaattagcagtaaatttaaacttat
atctctaaataatagcaaagacttaaaattaagaatcgatctaaaaaga
catatttcttatttaatactatacttaatgactttatttattttattatt
catgttaatctcacttagttatttgacaatgttcacaataatataatct
ctgtatttgaaatttcatttatattaaaaataattttaaacattaaacg
tcttctgttatgaacaaaatttacgcatgtaatcacggccgtgttaaat
gttttttatgtttacatacatctgtatcttatttacaaaaaaaaaaata
tatatccttataatcgcgtcagttccnacttccatgtaacgtaacgtta
attcttccctccatttcgtcaaactaactcatcattatcagtgtcggag
tcnaaaaatttattaaaaagtcaaaaatacgaagaatagaaatacgaga

SEQUENCE ANNEX IV
(SEQ ID NO: 15):

aatgcaagaggtcttatatataatatcggaaaatctttctggccagaag
aatttagataaaatttataaatgatattttacgttacctttttgaacat
tttcattttaactttagtatattttgattaaaaaataggaaaagagct
gtttattttaattcttttgaatttctgaacacttttttttgaccatttag
cactaccctttaaaccatatatatatatatatatgttcgacctttgcta
gctccaccctcgatcaagggtggagctagcttatggtcagcggttcatc
tactatttattaatagttaaatttactttatatatatactctatttgt
tcttacttgtctattttgacaaataaaaaattcttacctattatactct
taattgattactgtgaaaaatatagaattttttgctaaatcttaaatttt
taatttatccacgtcataattaatatgagtaaaatgataaactcgctaa
atcaaataatttattttcttaatagatgtgttaattcaagagtagacaaa
taactagggatagagaaagtatactgtagatgttgaactctcttgatta
attagtctgtatatttattctttcacctaataaaaatcgtcgatttttc
ggtagcaaaggcattgaatactagcgtgtggagtgtccctcttgtgttc
cctcattgccggttatgtgagggacaccattccctgttgcatcaaattt
gtgttccaaaactaacgtaacttccgtgcaaaaatcgcacccaacgtgc
gtctgtttacctggctgcaagcaagcgcgtattgacaacgaatcgtagg
cgagttgttttctccgtgttattatttatgagattcatgcacacacaaa
gaataactcgcctacatattgtcttttcctatataacaatcctcacaa
ttcacagcaattcaaatcaatcattcttttctaaatc

SEQUENCE ANNEX V
(SEQ ID NO: 16):

>pSIM108
agctttggcaggatatataccggtgtaaacgaagtgtgtggttgatc
caaaatctatcgtacctttagaaagtgtagctatgaaggatagtctcac
ttatgaagaactacctattgagattcttgatcgtcaggtccgaaggttg
agaaaaatagaagtcgcttcagttacggctttgtggaggagtaagggta
cccggggatcaattcccgatctagtaacatagatgacaccgcgcgcgat
aatttatcctagtttgcgcgctatattttgttttctatcgcgtattaaa
tgtataattgcgggactctaatcataaaaacccatctcataaataacgt
catgcattacatgttaattattacatgcttaacgtaattcaacagaaat
tatatgataatcatcgcaagaccggcaacaggattcaatcttaagaaac
tttattgccaaatgtttgaacgatcggggaaattcgagctctcagaaga
actcgtcaagaaggcgatagaaggcgatgcgctgcgaatcgggagcggc
gataccgtaaagcacgaggaagcggtcagcccattcgccgccaagctct
tcagcaatatcacgggtagccaacgctatgtcctgatagcggtccgcca
cacccagccggccacagtcgatgaatccagaaaagcggccattttccac
catgatattcggcaagcaggcatcgccatgggtcacgacgagatcatcg

SEQUENCE ANNEX V (SEQ ID NO: 16):

ccgtcgggcatgcgcgccttgagcctggcgaacagttcggctggcgcga
gccctgatgctcttcgtccagatcatcctgatcgacaagaccggcttc
catccgagtacgtgctcgctcgatgcgatgtttcgcttggtggtcgaat
gggcaggtagccggatcaagcgtatgcagccgccgcattgcatcagcca
tgatggatactttctcggcaggagcaaggtgagatgacaggagatcctg
ccccggcacttcgcccaatagcagccagtcccttcccgcttcagtgaca
acgtcgagcacagctgcgcaaggaacgcccgtcgtggccagccacgata
gccgcgctgcctcgtcctgcagttcattcagggcaccggacaggtcggt
cttgacaaaagaaccgggcgccctgcgctgacagccggaacacggcg
gcatcagagcagccgattgtctgttgtgcccagtcatagccgaatagcc
tctccacccaagcggccggagaacctgcgtgcaatccatcttgttcaat
catacccggggatcctctagagtccccgtgttctctccaaatgaaatg
aacttccttatatagaggaagggtcttgcgaaggatagtgggattgtgc
gtcatcccttacgtcagtggagatatcacatcaatccacttgctttgaa
gacgtggttggaacgtcttcttttttccacgatgctcctcgtgggtgggg
gtccatctttgggaccactgtcggcagaggcatcttcaacgatggcctt
tcctttatcgcaatgatggcatttgtaggagccaccttccttttccact
atcttcacaataaagtgacagatagctgggcaatggaatccgaggaggt
ttccggatattacccttgttgaaaagtctcaattgccctttggtcttc
tgagactgtatctttgatattttggagtagacaagtgtgtcgtgctcc
accatgttgacgaagattttcttcttgtcattgagtcgtaagagactct
gtatgaactgttcgccagtctttacggcgagttctgttaggtcctctat
ttgaatcttgtgactccatggcctttgattcagtgggaactacctttta
gagactccaatctctattacttgccttggtttgtgaagcaagccttgaa
tcgtccatactggaatagtacttctgatcttgagaaatatatctttctc
tgtgttcttgatgcagttagtcctgaatcttttgactgcatctttaacc
ttcttgggaaggtatttgatttcctggagattattgctcggtagatcg
tcttgatgagacctgctgcgtaagcctctctaaccatctgtgggttagc
attctttctgaaattggaaaaggctaatctggggacctgcagttatgct
ataaatttcatatatttagttgggagtaggctttataccgagttggact
acggtcagtcactttcaagtcctagaactacgtgccctgtaggttata
agtctcctctgtgggcatcaatttagtgatcatgccagtcatgcctcta
tacctctgacaggatatatggtactgtaaacactagttgtgaataagtc
gctgtgtatgtttgtttgagatctctaagagaaaagagcgtttattaga
ataacggatatttaaaagggcgtgaaaaggtttatccgttcgtccattt
gtatgtggtcacctatctcgagcatgccaaccacagggttcccctcggg
atcaaagtactttgatccaaccccctccgctgctatagtgcagtcggctt
ctgacgttcagtgcagccgtctcttctgaaaacgacatgtcgcacaagtcc taagttacgcgacaggctgccgccctgcccttttcctggcgttttcttg
tcgcgtgttttagtcgcataaagtagaatacttgcgactagaaccggag
acattacgccatgaacaagagcgccgccgctggcctgctgggctatgcc
cgcgtcagcaccgacgaccaggacttgaccaaccaacgggccgaactgc
acgcggccggctgcaccaagctgttttccgagaagatcaccggcaccag
gcgcgaccgcccgagctggccaggatgcttgaccacctacgccctggc
gacgttgtgacagtgaccaggctagaccgcctggcccgcagcacccgcg
acctactggacattgccgagcgcatccaggaggccggcgcgggcctgcg
tagcctggcagagccgtgggccgacaccaccacgccggccggccgcatg
gtgttgaccgtgttcgccggcattgccgagttcgagcgttccctaatca
tcgaccgcacccgagcgggcgcgaggccgccaaggcccgaggcgtgaa
gttttggccccgccctaccctcaccccggcacagatcgcgcacgcccgc
gagctgatcgaccaggaaggccgcaccgtgaaagaggcggctgcactgc
ttggcgtgcatcgctcgaccctgtaccgcgcacttgagcgcagcgagga
agtgacgcccaccgaggccaggcggcgcggtgccttccgtgaggacgca
ttgaccgaggccgacgccctggcggccgccgagaatgaacgccaagagg
aacaagcatgaaaccgcaccaggacggccaggacgaaccgttttcatt
accgaagagatcgaggcggagatgatcgcggccgggtacgtgttcgagc
cgccccgcgcacgtctcaaccgtgcggctgcatgaaatcctggccggttt
gtctgatgccaagctggcggcctggccggccagcttggccgctgaagaa
accgagcgccgccgtctaaaaaggtgatgtgtatttgagtaaaacagct
tgcgtcatgcggtcgctgcgtatatgatgcgatgagtaaataaacaaat
acgcaaggggaacgcatgaaggttatcgctgtacttaaccagaaaggcg
ggtcaggcaagacgaccatcgcaacccatctagcccgcgccctgcaact
cgccggggccgatgttctgttagtcgattccgatccccagggcagtgcc
cgcgattgggcggccgtgcgggaagatcaaccgctaaccgttgtcggca
tcgaccgcccgacgattgaccgcgacgtgaaggccatcggccggcgcga
cttcgtagtgatcgacggagcgccccaggcggcggacttggctgtgtcc
gcgatcaaggcagccgacttcgtgctgattccggtgcagccaagccctt
acgacatatgggccaccgccgacctggtggagctggttaagcagcgcat
tgaggtcacggatggaaggctacaagcggcctttgtcgtgtcgcgggcg
atcaaaggcacgcgcatcggcggtgaggttgccgaggcgctggccgggt
acgagctgcccattcttgagtcccgtatcacgcagcgcgtgagctaccc
aggcactgccgccgccggcacaaccgttcttgaatcagaacccgagggc
gacgctgcccgcgaggtccaggcgctggccgctgaaattaaatcaaaac
tcatttgagttaatgaggtaaagagaaaatgagcaaaagcacaaacacg
ctaagtgccggccgtccgagcgcacgcagcagcaaggctgcaacgttgg
ccagcctggcagacacgccagccatgaagcgggtcaactttcagttgcc

SEQUENCE ANNEX V
(SEQ ID NO: 16):

ggcggaggatcacaccaagctgaagatgtacgcggtacgccaaggcaag
accattaccgagctgctatctgaatacatcgcgcagctaccagagtaaa
tgagcaaatgaataaatgagtagatgaattttagcggctaaaggaggcg
gcatggaaaatcaagaacaaccaggcaccgacgccgtggaatgcccat
gtgtggaggaacgggcggttggccaggcgtaagcggctgggttgtctgc
cggccctgcaatggcactggaaccccaagcccgaggaatcggcgtgac
ggtcgcaaaccatccggcccggtacaaatcggcgcggcgctgggtgatg
acctggtggagaagttgaaggccgcgcaggccgcccagcggcaacgcat
cgaggcagaagcacgccccggtgaatcgtggcaagcggccgctgatcga
atccgcaaagaatcccggcaaccgccggcagccggtgcgccgtcgatta
ggaagccgcccaagggcgacgagcaaccagatttttttcgttccgatgct
ctatgacgtgggcacccgcgatagtcgcagcatcatggacgtggccgtt
ttccgtctgtcgaagcgtgaccgacgagctggcgaggtgatccgctacg
agcttccagacgggcacgtagaggtttccgcagggccggccggcatggc
cagtgtgtgggattacgacctggtactgatggcggtttcccatctaacc
gaatccatgaaccgataccgggaagggaagggagacaagcccggccgcg
tgttccgtccacacgttgcggacgtactcaagttctgccggcgagccga
tggcggaaagcagaaagacgacctggtagaaacctgcattcggttaaac
accacgcacgttgccatgcagcgtacgaagaaggccaagaacggccgcc
tggtgacggtatccgagggtgaagccttgattagccgctacaagatcgt
aaagagcgaaaccgggcggccggagtacatcgagatcgagctagctgat
tggatgtaccgcgagatcacagaaggcaagaacccggacgtgctgacgg
ttcaccccgattacttttttgatcgatcccggcatcggccgttttctcta
ccgcctggcacgccgcgccgcaggcaaggcagaagccagatggttgttc
aagacgatccacgaacgcagtggcagcgccggagagttcaagaagttct
gtttcaccgtgcgcaagctgatcgggtcaaatgacctgccggagtacga
tttgaaggaggaggcggggcaggctggcccgatcctagtcatgcgctac
cgcaacctgatcgagggcgaagcatccgccggttcctaatgtacggagc
agatgctagggcaaattgccctagcaggggaaaaaggtcgaaaaggtct
cttcctgtggatagcacgtacattgggaacccaaagccgtacattggg
aaccggaacccgtacattgggaacccaaagccgtacattgggaaccggt
cacacatgtaagtgactgatataaagagaaaaaggcgattttccgc
ctaaaactcttttaaaacttattaaaactcttaaaacccgcctggcctgt
gcataactgtctggccagcgcacagccgaagagctgcaaaaagcgccta
cccttcggtcgctgcgctccctacgccccgccgcttcgcgtcggcctat
cgcggccgctggccgcccaaaaatggctggcctacgccaggcaatcta
ccagggcgcggacaagccgcgccgtcgccactcgaccgccggcgcccac
atcaaggcaccctgcctcgcgcgtttcggtgatgacggtgaaaacctct

SEQUENCE ANNEX V
(SEQ ID NO: 16):

gacacatgcagctcccggagacggtcacagcttgtctgtaagcggatgc
cgggagcagacaagcccgtcagggcgcgtcagcgggtgttggcgggtgt
cggggcgcagccatgacccagtcacgtagcgatagcggagtgtatactg
gcttaactacgcggcatcagagcagattgtactgagagtgcaccatatg
cggtgtgaaataccgcacagatgcgtaaggagaaaataccgcatcaggc
gctcttccgcttcctcgctcactgactcgctgcgctcggtcgttcggct
gcggcgagcggtatcagctcactcaaaggcggtaatacggttatccaca
gaatcaggggataacgcaggaaagaacatgtgagcaaaaggccagcaaa
aggccaggaaccgtaaaaaggccgcgttgctggcgttttccataggct
ccgcccccctgacgagcatcacaaaaatcgacgctcaagtcagaggtgg
cgaaacccgacaggactataaagataccaggcgtttccccctggaagct
ccctcgtgcgctctcctgttccgaccctgccgcttaccggatacctgtc
cgcctttctcccttcgggaagcgtggcgctttctcatagctcacgctgt
aggtatctcagttcggtgtaggtcgttcgctccaagctgggctgtgtgc
acgaaccccccgttcagcccgaccgctgcgccttatccggtaactatcg
tcttgagtccaacccggtaagacacgacttatcgccactggcagcagcc
actggtaacaggattagcagagcgaggtatgtaggcggtgctacagagt
tcttgaagtggtggcctaactacggctacactagaaggacagtatttgg
tatctcgcgctctgctgaagccagttaccttcggaaaaagagttggtagc
tcttgatccggcaaacaaaccaccgctggtagcggtggttttttgttt
gcaagcagcagattacgcgcagaaaaaaaggatctcaagaagatcctttt
gatctttcctacggggtctgacgctcagtggaacgaaaactcacgttaa
gggattttggtcatgcattctaggtactaaaacaattcatccagtaaaa
tataatattttattttctcccaatcaggcttgatccccagtaagtcaaa
aaatagctcgacatactgttcttccccgatatcctccctgatcgaccgg
acgcagaaggcaatgtcataccacttgtccgccctgccgcttctcccaa
gatcaataaagccacttactttgccatctttcacaaagatgttgctgtc
tcccaggtcgccgtgggaaaagacaagttcctcttcgggcttttccgtc
tttaaaaaatcatacagctcgcgcggatctttaaatggagtgtcttctt
cccagttttcgcaatccacatcggccagatcgttattcagtaagtaatc
caattcggctaagcggctgtctaagctattcgtatagggacaatccgat
atgtcgatggagtgaaagagcctgatgcactccgcatacagctcgataa
tcttttcagggctttgttcatcttcatactcttccgagcaaaggacgcc
atcggcctcactcatgagcagattgctccagccatcatgccgttcaaag
tgcaggacctttggaacaggcagctttccttccagccatagcatcatgt
ccttttcccgttccacatcataggtggtcccctttataccggctgtccgt
cattttaaatataggttttcattttctcccaccagcttatataccttag
cagagacattccttccgtatctttttacgcagcggtattttttcgatca

SEQUENCE ANNEX V
(SEQ ID NO: 16):

gtttttcaattccggtgatatctcatttcagccatttattatttcct tcctcttttctacagtatttaaagataccccaagaagctaattataaca agacgaactccaattcactgttccttgcattctaaaaccttaaatacca gaaaacagcttttcaaagttgttttcaaagttggcgtataacatagta tcgacggagccgatttgaaaccgcggatcctgcagccaaagcacatac ttatcgatttaaatttcatcgaagagattaatatcgaataatcatatac atactttaaatacataacaaattttaaatacatatatctggtatataat taattttttaaagtcatgaagtatgtatcaaatacacatatggaaaaaa ttaactattcataattttaaaaaatagaaaagatacatctagtgaaatta ggtgcatgtatcaaatacattaggaaaagggcatatatcttgatctaga taattaacgattttgatttatgtataatttccaaatgaaggtttatatc tacttcagaaataacaatatactttttcagaacattcaacaaagtaac aaccaactagagtgaaaaatacacattgttctctaaacatacaaaattg agaaaagaatctcaaaatttagagaaacaaatctgaatttctagaagaa aaaaataattatgcactttgctattgctcgaaaaataaatgaaagaaat tagactttttttaaaagatgttagactagatatactcaaaagctatcaaa ggagtaatattcttcttacattaagtattttagttacagtcctgtaatt aaagacacattttagattgtatctaaacttaaatgtatctagaatacat atatttgaatgcatcatatacatgtatccgacacaccaattctcataaa aagcgtaatatcctaaactaatttatccttcaagtcaacttaagcccaa tatacattttcatctctaaaggcccaagtggcacaaaatgtcaggccca attacgaagaaaagggcttgtaaaaccctaataaagtggcactggcaga gcttacactctcattccatcaacaaagaaaccctaaaagccgcagcgcc actgatttctctcctccaggcgaagatgcagatcttcgtgaagacccta acggggaagacgatcacctагагagg ttgagtcttccgacaccatcgaca atgtcaaagccaagatccaggacaaggaagggattcccccagaccagca gcgtttgattttcgccggaaagcagcttgaggatggtcgtactcttgcc gactacaacatccagaaggagtcaactctccatctcgtgctccgtctcc gtggtggtggatccatggacctgcatctaattttcggtccaacttgcac aggaaagacgaccgcgatagctcttgcccagcagacagggcttcca gtcctttcgcttgatcgggtccaatgctgtcctcaactatcaaccgaa gcggacgaccaacagtggaagaactgaaaggaacgacgcgtctctacct tgatgatcggcctctggtggagggtatcatcgcagccaagcaagctcat cataggctgatcgaggaggtgtataatcatgaggccaacggcgggctta ttcttgagggaggatccacctcgttgctcaactgcatggcgcgaaacag ctattggagtgcagattttcgttggcatattattcgccacaagttaccc gaccaagagaccttcatgaaagcggccaaggccagagttaagcagatgt tgcaccccgctgcaggccattctattattcaagagttggtttatctttg gaatgaacctcggctgaggcccattctgaaagagatcgatggatatcga tatgccatgttgtttgctagccagaaccagatcacggcagatatgctat tgcagcttgacgcaaatatggaaggtaagttgattaatgggatcgctca ggagtatttcatccatgcgcgccaacaggaacagaaattcccccaagtt aacgcagccgctttcgacggattcgaaggtcatccgttcggaatgtatt aggttacgccagccctgcgtcgcacctgtcttcatctggataagatgtt cgtaattgttttggctttgtcctgttgtggcagggcggcaaatacttc cgacaatccatcgtgtcttcaaactttatgctggtgaacaagtcttagt ttccacgaaagtattatgttaaattttaaaatttcgatgtataatgtgg ctataattgtaaaaataaactatcgtaagtgtgcgtgttatgtataatt tgtctaaatgtttaatatatcatagaacgcaataaatattaaatata gcgcttttatgaaatataaatacatcattacaagttgtttatatttcgg gtggactagttttaatgttagcaaatgtcctatcagtttctctcttt tgtcgaacggtaatttagagttttttttgctatatggatttcgtttt gatgtatgtgacaaccctcgggattgttgatttatttcaaaactaagag ttttgcttattgttctcgtctatttggatatcaatcttagttttata tctttctagttctctacgtgttaaatgttcaacacactagcaatttgg ctgcagcgtatggattatggaactatcaagtctgtgggatcgataaata tgcttctcaggaatttgagattttacagtctttatgctcattgggttga gtataatatagtaaaaaataggaattctatccgcggtgatcacaggca gcaacgctctgtcatcgttacaatcaacatgctaccctccgcgagatca tccgtgtttcaaacccggcagcttagttgccgttcttccgaatagcatc ggtaacatgagcaaagtctgccgccttacaacggctctcccgctgacgc cgtcccggactgatgggctgcctgtatcgagtggtgattttgtgccgag ctgccggtcggggagctgttggctggctgga SEQUENCE ANNEX VI
(SEQ ID NO: 17, nucleotide sequence;
SEQ ID NO: 18, amino acid sequence):

>Ant1 nucleotide sequence
Atgagtactcctatgatgtgtacattttgggagtaataaggaaaggtt catggactgaagaagaagatattcttttgaggaaatgtattgataagta tggagaaggaaagtggcatcttgttccaactagagctggattaaacaga tgcagaaaagttgtagactgaggtggctaaattatctaaggccacata tcaagagaggtgactttgaaccagatgaagtggatctcatcttgagact tcataagctcttaggcaaccgatggtcacttattgctggtagacttcca ggaaggacagctaacgatgtgaaaaactattggaacactaaccttctaa ggaagctaaatactagtactaaatttgctcctcaacccaagaaggaat taatactagtactattgctcctcaaccacaagaaggaattaagtatggg

SEQUENCE ANNEX VI
(SEQ ID NO: 17, nucleotide sequence;
SEQ ID NO: 18, amino acid sequence):

caagccaatgccataataagacctcaacctcagaaattcacaagctcca tgaagattaatgtctcttggtgcaacaacaatagtatggtaaataatga agaagcatcgaaagacaacaacgatatgcaatggtgggcaaatatactg gaaaactgcaatgacattggagaaggagaagctgaaagaacactacctt catgtaaggaaattaattgcaatgaaattgataaagcaccaagtttgtt acatgagggaggcaactccatgcaacaaggacaaggtgatggtggttgg gatgaatttgctctagatgatatatggaatctacttaattag >Ant1 protein sequence
mstpmmctflgvirkgswteeedillrkcidkygegkwhlvptraglnr crkscrlrwlnylrphikrgdfepdevdlilrlhkllgnrwsliagrlp grtandvknywntnllrklntstkfapqpqegintstiapqpqegikyg ganaiirpqpqkftssmkinvswcnnnsmvnneeaskdnndmqwwanil encndigegeaertlpsckeincneidkapsllheggnsmqqgqgdggw defalddiwnlln

---

SEQUENCE ANNEX VII
(SEQ ID NO: 19, nucleotide sequence;
SEQ ID NO: 20, amino acid sequence):

>pan1
atgagtactcctatgatgtgtacattttttgggagtaataaggaaaggtt catggactgaagaagaagatattcttttgaggaaatgtattgataagta tggagaaggaaagtggcatcttgttccaactagagctggattaaacaga tgcagaaaaagttgtagactgaggtggctaaattatctaaggccacata tcaagagaggtgactttgaaccagatgaagtggatctcatcttgagact tcataagctcttaggcaaccgatggtcacttattgctggtagacttcca ggaaggacagctaacgatgtgaaaaactattggaacactaaccttctaa ggaagctaaatactagtactaaatttgctcctcaaccacaagaaggaat taatactagtactattgctcctcaaccacaagaaggaattaagtatggg caagccaatgccataataagacctcaacctcagaaattcacaagctcca tgaagattaatgtctcttggtgcaacaacaatagtatggtaaataatga agaagcatcgaaagacaacaacgatatgcaatggtgggcaaatatactg gaaaactgcaatgacattggagaaggagaagctgaaagaacactacctt catgtaaggaaattaattgcaatgaaattgataaagcaccaagtttgtt acatgagggaggcaactccatgcaacaaggacaaggtgatggtggttgg gatgaatttgctctagatgatatatggaatctacttaattag

>PAN1
MSTPMMCTFLGVIRKGSWTEEEDILLRKCIDKYGEGKWHLVPTRAGLNR

CRKSCRLRWLNYLRPHIKRGDFEPDEVDLILRLHKLLGNRWSLIAGRLP

GRTANDVKNYWNTNLLRKLNTSTKFAPQPQEGINTSTIAPQPQEGIKYG

---

SEQUENCE ANNEX VII
(SEQ ID NO: 19, nucleotide sequence;
SEQ ID NO: 20, amino acid sequence):

QANAIIRPQPQKFTSSMKINVSWCNNNSMVNNEEASKDNNDMQWWANIL

ENCNDIGEGEAERTLPSCKEINCNEIDKAPSLLHEGGNSMQQGQGDGGW

DEFALDDIWNLLN

---

SEQUENCE ANNEX VIII
(StMyb12, SEQ ID NO: 20; SlMyb12, SEQ ID NO: 21;
AtMyb12, SEQ ID NO: 22

CLUSTAL W (1.83) multiple sequence alignment

StMyb12/1-362      MGRTPCCEKVGIKRGRWTAEEDQILTNYIL
                   SNGEGSWRSLPKNAGLLRCGKSCRLRWINY

SlMyb12/1-339      MGRTPCCEKVGIKRGRWTAEEDQILTNYII
                   SNGEGSWRSLPKNAGLLRCGKSCRLRWINY

AtMyb12/1-371      MGRAPCCEKVGIKRGRWTAEEDQILSNYIQ
                   SNGEGSWRSLPKNAGLKRCGKSCRLRWINY

StMyb12/1-362      LRSDLKRGNITSQEEDIIIKLHATLGNRWS
                   LIAGHLSGRTDNEIKNYWNSHLSRKVD-SL

SlMyb12/1-339      LRSDLKRGNITSQEEDIIIKLHATLGNRWS
                   LIAEHLSGRTDNEIKNYWNSHLSRKVD-SL

AtMyb12/1-371      LRSDLKRGNITPEEEELVVKLHSTLGNRWS
                   LIAGHLPGRTDNEIKNYWNSHLSRKLHNFI

StMyb12/1-362      RIPSDEKLPKAVVDLAKKGTLKPIKHCRKS
                   LISRSKNKKSNLLEAKENSTSGALIGIVPM

SlMyb12/1-339      RIPSDEKLPKAVVDLAKKGIPKPIK---KS
                   SISRPKNKKSNLLEK--------------

AtMyb12/1-371      RKPSISQDVSAVIMTNASSAPPPPQAKRRL
                   GRTSRSAMKPKIHRTKTRKTKKTSAPPEPN

StMyb12/1-362      PSTPNIEKEALCCTNMPACDSAMALMQEDV
                   AKVEVPNSWAGSIEAKG-SLSSDSGMEWPR

SlMyb12/1-339      --------EALCCTNMPACDSAMELMQEDL
                   AKIEVPNSWGRTYRGQGKPLVQIVISNGPR

AtMyb12/1-371      ADVAGADKEALMVE---SSGAEAELGRPCD
                   YYGDDCNKNLMSINGDNGVLTFDDDIIDLL

StMyb12/1-362      LEEIMPDVVIDDEDMNPNFILNGLEEEVMS
                   NNAGNNYS-----CIDEGNKNVSSDDEKSK

SlMyb12/1-339      LEEIMPDVVIDDEDKNTNFILNCFREEVTS
                   NNVGNSYS-----CIEEGNKKISSDDEKIK

AtMyb12/1-371      LDESDPGHLYTNTTCGGDGELHNIRDSEGA
                   RGFSDTWNQGNLDCLLQSCPSVESFLNYDH

StMyb12/1-362      LLMDWQDDDELVWPTPPWELETDIIPSWPQ
                   WDDTDTDLLQN---CTN--NNYEEATTMEI

SlMyb12/1-339      LLMDWQDNDELVWPTLPWELETDIVPSWPQ
                   WDDIDINLLQN---CTNDNNNYEEATTMEI

AtMyb12/1-371      QVNDASTDEFIDWDCVWQEGSDNNLWHEKE
                   NPDSMVSWLLDGDDEATIGNSNCENFGEPL

StMyb12/1-362      NNQNHSAIVSWLLS

SlMyb12/1-339      NNQNHSTIVSWLLS

AtMyb12/1-371      DHDDESALVAWLLS

The invention claimed is:

1. A method for increasing the level of antioxidant compounds in a plant of the family Solanaceae or in at least one part of the plant, said method comprising causing or allowing within the plant or in at least one part, the expression of a heterologous nucleic acid comprising a MYB12 nucleotide sequence which encodes SlMYB12, StMYB12, or AtMYB12, or a functional variant of SlMYB12, StMYB12, or AtMYB12, said functional variant comprising at least 90% amino acid sequence identity to at least one amino acid sequence selected from the group consisting of SEQ ID NO: 12, 14, and 22; wherein the level of at least one antioxidant compound selected from the group consisting of flavonols, flavonol derivatives and chlorogenic acid is increased in the plant or in at least one part thereof when compared to the level of the one antioxidant compound in a wild-type plant or part thereof.

2. The method of claim 1, wherein the MYB12 nucleotide sequence encodes a polypeptide comprising the amino acid sequence set forth in SEQ ID NO: 12, 14, or 22.

3. The method of claim 1, further comprising causing or allowing within the plant or in at least one part the expression of a second heterologous nucleic acid and a third heterologous nucleic acid, wherein said second heterologous nucleic acid comprises a second nucleotide sequence which encodes Delila or a functional variant of Delila comprising at least 90% amino acid sequence identity to SEQ ID NO: 86, wherein said third heterologous nucleic acid comprises a third nucleotide sequence which encodes Rosea1 or Pan1, or a functional variant of Rosea1 or Pan1, said functional variant comprising at least 90% amino acid sequence identity to at least one amino acid sequence selected from the group consisting of SEQ ID NO: 20 or 84, and wherein the level of at least one anthocyanin is increased in the plant or in at least one part thereof when compared to the level of the anthocyanin in a wild-type plant or part thereof.

4. The method of claim 1, wherein the heterologous nucleic acid further comprises a promoter operably linked to the MYB12 nucleotide sequence.

5. The method of claim 1, wherein the heterologous nucleic acid is stably incorporated into the genome of the plant or part thereof.

6. A plant or plant part produced by the method of claim 1, wherein said plant or plant part comprises the heterologous nucleic acid.

7. A plant or part thereof comprising in its genome a heterologous nucleic acid comprising a MYB12 nucleotide sequence selected from the group consisting of:
   (a) a nucleotide sequence encoding SlMYB12;
   (b) a nucleotide sequence encoding StMYB12;
   (c) the nucleotide sequence set forth in SEQ ID NO: 11 or 13; and
   (d) a nucleotide sequence encoding a functional variant of StMYB12 or SlMYB12, said functional variant comprising at least 90% amino acid sequence identity to at least one amino acid sequence selected from the group consisting of SEQ ID NO: 12 and 14;
wherein the level of at least one antioxidant compound selected from the group consisting of flavonols, flavonol derivatives and chlorogenic acid is increased in the plant or in at least one part thereof when compared to the level of the one antioxidant compound in a wild-type plant or part thereof.

8. The plant or part thereof of claim 7, wherein the nucleotide sequence of (a) encodes a polypeptide comprising the amino acid sequence set forth in SEQ ID NO: 12.

9. The plant or part thereof of claim 7, wherein the nucleotide sequence of (b) encodes a polypeptide comprising the amino acid sequence set forth in SEQ ID NO: 14.

10. The plant or part thereof of claim 7, further comprising in its genome a second heterologous nucleic acid and a third heterologous nucleic acid, wherein said second heterologous nucleic acid comprises a second nucleotide sequence which encodes Delila or a functional variant comprising at least 90% amino acid sequence identity to SEQ ID NO: 86, and wherein said third heterologous nucleic acid comprises a third nucleotide sequence which encodes Rosea1 or Pan1, or a functional variant of Rosea1 or Pan1, said functional variant comprising at least 90% amino acid sequence identity to at least one amino acid sequence selected from the group consisting of SEQ ID NO: 20 or 84.

11. The plant or part thereof of claim 7, wherein the heterologous nucleic acid further comprises a promoter operably linked to the MYB12 nucleotide sequence.

12. The plant or part thereof of claim 7, wherein the heterologous nucleic acid is stably incorporated into the genome of the plant or part thereof.

13. The plant or part thereof of claim 7, wherein the plant is a plant of the family Solanaceae.

14. The plant or part thereof of claim 7, wherein the plant is a tomato plant or potato plant.

15. The plant or part thereof of claim 7, wherein the part is a tomato fruit or a potato tuber.

16. The plant or part thereof of claim 7, wherein the plant is a seed.

17. The plant or part thereof of claim 7, wherein the part is a cell.

18. A food product produced from the plant or part thereof of claim 7, wherein the food product comprises the heterologous nucleic acid.

19. A nucleic acid molecule comprising a member selected from the group consisting of:
(a) a nucleic acid molecule comprising a nucleotide sequence consisting of SEQ ID NO: 11 or 13, wherein the nucleic acid molecule comprises DNA;
(b) a recombinant vector comprising a nucleotide sequence encoding SlMYB12 or StMYB12 or a functional variant of SlMYB12 or StMYB12, said functional variant comprising at least 90% amino acid sequence identity to at least one amino acid sequence selected from the group consisting of SEQ ID NO: 12 and 14; and
(c) a recombinant DNA construct comprising a promoter operably linked to a nucleotide sequence encoding SlMYB12 or StMYB12 or a functional variant of SlMYB12 or StMYB12, said functional variant comprising at least 90% amino acid sequence identity to at least one amino acid sequence selected from the group consisting of SEQ ID NO: 12 and 14.

20. A plant or cell comprising a nucleic acid molecule of claim 19.

* * * * *